(12) United States Patent
Jang et al.

(10) Patent No.: US 9,957,441 B2
(45) Date of Patent: May 1, 2018

(54) AMINE-BASED COMPOUND AND ORGANIC LIGHT-EMITTING DEVICE INCLUDING THE SAME

(71) Applicant: SAMSUNG DISPLAY CO., LTD., Yongin-si, Gyeonggi-Do (KR)

(72) Inventors: Hyungseok Jang, Yongin-si (KR); Youngkook Kim, Yongin-si (KR); Jongwoo Kim, Yongin-si (KR); Jino Lim, Yongin-si (KR); Seokhwan Hwang, Yongin-si (KR)

(73) Assignee: SAMSUNG DISPLAY CO., LTD., Yongin-Si, Gyeonggi-Do (KR)

( * ) Notice: Subject to any disclaimer, the term of this patent is extended or adjusted under 35 U.S.C. 154(b) by 168 days.

(21) Appl. No.: 14/963,281

(22) Filed: Dec. 9, 2015

(65) Prior Publication Data
US 2016/0190467 A1    Jun. 30, 2016

(30) Foreign Application Priority Data

Dec. 30, 2014  (KR) .................. 10-2014-0194320

(51) Int. Cl.
*C09K 11/00*    (2006.01)
*C09K 11/06*    (2006.01)
(Continued)

(52) U.S. Cl.
CPC ............ *C09K 11/06* (2013.01); *C07D 261/00* (2013.01); *C07D 273/01* (2013.01);
(Continued)

(58) Field of Classification Search
CPC .. C09D 309/71; C09D 261/00; C09D 273/01; C09D 273/02; C09K 11/06;
(Continued)

(56) References Cited

U.S. PATENT DOCUMENTS 6,465,115 B2    10/2002  Shi et al.
6,596,415 B2    7/2003   Shi et al.
(Continued)

FOREIGN PATENT DOCUMENTS

KR    10-2012-0052993 A    5/2012
KR    10-2012-0066076 A    6/2012
(Continued)

*Primary Examiner* — Amanda C Walke
(74) *Attorney, Agent, or Firm* — Lee & Morse, P.C.

(57) ABSTRACT

An amine-based compound and an organic light-emitting device, the amine-based compound being represented by Formula 1 below:

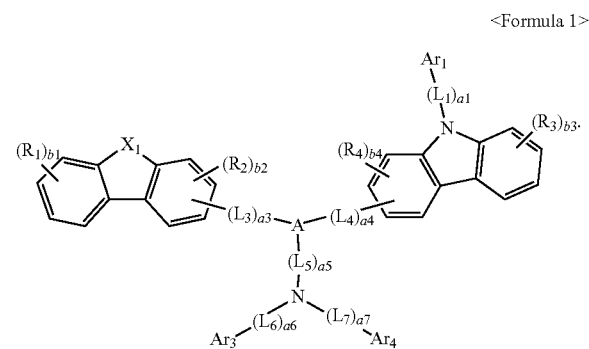

<Formula 1>

20 Claims, 1 Drawing Sheet

(51) Int. Cl.
  *H01L 51/00* (2006.01)
  *C07D 405/10* (2006.01)
  *C07D 309/00* (2006.01)
  *C07D 273/01* (2006.01)
  *C07D 261/00* (2006.01)
  *C07D 273/02* (2006.01)
  *H01L 51/50* (2006.01)

(52) U.S. Cl.
  CPC ......... *C07D 273/02* (2013.01); *C07D 309/00* (2013.01); *C07D 405/10* (2013.01); *H01L 51/006* (2013.01); *H01L 51/0058* (2013.01); *H01L 51/0059* (2013.01); *H01L 51/0072* (2013.01); *H01L 51/0073* (2013.01); *H01L 51/5056* (2013.01)

(58) Field of Classification Search
  CPC .. C07D 309/00; C07D 261/00; C07D 273/01; C07D 273/02
  USPC ....... 257/E51.026, 40; 548/440; 549/43, 460
  See application file for complete search history.

(56) References Cited

U.S. PATENT DOCUMENTS

| | | |
|---|---|---|
| 2009/0160323 A1 | 6/2009 | Nomura et al. |
| 2012/0146014 A1 | 6/2012 | Kato |
| 2012/0248426 A1* | 10/2012 | Kato ................... C07D 209/86 257/40 |
| 2013/0270540 A1 | 10/2013 | Numata |
| 2013/0300638 A1* | 11/2013 | Kamatani ............... C09K 11/06 345/76 |
| 2014/0159023 A1 | 6/2014 | Matsumoto et al. |
| 2014/0374723 A1* | 12/2014 | Kamatani ............. C07C 211/61 257/40 |
| 2015/0105563 A1* | 4/2015 | Ahn ...................... C07F 7/0812 548/418 |
| 2015/0270492 A1* | 9/2015 | Kang .................. H01L 51/0059 257/40 |
| 2016/0190464 A1* | 6/2016 | Lim ..................... C07D 307/91 257/40 |
| 2016/0190468 A1* | 6/2016 | Ueno .................. H01L 51/0059 257/40 |
| 2016/0226000 A1* | 8/2016 | Kim ....................... H01L 51/006 |
| 2016/0293843 A1* | 10/2016 | Itoi ...................... C07D 307/91 |
| 2016/0322579 A1* | 11/2016 | Hwang ............... H01L 51/0061 |

FOREIGN PATENT DOCUMENTS

| | | |
|---|---|---|
| KR | 10-2013-0058086 A | 6/2013 |
| KR | 10-2014-0015285 A | 2/2014 |
| KR | 10-2014-0034183 A | 3/2014 |
| KR | 10-2014-0061241 A | 5/2014 |

* cited by examiner

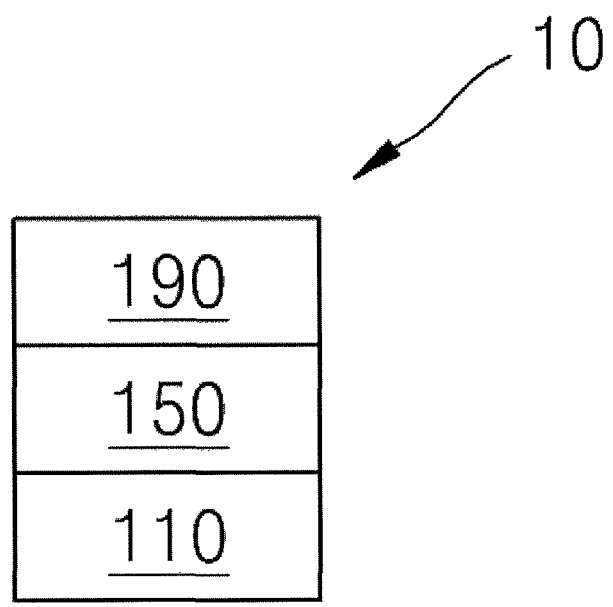

AMINE-BASED COMPOUND AND ORGANIC LIGHT-EMITTING DEVICE INCLUDING THE SAME

CROSS-REFERENCE TO RELATED APPLICATION

Korean Patent Application No. 10-2014-0194320, filed on Dec. 30, 2014, in the Korean Intellectual Property Office, and entitled: "Amine-Based Compound and Organic Light-Emitting Device Including the Same," is incorporated by reference herein in its entirety.

BACKGROUND

1. Field

Embodiments relate to an amine-based compound and an organic light-emitting device including the same.

2. Description of the Related Art

Organic light-emitting devices are self-emission devices that have wide viewing angles, high contrast ratios, short response times, and excellent brightness, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, are recombined in the emission layer to produce excitons. These excitons change from an excited state to a ground state, thereby generating light.

SUMMARY

Embodiments are directed to an amine-based compound and an organic light-emitting device including the same.

An aspect provides an amine-based compound represented by Formula 1 below:

<Formula 1>

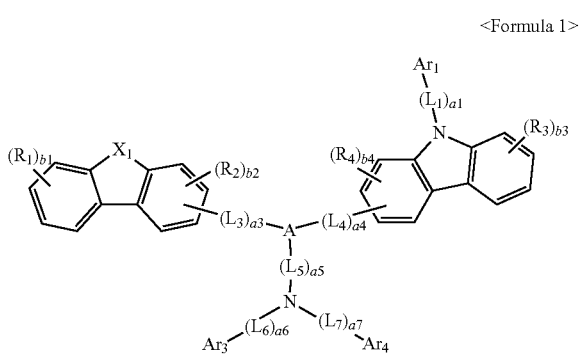

wherein in Formula 1,

A may be a substituted or unsubstituted $C_6$-$C_{20}$ aromatic ring;

$X_1$ may be selected from N-$(L_2)_{a2}$-$(Ar_2)$, an oxygen atom (O), and a sulfur atom (S);

$L_1$ to $L_7$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a7 may each independently be an integer selected from 0 to 3;

$Ar_1$ to $Ar_4$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted heteroaryl group, a substituted or unsubstituted monovalent non-aromatic condensed polycyclic group, and a substituted or unsubstituted monovalent non-aromatic condensed heteropolycyclic group;

$R_1$ to $R_4$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, and —B$(Q_4)(Q_5)$;

b1 and b3 may each independently be an integer selected from 0 to 4, b2 and b4 are each independently an integer selected from 0 to 3;

at least one substituent of the substituted $C_6$-$C_{20}$ aromatic ring, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted a divalent non-aromatic condensed polycyclic group, substituted a divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), and —B($Q_{14}$)($Q_{15}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{31}$)($Q_{32}$)($Q_{33}$), and —B($Q_{34}$)($Q_{35}$), each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), and —B($Q_{24}$)($Q_{25}$); and $Q_1$ to $Q_5$, $Q_{11}$ to $Q_{15}$, $Q_{21}$ to $Q_{25}$ and $Q_{31}$ to $Q_{35}$ may each independently be a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

Another aspect provides an organic light-emitting device that includes: a first electrode; a second electrode facing the first electrode; and an organic layer that is disposed between the first electrode and the second electrode and includes an emission layer, wherein the organic layer includes at least one of the amine-based compound described above.

BRIEF DESCRIPTION OF THE DRAWING

Features will be apparent to those of skill in the art by describing in detail exemplary embodiments with reference to the attached drawing in which:

FIG. 1 illustrates a schematic view of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

An amine-containing (e.g., tertiary amine-containing) or amine-based compound according to an embodiment may be represented by Formula 1 below.

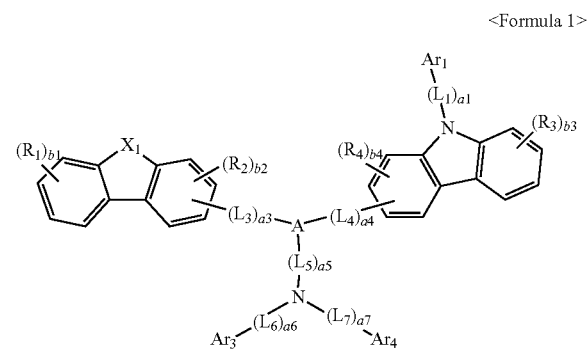

<Formula 1>

A in Formula 1 may be or may include, e.g., a substituted or unsubstituted $C_6$-$C_{20}$ aromatic ring.

In an implementation, A in Formula 1 may be selected from or include, e.g., a substituted or unsubstituted a benzene group, a substituted or unsubstituted a naphthalene group, a substituted or unsubstituted an anthracene group, a substituted or unsubstituted a pyrene group, a substituted or unsubstituted a phenanthrene group, a substituted or unsubstituted a chrysene group, and a substituted or unsubstituted triphenylene group.

In an implementation, A may be a group represented by one of the following Formulae 2-1 to 2-19.

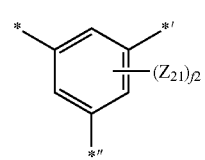

Formula 2-1

-continued
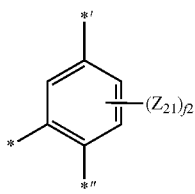
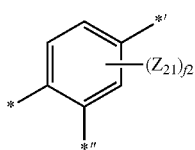
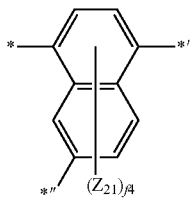
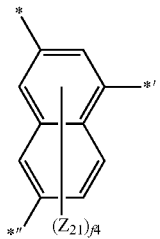
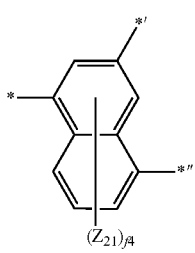
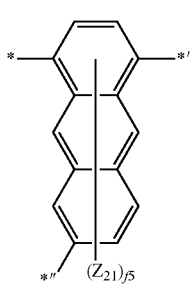
Formula 2-2
Formula 2-3
Formula 2-4
Formula 2-5
Formula 2-6
Formula 2-7
-continued
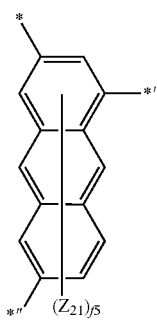
Formula 2-8
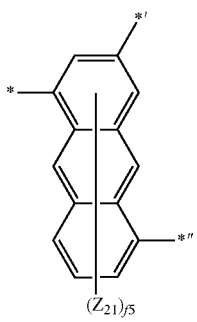
Formula 2-9
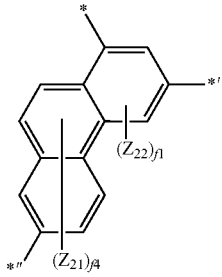
Formula 2-10
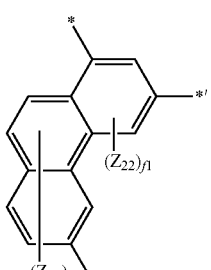
Formula 2-11
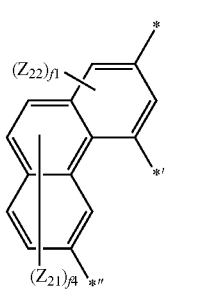
Formula 2-12

-continued

Formula 2-13

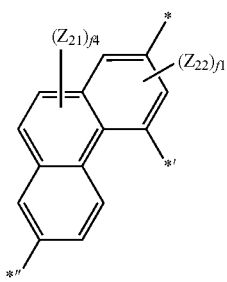

Formula 2-14

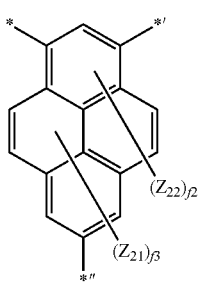

Formula 2-15

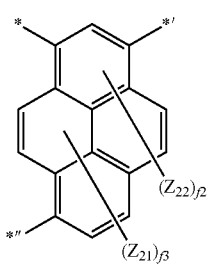

Formula 2-16

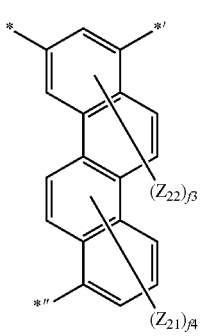

Formula 2-17

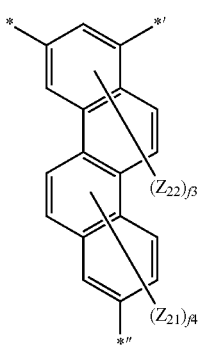

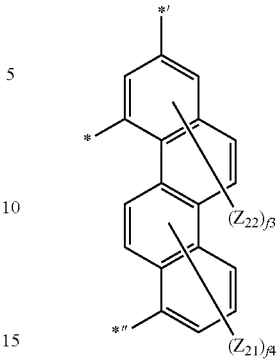

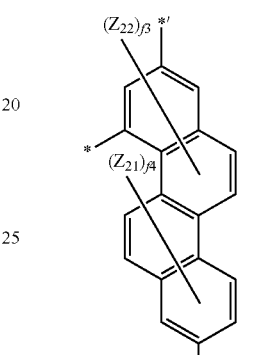

Formula 2-18

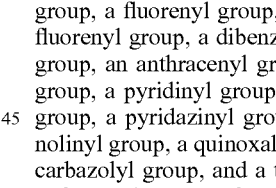

Formula 2-19

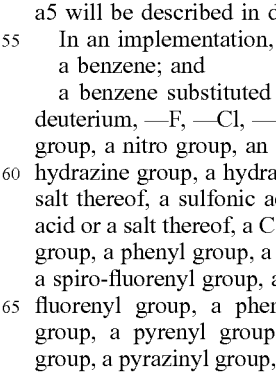

In Formulae 2-1 to 2-19, $Z_{21}$ and $Z_{22}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

f1 may be 1 or 2, f2 may be an integer selected from 1 to 3, f3 may be an integer selected from 1 to 4, f4 may be an integer selected from 1 to 5, and f5 may be an integer selected from 1 to 7;

\* and \*' indicate binding sites to neighboring atoms, and \*'' indicates a binding site to $L_5$ in -$(L_5)_{a5}$- or to N. $L_5$ and a5 will be described in detail below.

In an implementation, A may be selected from:

a benzene; and a benzene substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

$X_1$ in Formula 1 may be selected from, e.g., N-$(L_2)_{a2}$-$(Ar_2)$, O (oxygen atom) and S (sulfur atom). For example, $X_1$ may be O or S.

In an implementation, $X_1$ may be O.

$L_1$ to $L_7$ may each independently be selected from or include, e.g., a substituted or unsubstituted $C_3$-$C_{10}$ cycloalkylene group, a substituted or unsubstituted heterocycloalkylene group, a substituted or unsubstituted $C_1$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In an implementation, $L_1$ to $L_7$ in Formula 1 may each independently be selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a furinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a furinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a pherylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In an implementation, $L_1$ to $L_7$ in Formula 1 may each independently be a group represented by one of Formulae 3-1 to 3-33 below.

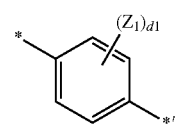

Formula 3-1

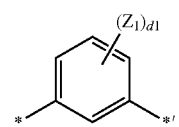

Formula 3-2

-continued
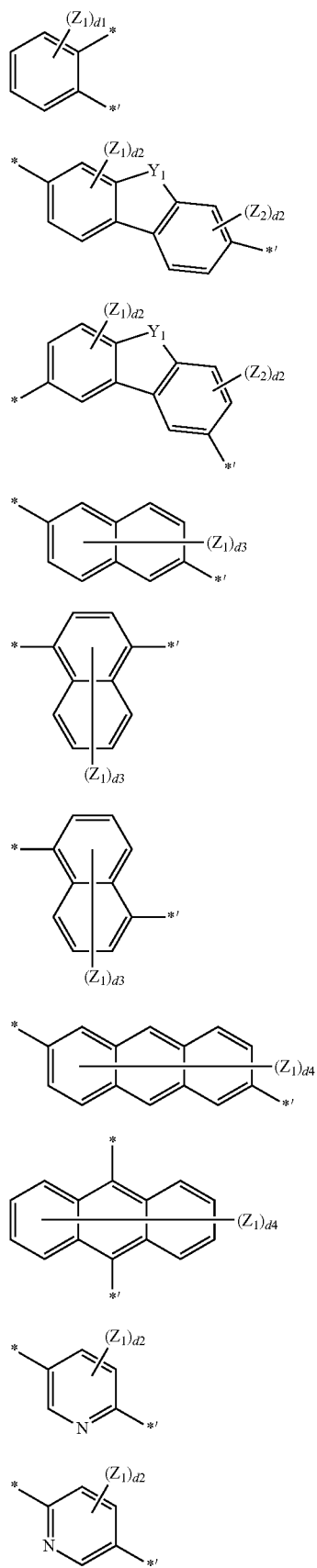
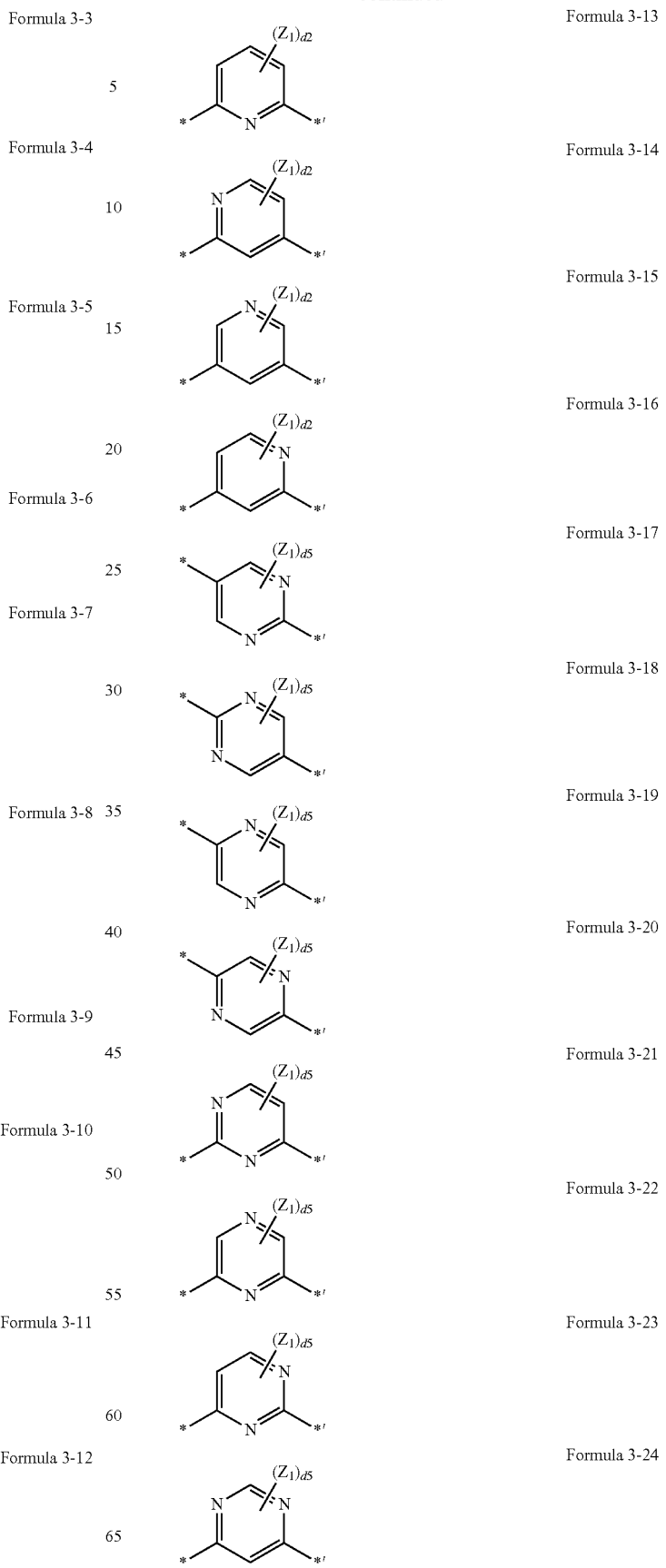

-continued

Formula 3-25
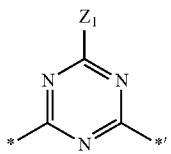

Formula 3-26
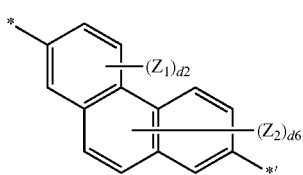

Formula 3-27
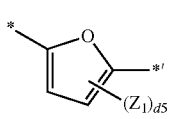

Formula 3-28
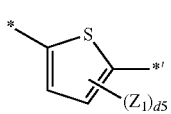

Formula 3-29
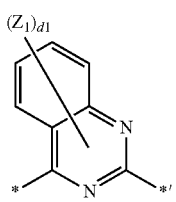

Formula 3-30
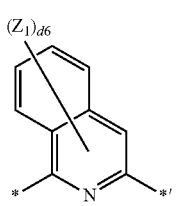

Formula 3-31
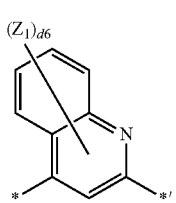

Formula 3-32
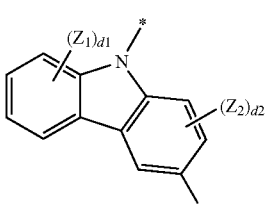

Formula 3-33
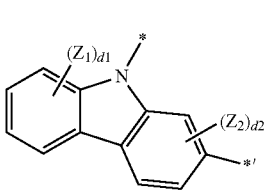

In Formulae 3-1 to 3-33, $Y_1$ may be O, S, $C(Z_3)(Z_4)$, $N(Z_5)$, or $Si(Z_6)(Z_7)$;

$Z_1$ to $Z_7$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 may be an integer selected from 1, 2, 3, and 4, d2 may be an integer selected from 1, 2, and 3, d3 may be an integer selected from 1, 2, 3, 4, 5, and 6, d4 may be an integer selected from 1, 2, 3, 4, 5, 6, 7, and 8, d5 may be 1 or 2, and d6 may be an integer selected from 1, 2, 3, 4, and 5, and * and *' indicate binding sites to neighboring atoms.

a1, a2, a3, a4, a5, a6, and a7 in Formula 1 respectively indicate numbers of $L_1$, $L_2$, $L_3$, $L_4$, $L_5$, $L_6$, and $L_7$, and may each independently be an integer selected from 0 to 3.

For example, a1, a2, a5, a6, and a7 may each independently be 0, 1, 2, or 3, and a3 and a4 may each independently be 0 or 1.

When a1, a2, a3, a4, a5, a6, or a7 are 2 or more, 2 or more $L_1$, $L_2$, $L_3$, $L_4$, $L_5$, $L_6$, or $L_7$ may be identical or different.

*-$(L_1)_{a1}$-*', *-$(L_2)_{a2}$-*', *-$(L_3)_{a3}$-*', *-$(L_6)_{a6}$-*, and *-$(L_7)_{a7}$-* in Formula 1 may each independently be a single bond or may be a group represented by one of the following Formulae 4-1 to 4-27.

Formula 4-1
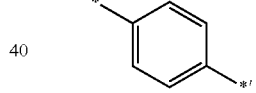

Formula 4-2
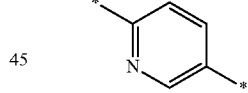

Formula 4-3
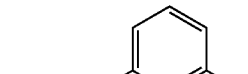

Formula 4-4
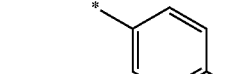

Formula 4-5
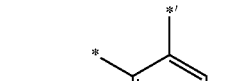

Formula 4-6
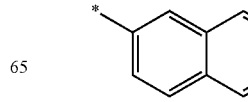

-continued
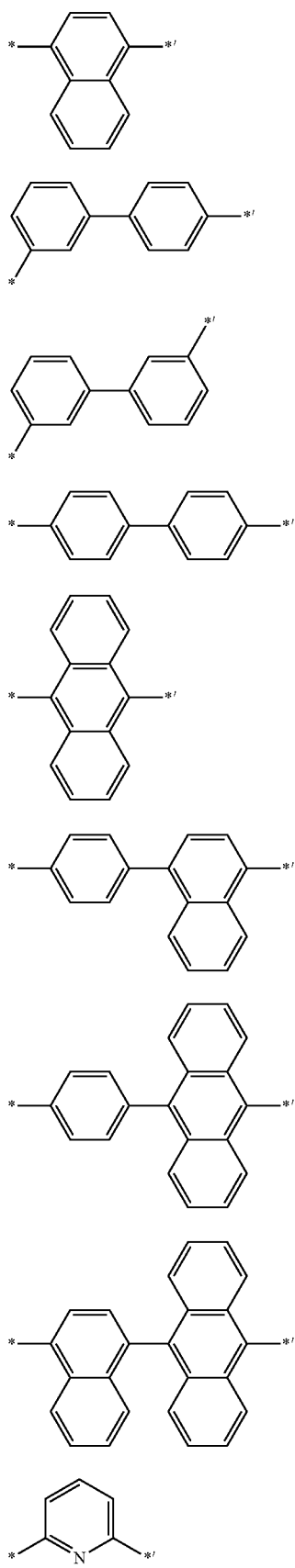
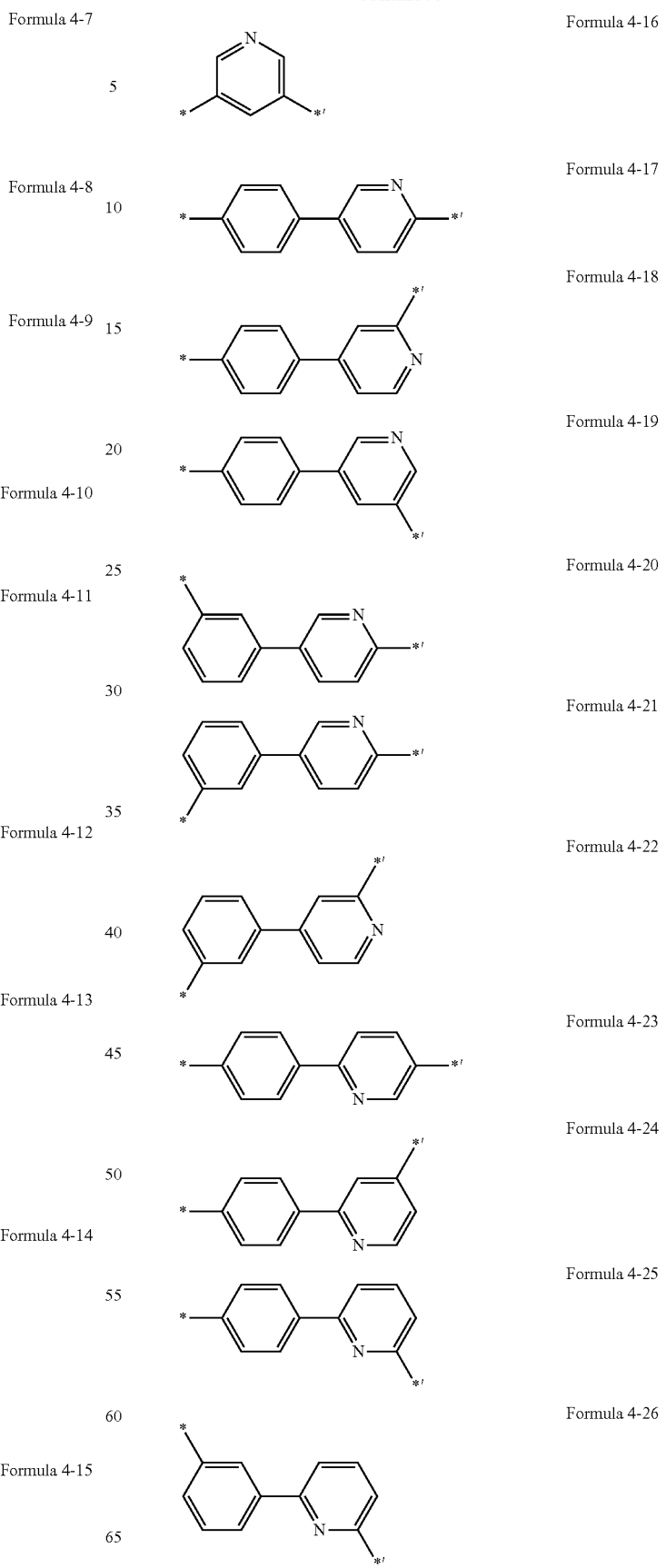

Formula 4-27

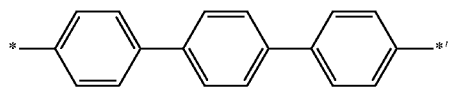

* and *' in Formulae 4-1 to 4-27 indicate binding sites to neighboring atoms.

$Ar_1$ to $Ar_4$ in Formula 1 may each independently be selected from or include, e.g., a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted heteroaryl group, a substituted or unsubstituted monovalent non-aromatic condensed polycyclic group, and a substituted or unsubstituted monovalent non-aromatic condensed heteropolycyclic group.

In an implementation, $Ar_1$ to $Ar_4$ in Formula 1 may each independently be selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzofuranyl group, a thiadiazolyl group, an imidazopyridinyl group, or an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, an imidazopyrimidinyl group, —Si($Q_{31}$)($Q_{32}$)($Q_{33}$), and —B($Q_{34}$)($Q_{35}$)

$Q_{31}$ to $Q_{35}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In an implementation, $Ar_1$ to $Ar_4$ in Formula 1 may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group, and a dibenzocarbazolyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group, a dibenzocarbazolyl group, —Si($Q_{31}$)($Q_{32}$)($Q_{33}$), and —B($Q_{34}$)($Q_{35}$)

$Q_{31}$ to $Q_{35}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In an implementation, $Ar_1$ to $Ar_4$ in Formula 1 may each independently be a group represented by one of Formulae 5-1 to 5-16 below.

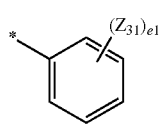

Formula 5-1

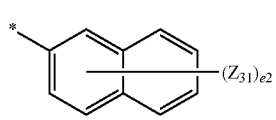

Formula 5-2

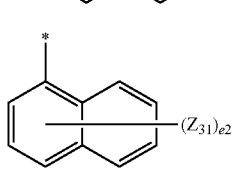

Formula 5-3

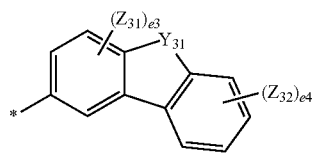

Formula 5-4

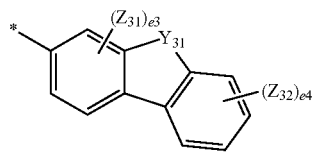

Formula 5-5

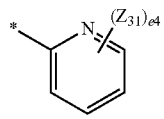

Formula 5-6

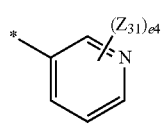

Formula 5-7

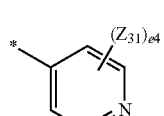

Formula 5-8

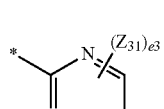

Formula 5-9

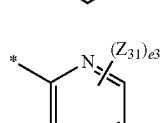

Formula 5-10

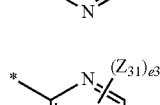

Formula 5-11

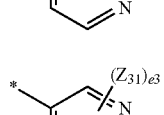

Formula 5-12

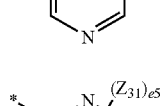

Formula 5-13

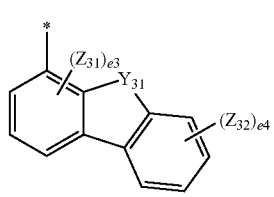

Formula 5-14

Formula 5-15

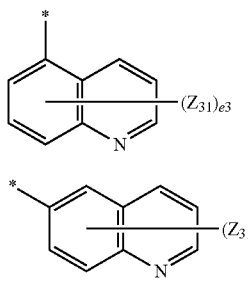

Formula 5-16

In Formulae 5-1 to 5-16, $Y_{31}$ may be $C(Z_{33})(Z_{34})$ or $N(Z_{35})$;

$Z_{31}$ to $Z_{35}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group, and a dibenzocarbazolyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, and a naphthyl group; and —Si($Q_{31}$)($Q_{32}$)($Q_{33}$).

$Q_{31}$ to $Q_{33}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

e1 may be an integer of 1 to 5; e2 may be an integer of 1 to 7; e3 may be an integer of 1 to 3; e4 may be an integer of 1 to 4; e5 may be 1 or 2; and * indicates a binding site to a neighboring atom.

In an implementation, $Ar_1$ to $Ar_4$ in Formula 1 may each independently be a group represented by one of Formulae 6-1 to 6-24 below.

Formula 6-1

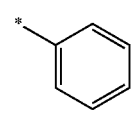

Formula 6-2

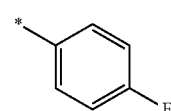

Formula 6-3

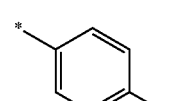

Formula 6-4

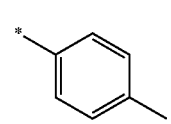

Formula 6-5

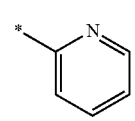

Formula 6-6

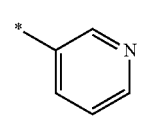

Formula 6-7

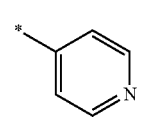

Formula 6-8

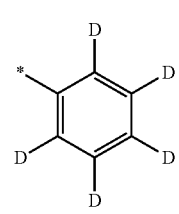

Formula 6-9

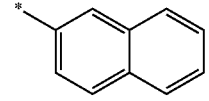

Formula 6-10

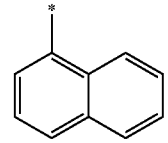

Formula 6-11
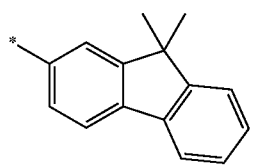

Formula 6-12
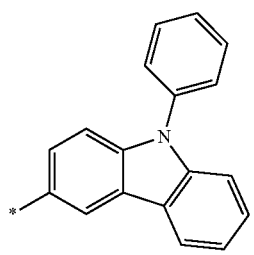

Formula 6-13
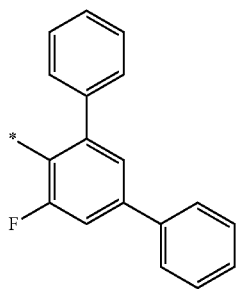

Formula 6-14
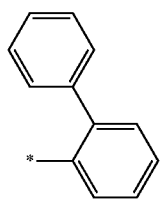

Formula 6-15
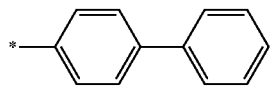

Formula 6-16
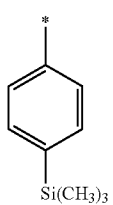

Formula 6-17
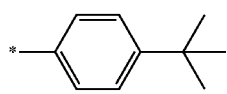

Formula 6-18
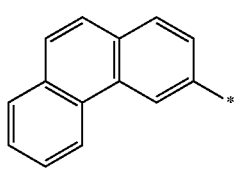

Formula 6-19
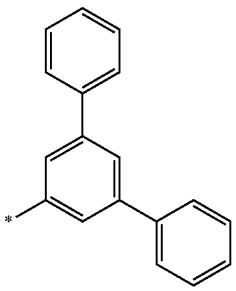

Formula 6-20
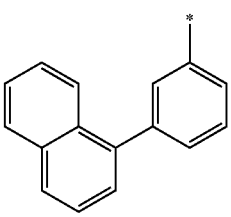

Formula 6-21
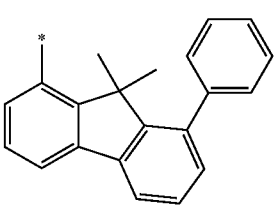

Formula 6-22
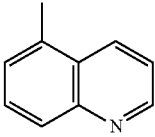

Formula 6-23
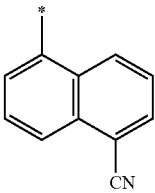

Formula 6-24
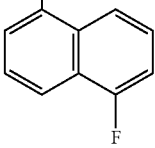

wherein * in Formulae 6-1 to 6-24 indicates a binding site to a neighboring atom.

In an implementation, $Ar_1$ to $Ar_4$ in Formula 1 may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and —Si($Q_{31}$)($Q_{32}$)($Q_{33}$).

$Q_{31}$ to $Q_{33}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

$R_1$ to $R_4$ in Formula 1 may each independently be selected from or include, e.g., a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —B($Q_4$)($Q_5$). $Q_1$ to $Q_5$ may be the same as described below.

In an implementation, $R_1$ to $R_4$ in Formula 1 may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —Si($Q_{31}$)($Q_{32}$)($Q_{33}$) and —B($Q_{34}$)($Q_{35}$); and —Si($Q_1$)($Q_2$)($Q_3$).

$Q_1$ to $Q_3$ and $Q_{31}$ to $Q_{33}$ may each independently be selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

In an implementation, $R_1$ to $R_4$ in Formula 1 may each independently be selected from a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one selected from —F, a cyano group, a nitro group, a phenyl group, a naphthyl group, a pyridinyl group, a pyrimidinyl group, a triazinyl group, and —Si($Q_{33}$)($Q_{34}$)($Q_{35}$); and —Si($Q_1$)($Q_2$)($Q_3$).

$Q_1$ to $Q_3$ and $Q_{33}$ to $Q_{35}$ may each independently be selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

b1, b2, b3, and b4 in Formula 1 respectively indicate numbers of $R_1$, $R_2$, $R_3$, and $R_4$, and b1 and b3 may be each independently 1, 2, 3, or 4 and b2 and b4 may be each independently 1, 2, or 3. When b1, b2, b3, or b4 is 2 or more, 2 or more $R_1$, $R_2$, $R_3$ or $R_4$ may be identical or different.

In an implementation, $Q_1$ to $Q_5$, $Q_{11}$ to $Q_{15}$, $Q_{21}$ to $Q_{25}$ and $Q_{31}$ to $Q_{35}$ may each independently be, e.g., a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

In an implementation, the amine-based compound represented by Formula 1 may be represented by one of the following Formulae 1A to 1F.

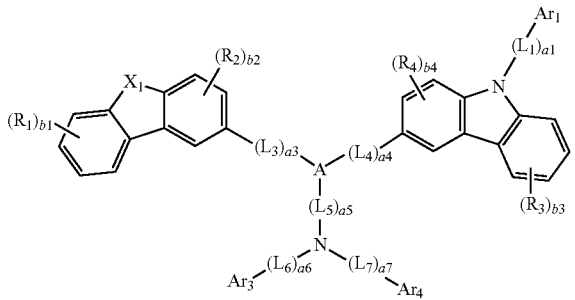

<Formula 1A>

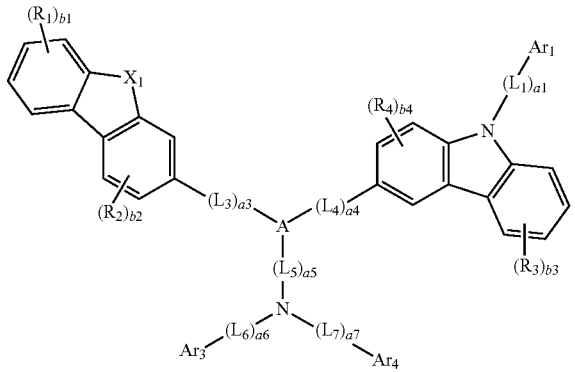

<Formula 1B>

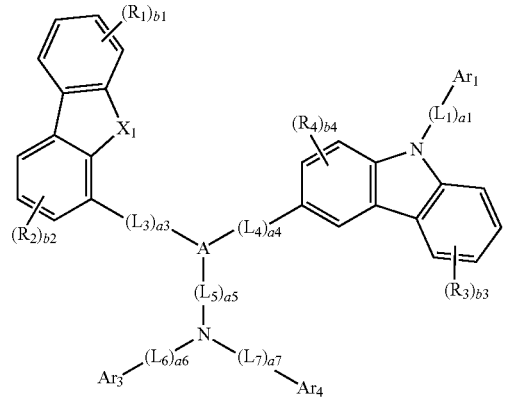

<Formula 1C>

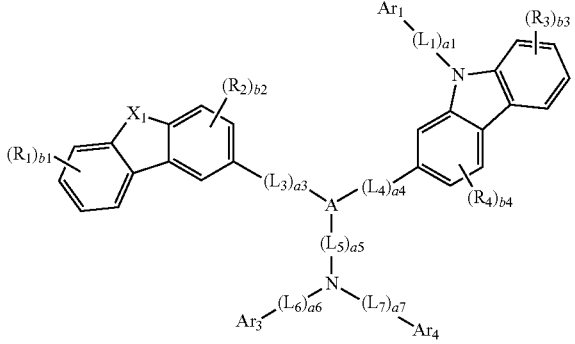

<Formula 1D>

<Formula 1E>
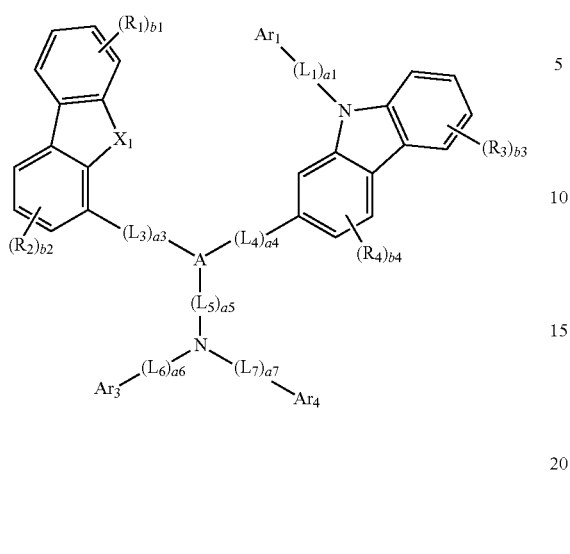
<Formula 1F>
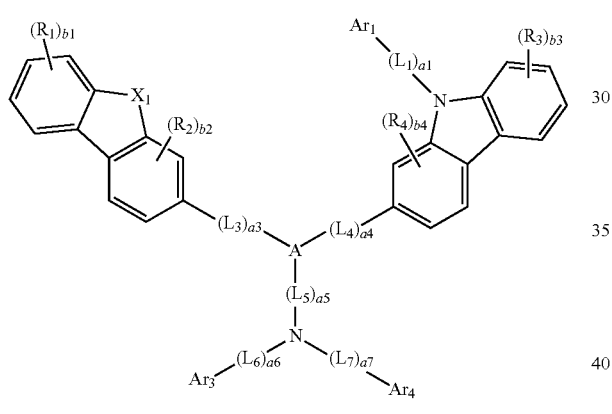
Descriptions of $X_1$, A, $L_1$ to $L_7$, a1 to a7, $Ar_1$ to $Ar_4$, $R_1$ to $R_4$, and b1 to b4 in Formulae 1A to 1F may be the same as described above.
In an implementation, the amine-based compound represented by Formula 1 may be represented by one of the following Formulae 1A-1, 1A-2, 1B-1, 1B-2, 1C-1, 1C-2, 1D-1, 1D-2, 1E-1, 1E-2, 1F-1, and 1F-2.
<Formula 1A-1>
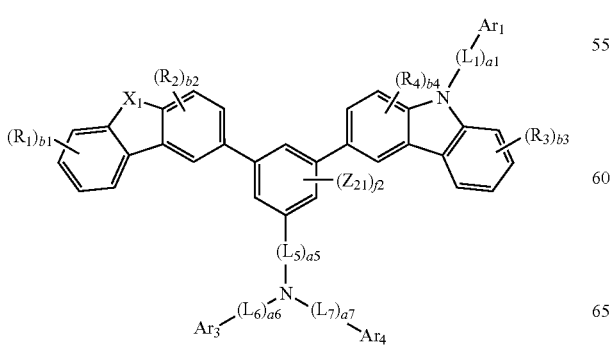
<Formula 1A-2>
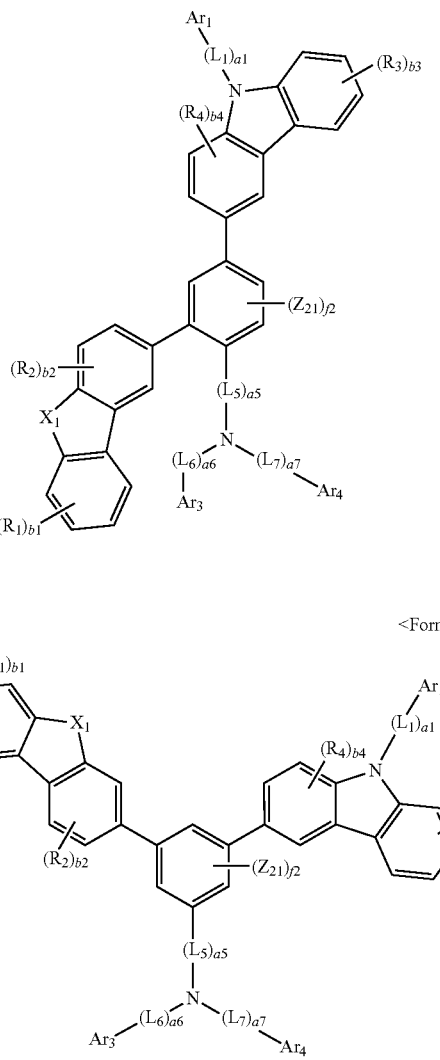
<Formula 1B-1>
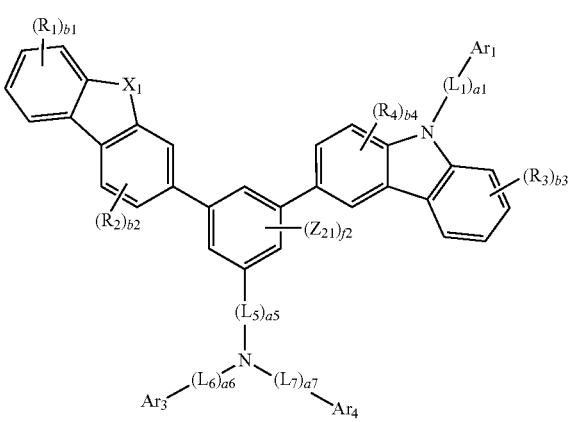
<Formula 1B-2>
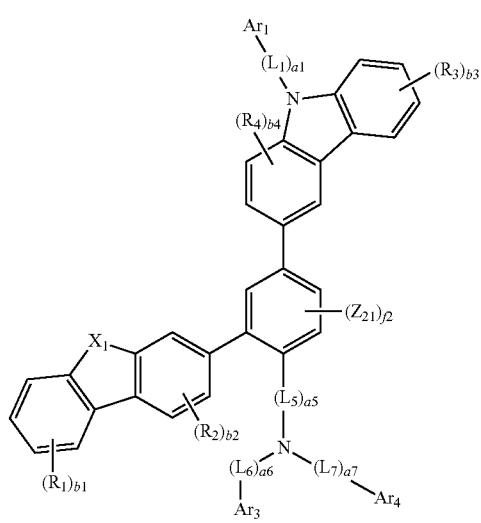

<Formula 1C-1>
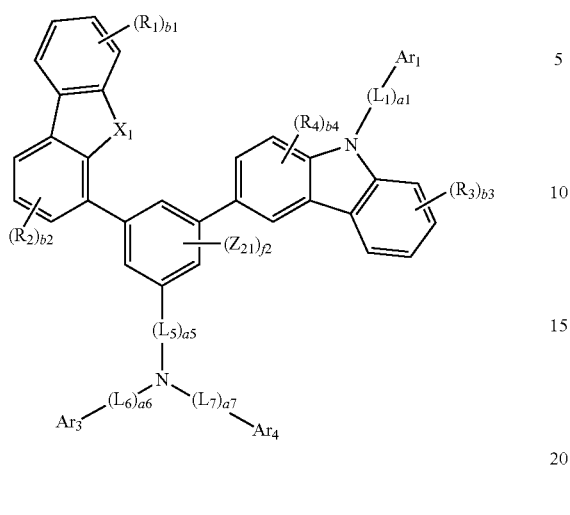
<Formula 1D-2>
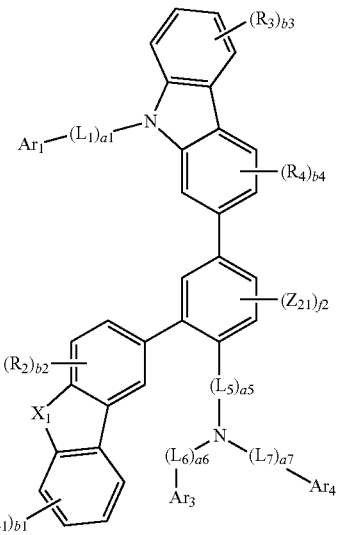
<Formula 1C-2>
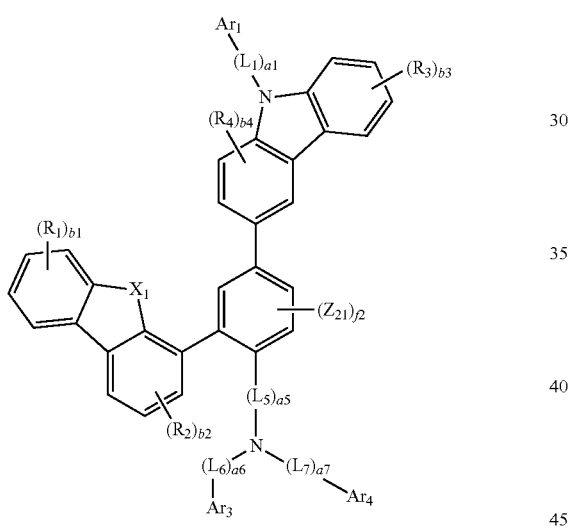
<Formula 1E-1>
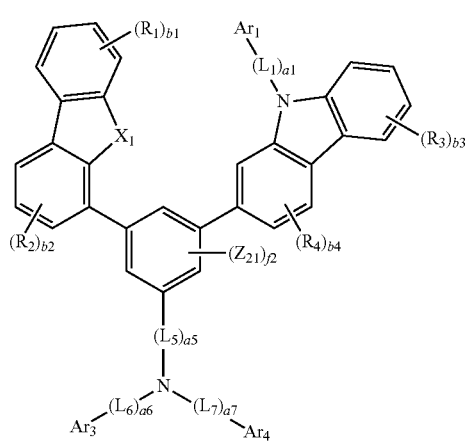
<Formula 1D-1>
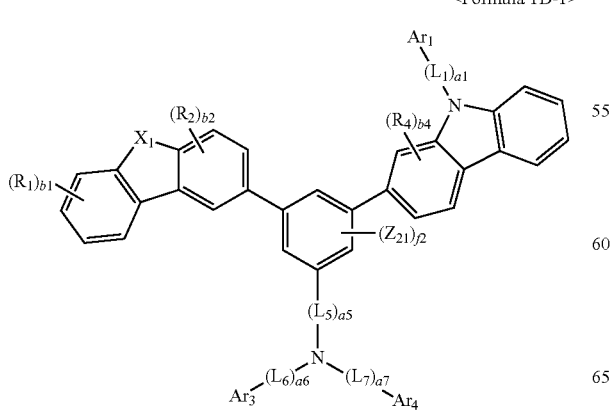
<Formula 1E-2>
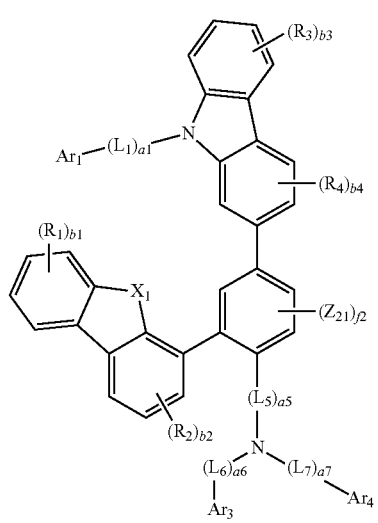

-continued

<Formula 1F-1>

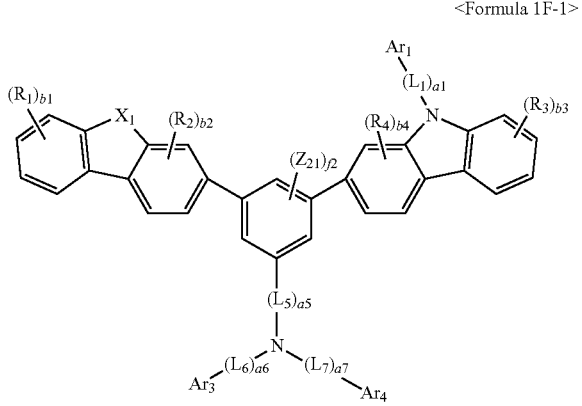

<Formula 1F-2>

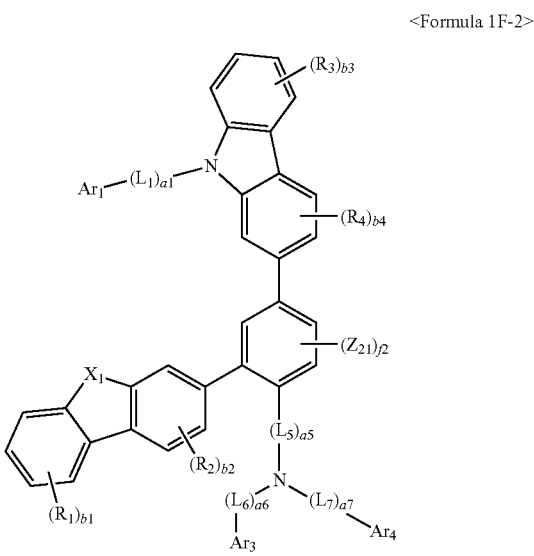

In Formulae 1A-1, 1A-2, 1B-1, 1B-2, 1C-1, 1C-2, 1D-1, 1D-2, 1E-1, 1E-2, 1F-1, and 1F-2, $Z_{21}$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

f2 may be an integer selected from 0 to 3;

$X_1$ may be O or S;

$L_1$, $L_5$, $L_6$, and $L_7$ may each independently be selected from a phenylene group, a naphthylene group, a pyridinylene group, a pyrimidinylene group, and a triazinylene group; and a phenylene group, a naphthylene group, a pyridinylene group, a pyrimidinylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a1 may be 0 or 1, and a5, a6, and a7 may each independently be an integer selected from 0 to 3;

$Ar_1$ to $Ar_4$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, —Si($Q_{31}$)($Q_{32}$)($Q_{33}$), and —B($Q_{34}$)($Q_{35}$), $Q_{31}$ to $Q_{35}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_1$ to $R_4$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, and a substituted or unsubstituted $C_1$-$C_{20}$ alkoxy group;

b1 and b3 may each independently be an integer selected from 0 to 4, and b2 and b4 may each independently be an integer selected from 0 to 3.

In an implementation, the amine-based compound represented by Formula 1 may be one of the following Compounds 1 to 300.

1
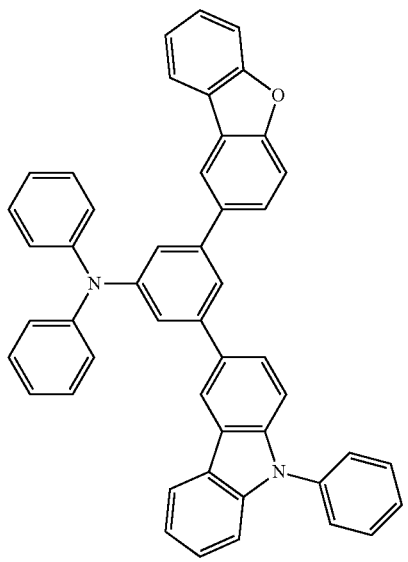
2
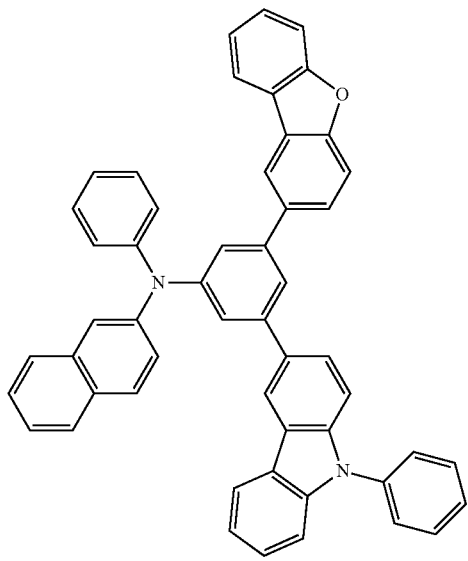
3
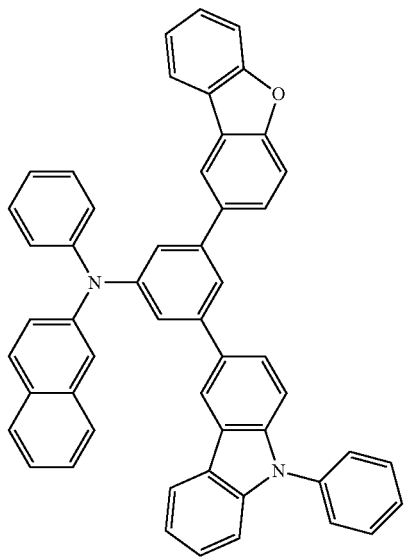
4
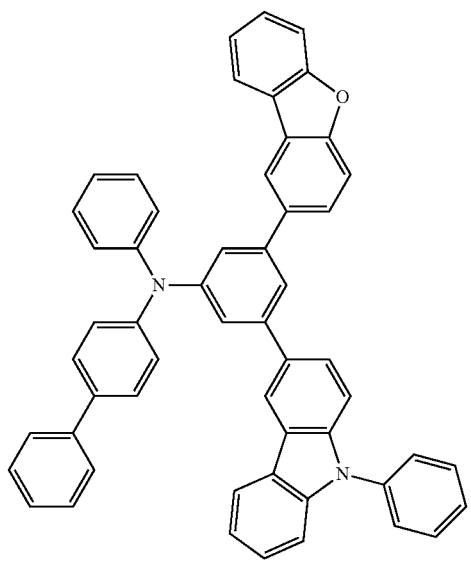

5
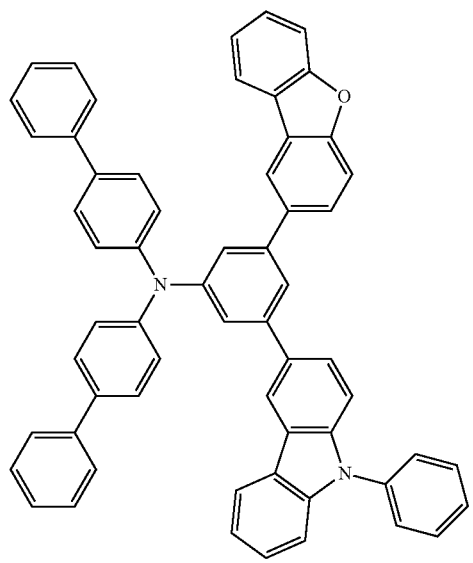
6
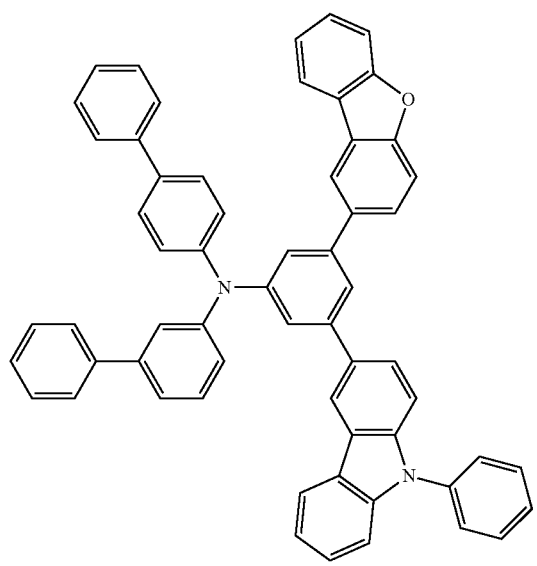
7
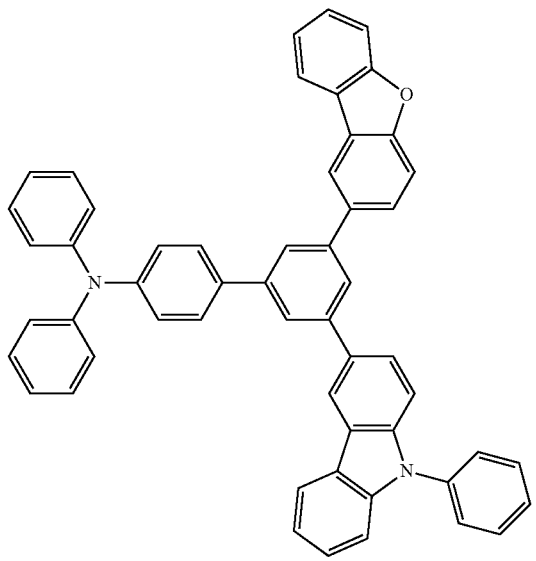
8
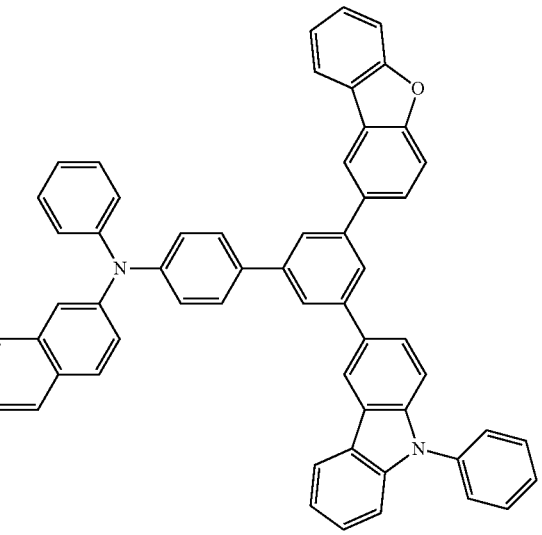

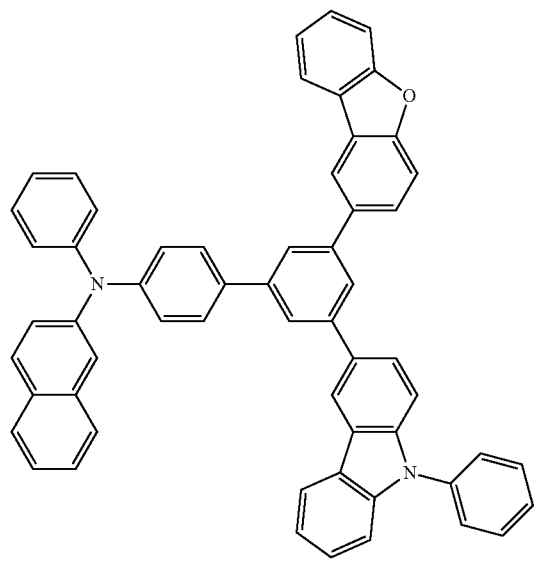
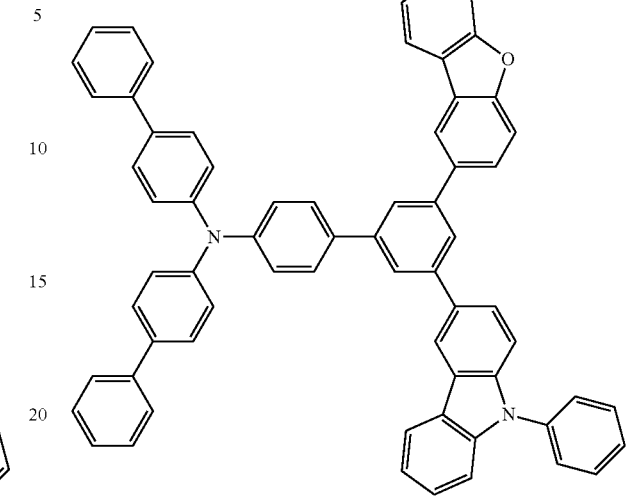
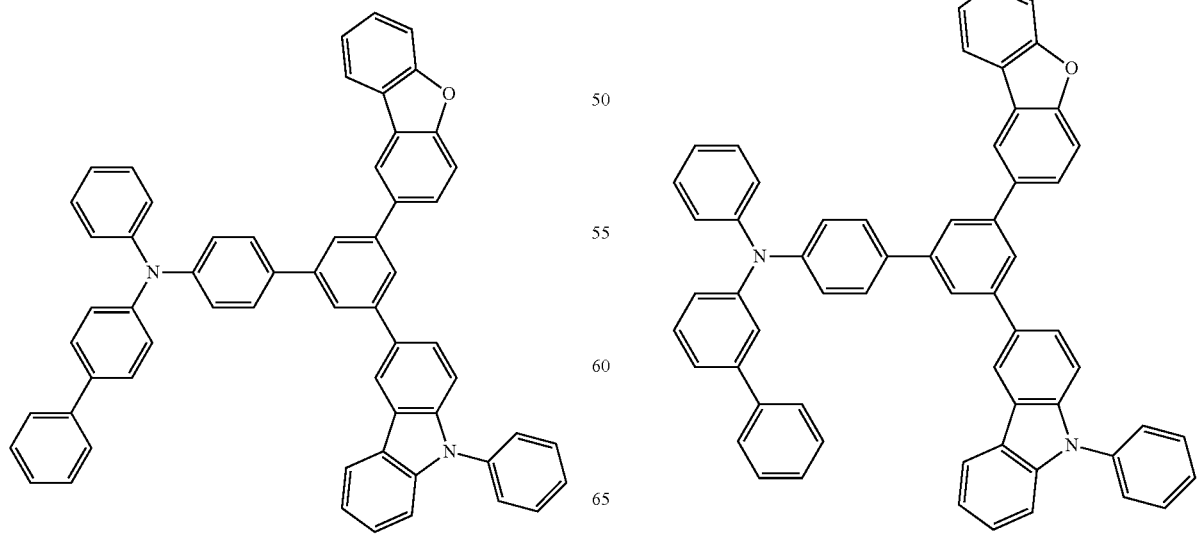

13
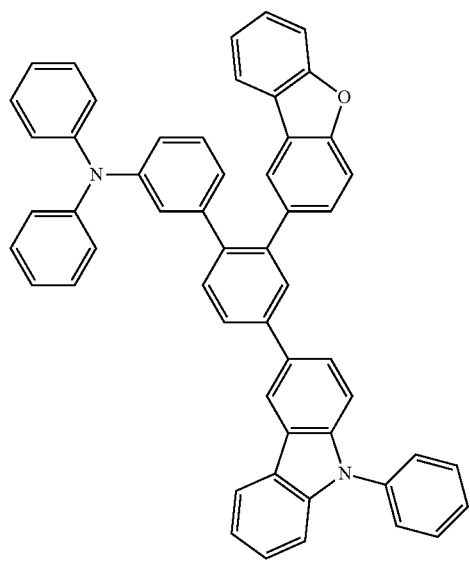
14
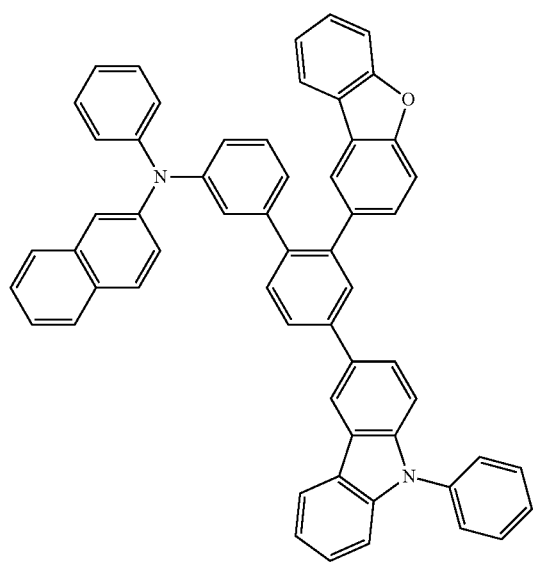
15
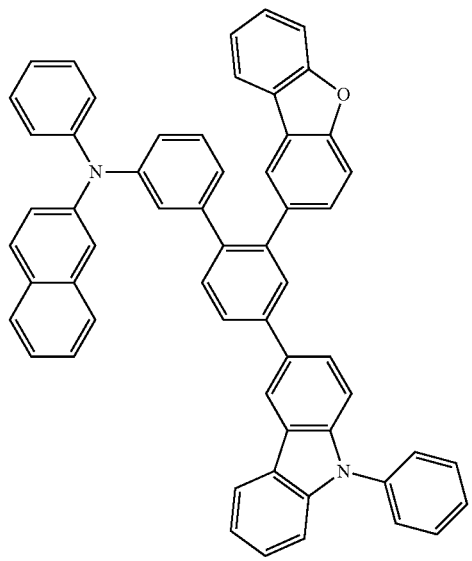
16
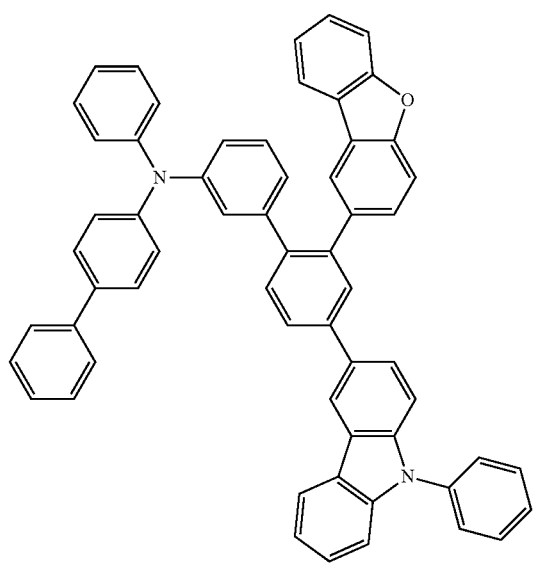

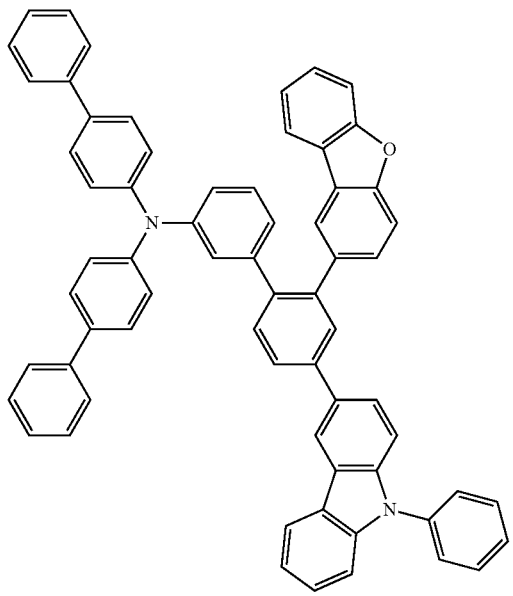
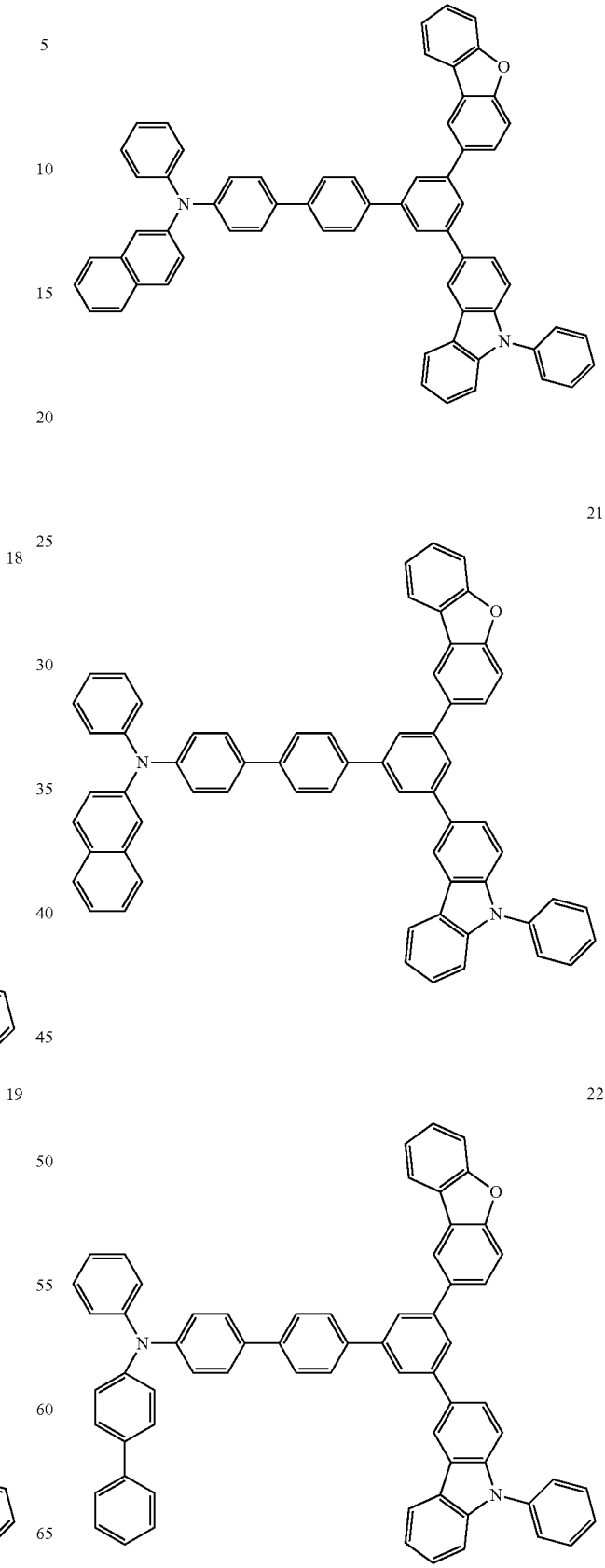

23
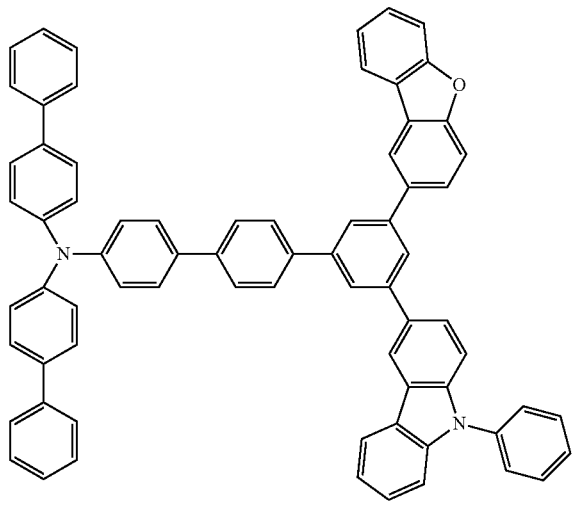
24
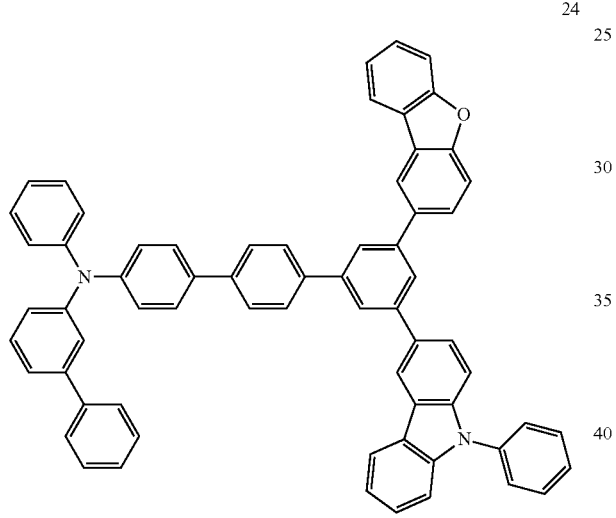
26
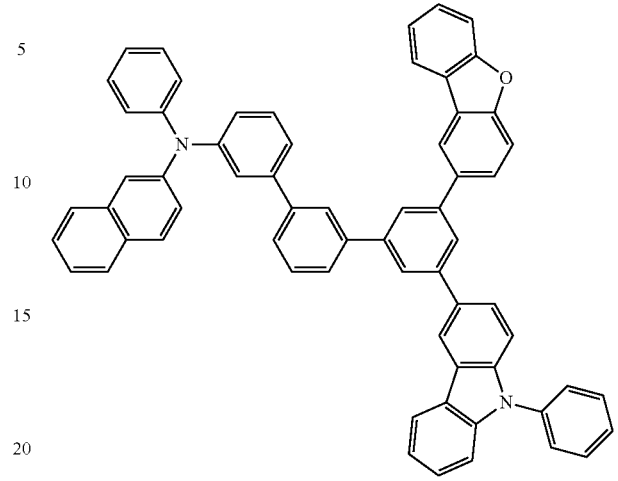
27
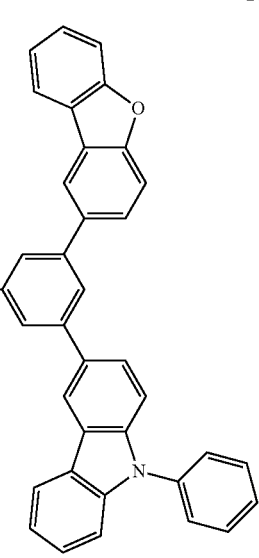
25
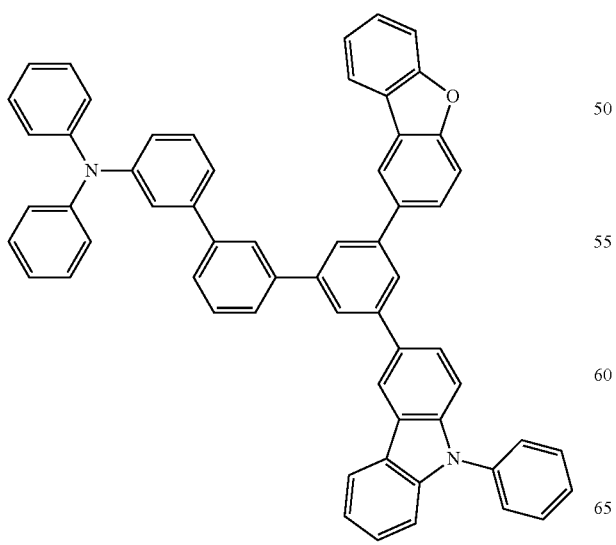
28
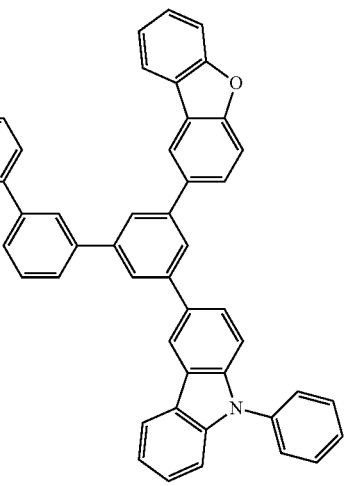

29
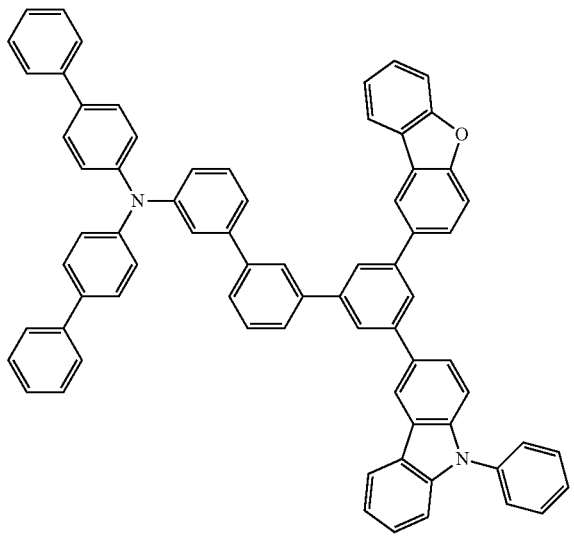
31
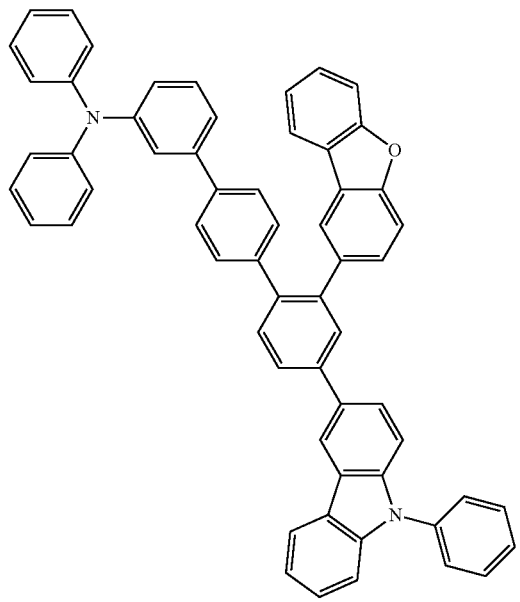
30
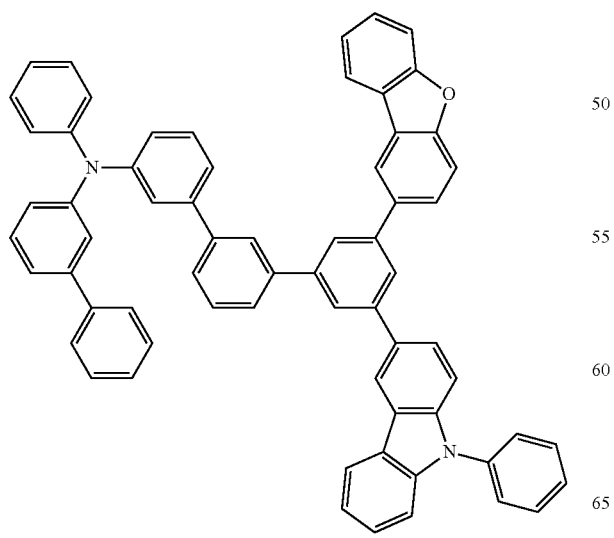
32
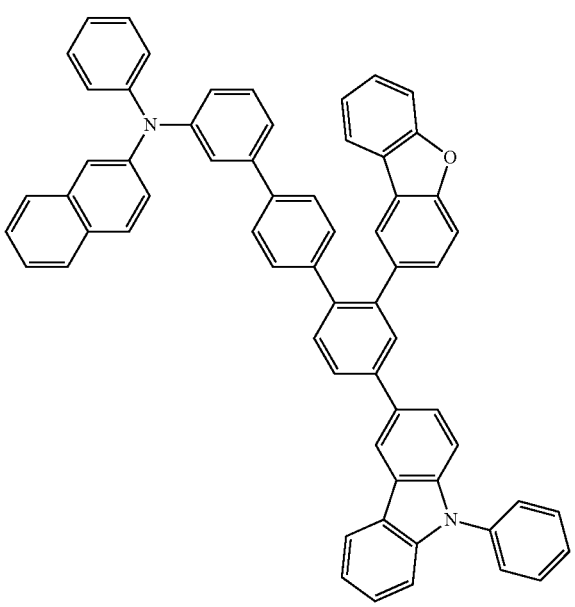

33
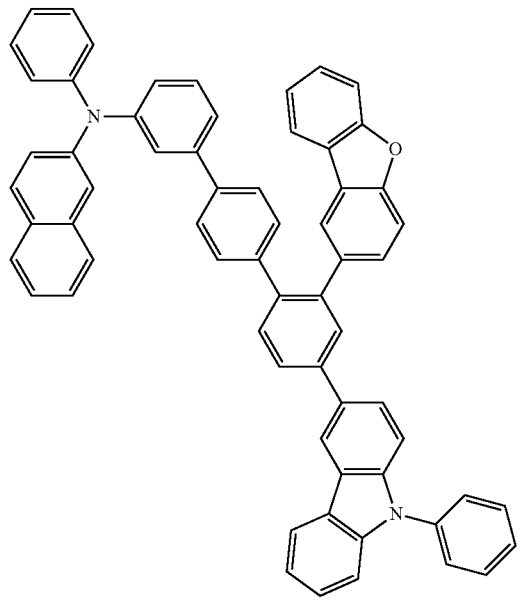
34
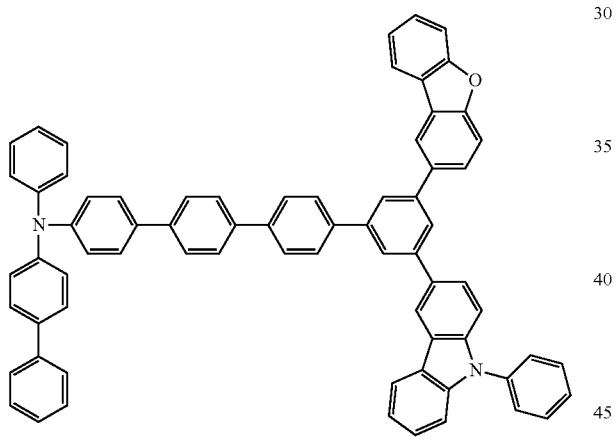
35
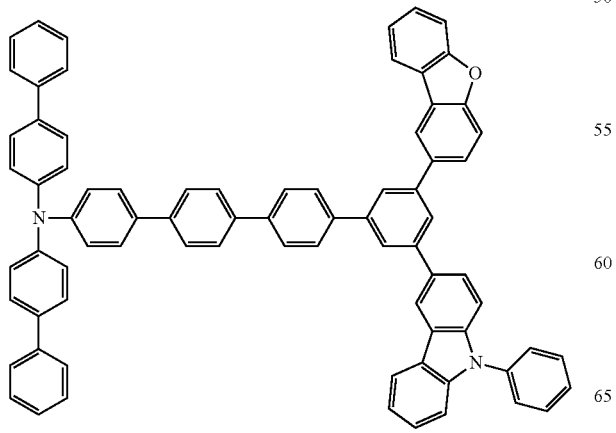
36
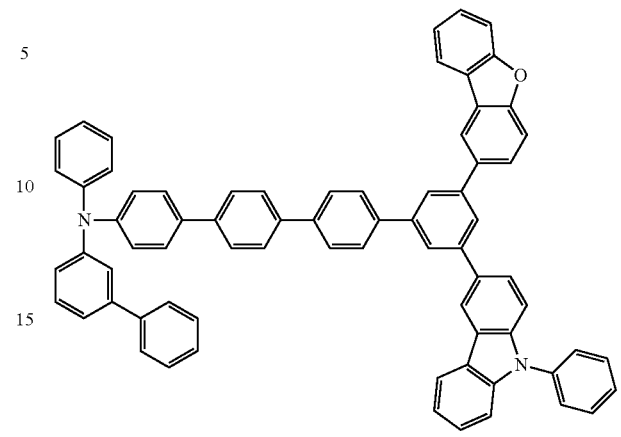
37
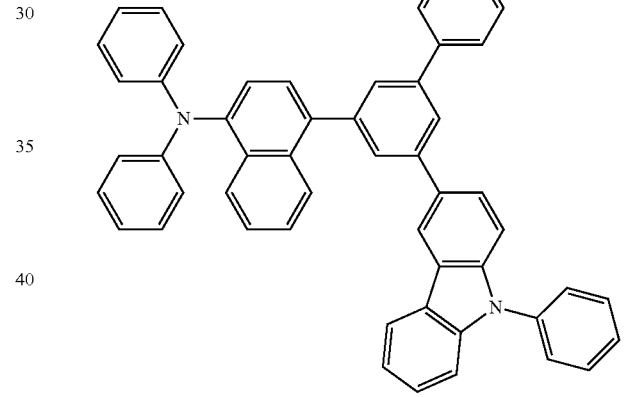
38
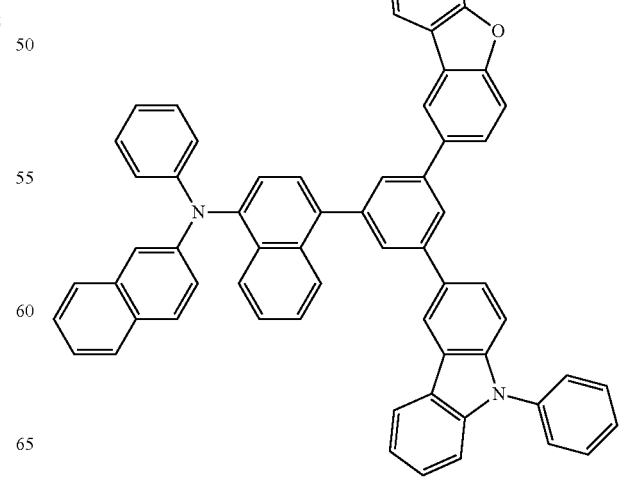

39
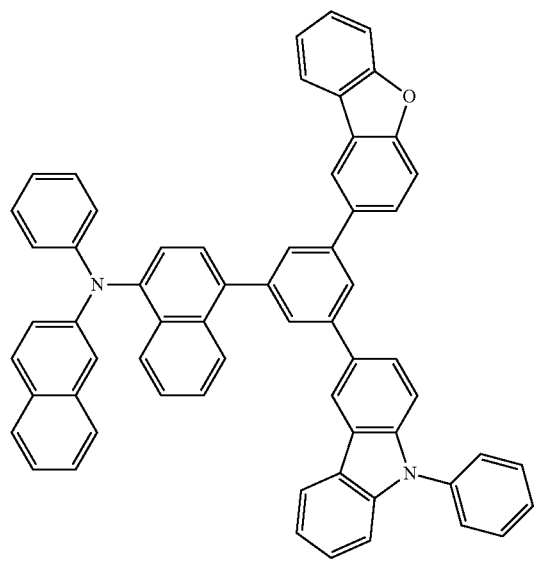
40
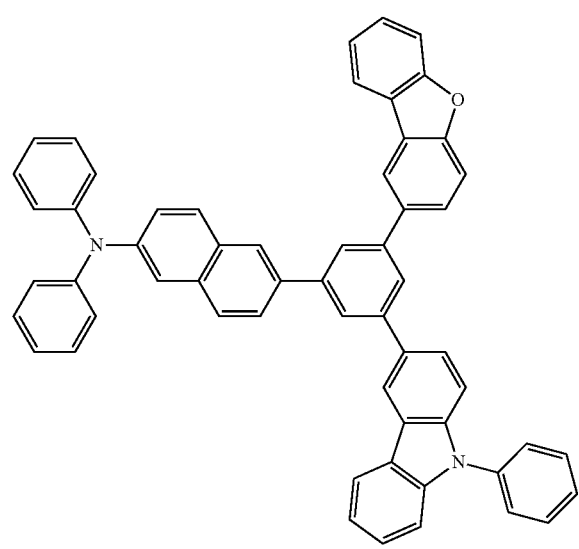
41
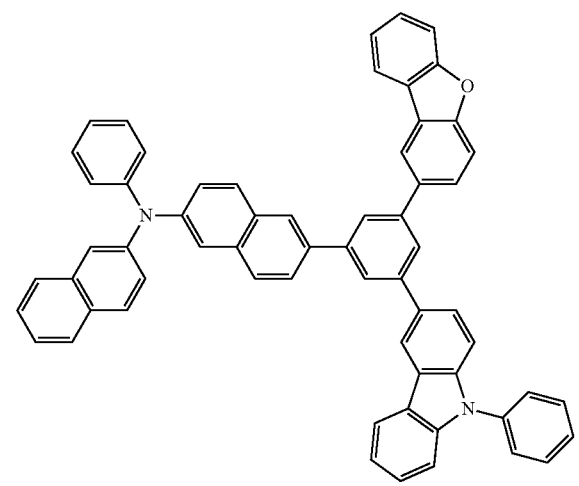
42
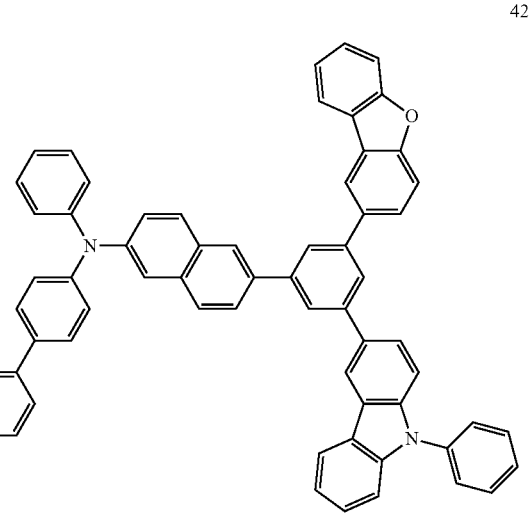
43
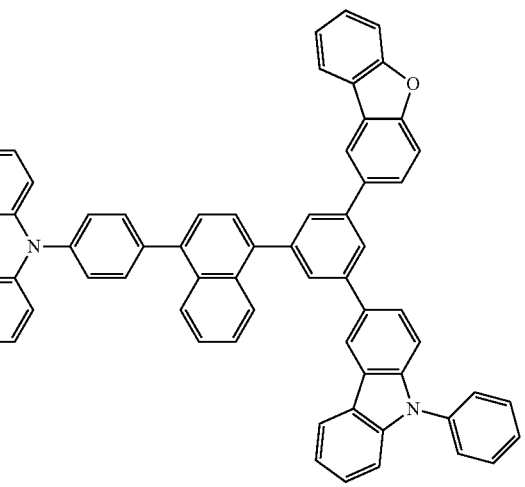
44

45
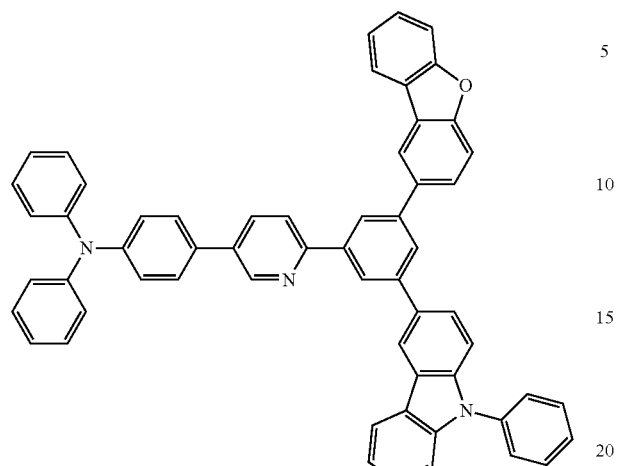
46
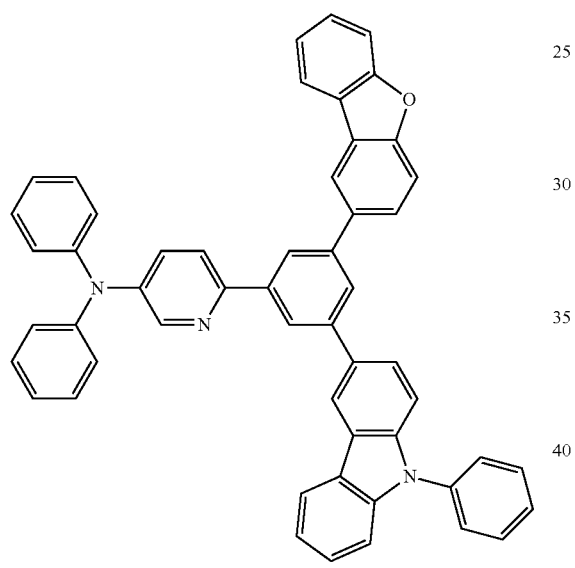
47
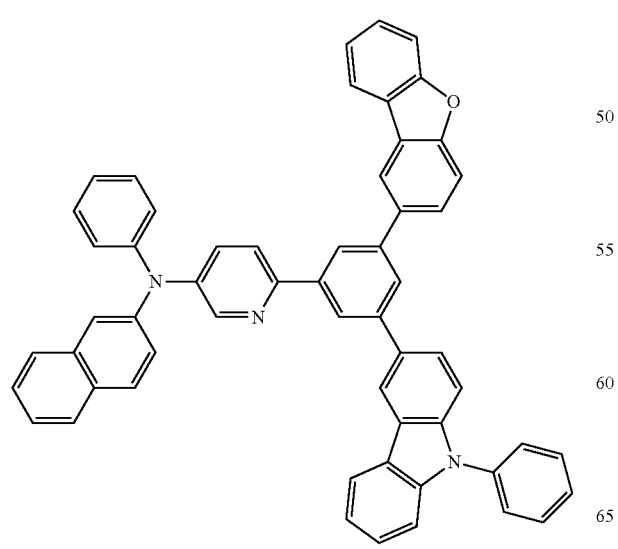
48
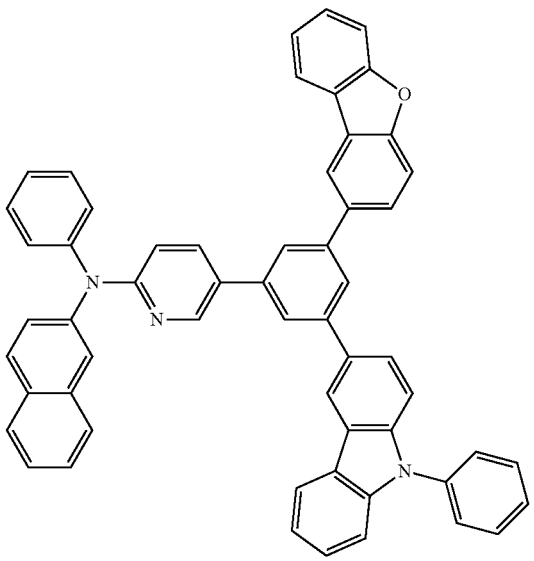
49
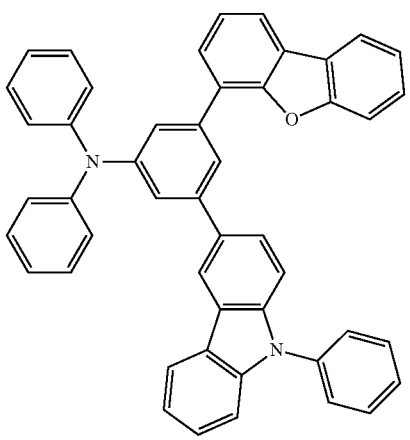
50
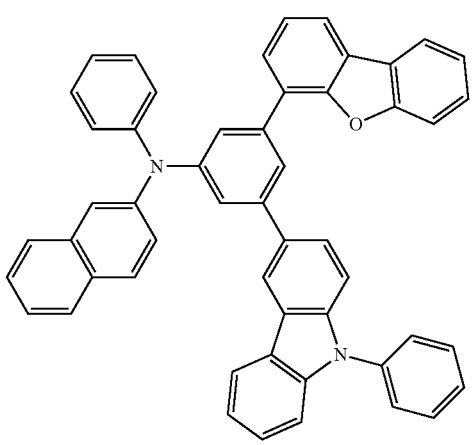

51
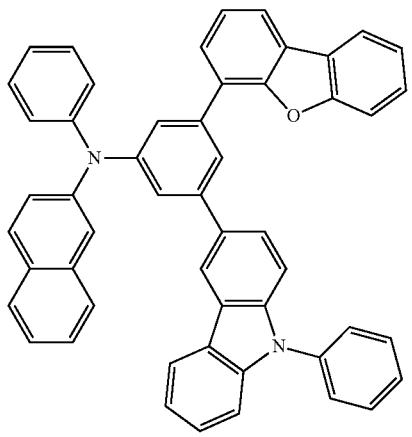
54
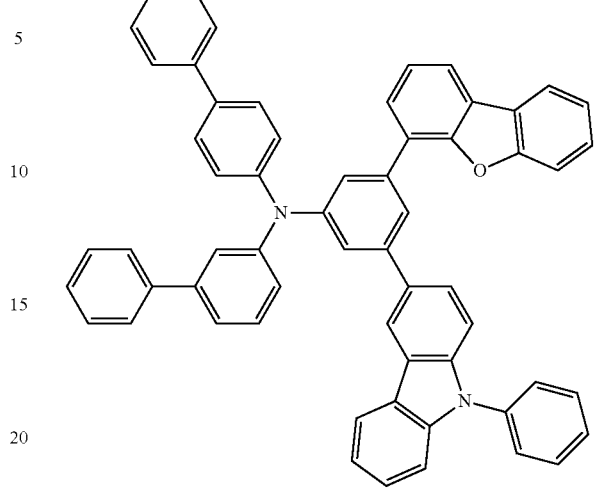
52
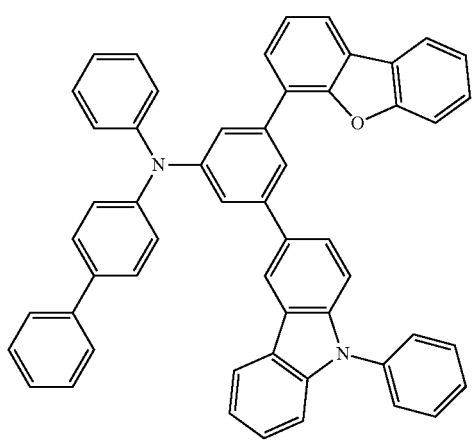
55
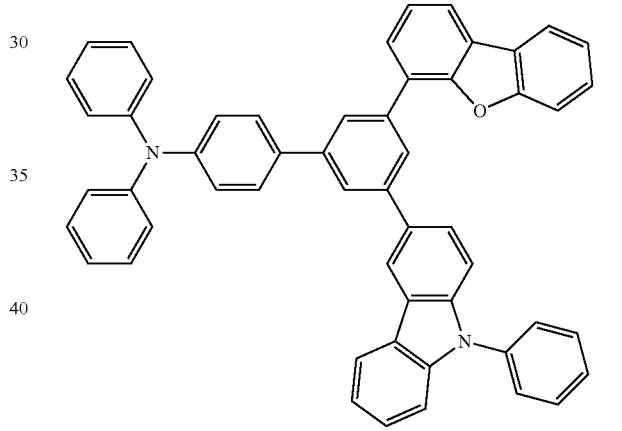
53
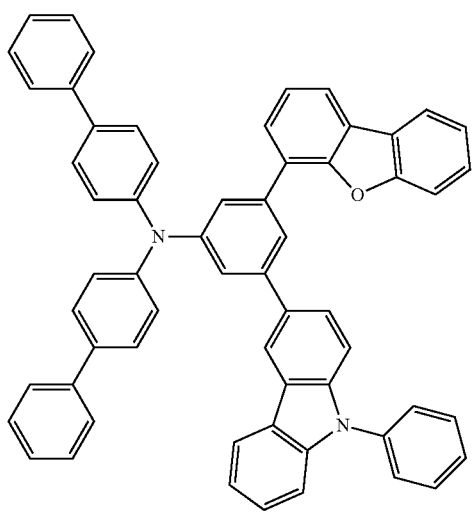
56
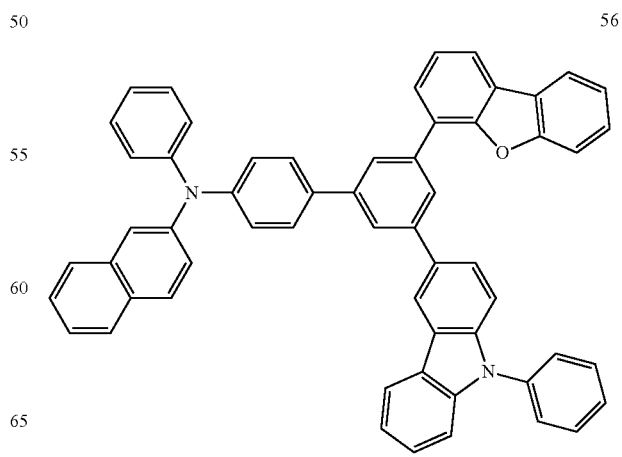

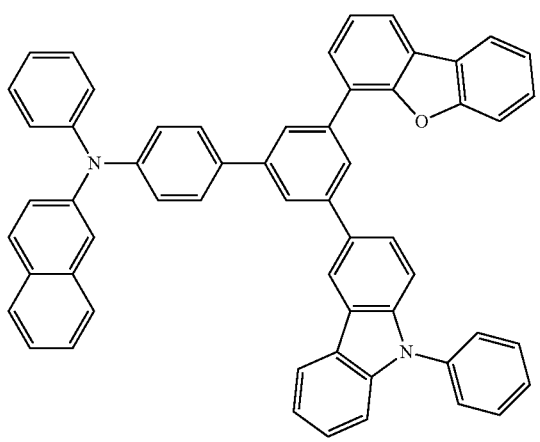
57
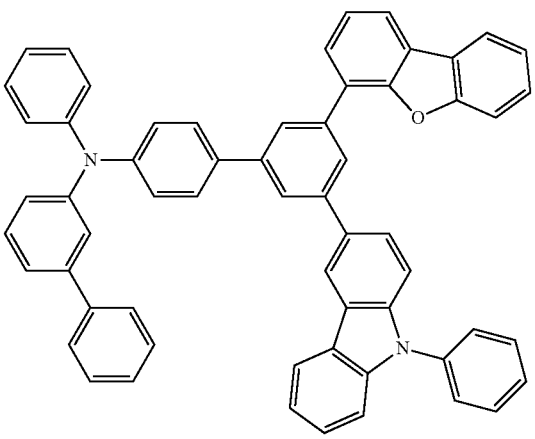
60
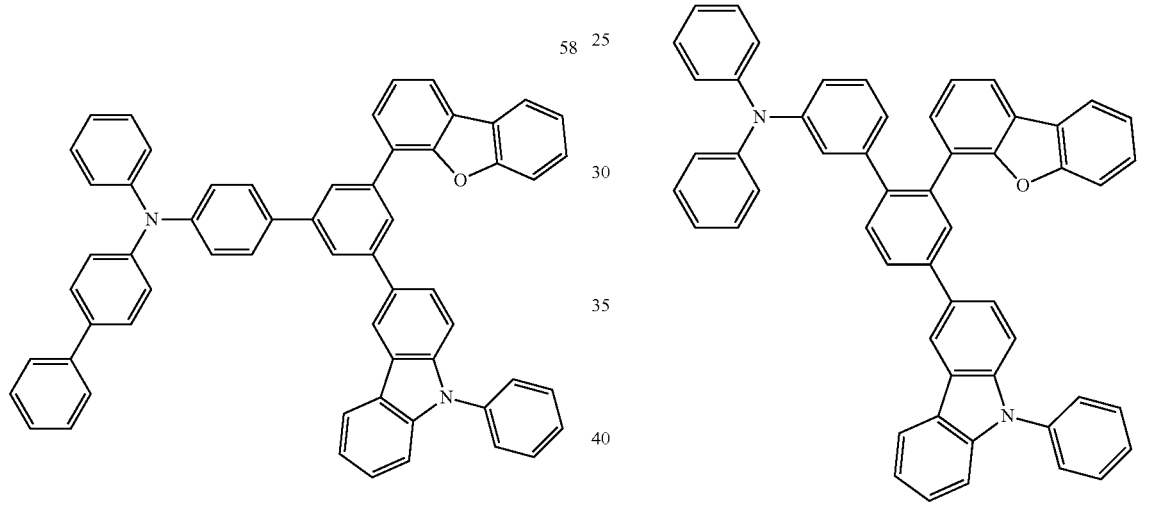
58
61
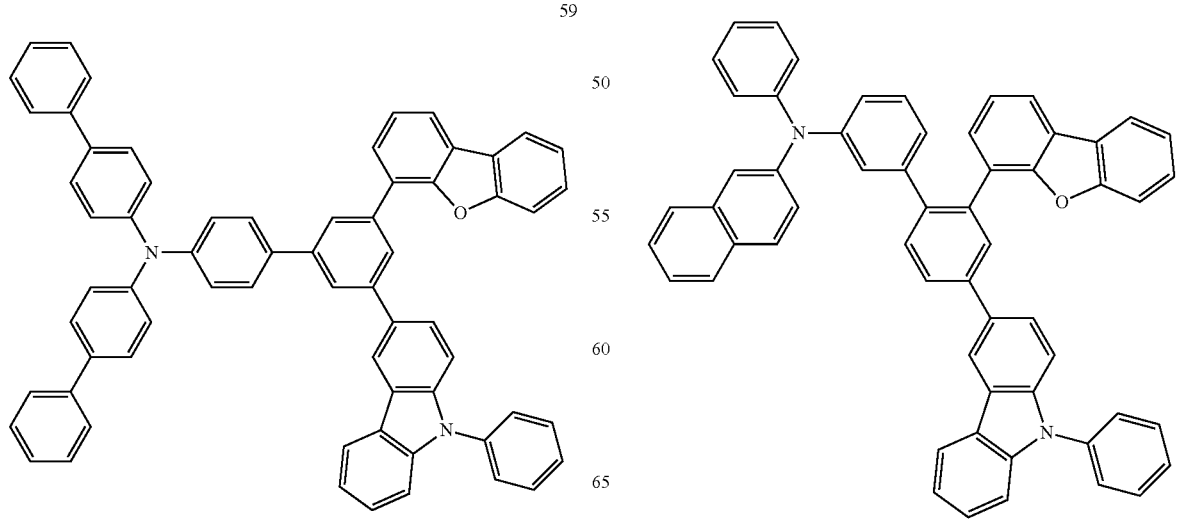
59
62

63
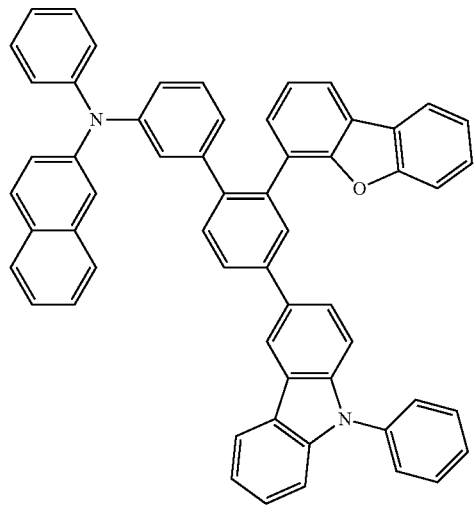
64
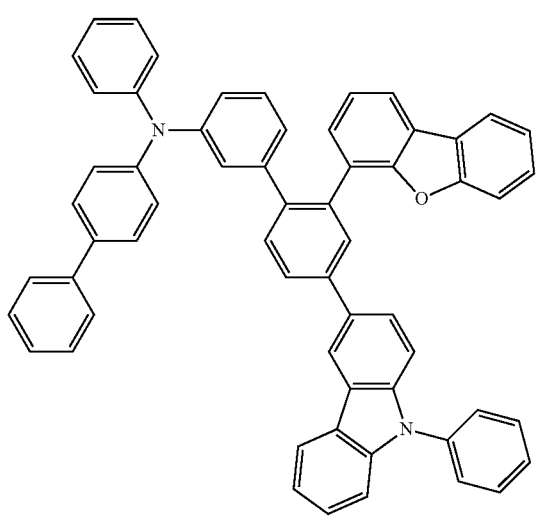
65
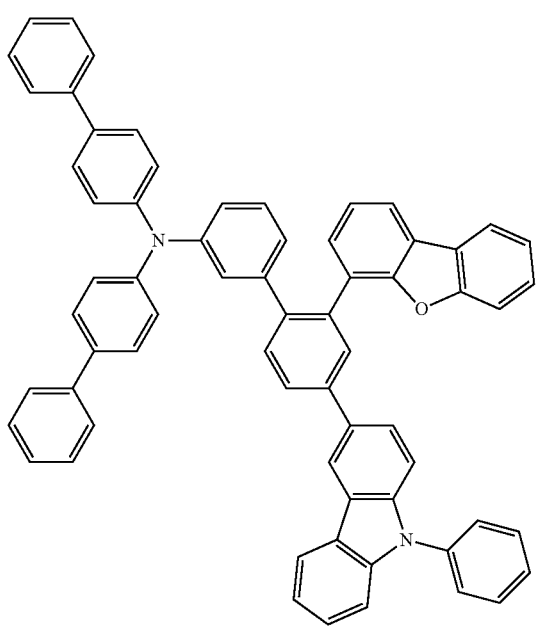
66
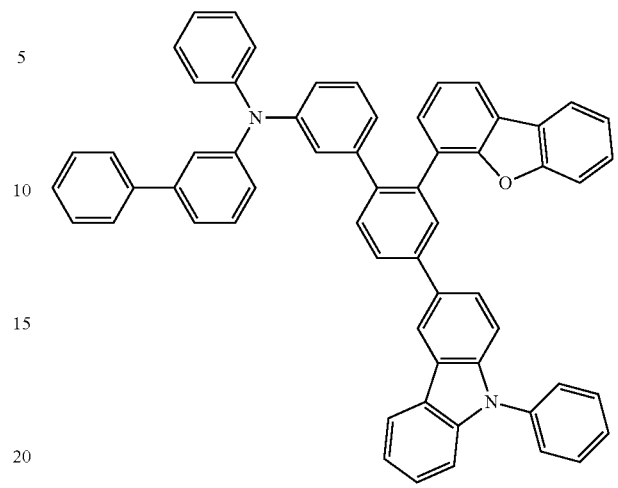
67
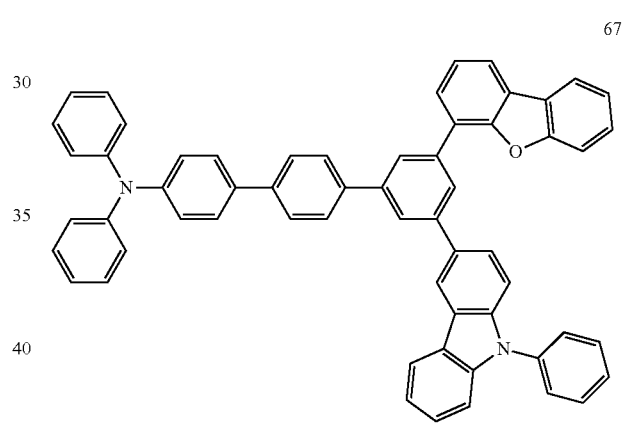
68
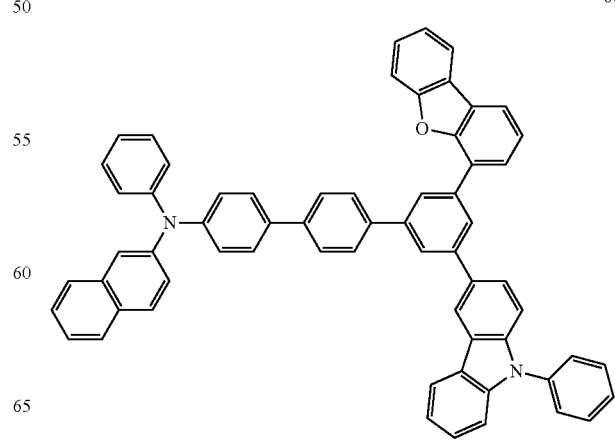

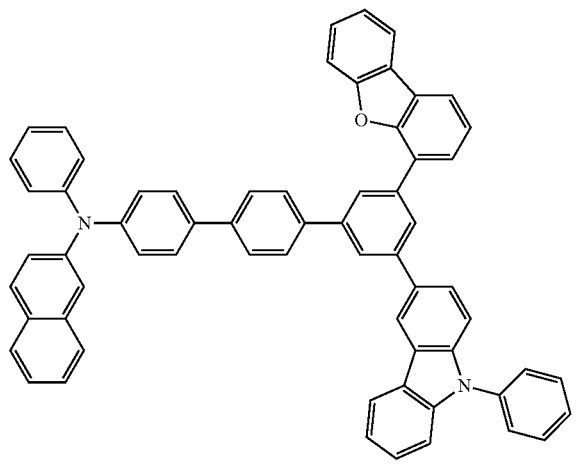
69
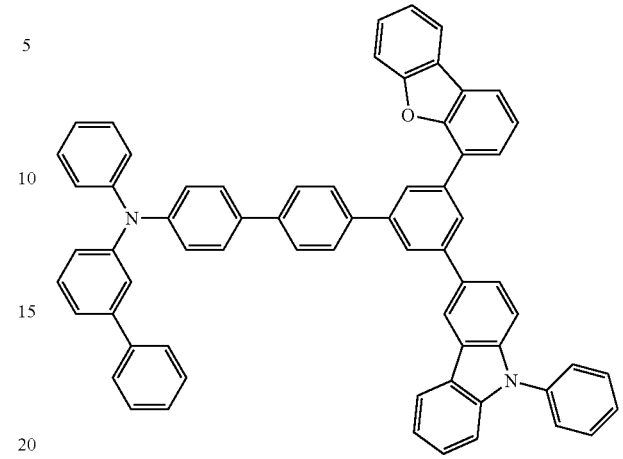
72
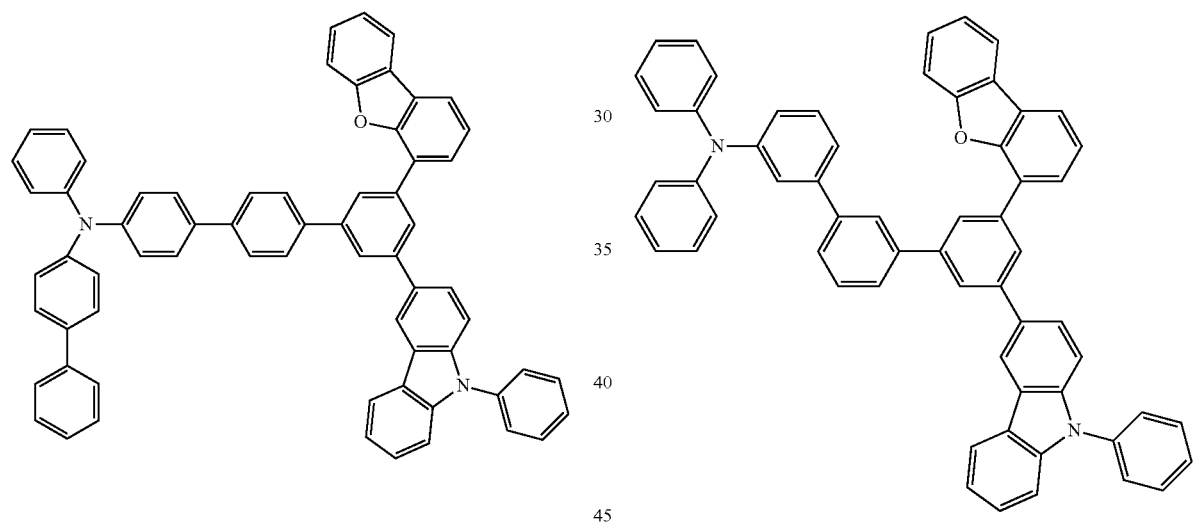
70
73
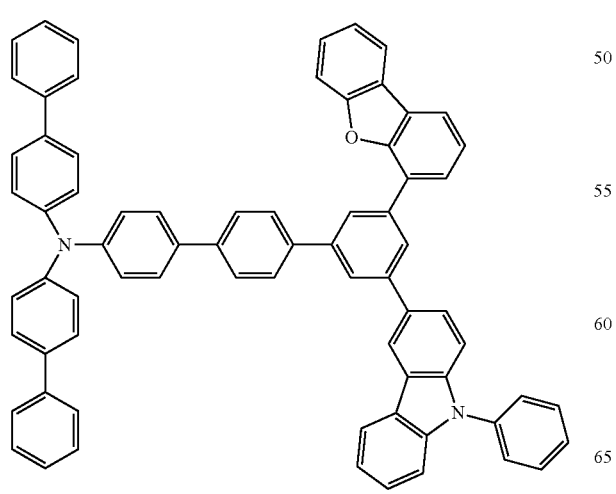
71
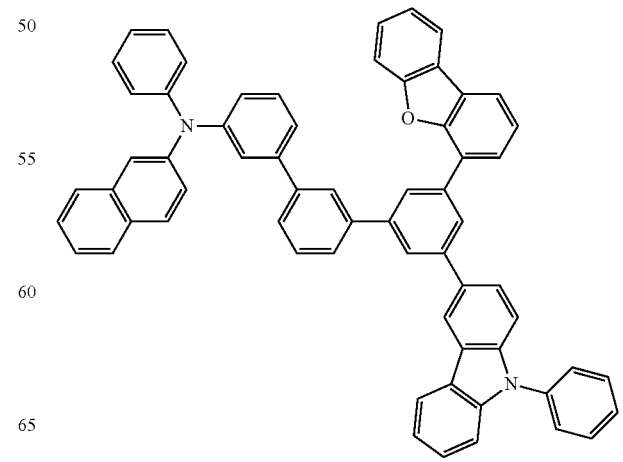
74

75
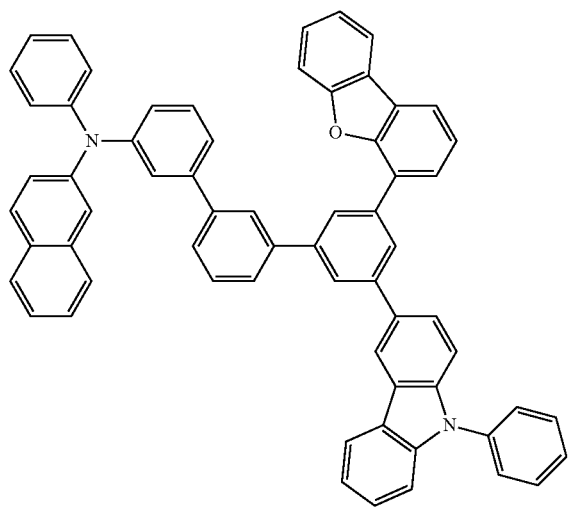
76
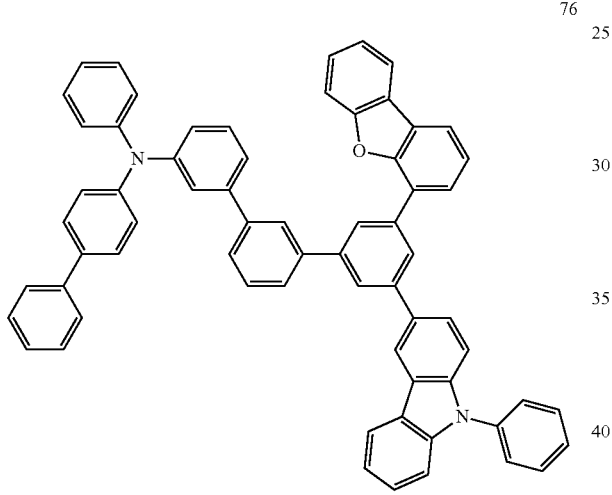
77
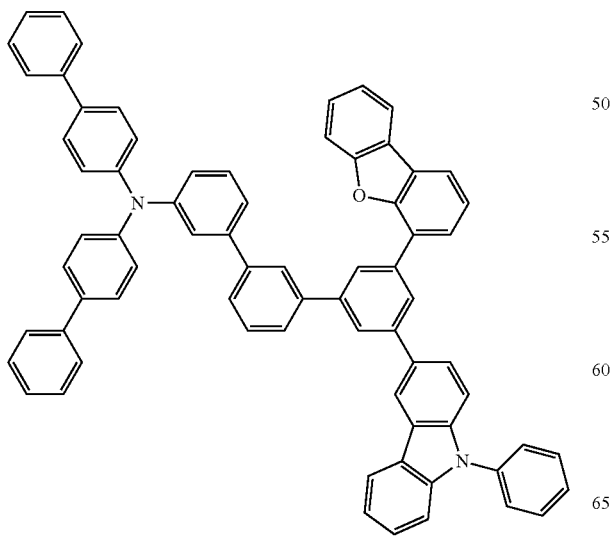
78
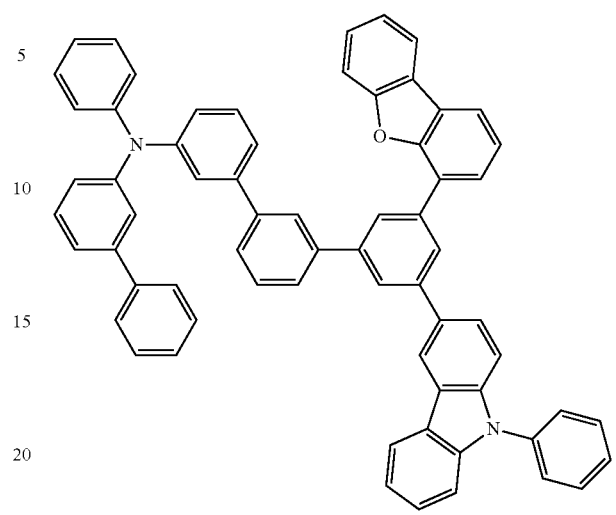
79
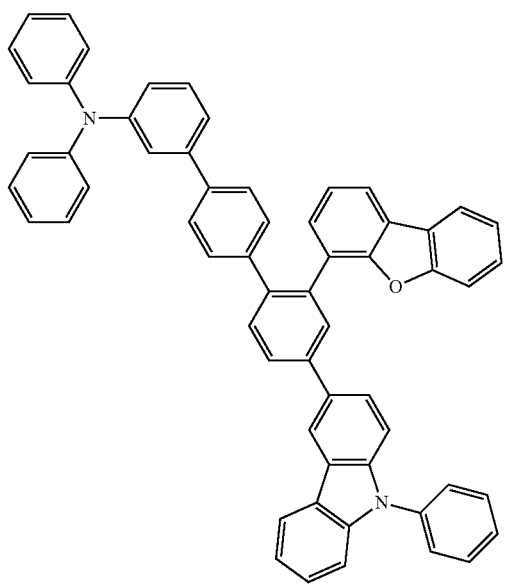

80
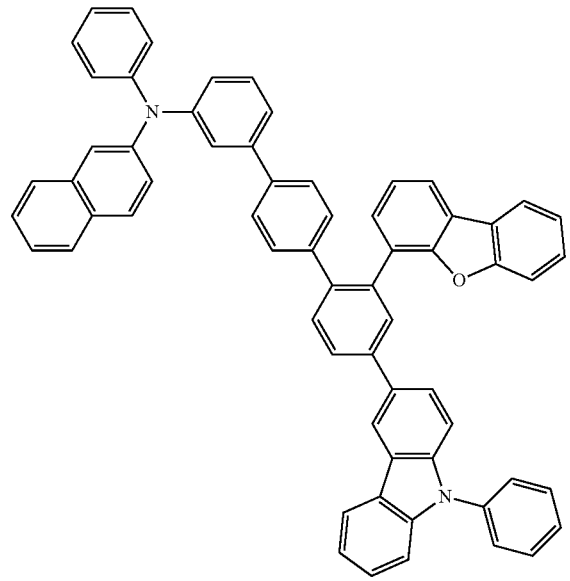
81
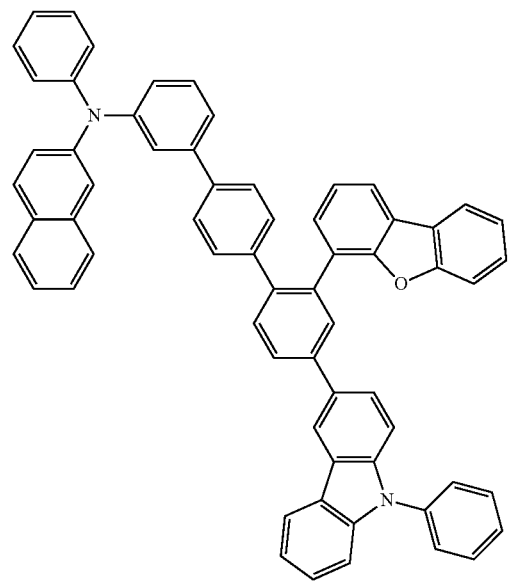
82
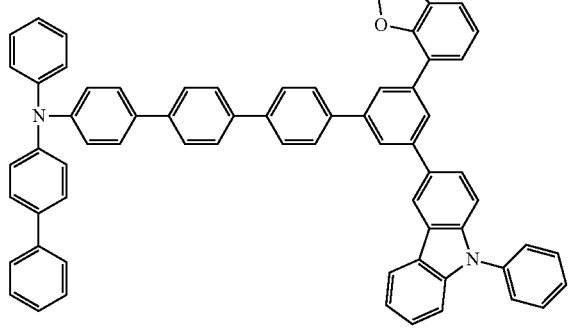
83
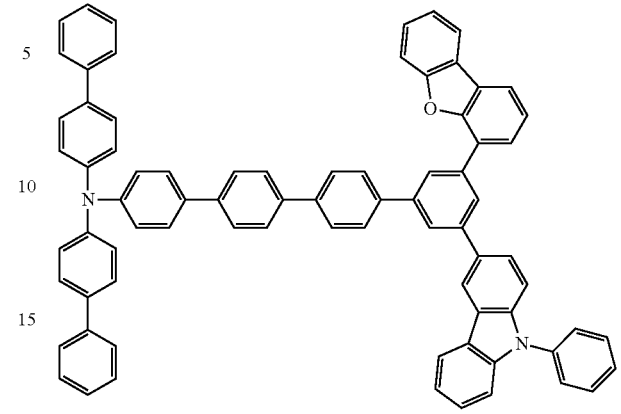
84
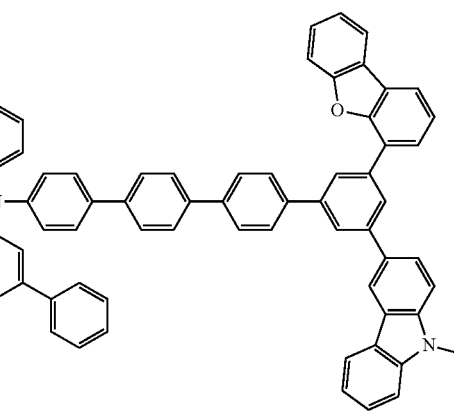
85
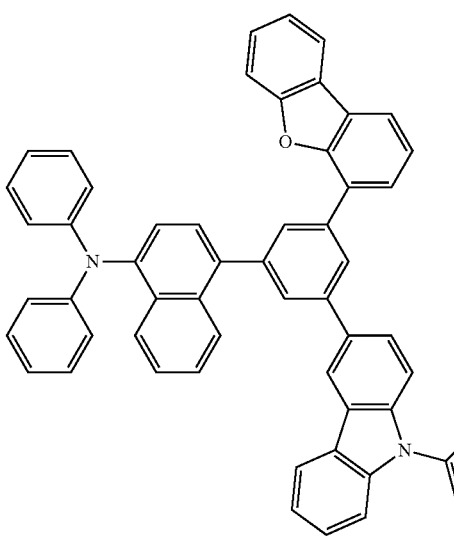

86
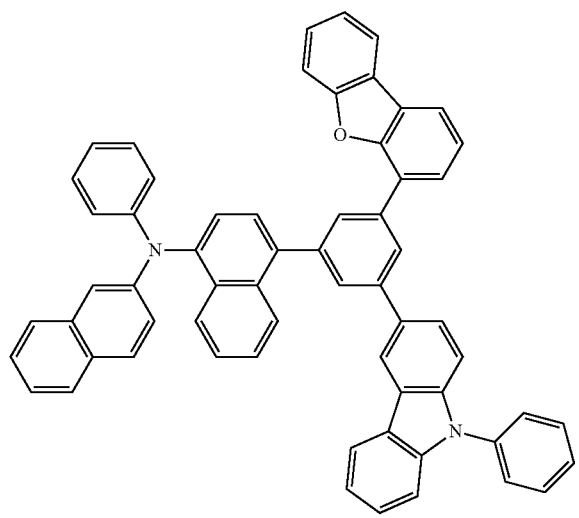
87
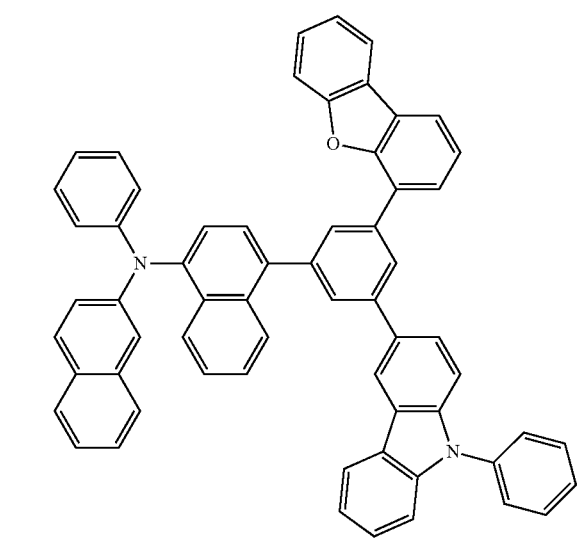
88
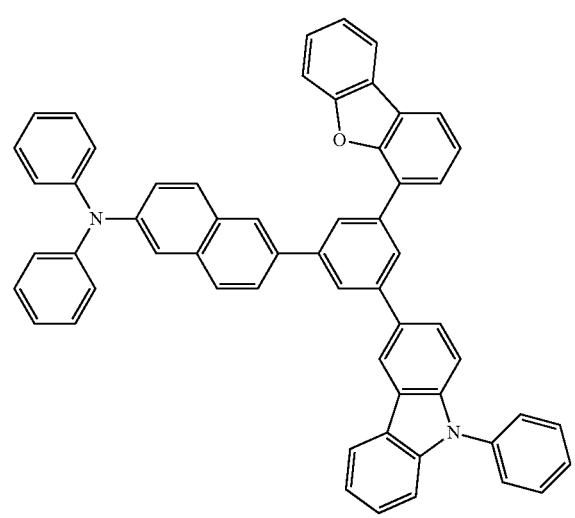
89
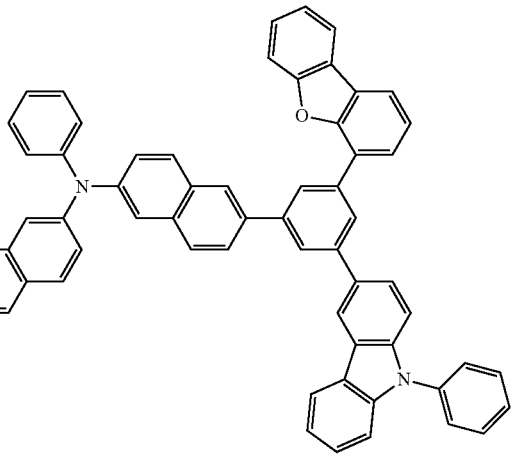
90
91
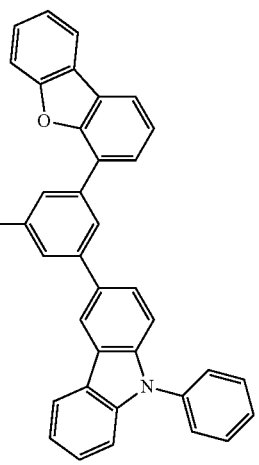

92
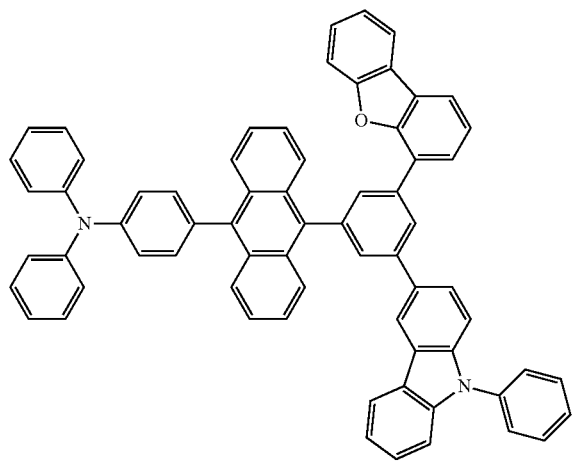
93
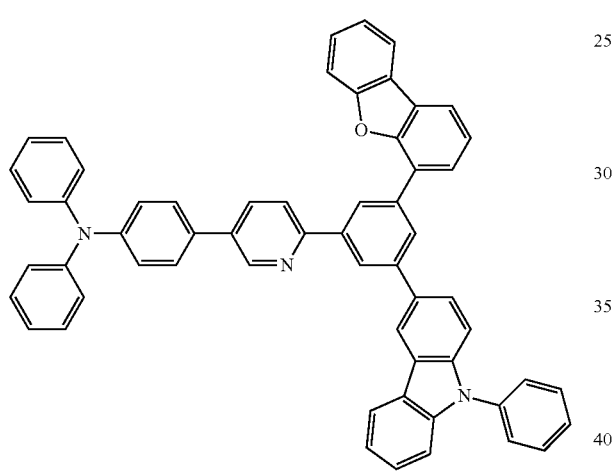
94
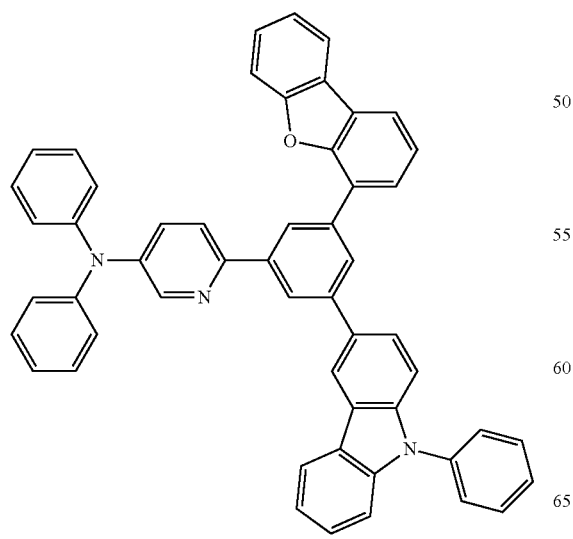
95
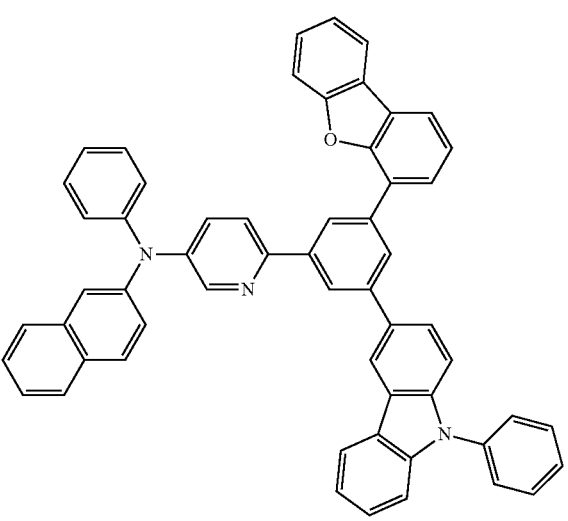
96
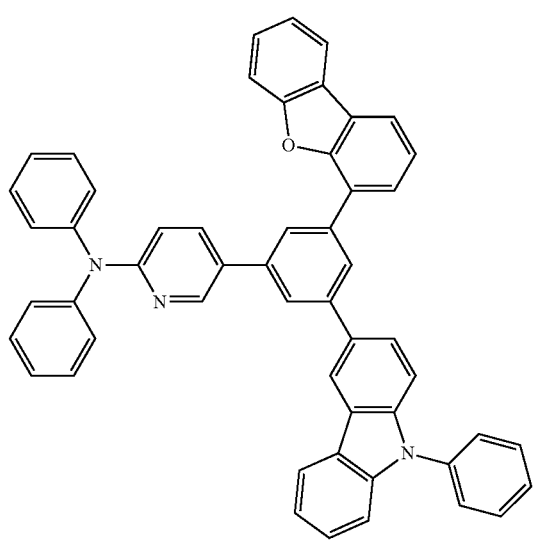
97

98
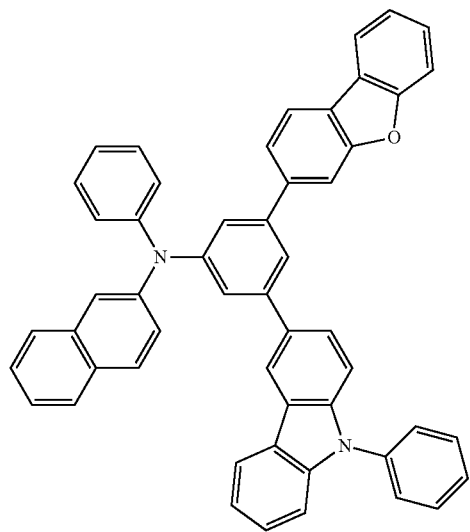
99
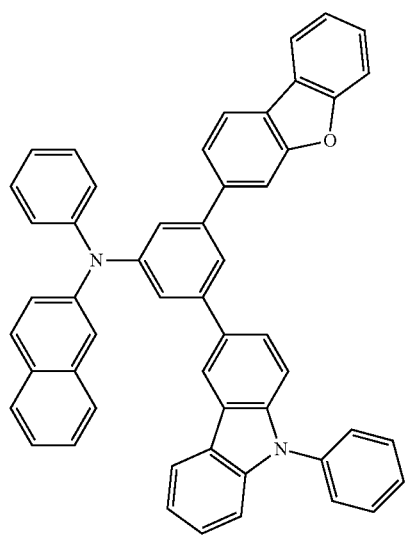
100
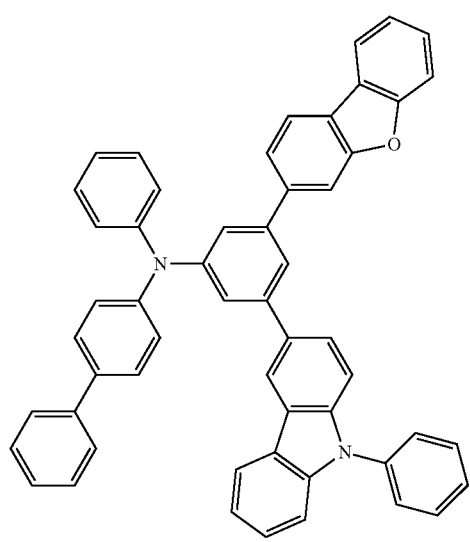
101
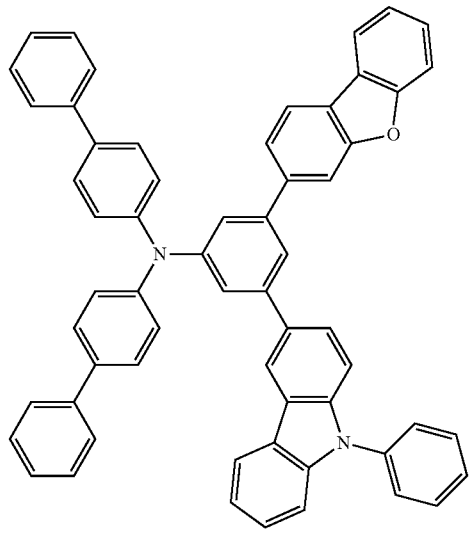
102
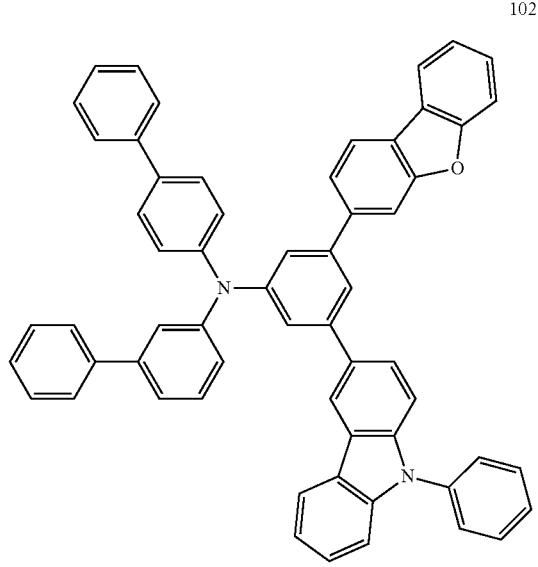
103
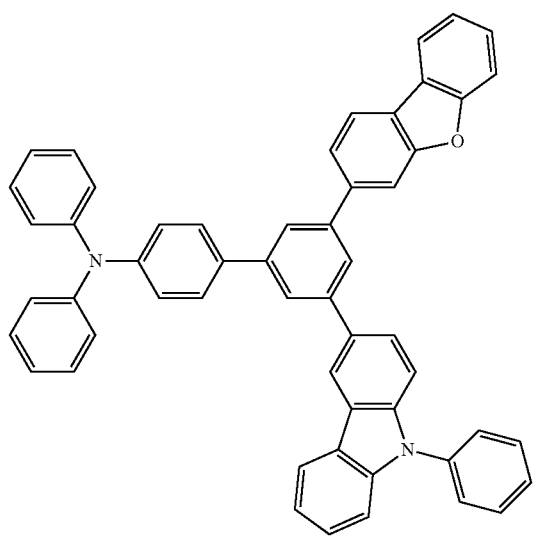

104
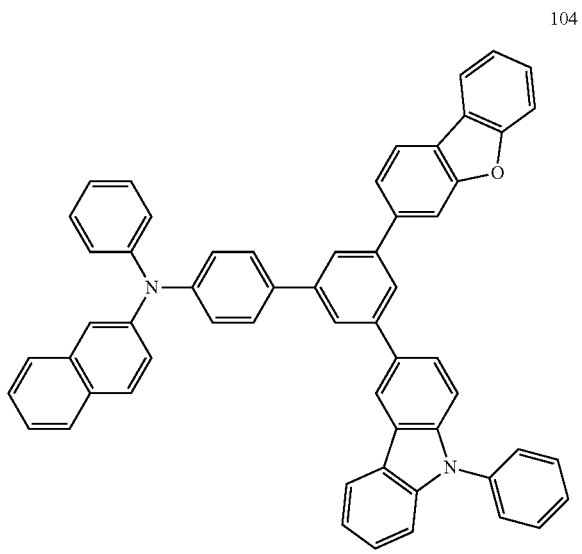
105
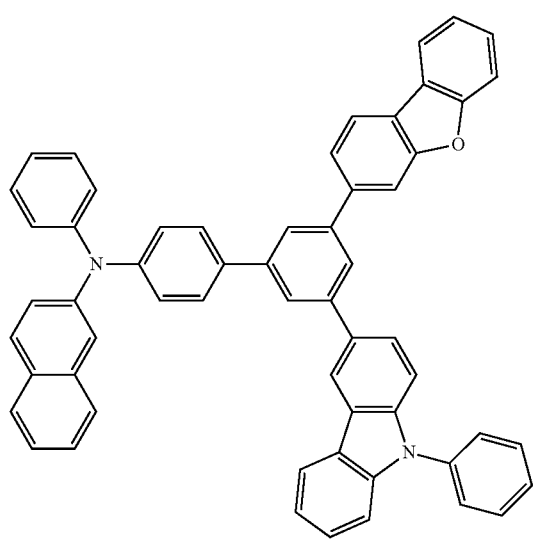
106
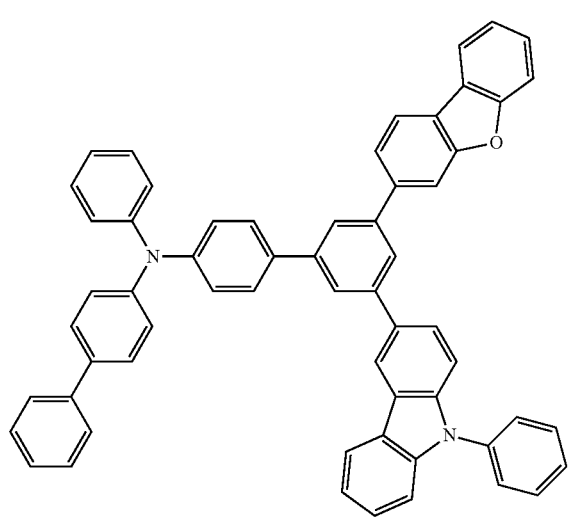
107
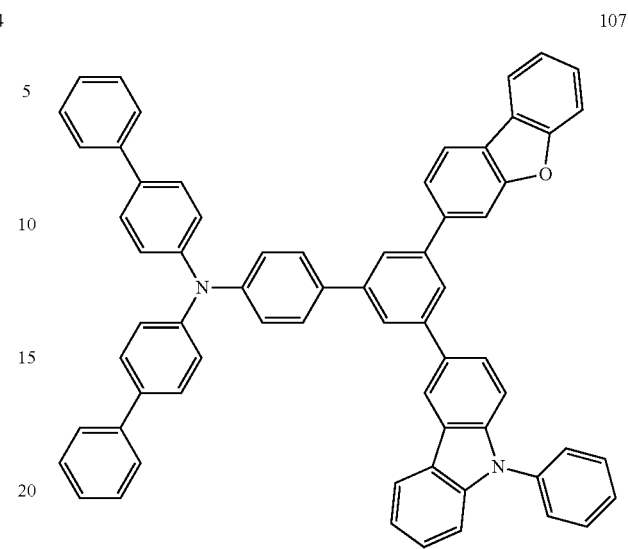
108
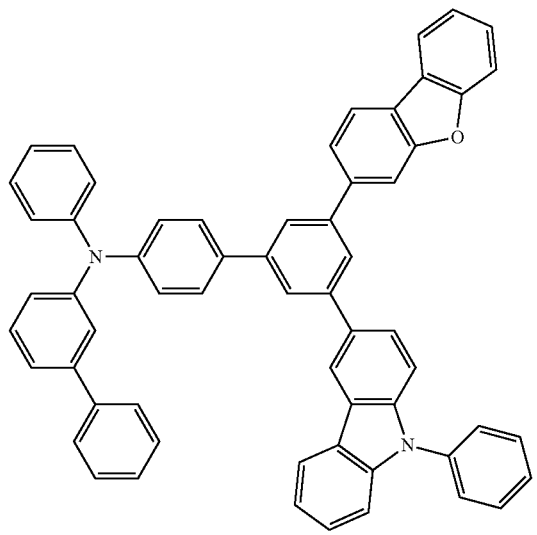
109
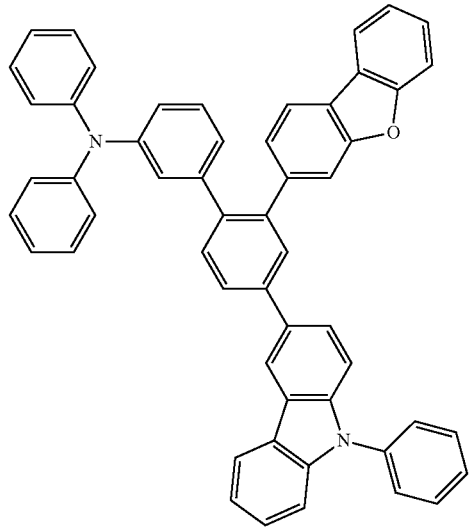

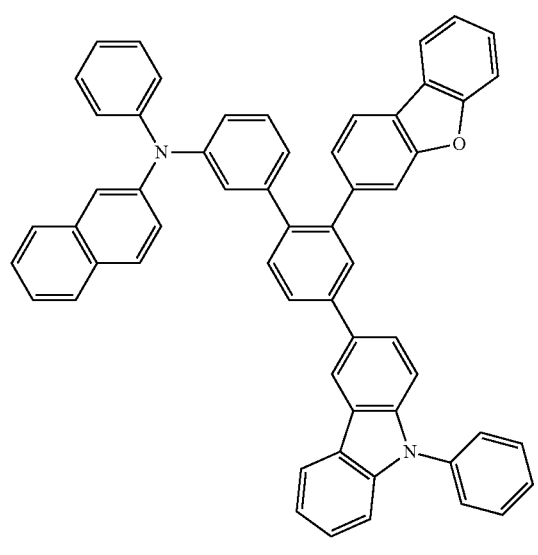
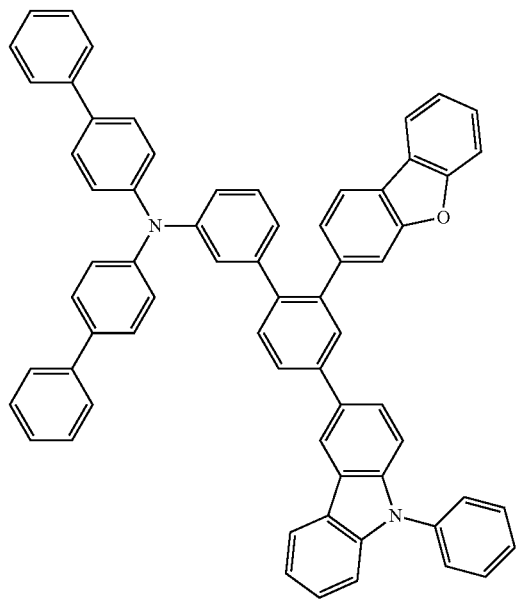

116
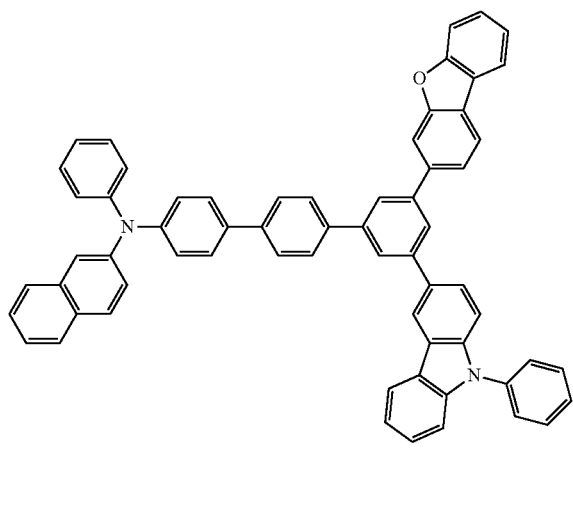
117
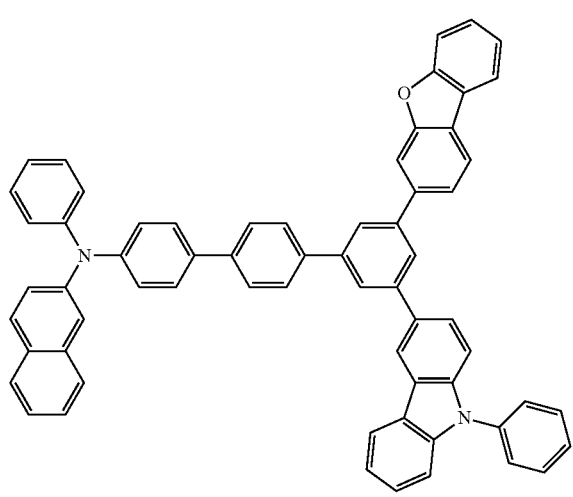
118
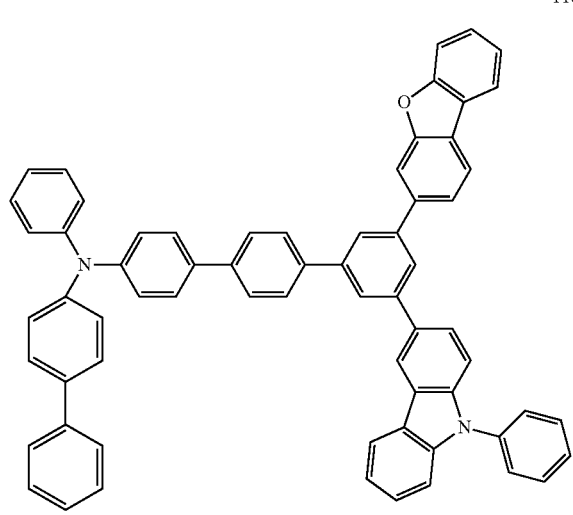
119
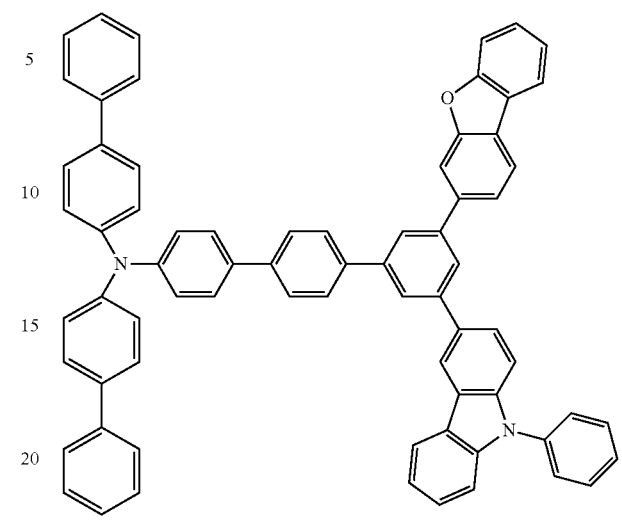
120
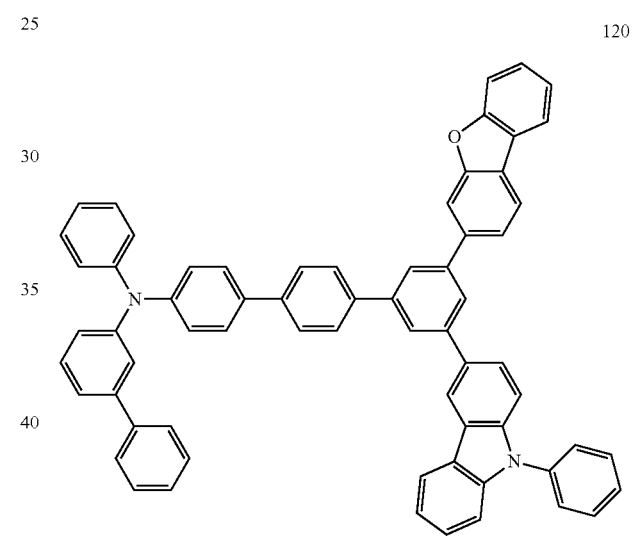
121
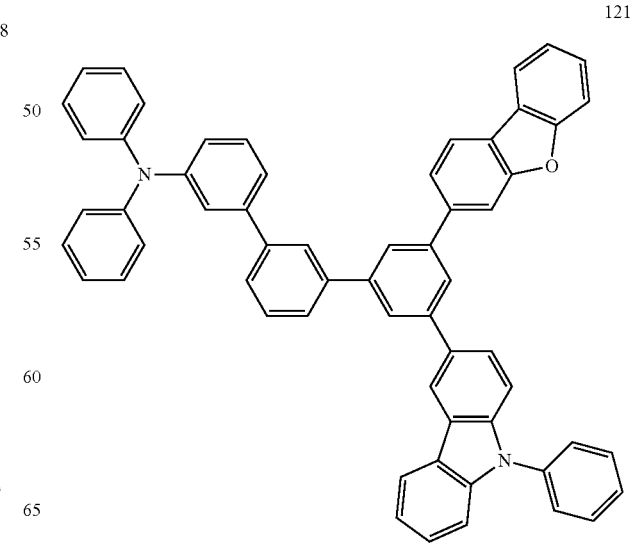

122
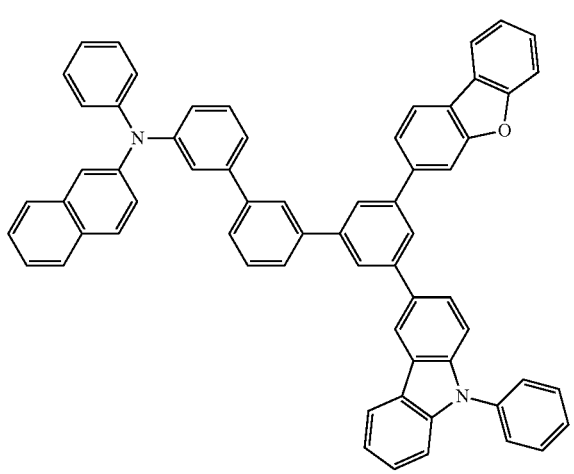
123
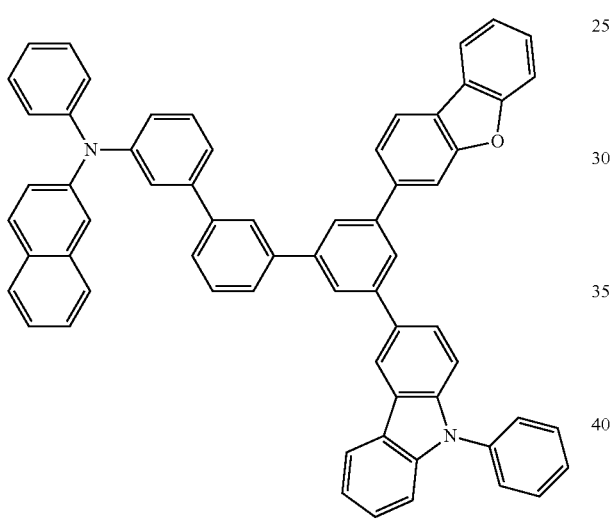
124
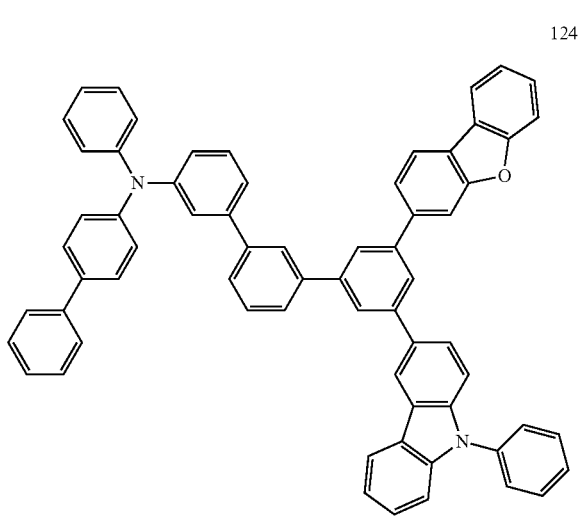
125
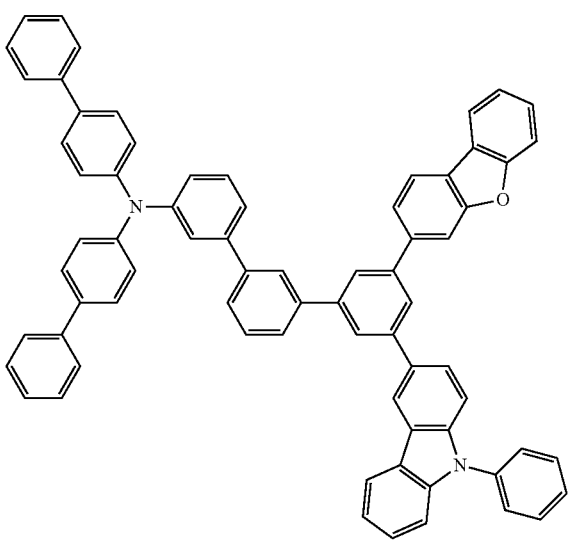
126
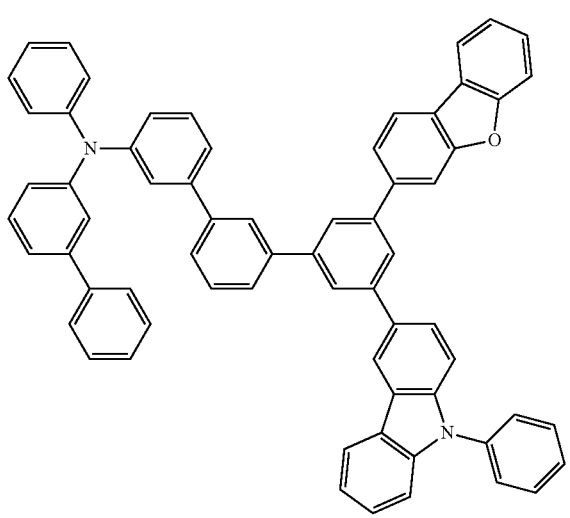

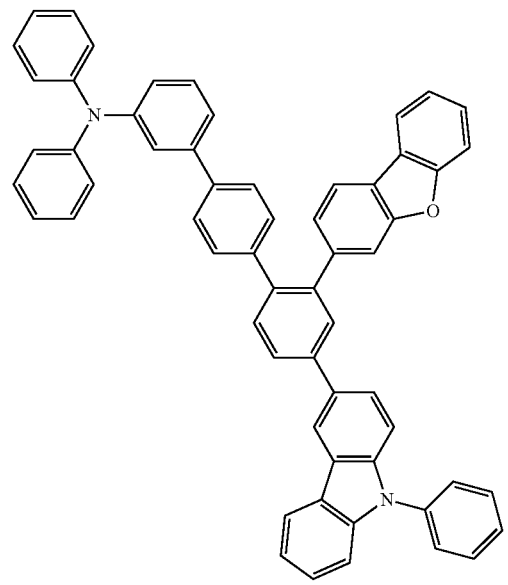
127
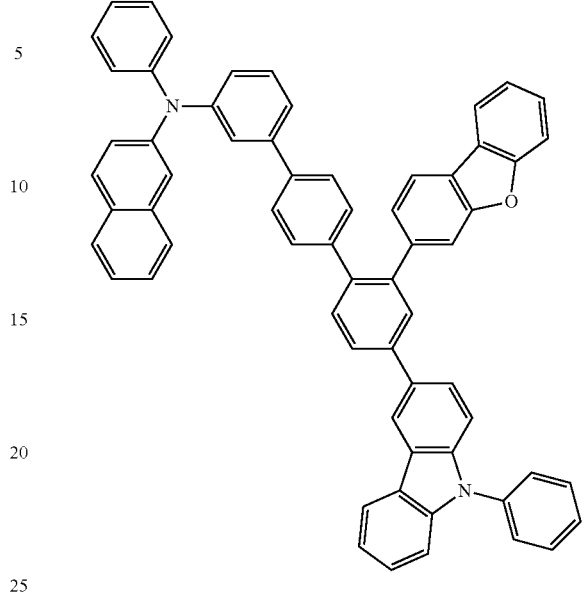
129
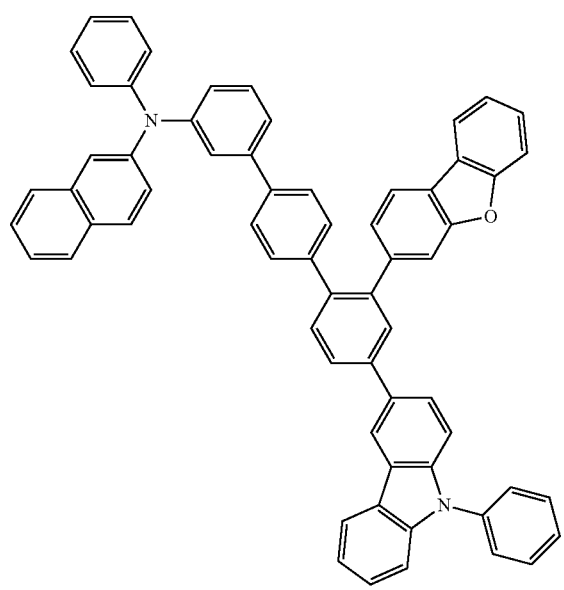
128
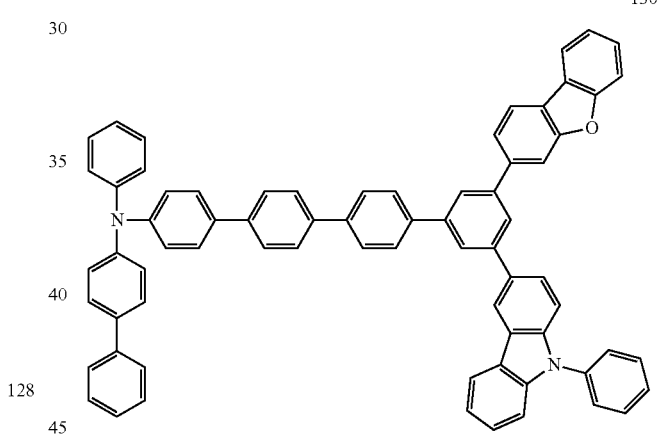
130
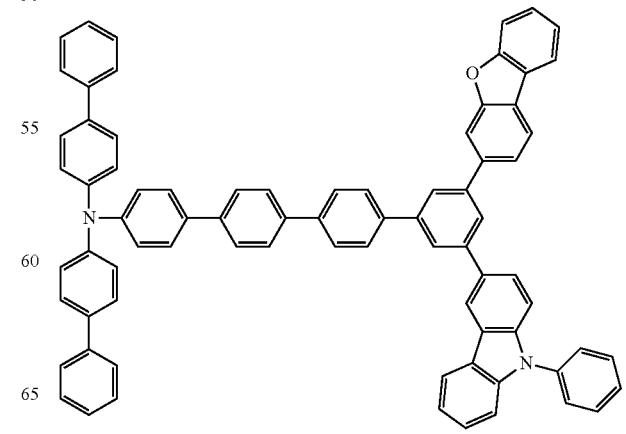
131

132
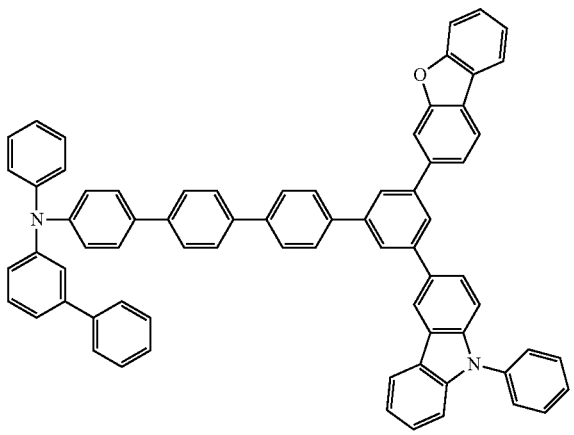
133
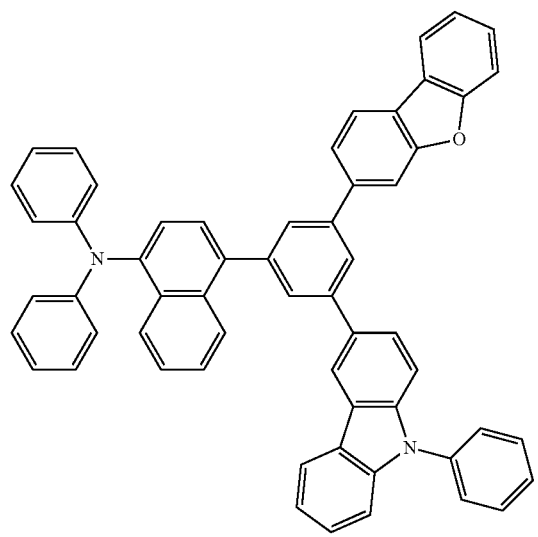
134
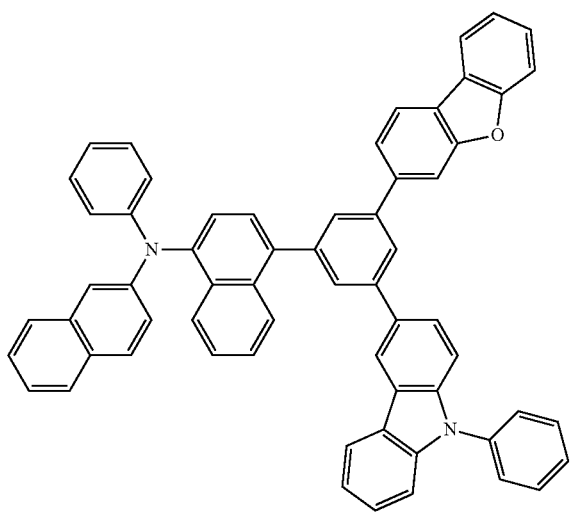
135
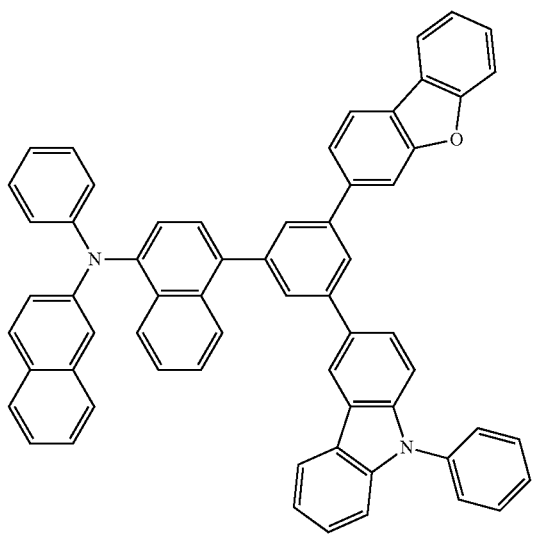
136
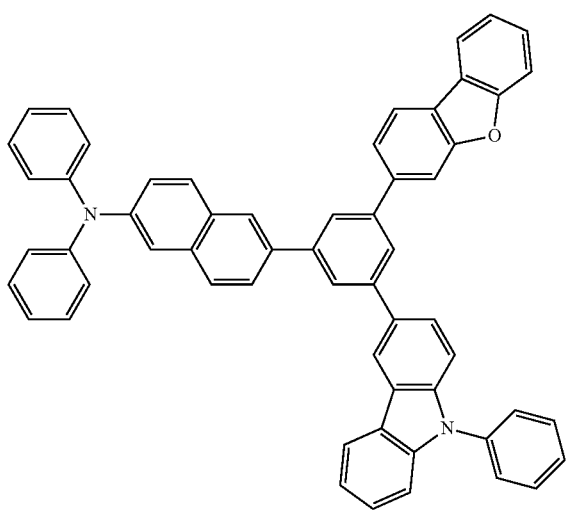
137
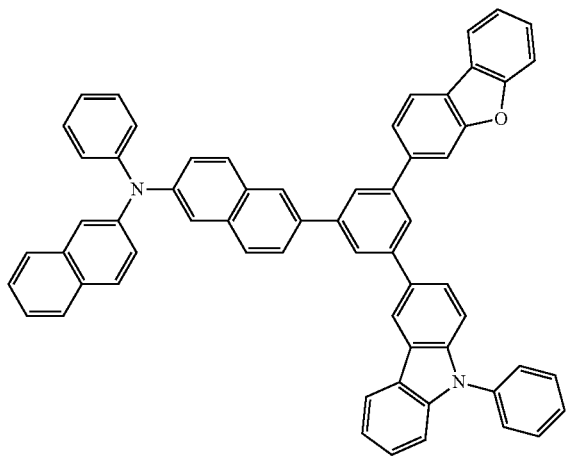

-continued
138
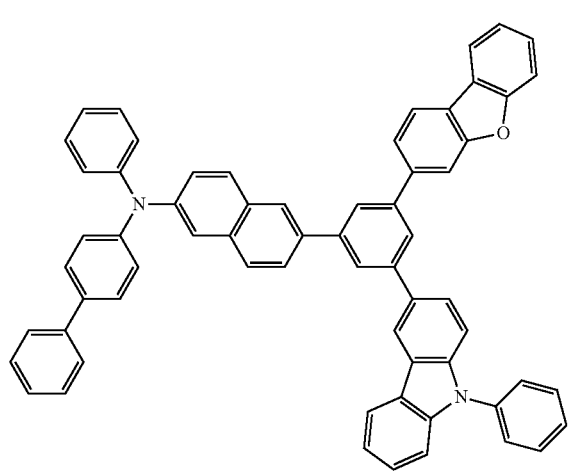
139
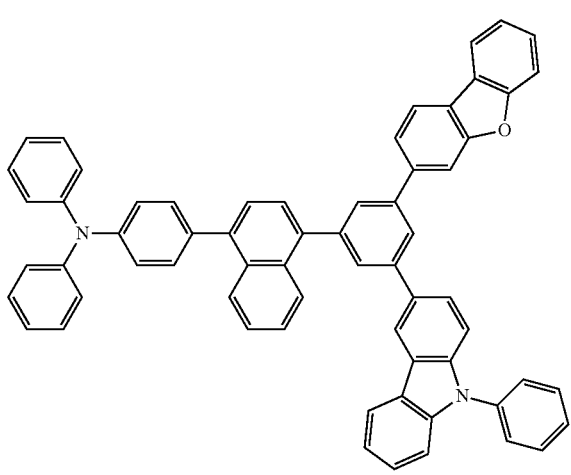
140
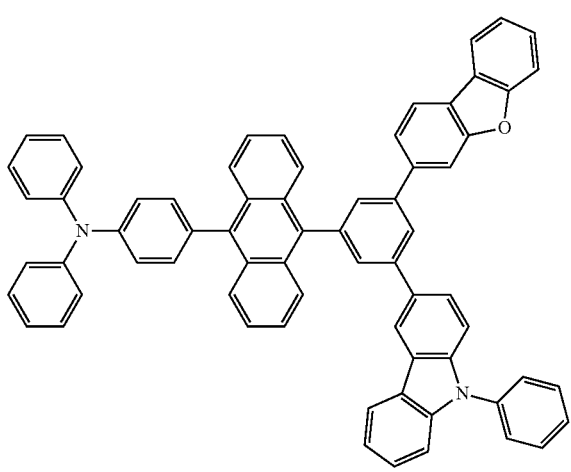
-continued
141
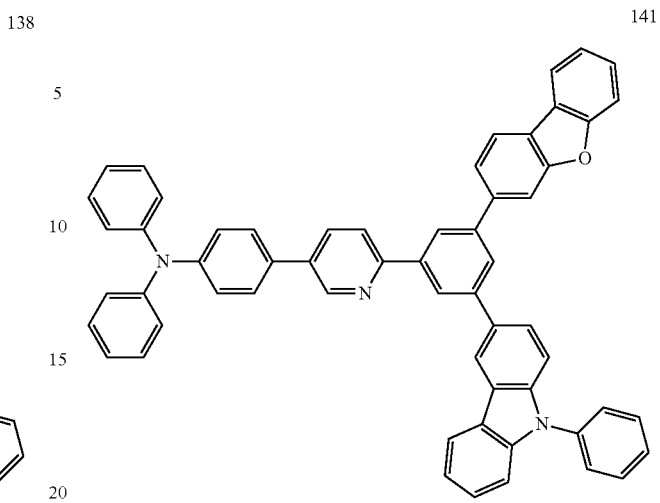
142
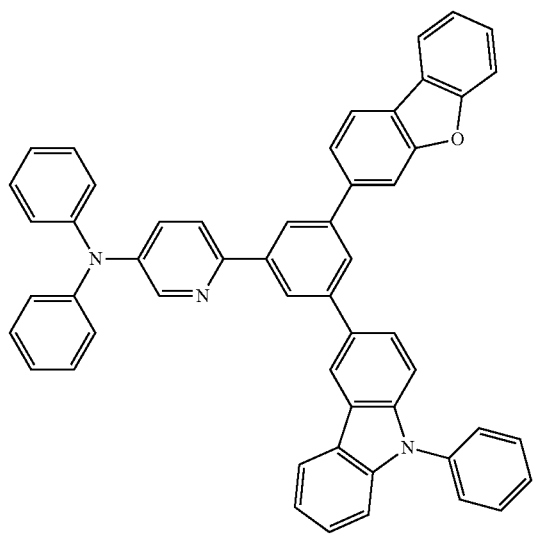
143
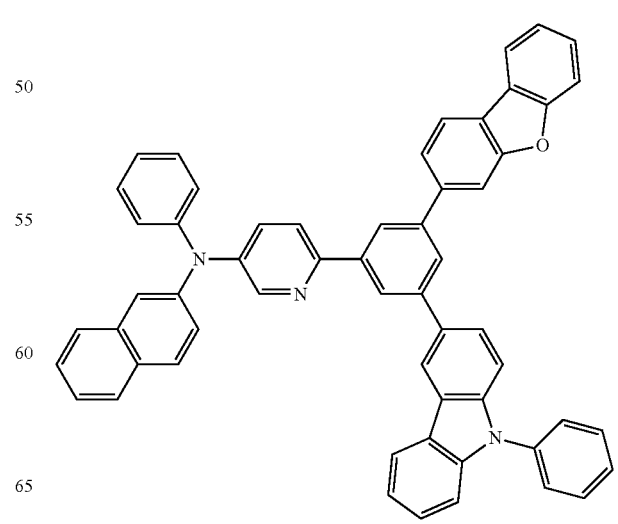

144
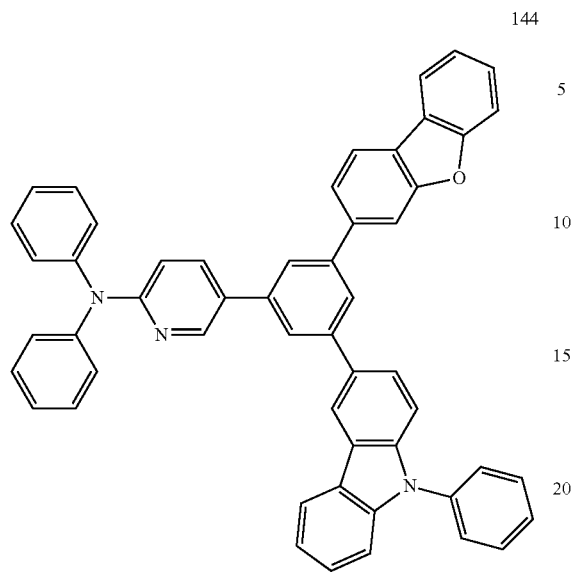
145
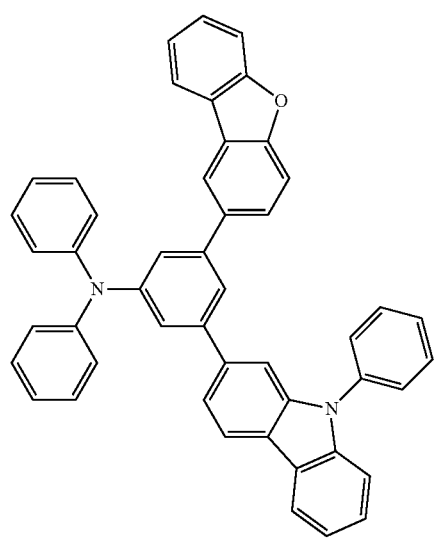
146
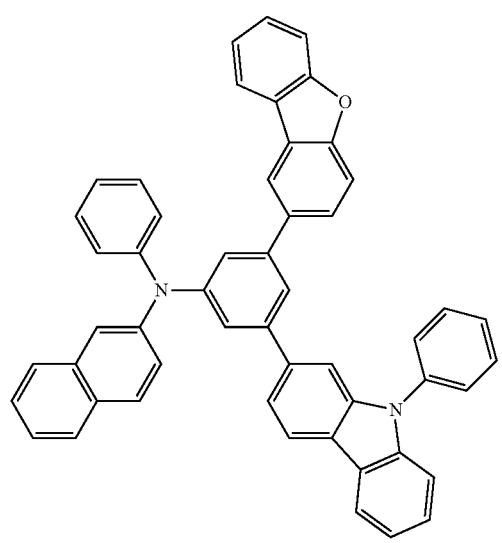
147
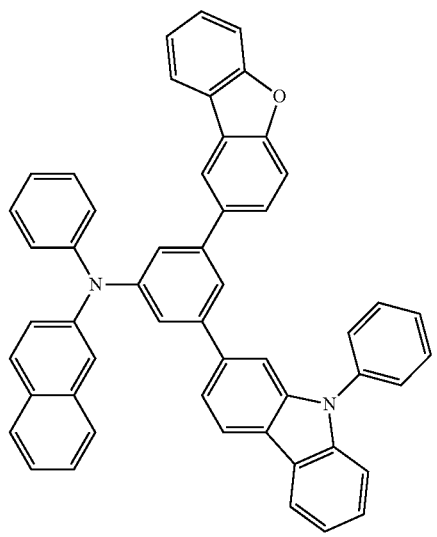
148
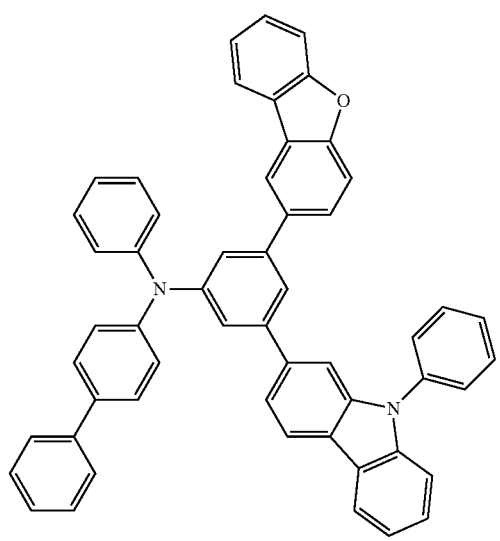
149
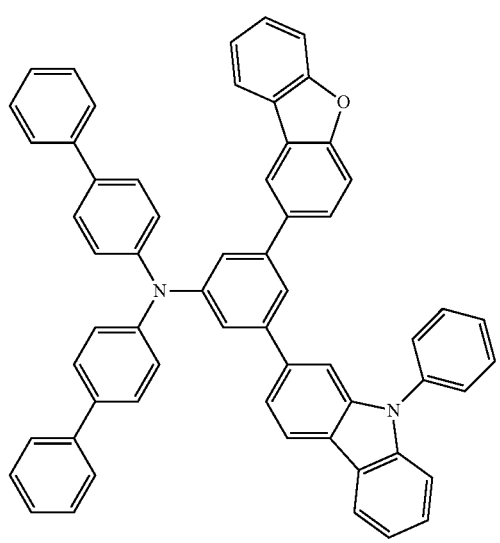

150
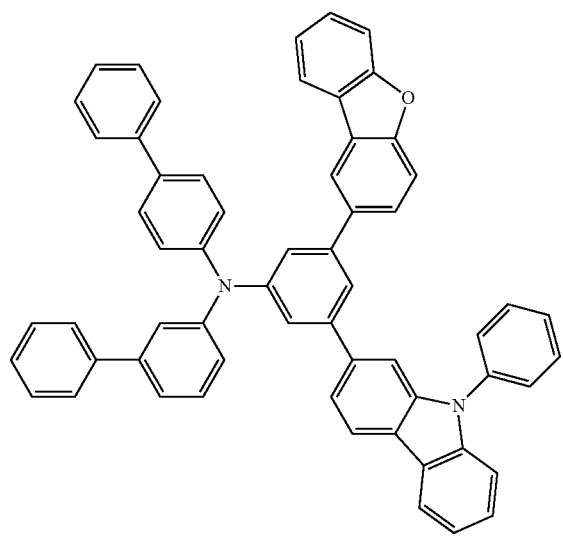
151
153
154
152
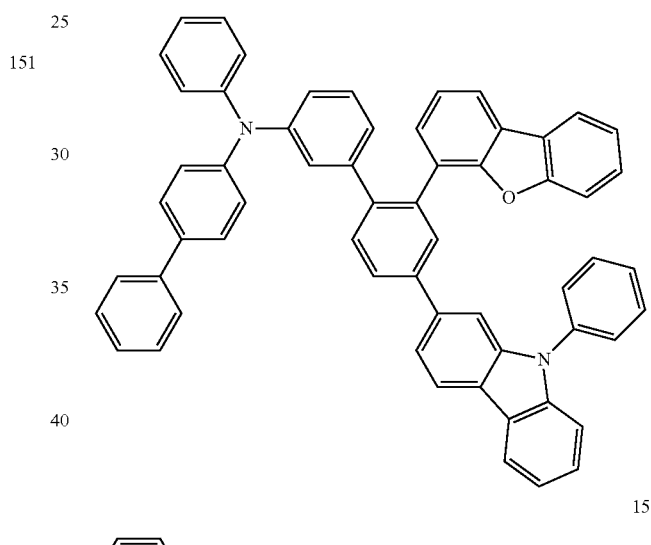
155
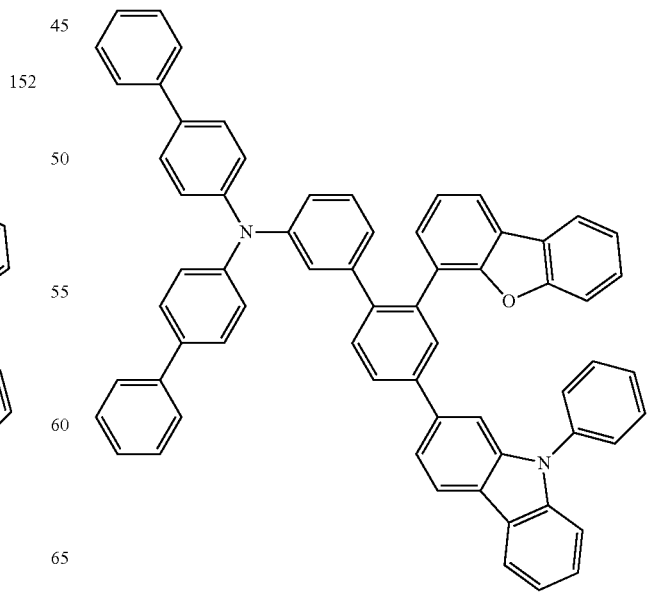

156
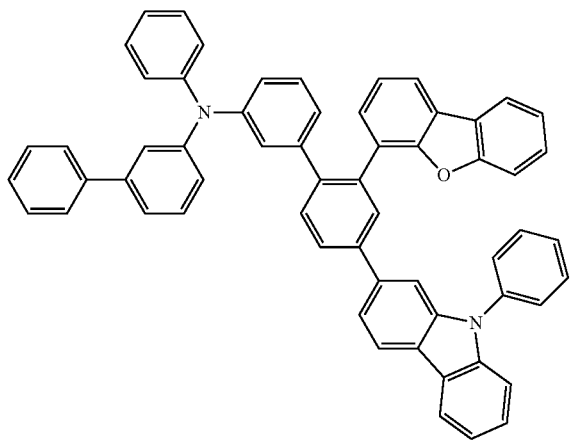
157
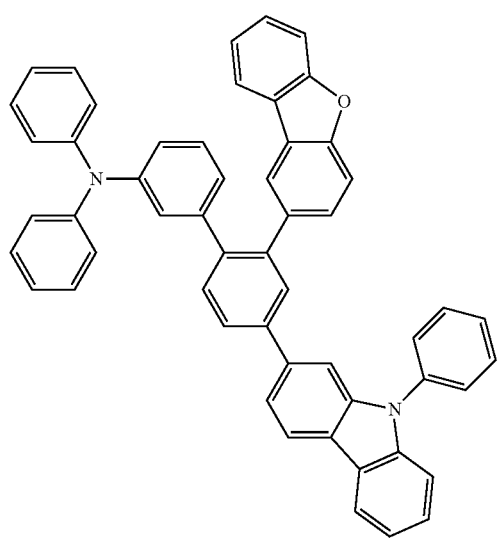
158
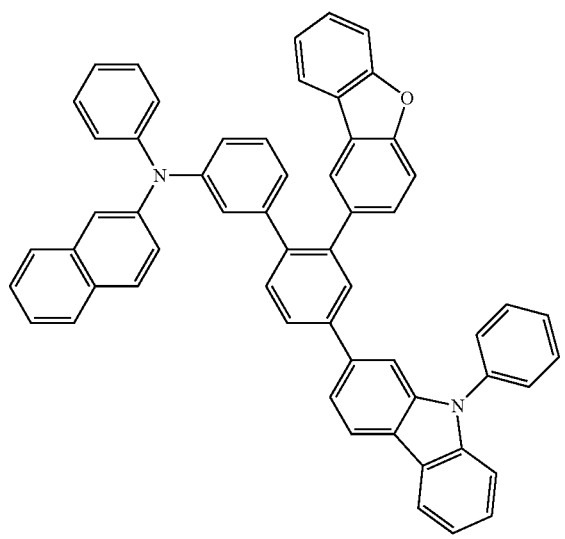
159
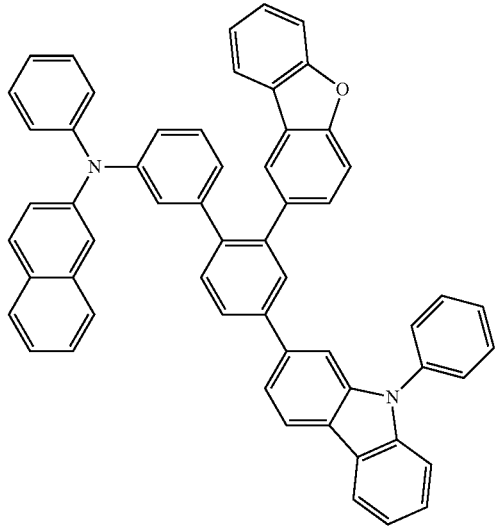
160
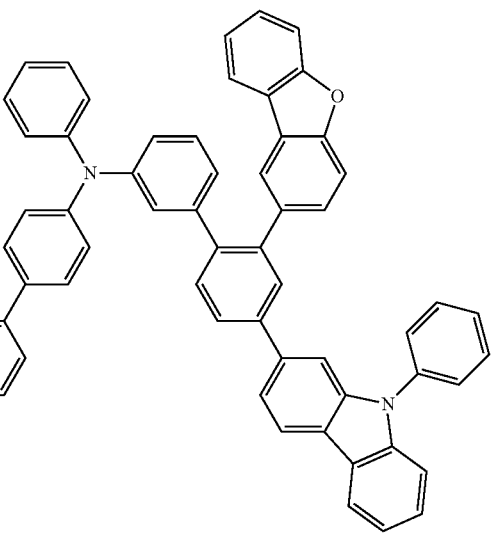

161
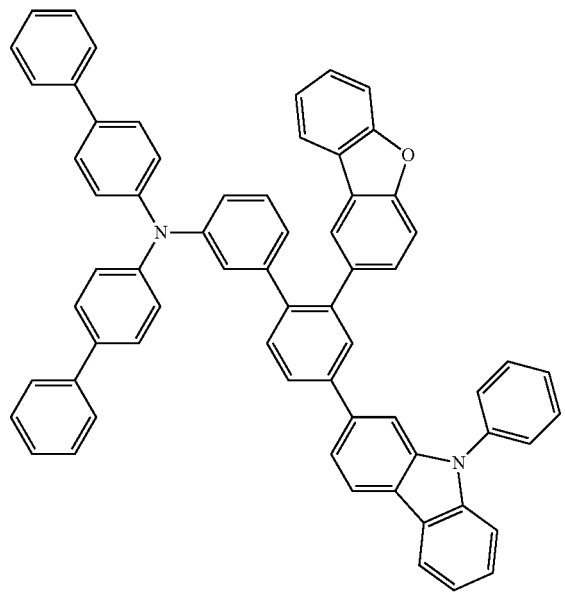
162
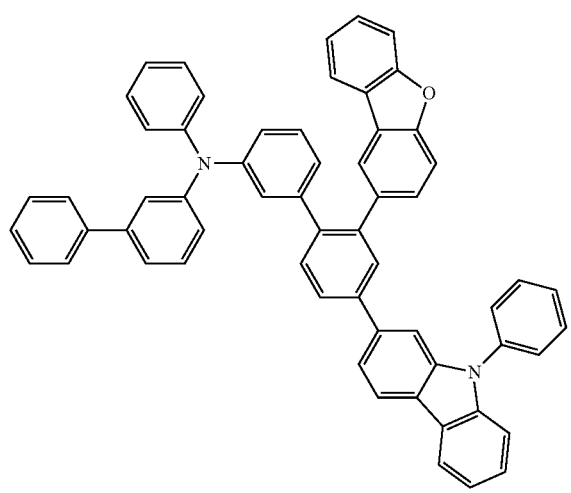
163
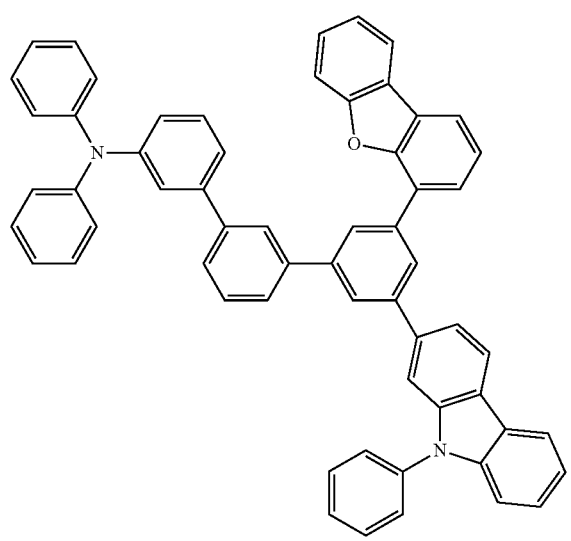
164
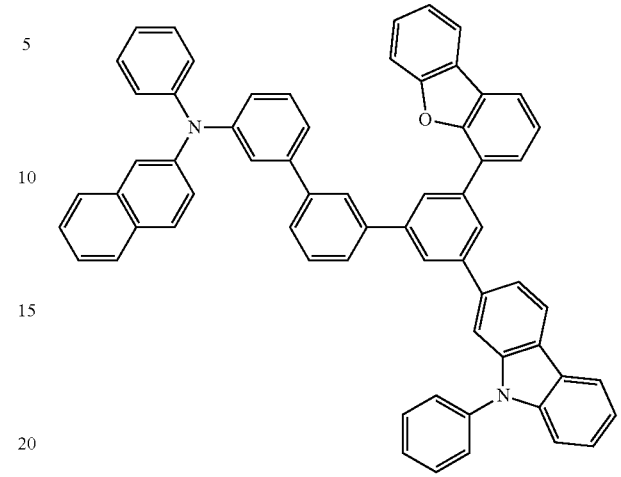
165
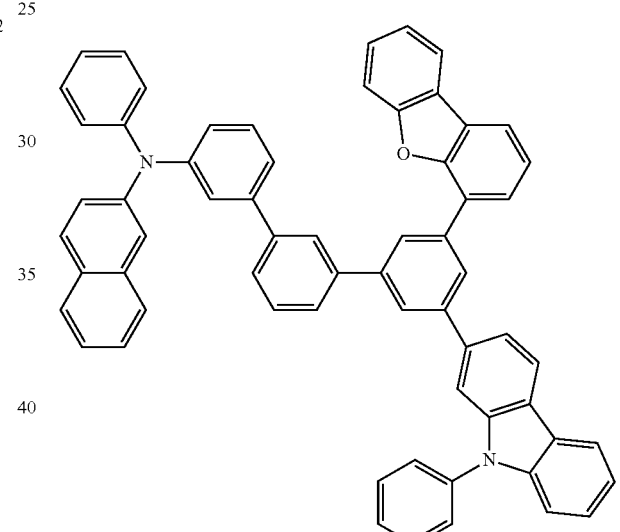
166

167
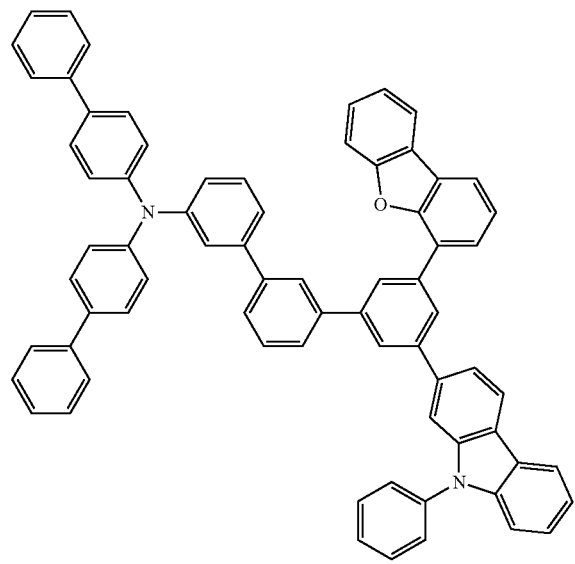
168
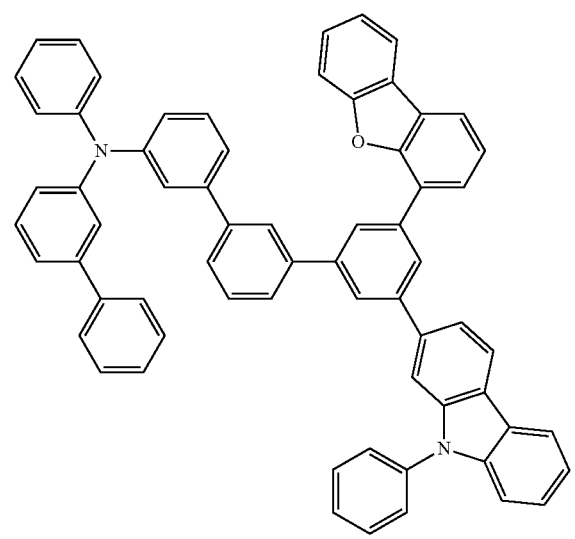
169
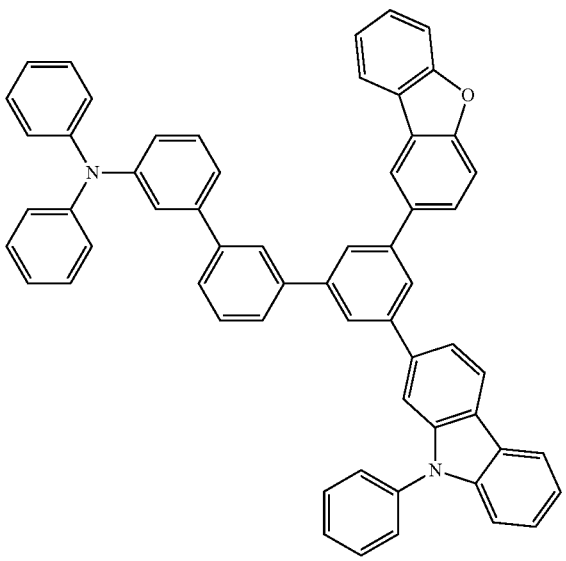
170

171
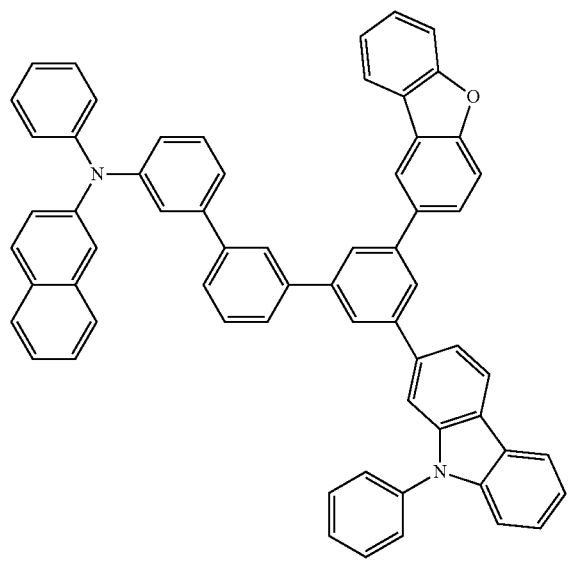
172
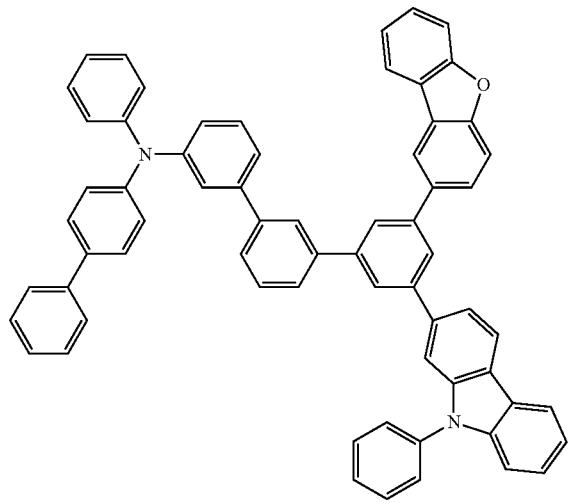
173
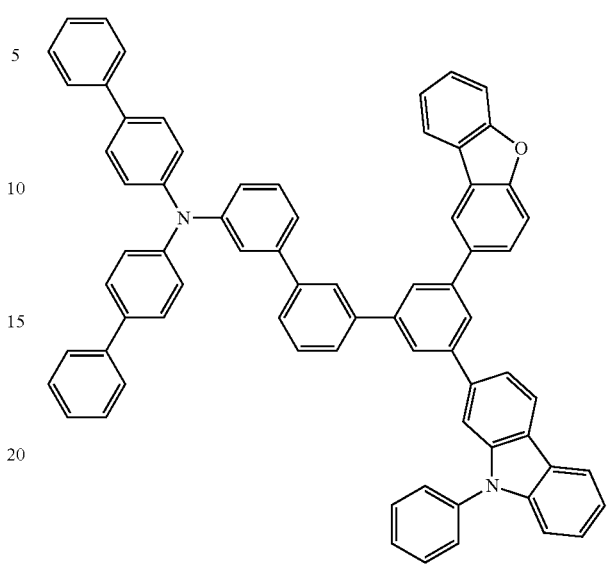
174
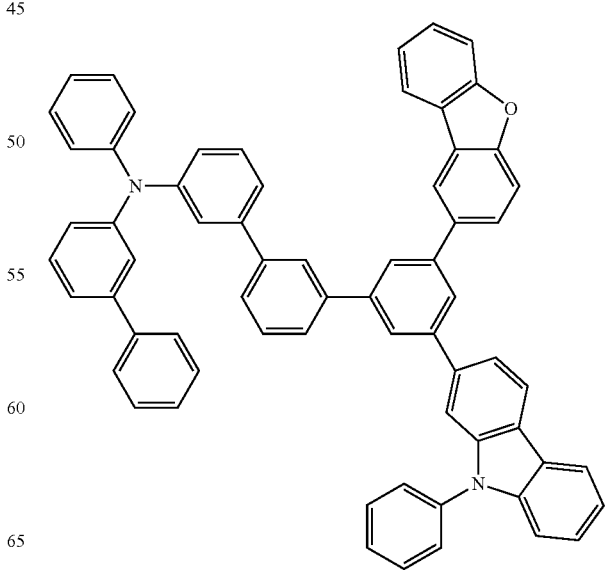

175
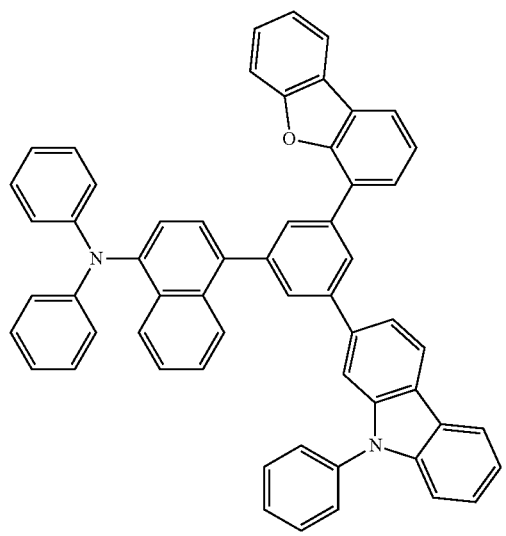
176
178
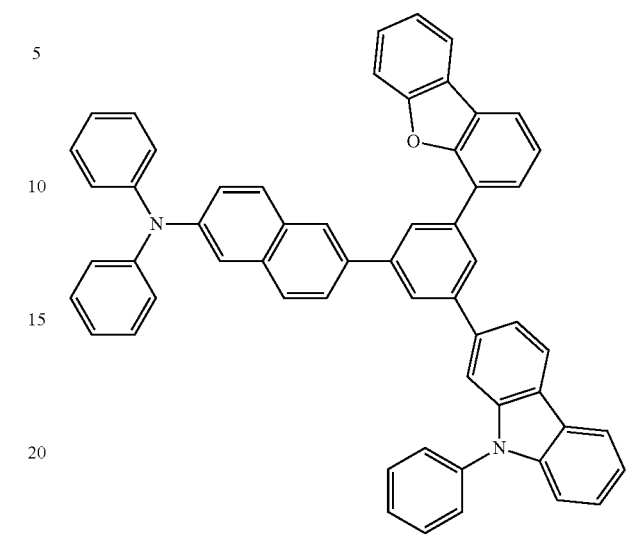
179
177
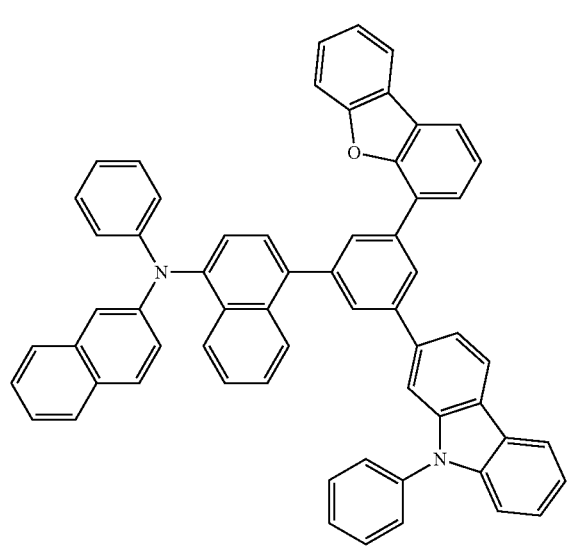
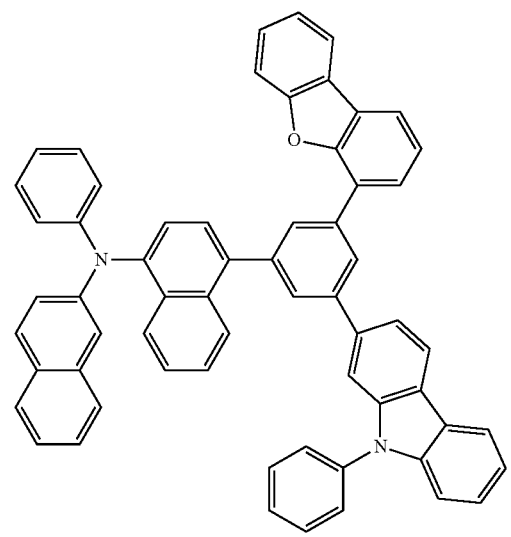
180
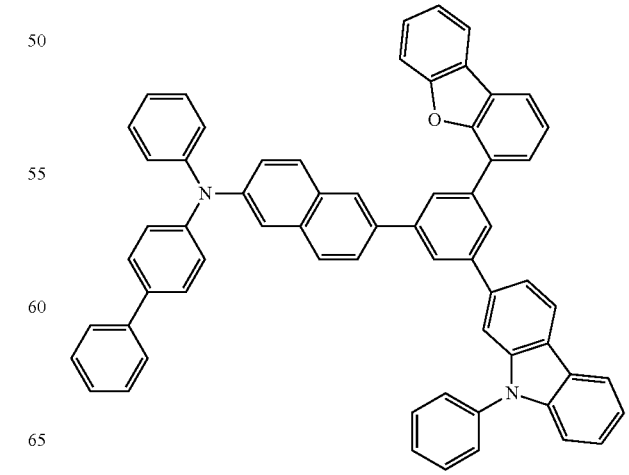

101
-continued
181
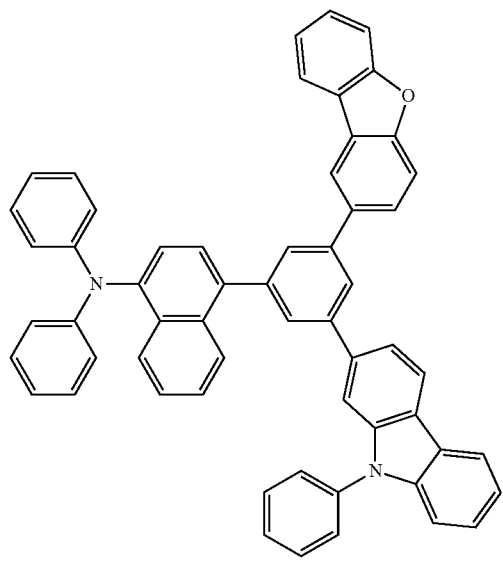
182
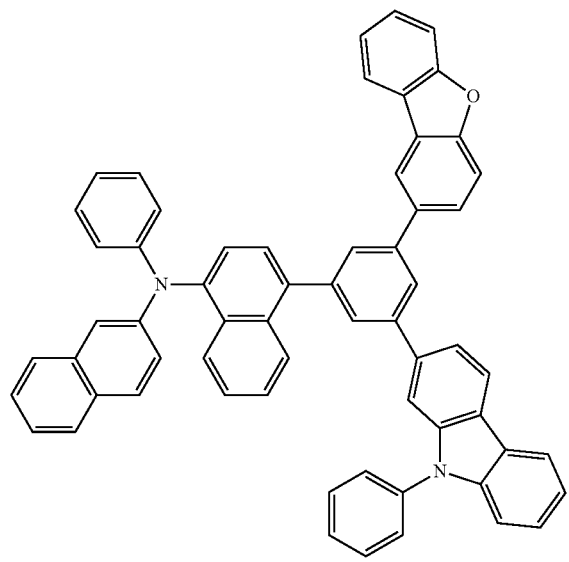
102
-continued
183
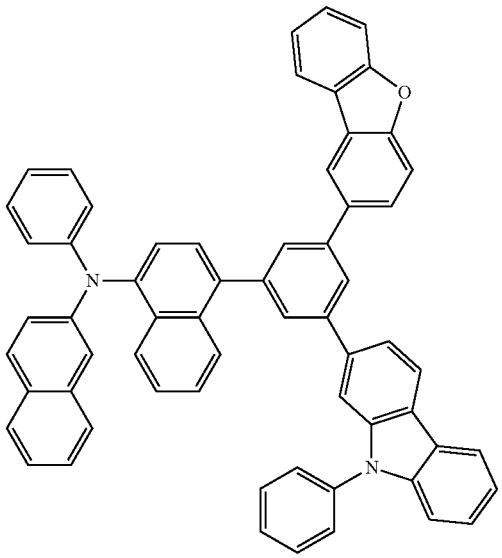
184
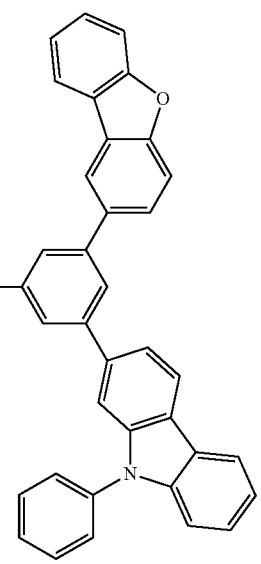

-continued
185
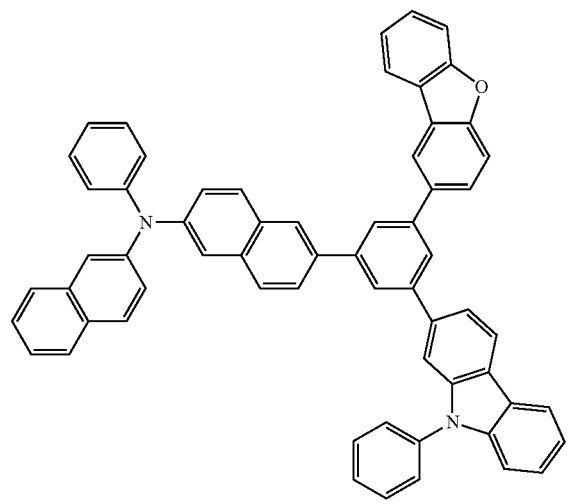
186
187
-continued
188
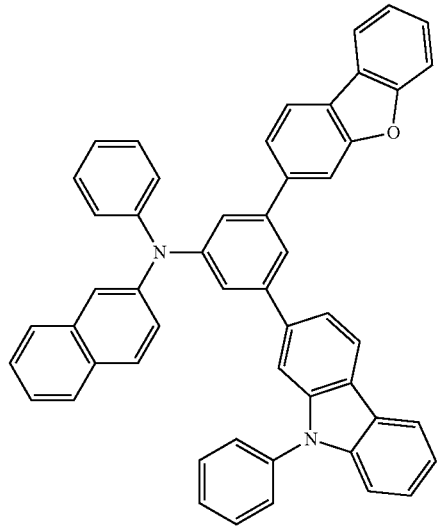
189
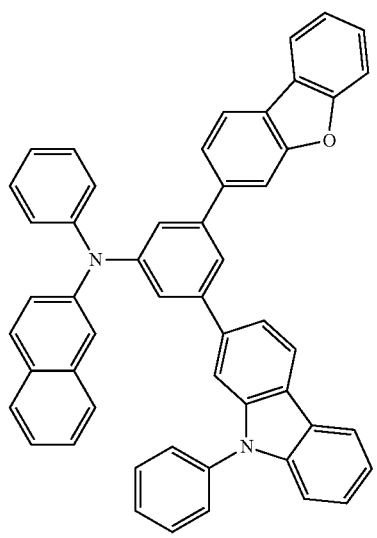
190
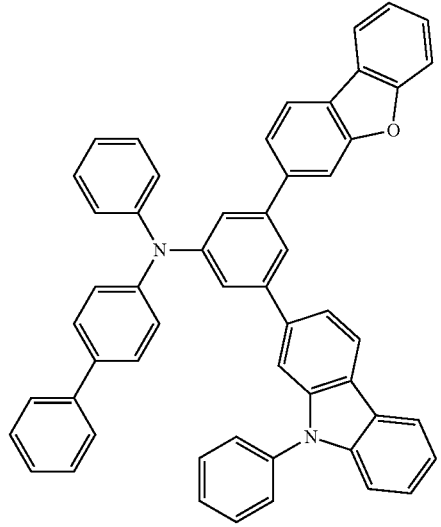

-continued
191
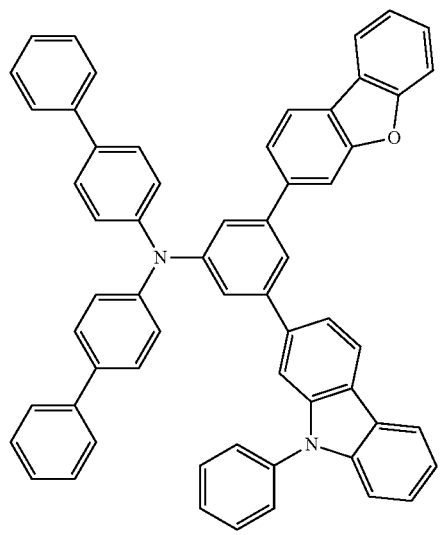
192
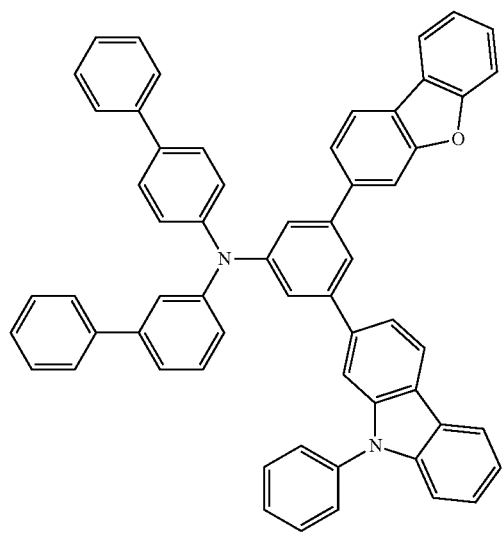
193
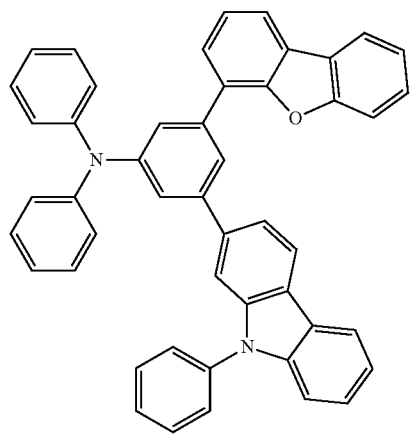
-continued
194
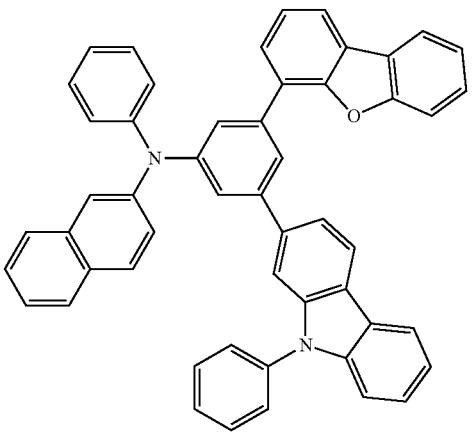
195
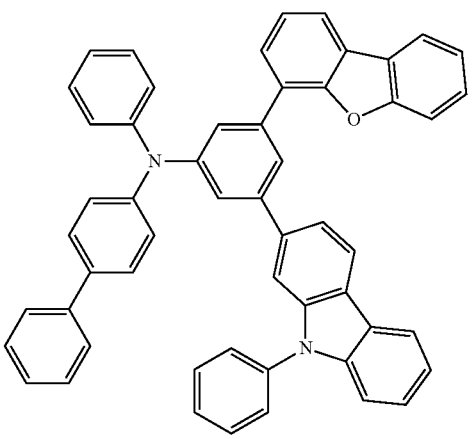
196

107
-continued
197
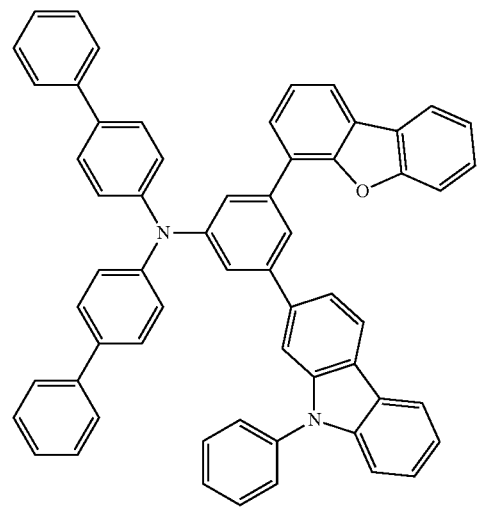
198
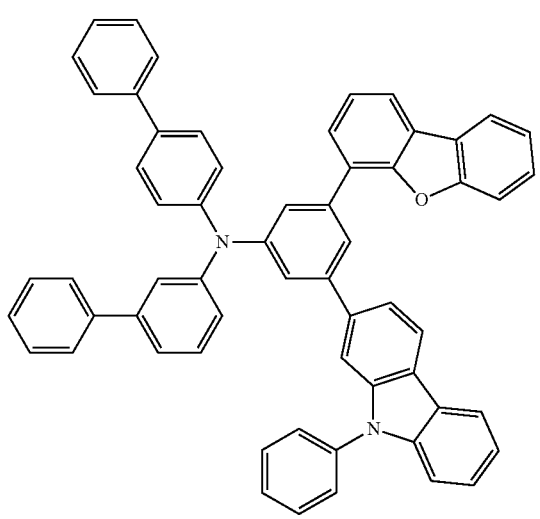
199
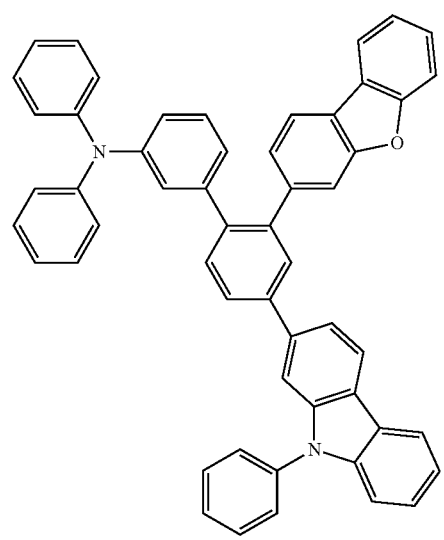
108
-continued
200
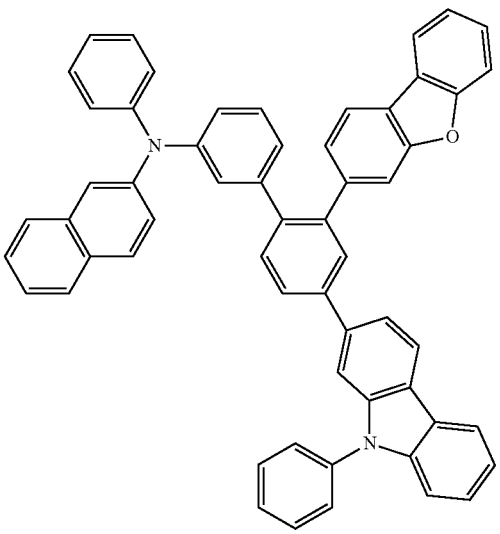
201
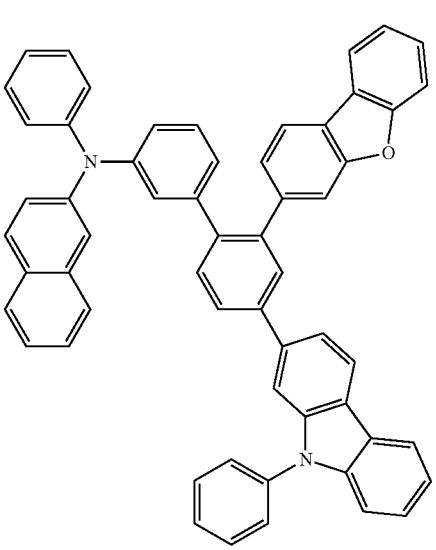
202
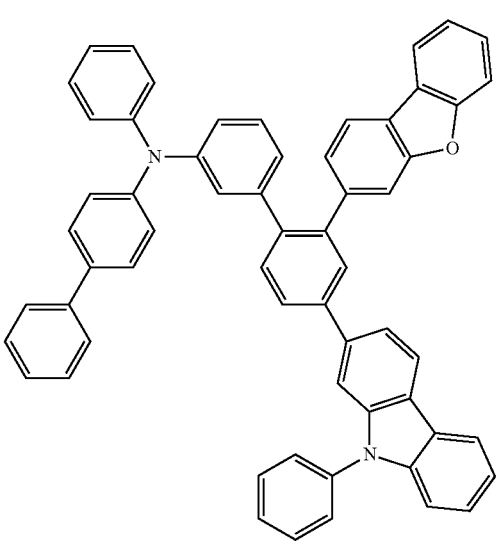

203
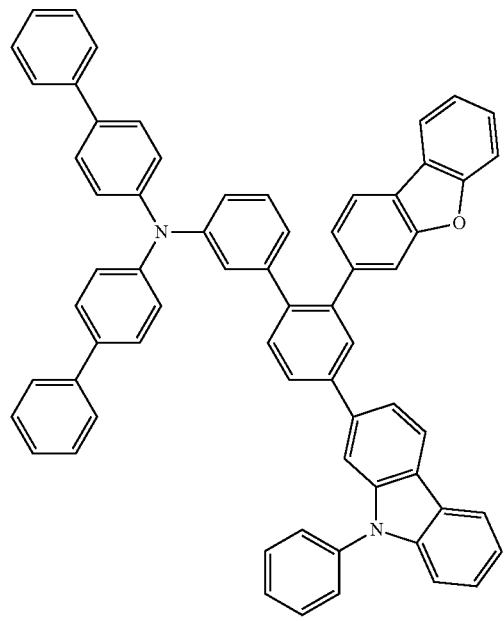
204
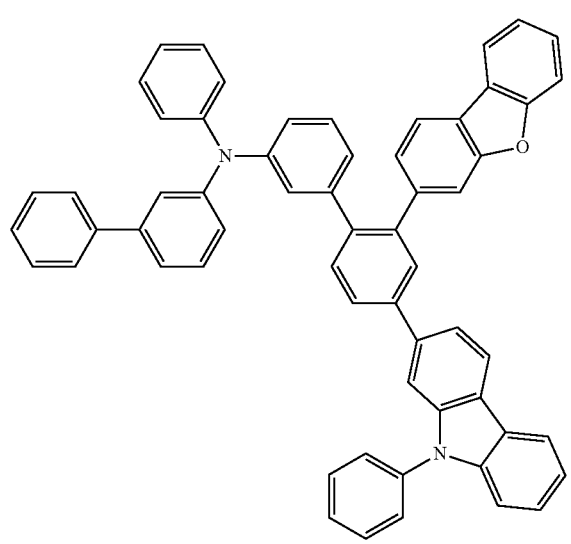
205
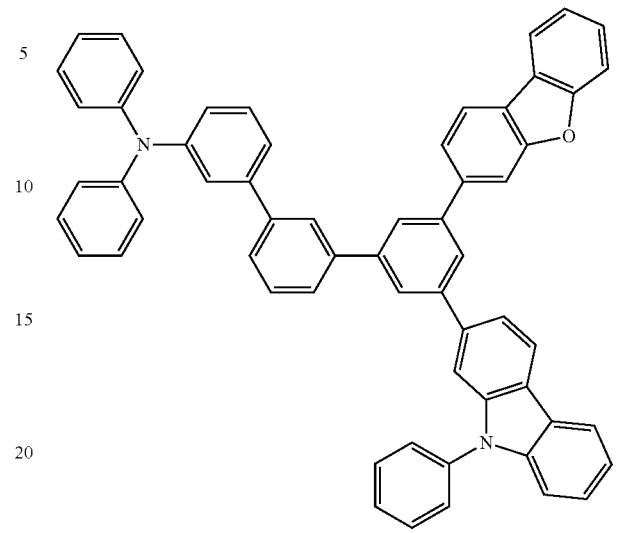
206
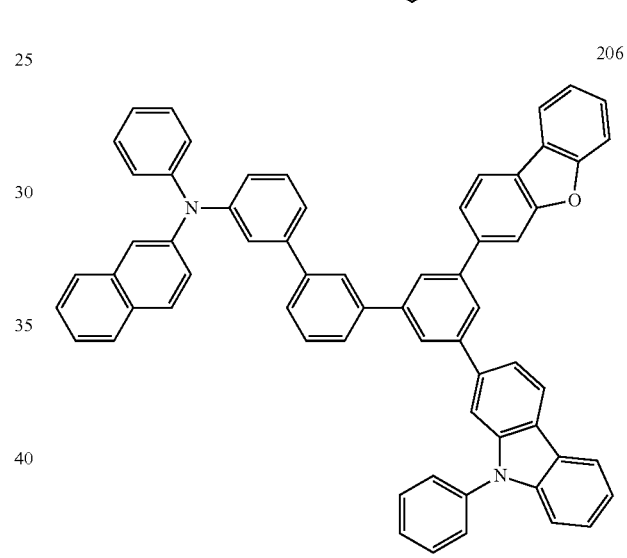
207
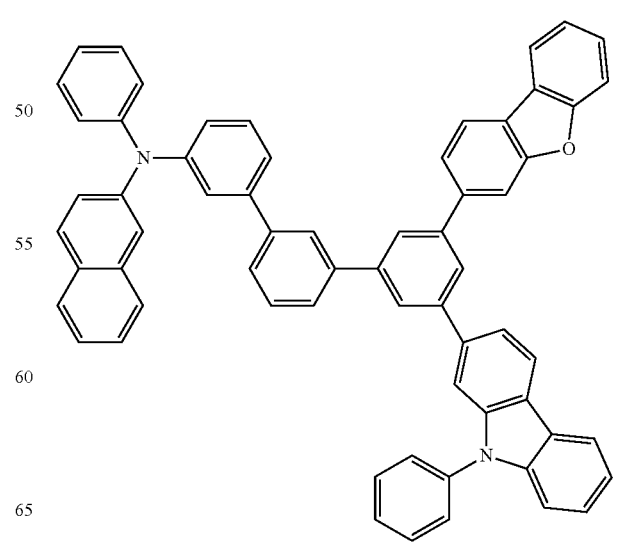

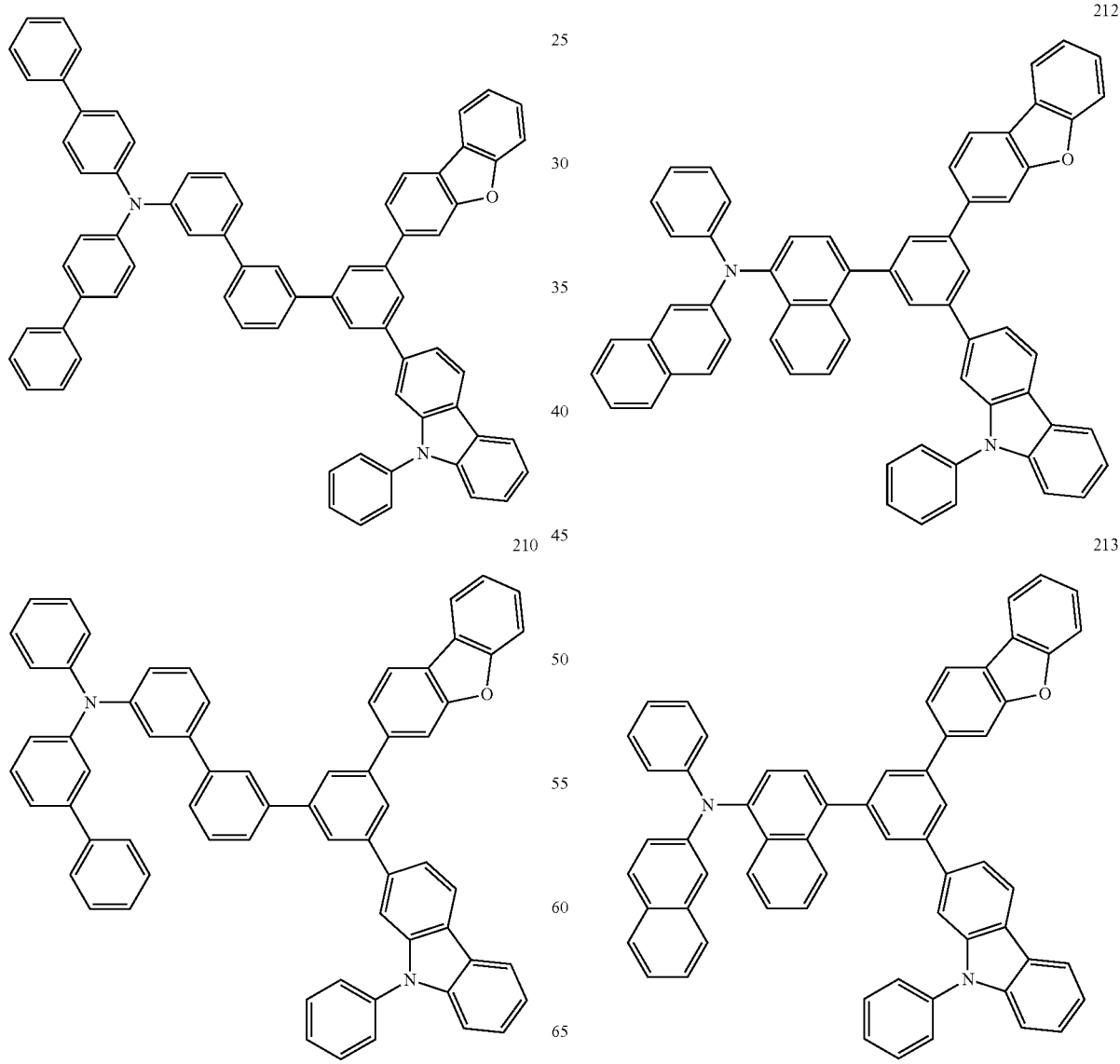

214
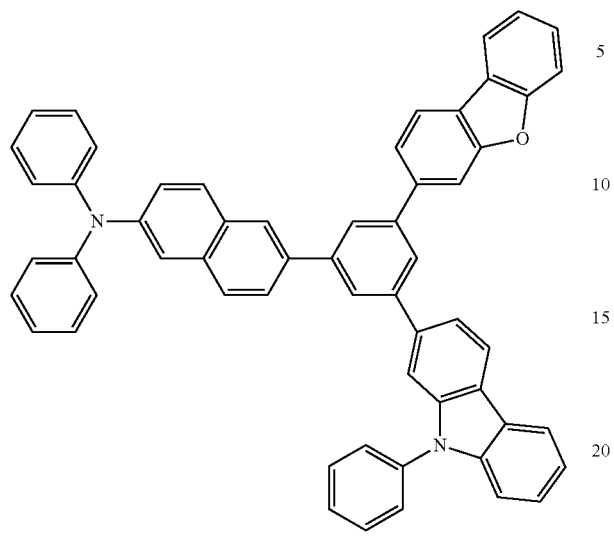
215
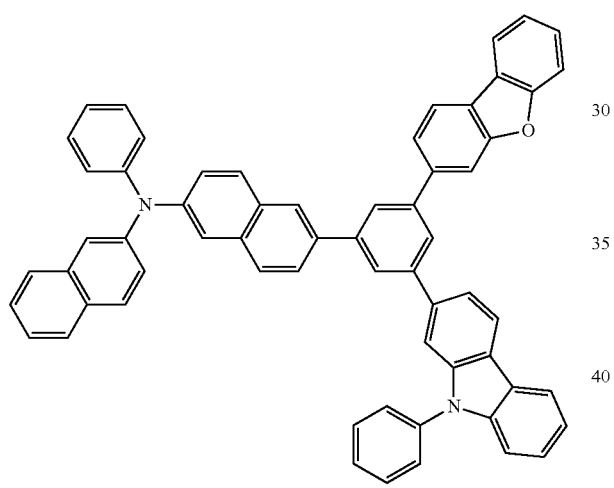
216
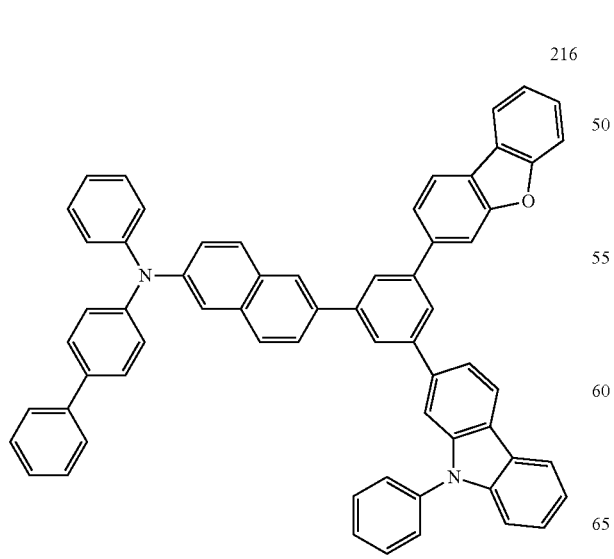
217
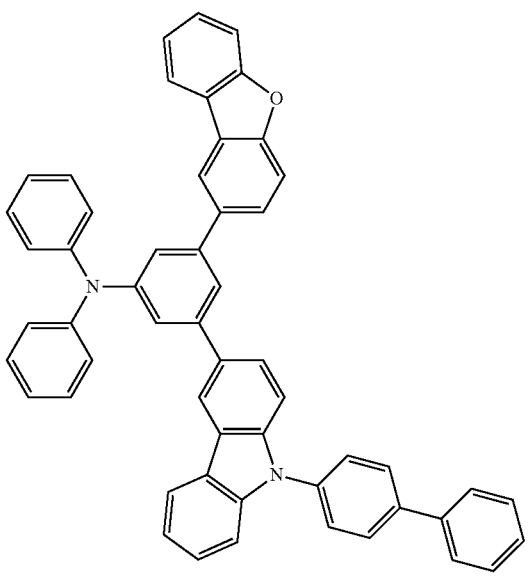
218
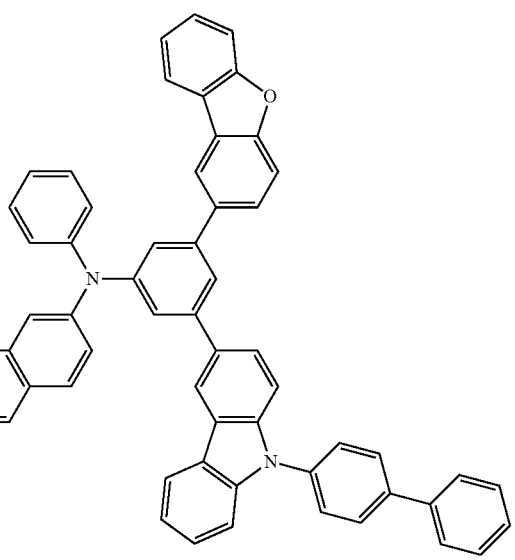

219
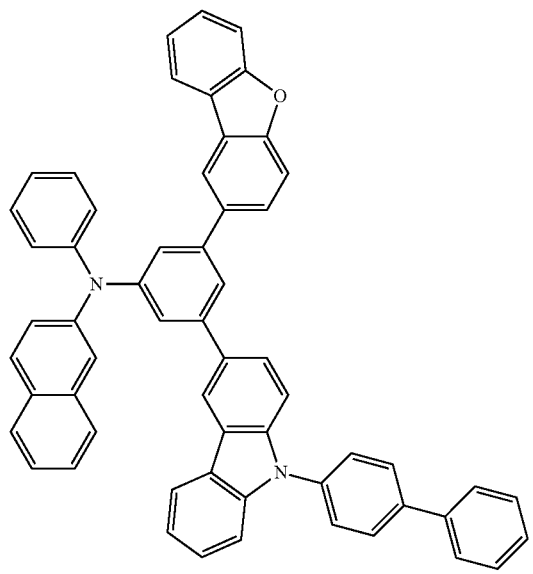
220
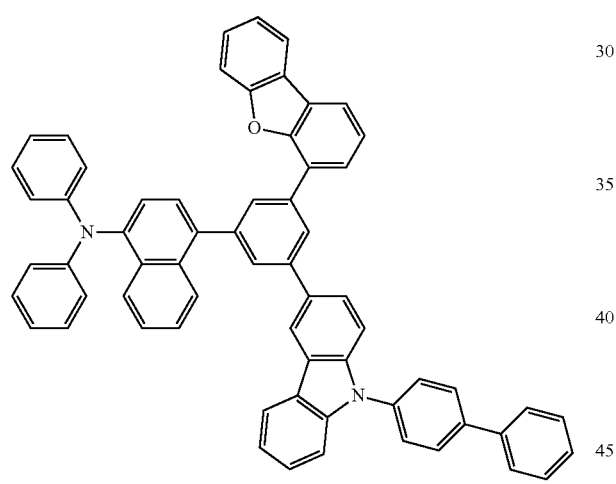
221
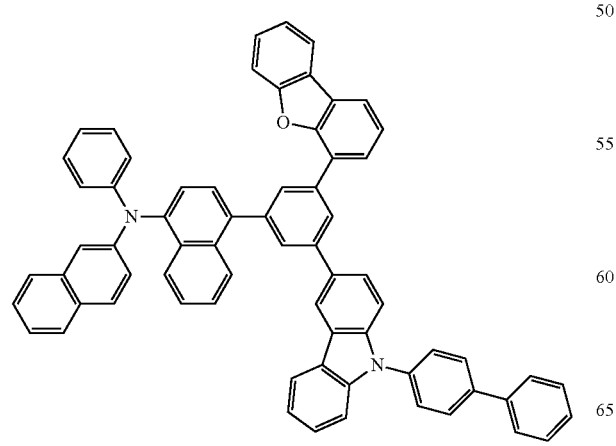
222
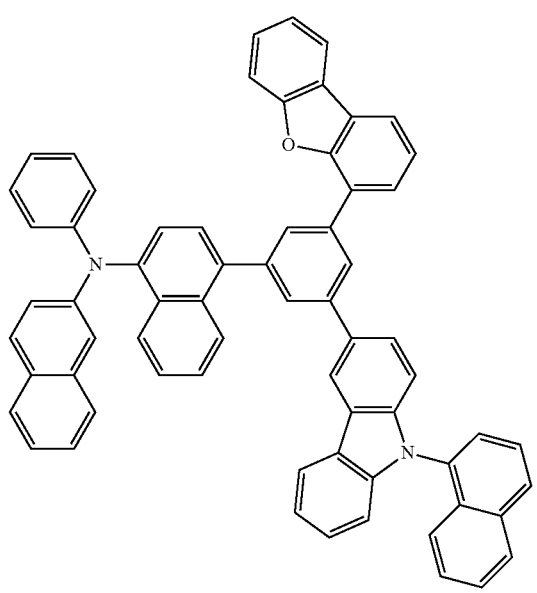
223
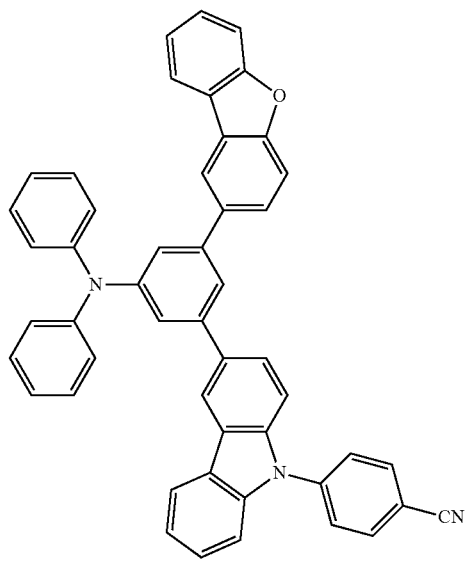

-continued
224
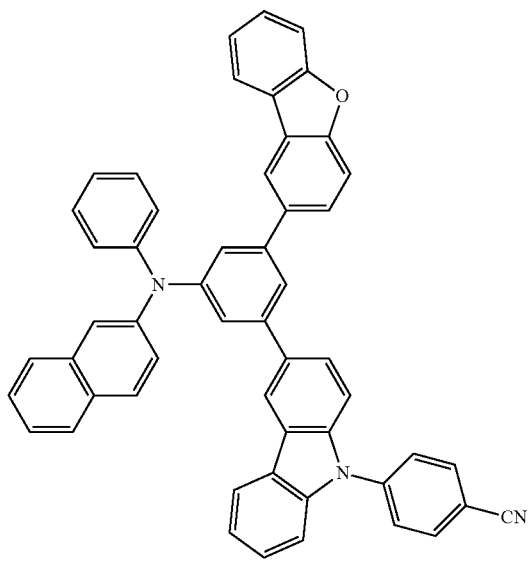
225
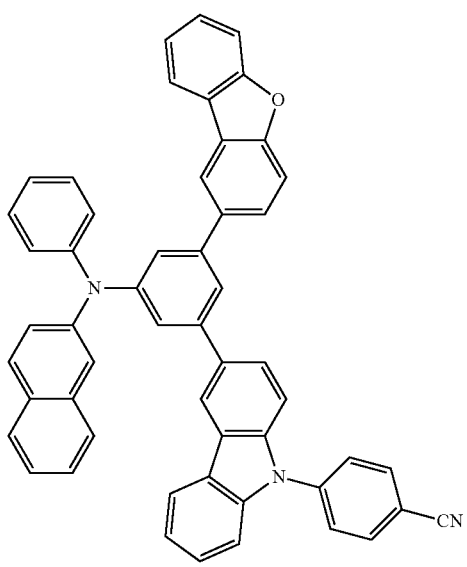
226
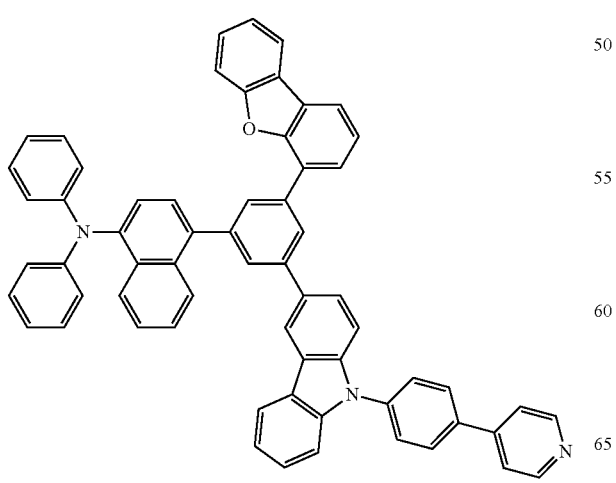
-continued
227
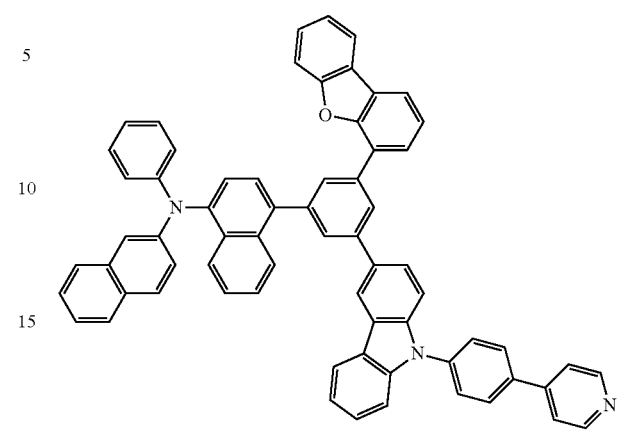
228
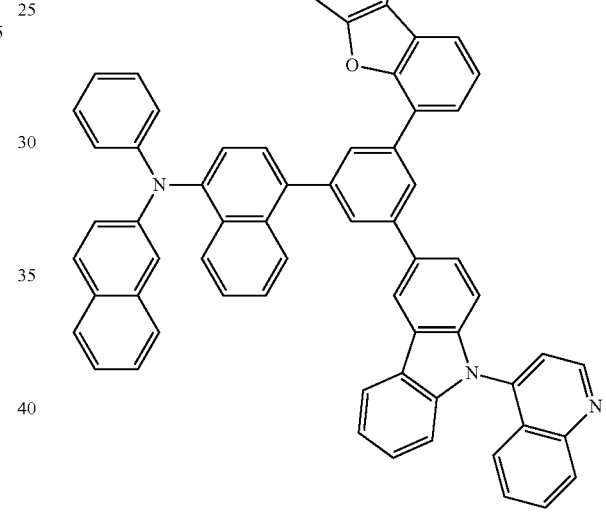
229
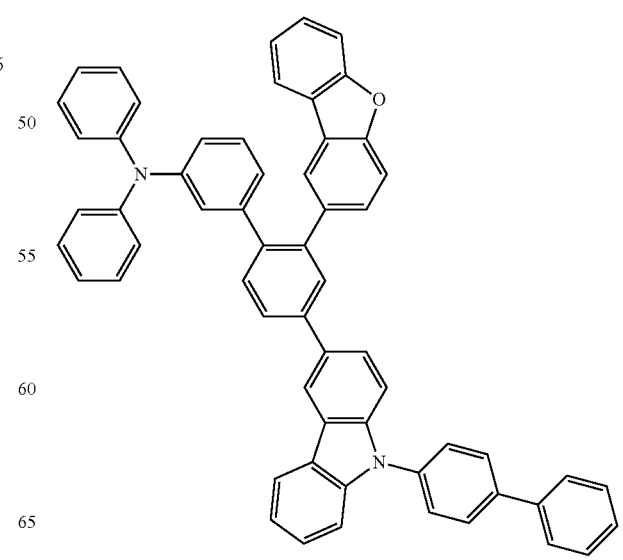

119
-continued
230
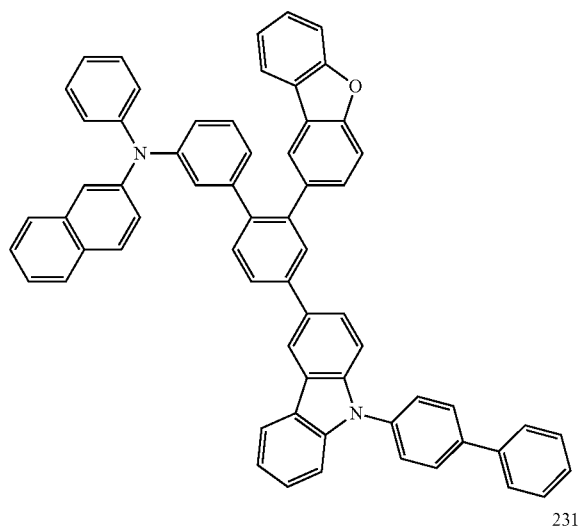
231
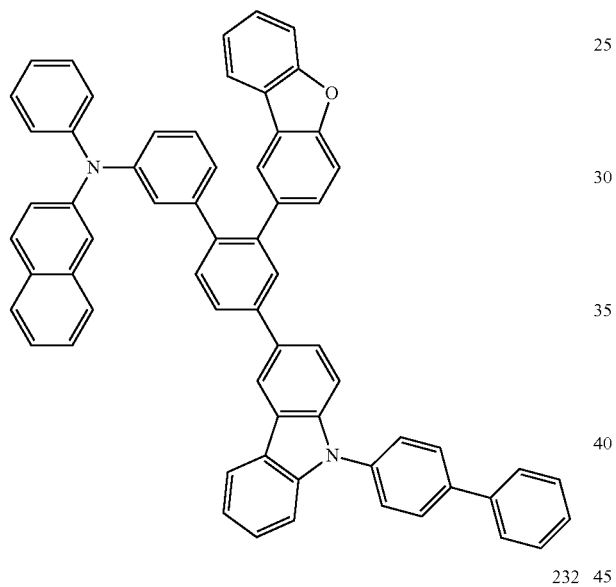
232
120
-continued
233
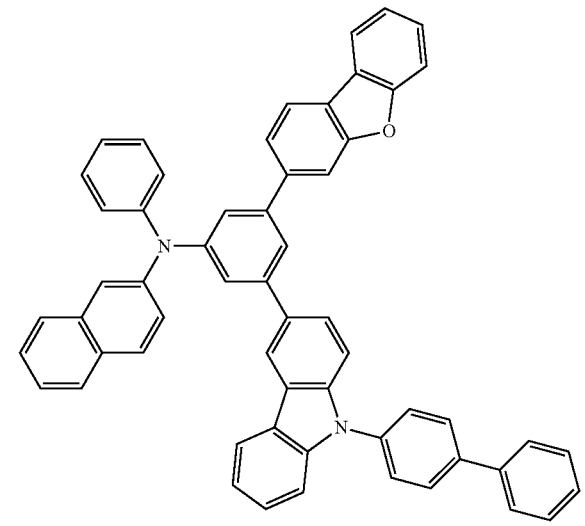
234
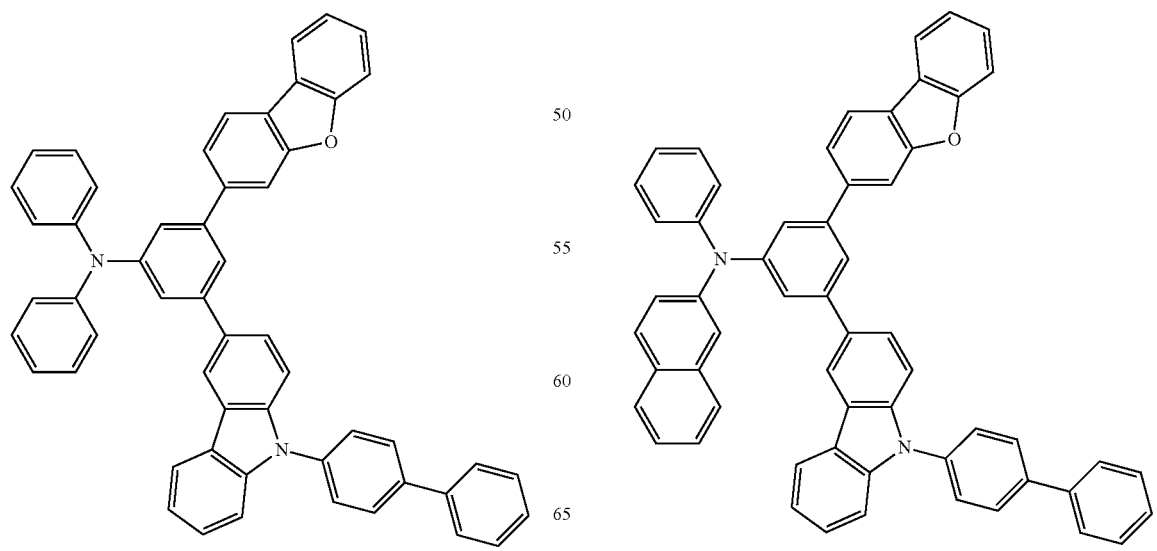

121
-continued
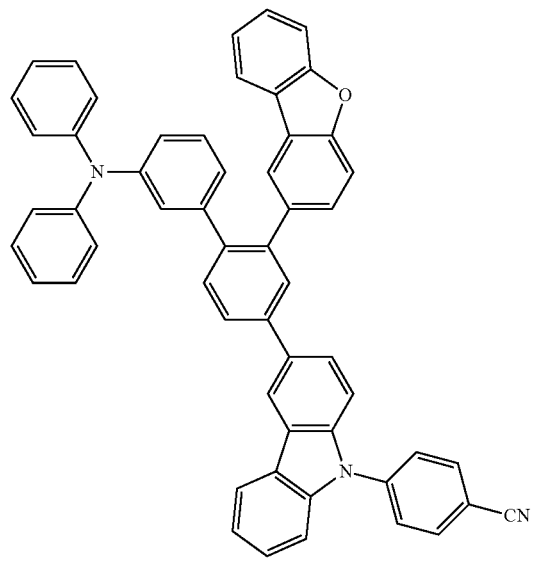
235
122
-continued
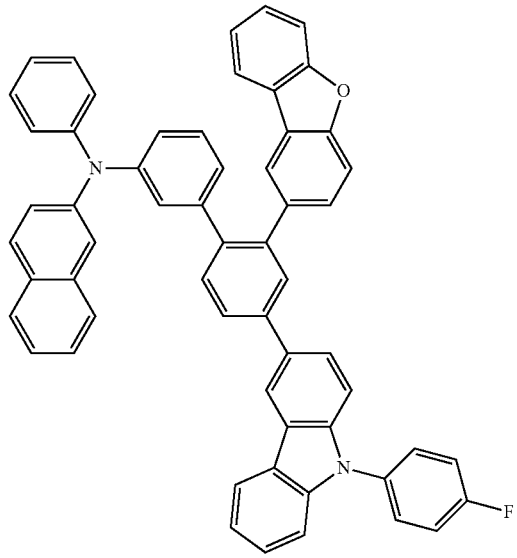
237
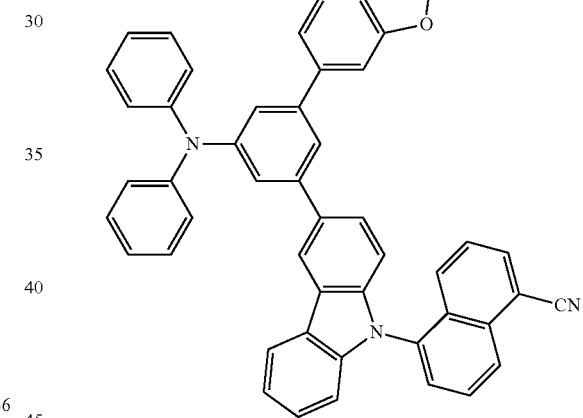
238
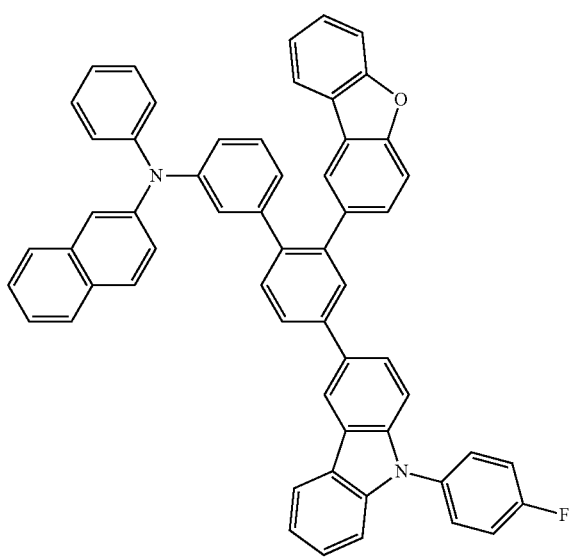
236
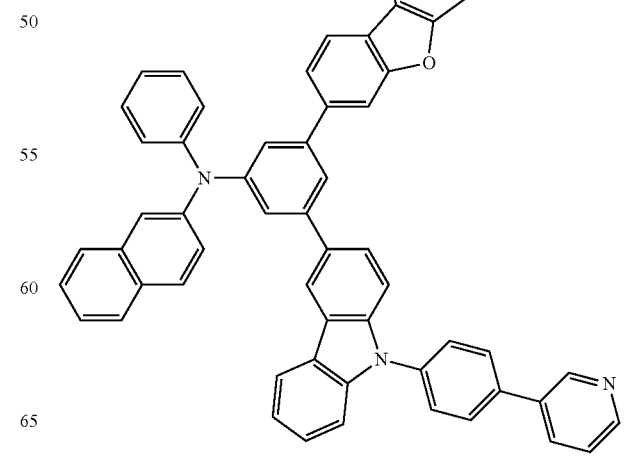
239

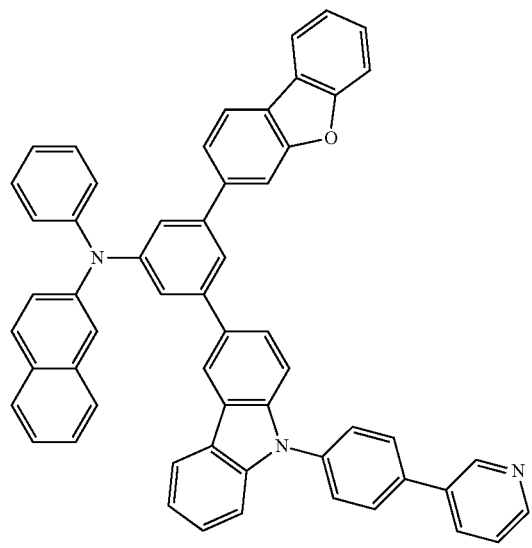
240
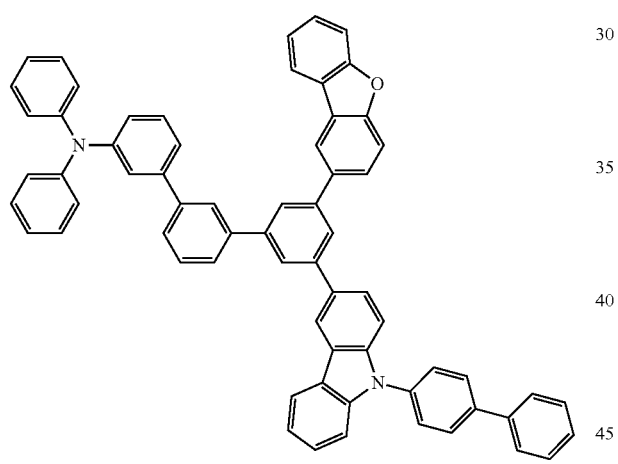
241
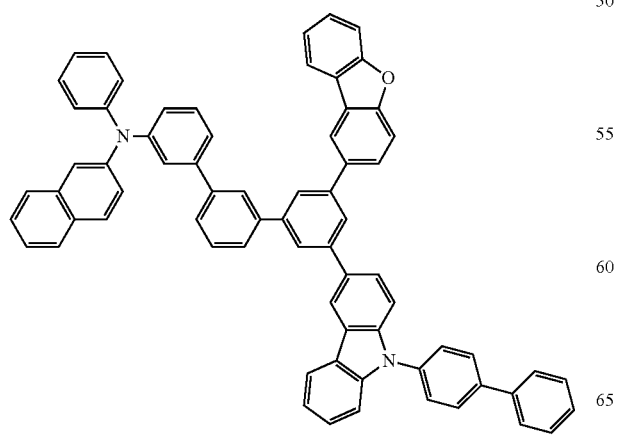
242
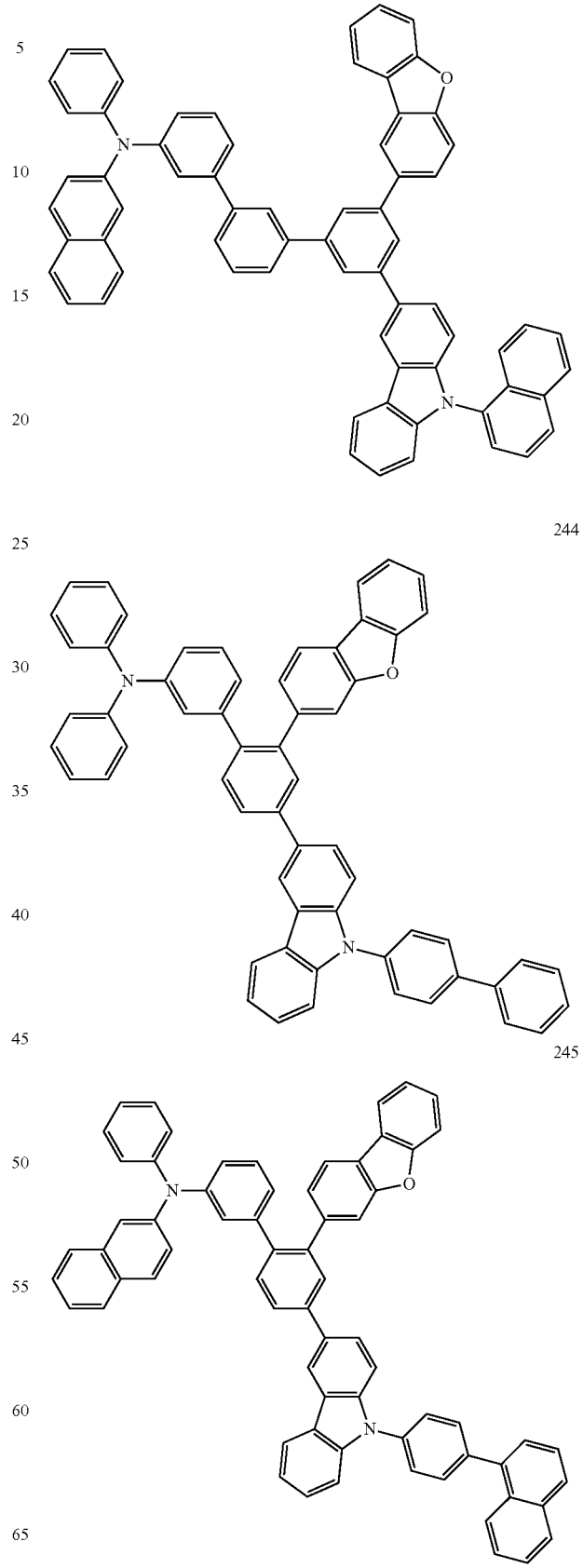
243
244
245

246
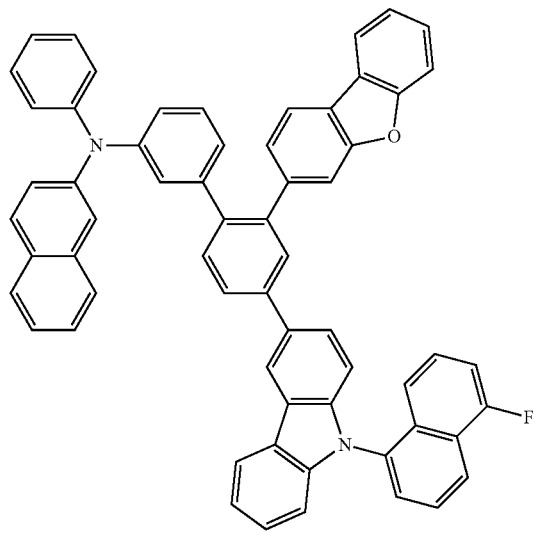
247
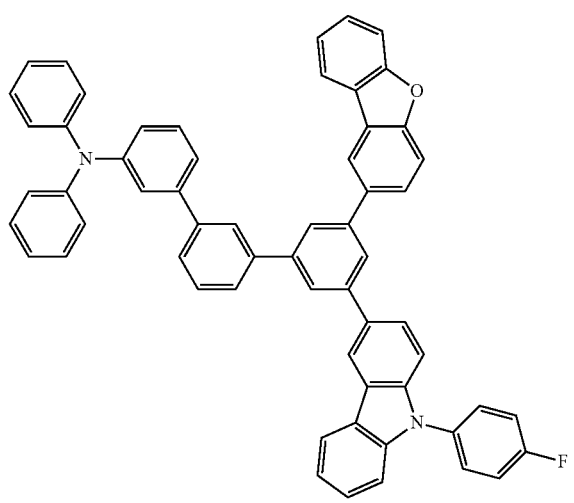
248
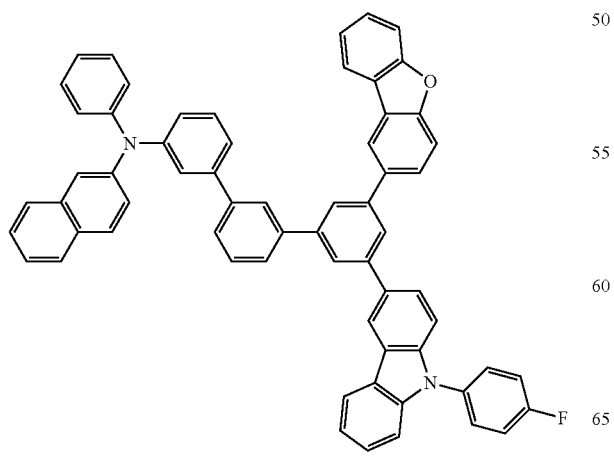
249
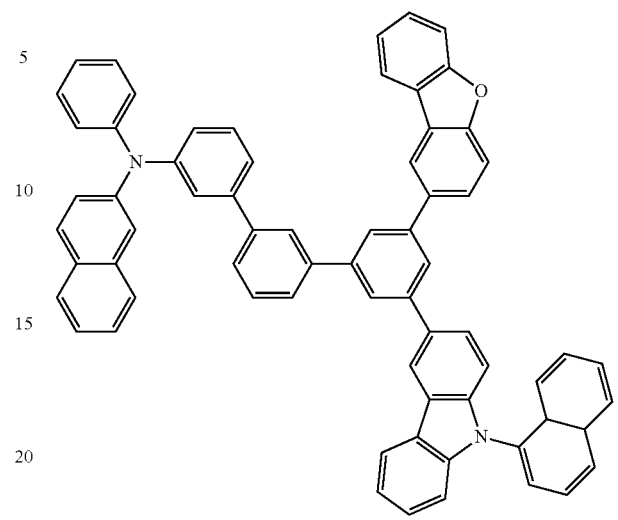
250
251
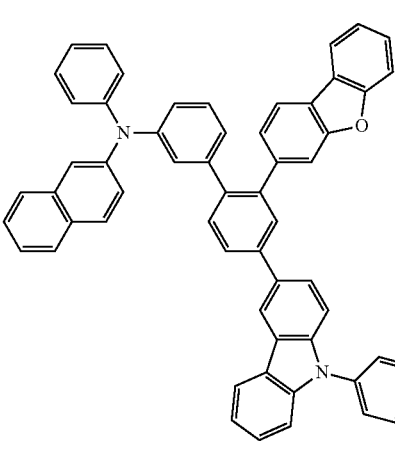

252
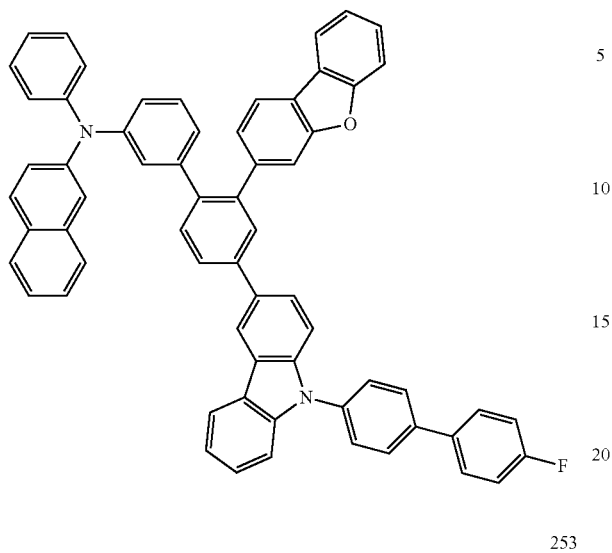
253
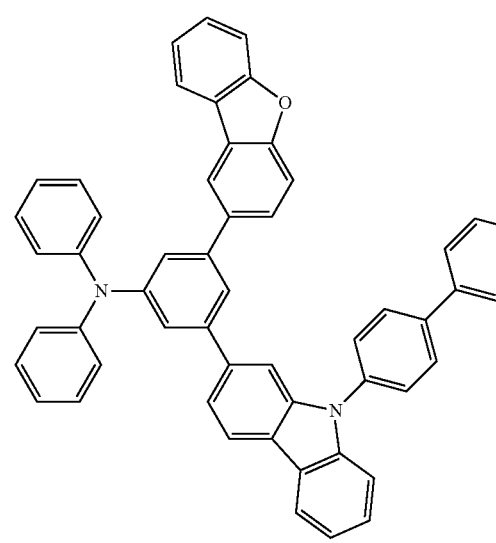
264
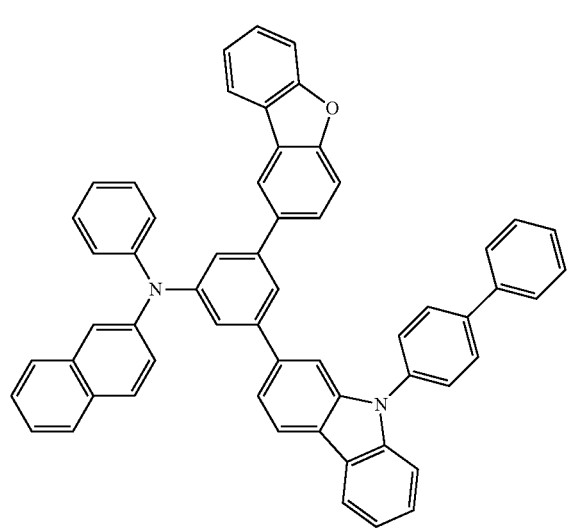
255
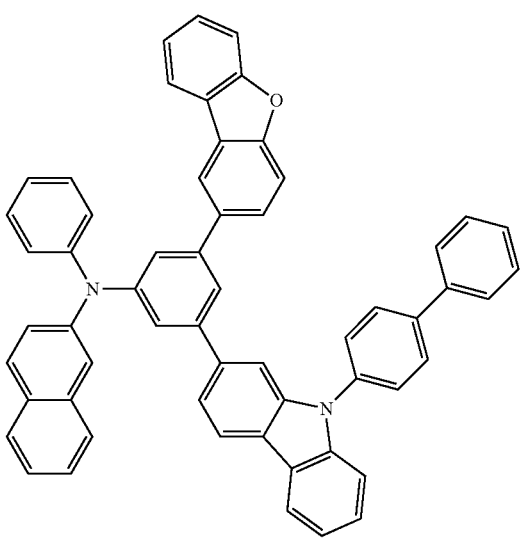
256
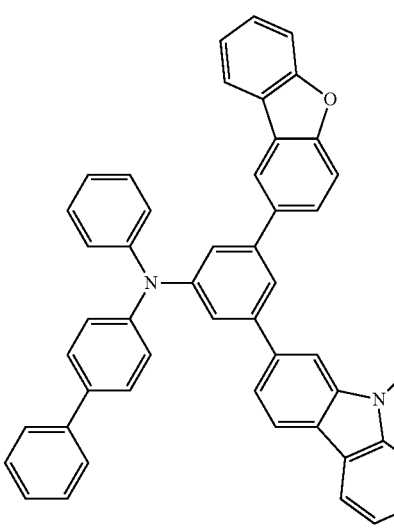
257
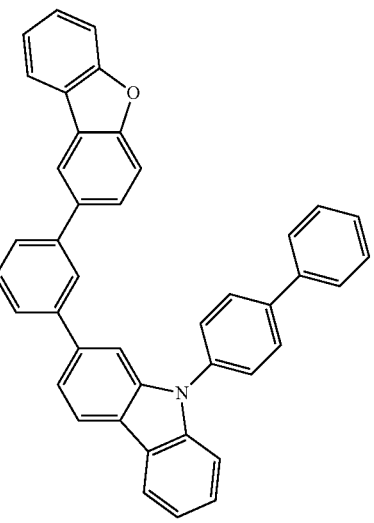

258
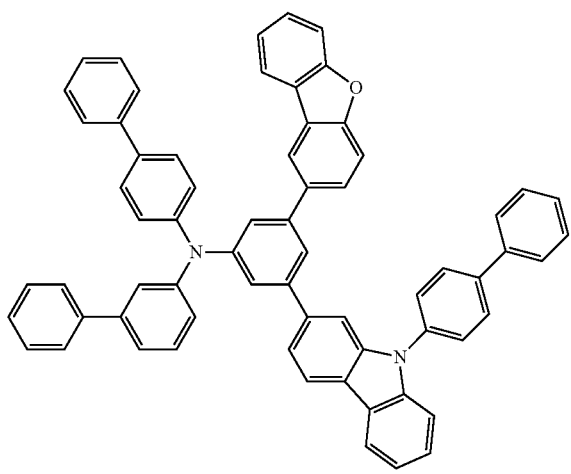
259
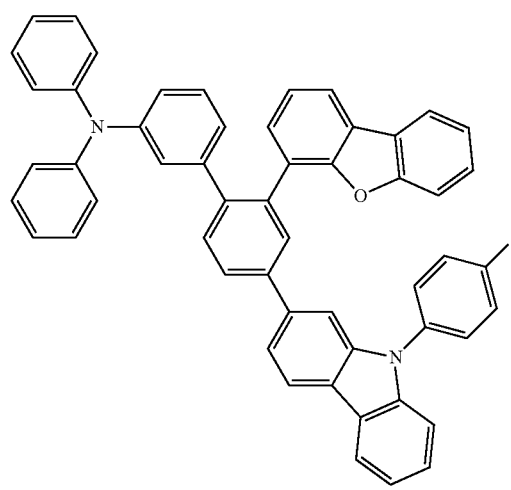
260
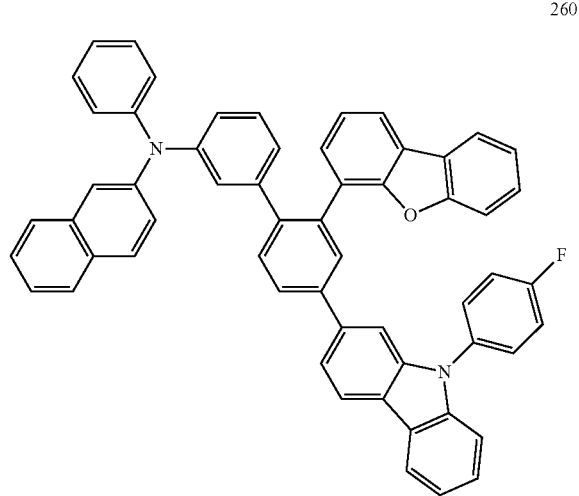
261
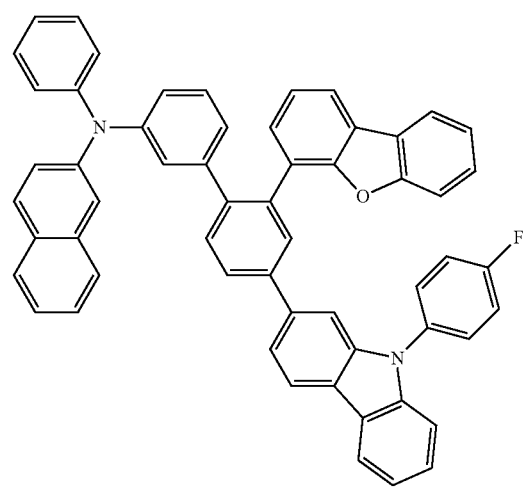
262
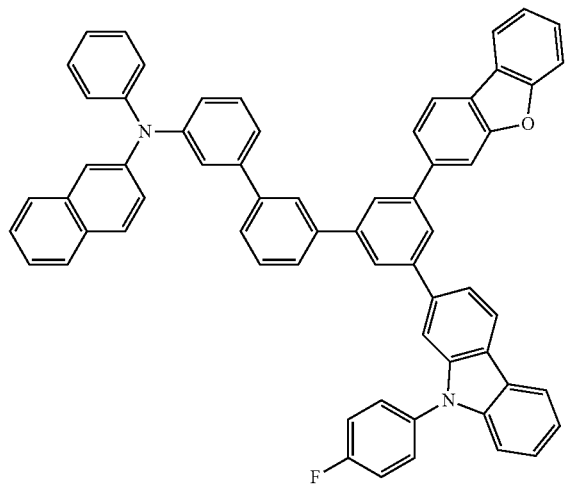
263

264
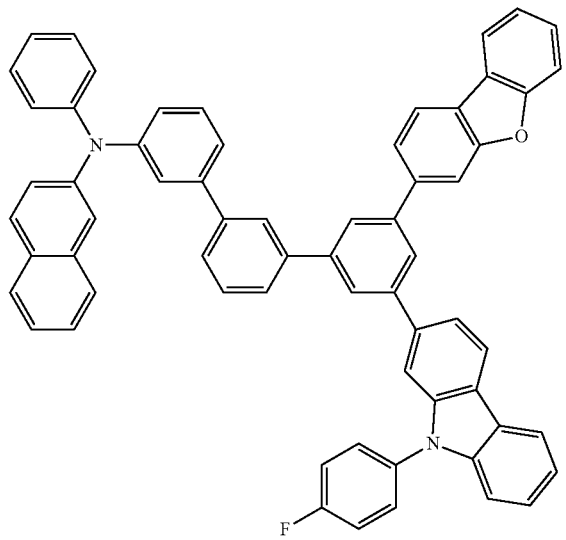
267
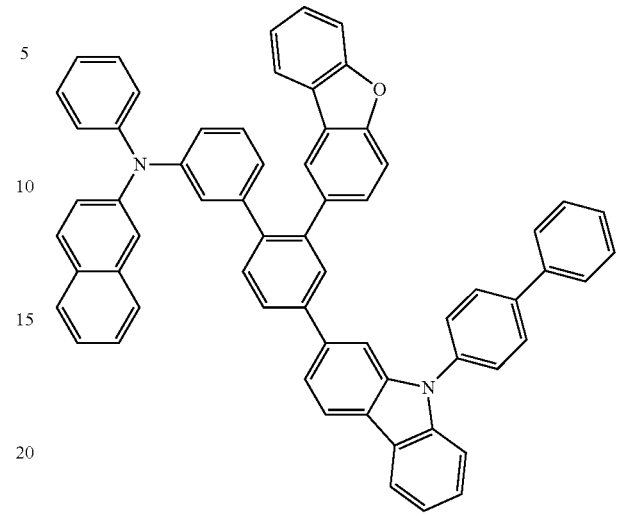
265
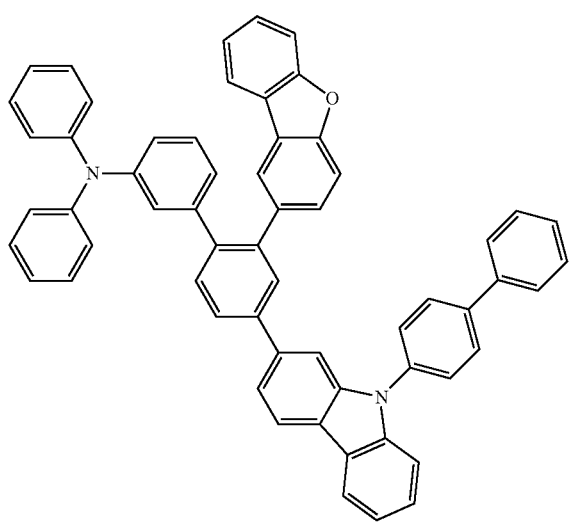
268
266
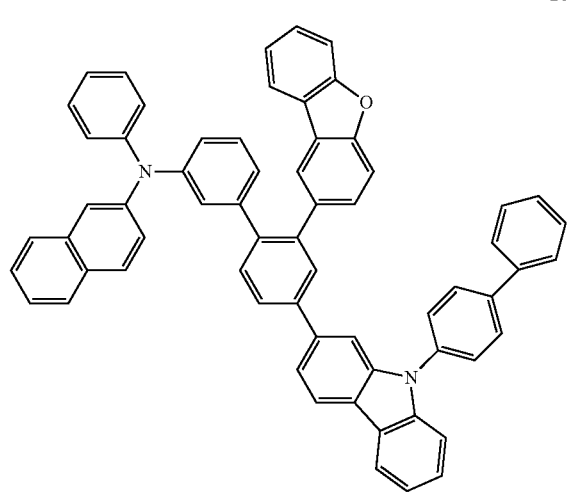
269
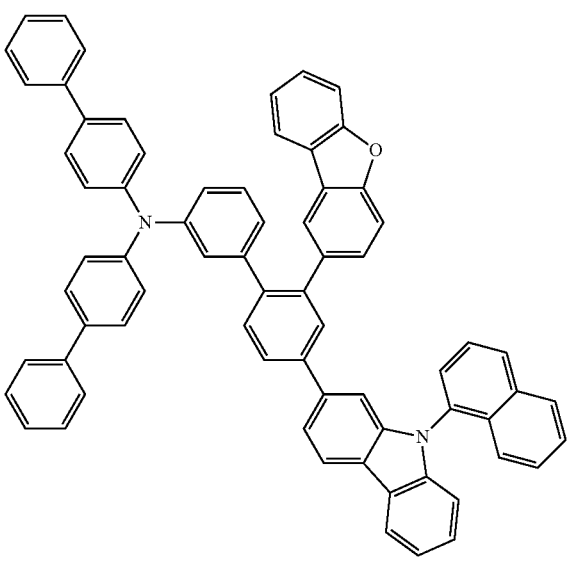

270
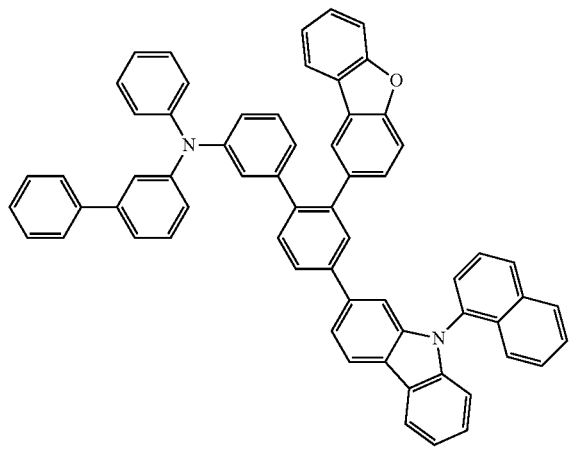
271
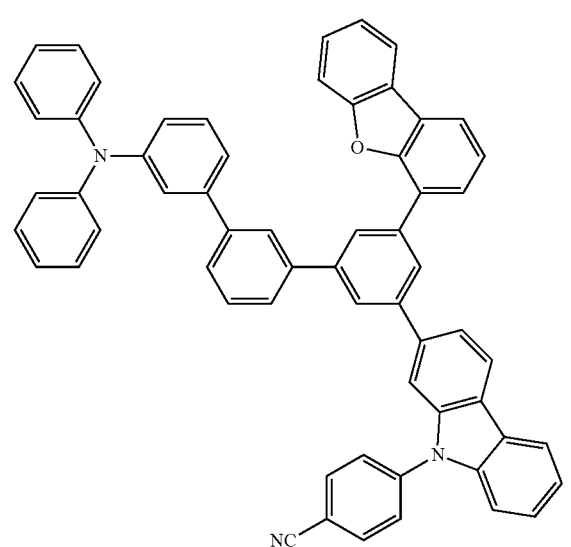
272
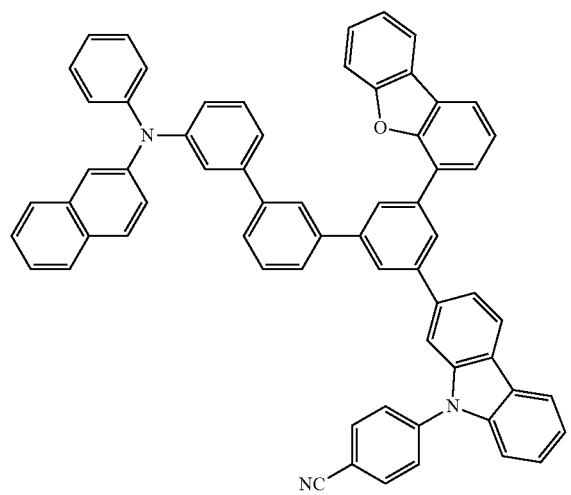
273
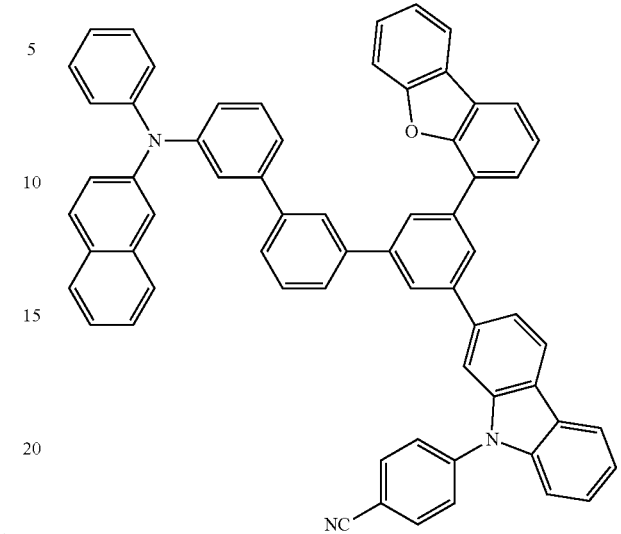
274
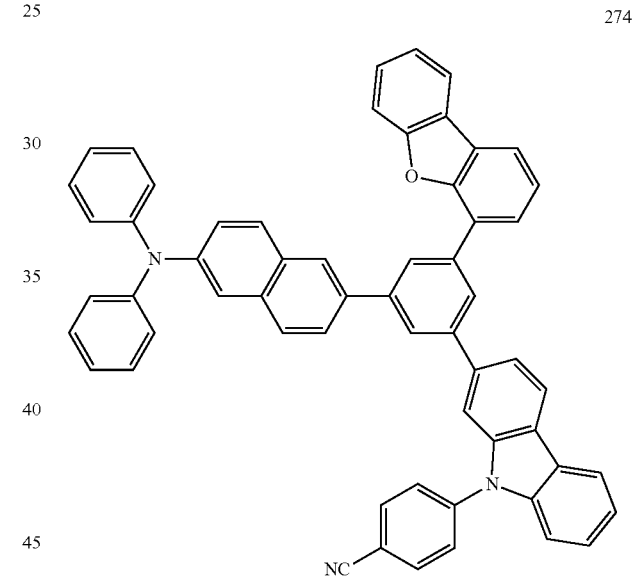
275
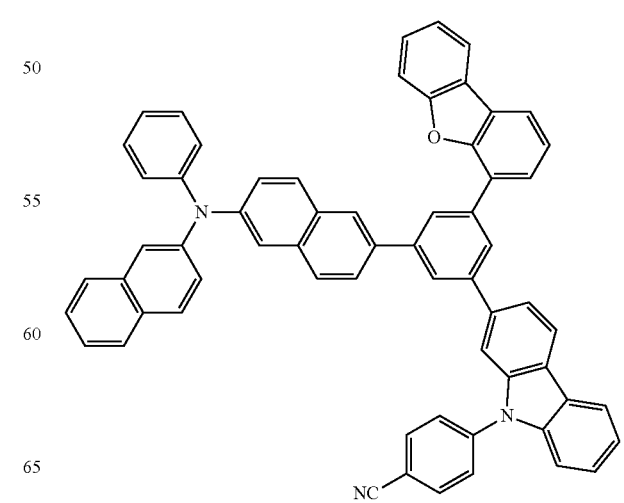

135
-continued
276
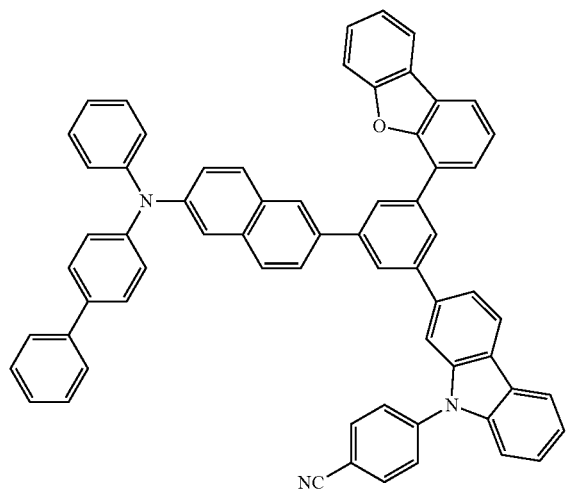
277
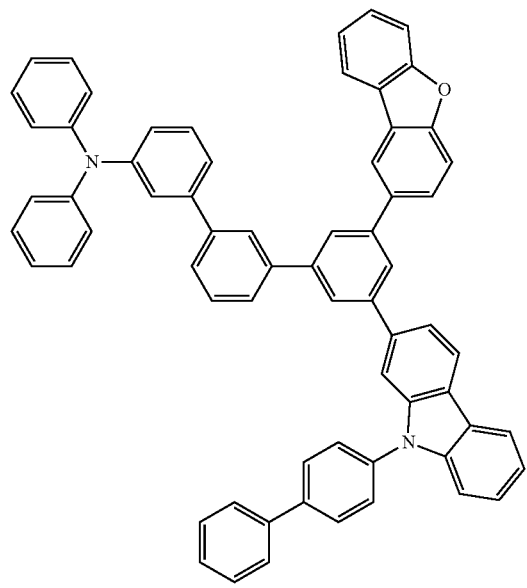
136
-continued
278
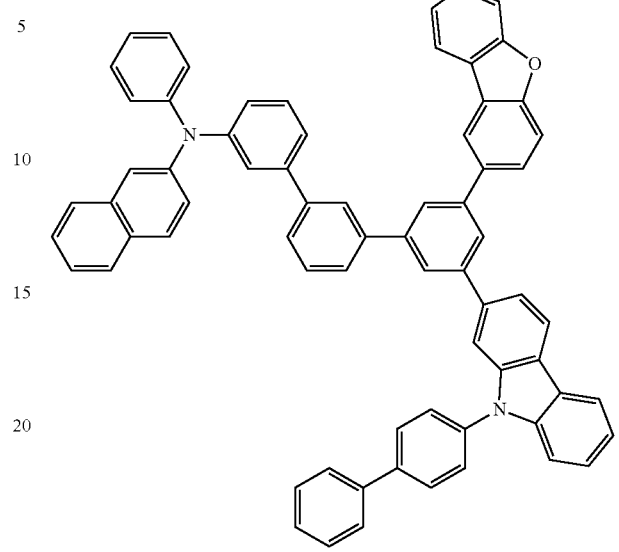
279
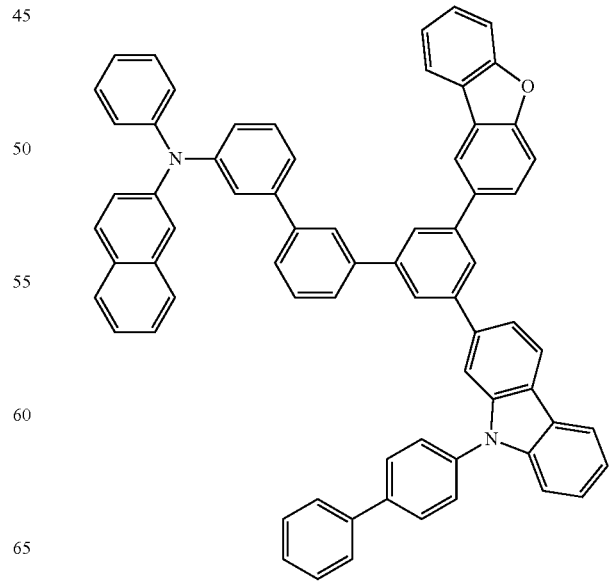

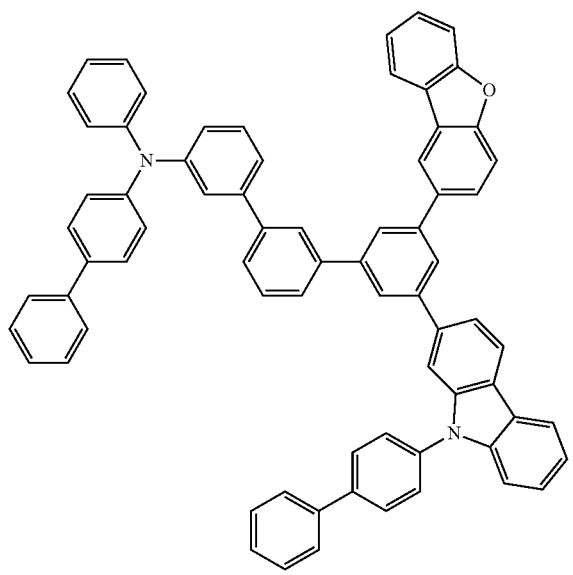
280
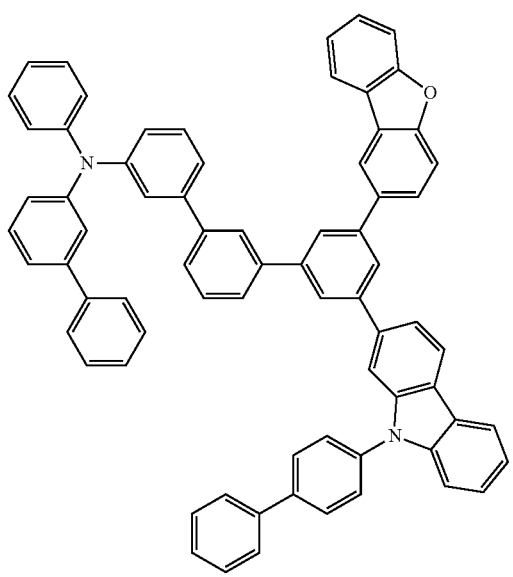
282
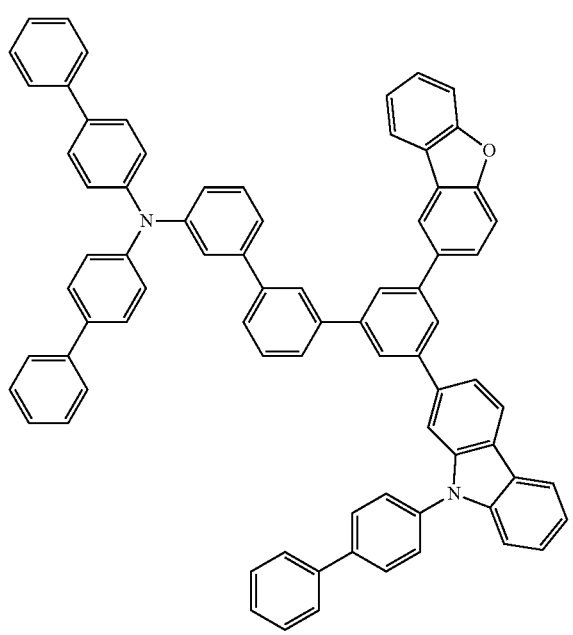
281
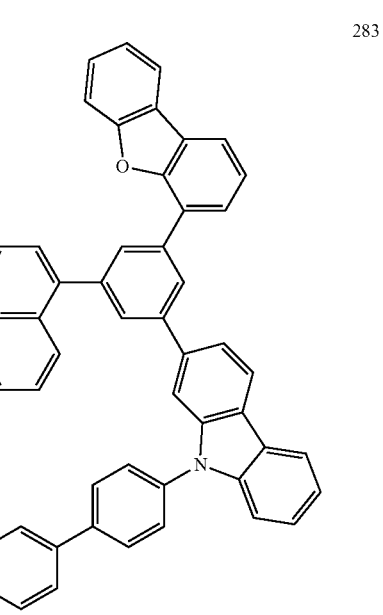
283

284
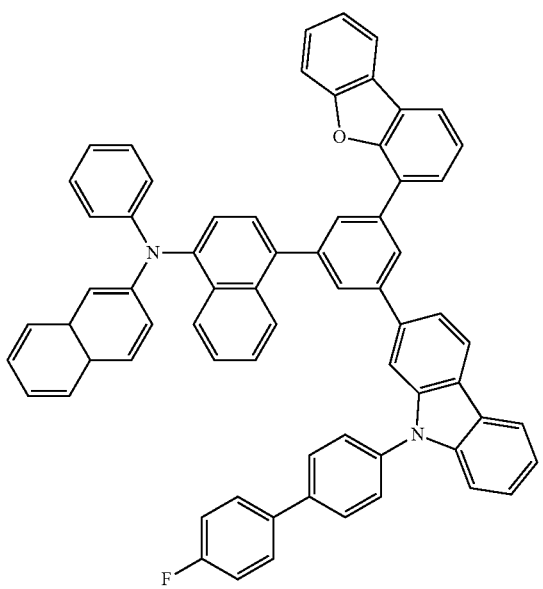
286
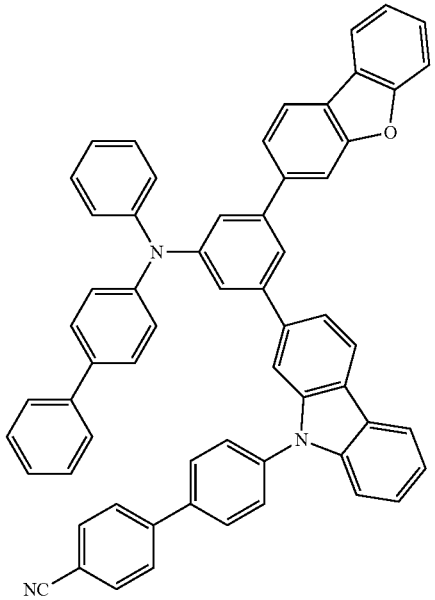
285
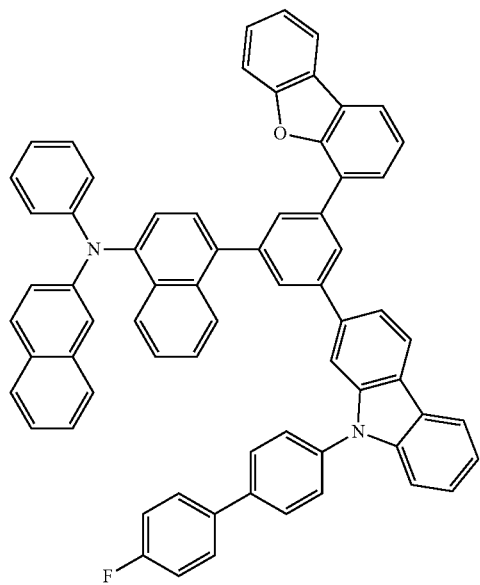
287
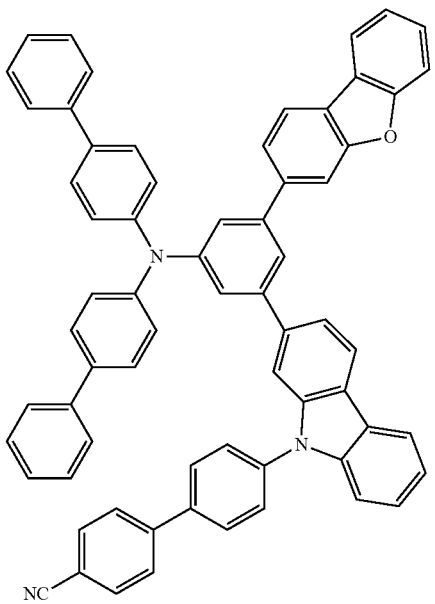

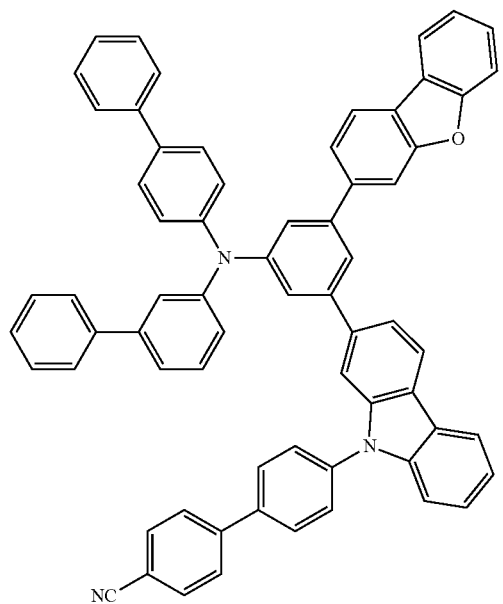
288
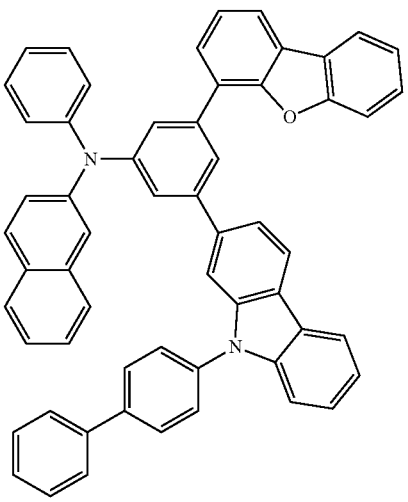
291
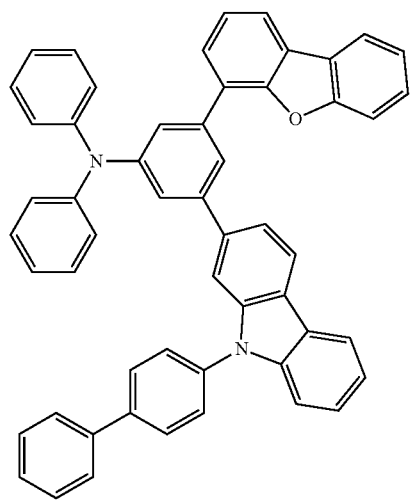
289
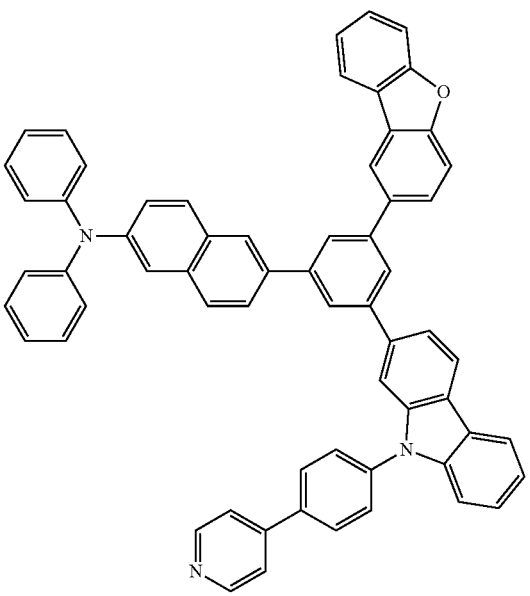
292

293
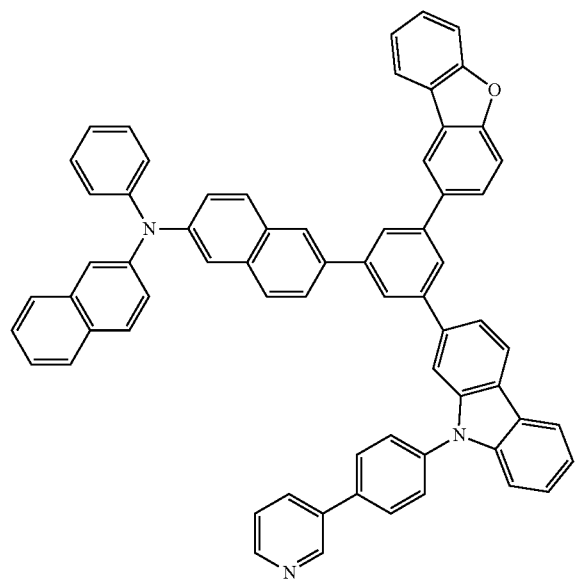
294
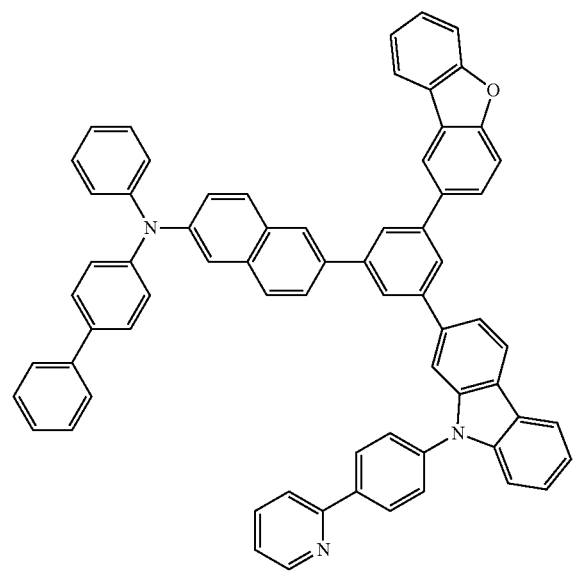
295
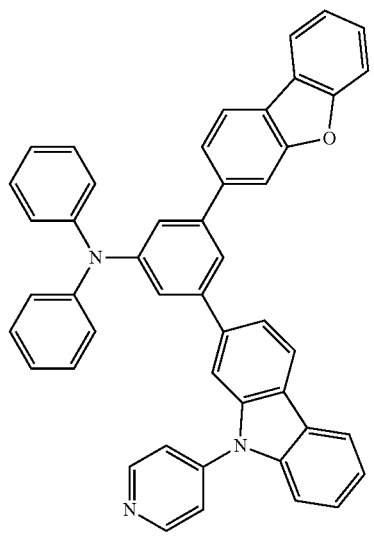
296
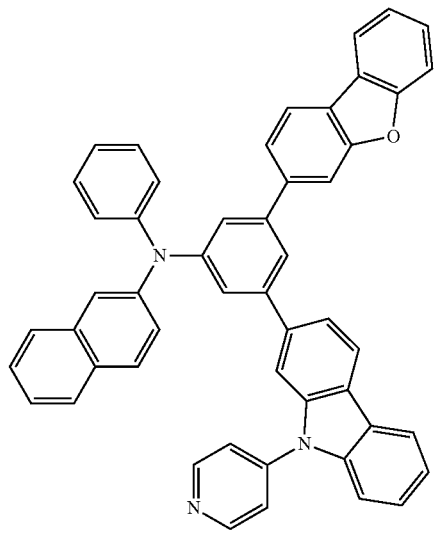
297

298

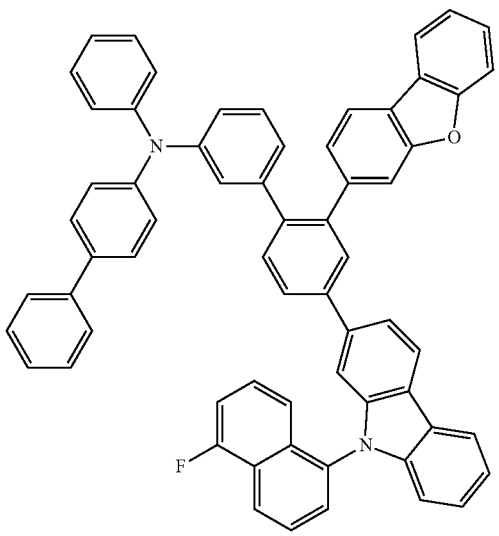

300

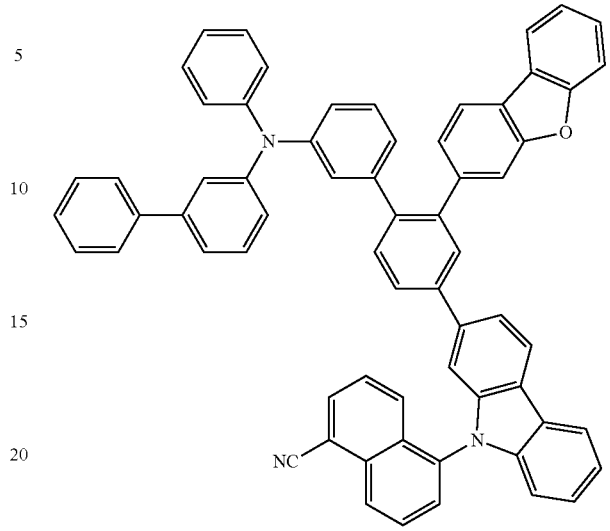

299

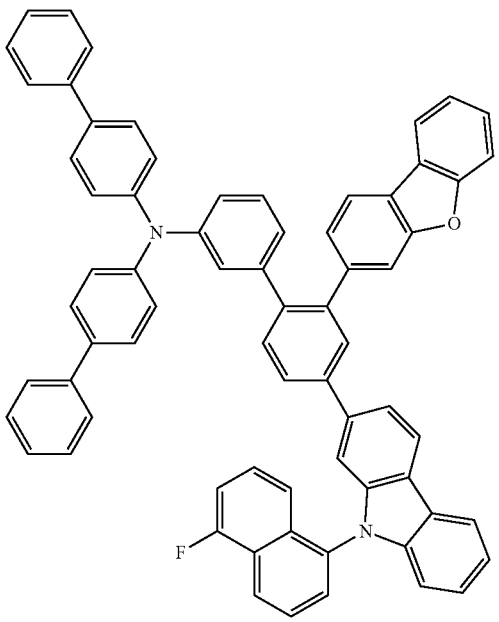

In the amine-based compound represented by Formula 1, as shown in Formula 1A-1', below, either one substituted or unsubstituted dibenzofuran or one substituted or unsubstituted a dibenzothiophene (when $X_1$ is O or S), and one substituted or unsubstituted carbazole may be bound to a core. Accordingly, due to an orbital principle, a planar structure may be easily formed, facilitating film formation in a deposition process and helping to provide high charge mobility efficiency of an organic light-emitting device.

Also, in the amine-based compound represented by Formula 1, as shown in Formula Formula 1A-1', a carbon atom a benzene ring of the carbazole may be directly bound to the core. Accordingly, due to the orbital principle, intermolecular hydrogen bonding and pi-pi stacking may easily occur. Thus, a planar structure may be easily formed, leading to an increase in efficiency and lifespan of an organic light-emitting device.

<Formula 1A-1'>

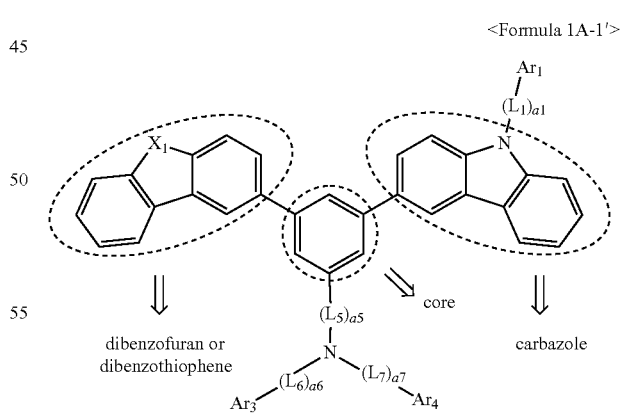

The amine-based compound represented by Formula 1 may be synthesized by using a suitable organic synthetic method. A synthesis method of the amine-based compound may be understood in view of the following embodiments.

The amine-based compound of Formula 1 may be used or included between a pair of electrodes of an organic light-emitting device. In an implementation, the amine-based compound may be included in a hole transport region, e.g., a hole transport layer. In an implementation, an organic light-emitting device may include, e.g., a first electrode; a second electrode facing the first electrode; and an organic layer between the first electrode and the second electrode and including an emission layer. The organic layer may include at least one of the amine-based compound described above.

The expression that "(an organic layer) includes at least one amine-based compound" used herein may include a case in which "(an organic layer) includes identical amine-based compounds represented by Formula 1 and a case in which (an organic layer) includes two or more different amine-based compounds represented by Formula 1.

For example, the organic layer may include, as the amine-based compound, only Compound 1. In this regard, Compound 1 may exist in a hole transport layer of the organic light-emitting device. In some embodiments, the organic layer may include, as the amine-based compound, Compound 1 and Compound 2. In this regard, Compound 1 and Compound 2 may exist in an identical layer (for example, Compound 1 and Compound 2 may all exist in a hole transport layer), or different layers (for example, Compound 1 may exist in an emission layer and Compound 2 may exist in a hole transport layer).

The organic layer may include, e.g., i) a hole transport region that is disposed between the first electrode (anode) and the emission layer and includes at least one of a hole injection layer, a hole transport layer, a buffer layer, and an electron blocking layer, and/or ii) an electron transport region that is disposed between the emission layer and the second electrode (cathode) and includes at least one selected from a hole blocking layer, an electron transport layer, and an electron injection layer. The amine-based compound represented by Formula 1 may be included in the hole transport region. For example, the hole transport region may include a hole transport layer, and the hole transport layer may include the amine-based compound represented by Formula 1.

The term "organic layer" used herein refers to a single layer and/or a plurality of layers disposed between the first electrode and the second electrode of the organic light-emitting device. A material included in the "organic layer" is not limited to an organic material.

FIG. 1 illustrates a schematic view of an organic light-emitting device 10 according to an embodiment. The organic light-emitting device 10 may include a first electrode 110, an organic layer 150, and a second electrode 190.

Hereinafter, the structure of an organic light-emitting device according to an embodiment and a method of manufacturing an organic light-emitting device according to an embodiment will be described in connection with FIG. 1.

In FIG. 1, a substrate may be additionally disposed under the first electrode 110 or above the second electrode 190. The substrate may be a glass substrate or transparent plastic substrate, each with excellent mechanical strength, thermal stability, transparency, surface smoothness, ease of handling, and water-resistance.

The first electrode 110 may be formed by depositing or sputtering a material for forming the first electrode on the substrate. When the first electrode 110 is an anode, the material for the first electrode 110 may be selected from materials with a high work function to make holes be easily injected. The first electrode 110 may be a reflective electrode or a transmissive electrode. The material for the first electrode 110 may be a transparent and highly conductive material, and examples of such a material are indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one of magnesium (Mg), aluminum (Al), aluminum-lithium (Al—Li), calcium (Ca), magnesium-indium (Mg—In), magnesium-silver (Mg—Ag) may be used.

The first electrode 110 may have a single-layer structure, or a multi-layer structure including two or more layers. For example, the first electrode 110 may have a three-layered structure of ITO/Ag/ITO.

An organic layer 150 may be disposed on the first electrode 110. The organic layer 150 may include an emission layer.

The organic layer 150 may further include a hole transport region between the first electrode and the emission layer, and/or an electron transport region between the emission layer and the second electrode.

The hole transport region may include the amine-based compound represented by Formula 1.

The hole transport region may include at least one selected from a hole injection layer (HIL), a hole transport layer (HTL), a buffer layer, and an electron blocking layer (EBL). The electron transport region may include at least one selected from a hole blocking layer (HBL), an electron transport layer (ETL), and an electron injection layer (EIL).

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order.

When the hole transport region includes a hole injection layer, the hole injection layer may be formed on the first electrode 110 by using various methods, e.g., vacuum deposition, spin coating casting, a Langmuir-Blodgett (LB) method, ink-jet printing, laser-printing, or laser-induced thermal imaging.

When a hole injection layer is formed by vacuum deposition, e.g., the vacuum deposition may be performed at a temperature of a deposition temperature of about 100 to about 500° C., at a vacuum degree of about $10^{-8}$ to about $10^{-3}$ torr, and/or at a deposition rate of about 0.01 to about 100 Å/sec in consideration of a compound for a hole injection layer to be deposited, and the structure of a hole injection layer to be formed.

When a hole injection layer is formed by spin coating, the spin coating may be performed at a coating rate of about 2,000 rpm to about 5,000 rpm, and/or at a temperature of about 80° C. to 200° C. in consideration of a compound for a hole injection layer to be deposited, and the structure of a hole injection layer to be formed.

As a hole injection material, a suitable hole injection material may be used, and examples may include N,N'-diphenyl-N,N'-bis-[4-(phenyl-m-tolyl-amino)-phenyl]-biphenyl-4,4'-diamine (DNTPD), a phthalocyanine compound, such as a copper phthalocyanine, 4,4',4"-tris(3-methylphenylphenylamino) triphenylamine [m-MT-DATA], N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and (polyaniline)/poly(4-styrenesulfonate) (PANI/PSS).

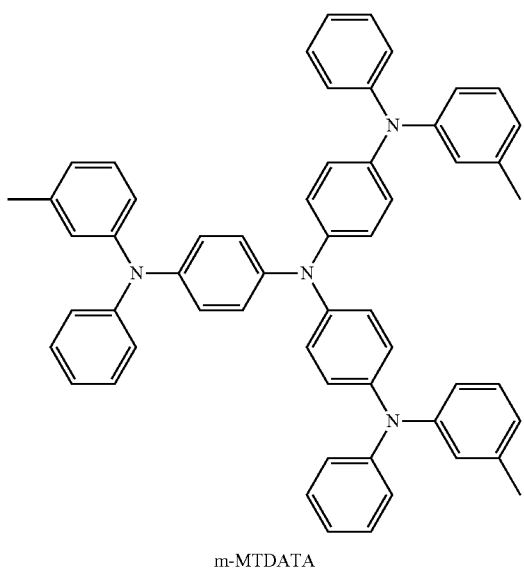

m-MTDATA

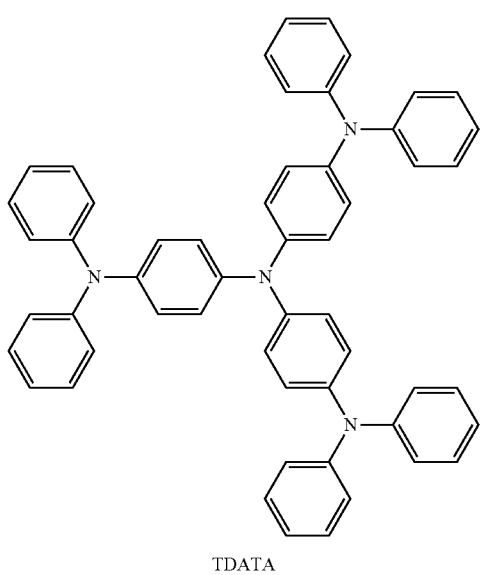

TDATA

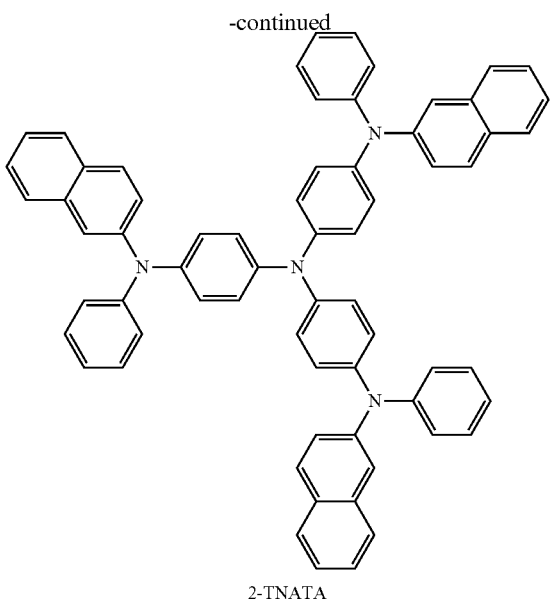

2-TNATA

A hole transport layer may be formed on the first electrode 110 or the hole injection layer by using various methods, e.g., vacuum deposition, spin coating, casting, a LB method, ink-jet printing, laser-printing, or laser-induced thermal imaging (LITI). When the hole transport layer is formed by vacuum deposition or spin coating, deposition and coating conditions for the hole transport layer may be the same as the deposition and coating conditions for the hole injection layer.

A thickness of the hole transport region may be in a range of about 100 Å to about 10,000 Å, e.g., about 100 Å to about 1,000 Å. When the hole transport region includes both a hole injection layer and a hole transport layer, a thickness of the hole injection layer may be in a range of about 100 Å to about 10,000 Å, e.g., about 100 Å to about 1,000 Å, and a thickness of the hole transport layer may be in a range of about 50 Å to about 2,000 Å, e.g., about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to the amine-based compound represented by Formula 1, a charge-generation material for the improvement of conductive properties. The charge-generation material may be homogeneously or unhomogeneously dispersed in the hole transport region.

The charge-generation material may be, e.g., a p-dopant. The p-dopant may be one selected from a quinone derivative, a metal oxide, and a cyano group-containing compound. Examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below.

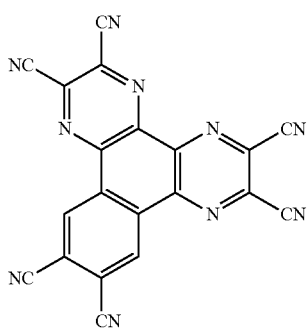

<Compound HT-D1>

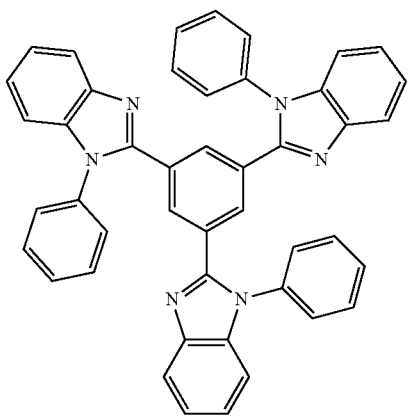

TPBi

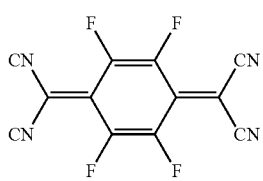

<F4-TCNQ>

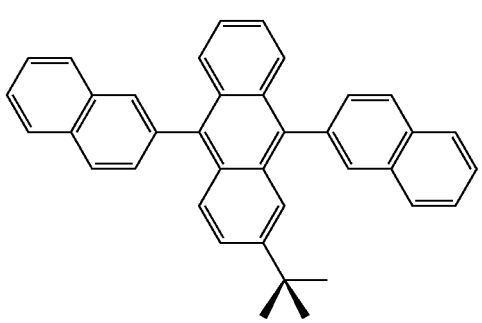

TBADN

The hole transport region may further include, in addition to the hole injection layer and the hole transport layer, at least one of a buffer layer and an electron blocking layer. Since the buffer layer may compensate for an optical resonance distance according to a wavelength of light emitted from the emission layer, light-emission efficiency of a formed organic light-emitting device may be improved. For use as a material included in the buffer layer, materials that are included in the hole transport region may be used. The electron blocking layer prevents injection of electrons from the electron transport region.

An emission layer may be formed on the first electrode 110 or the hole transport region by using various methods, e.g., vacuum deposition, spin coating, casting, a LB method, ink-jet printing, laser-printing, or laser-induced thermal imaging. When an emission layer is formed by vacuum deposition or spin coating, deposition and coating conditions for the emission may be the same as those for the hole injection layer.

When the organic light-emitting device 10 is a full color organic light-emitting device, the emission layer may be patterned into a red emission layer, a green emission layer, or a blue emission layer, according to a sub pixel. In an implementation, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include a host and a dopant.

The host may include at least one selected from TPBi, TBADN, ADN (also referred to as "DNA"), CBP, CDBP, and TCP:

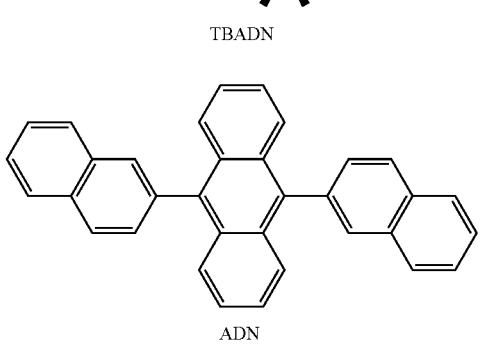

ADN

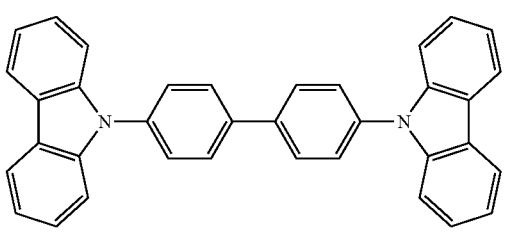

CBP

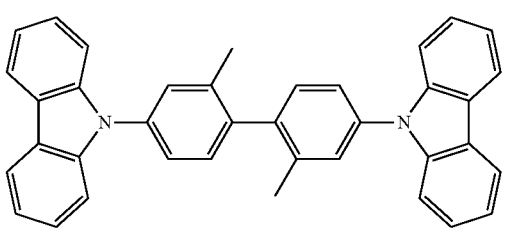

CDBP

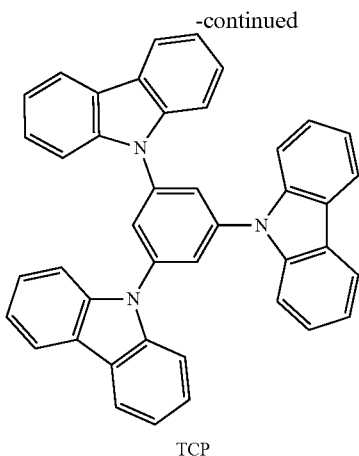

TCP

In an implementation, the host may include a compound represented by Formula 301 below.

$$Ar_{301}-[(L_{301})_{xb1}-R_{301}]_{xb2}$$ <Formula 301>

In Formula 301, $Ar_{301}$ may be selected from a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, monovalent non-aromatic condensed heteropolycyclic group, and —Si($Q_{301}$)($Q_{302}$)($Q_{303}$) ($Q_{301}$ to $Q_{303}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

a description of $L_{301}$ may be understood by referring to the description provided in connection with $L_1$;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazol group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xb1 may be selected from 0, 1, 2, and 3;

xb2 may be selected from 1, 2, 3, and 4.

In Formula 301, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

For example, the host may include a compound represented by Formula 301A below.

<Formula 301A>

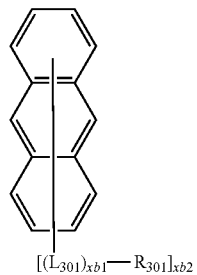

$[(L_{301})_{xb1}\text{—}R_{301}]_{xb2}$

Descriptions of substituents of Formula 301A may be understood by referring to the descriptions of similar groups provided herein.

The compound represented by Formula 301 may include at least one of Compounds H1 to H42.

H1

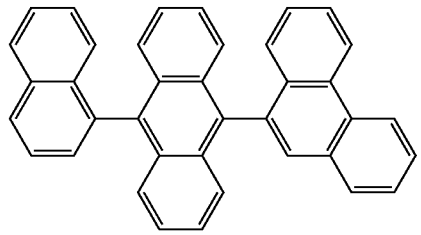

H2

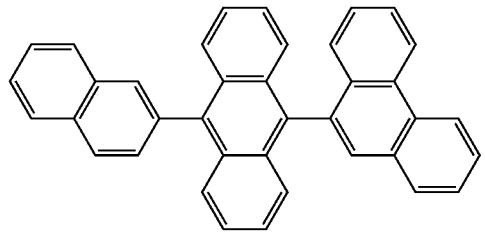

H3

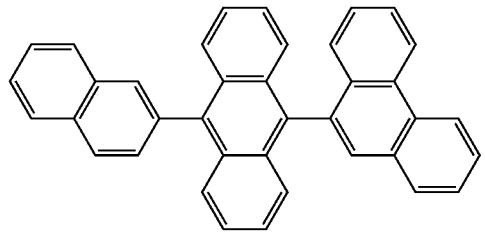

H4

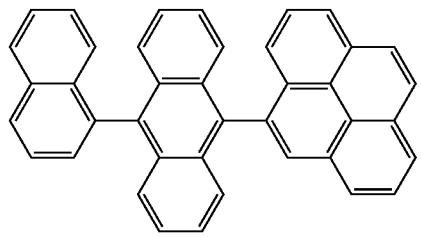

H5

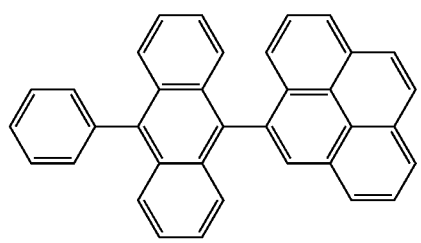

H6

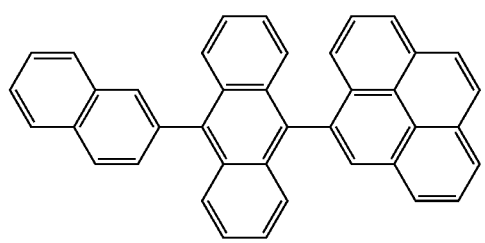

H7

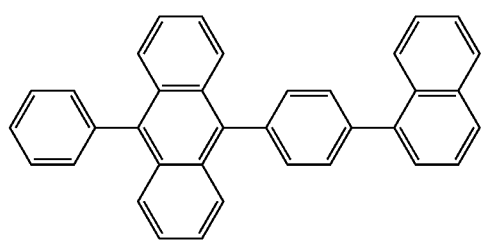

H8

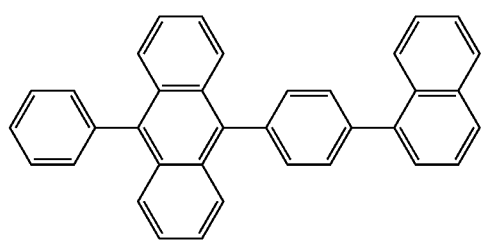

157
-continued
H9
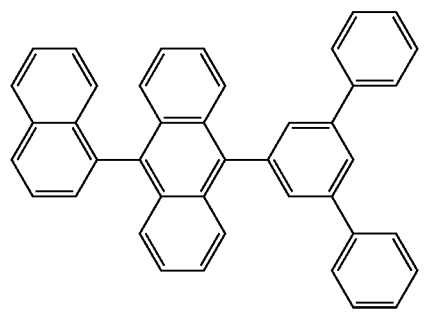
H10
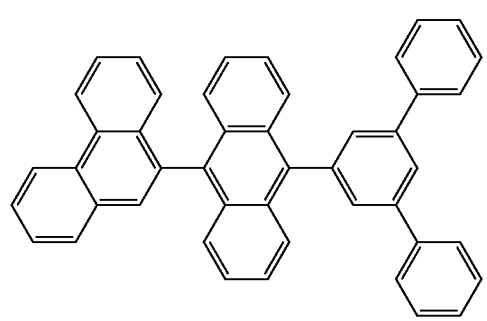
H11
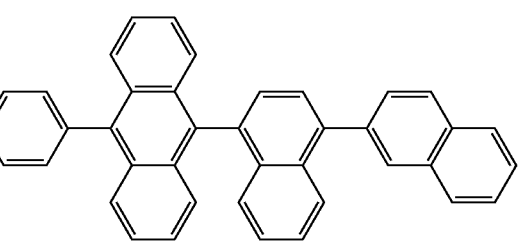
H12
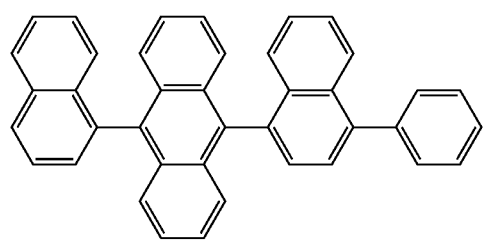
H13
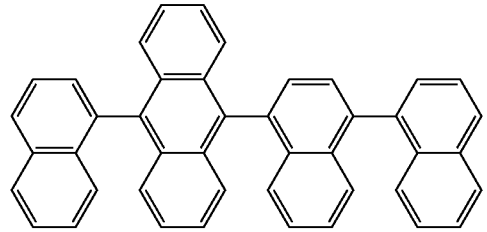
H14
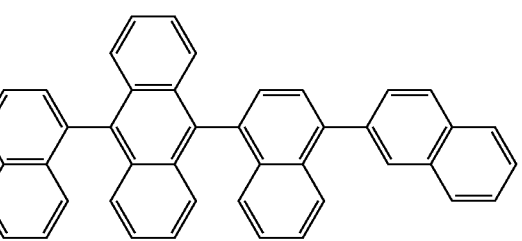
158
-continued
H15
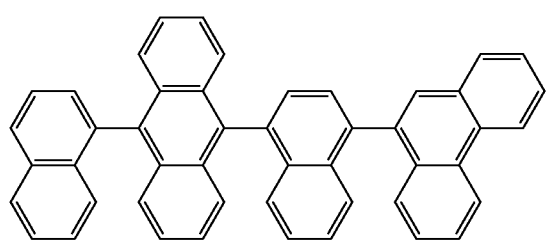
H16
H17
H18
H19

H20
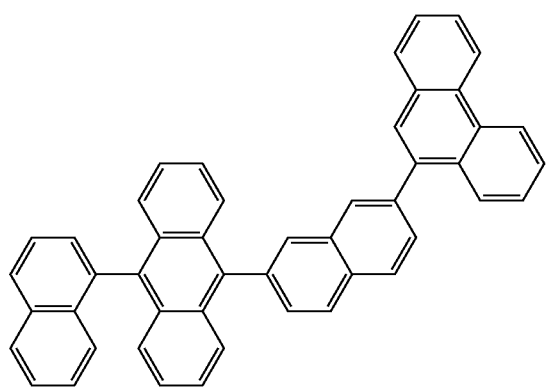
H21
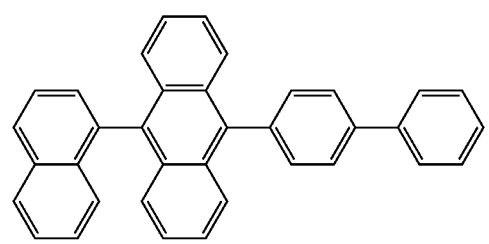
H22
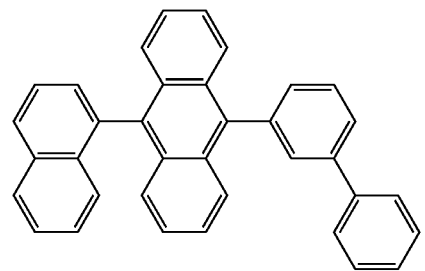
H23
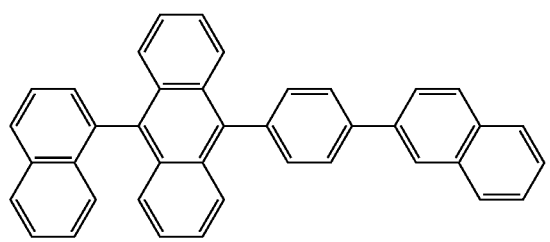
H24
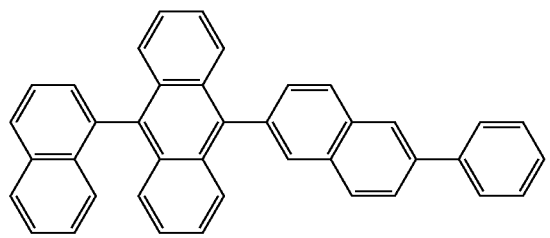
H25
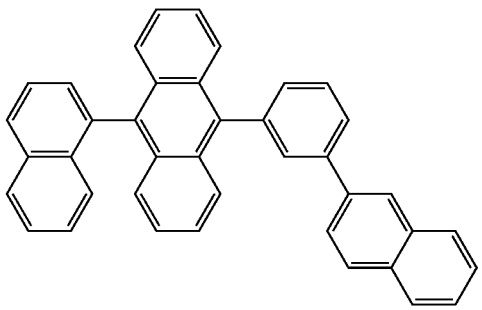
H26
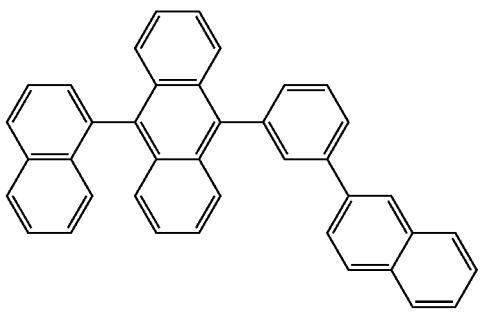
H27
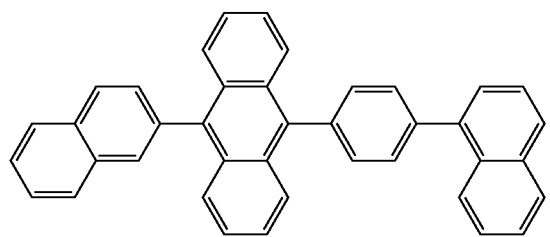
H28
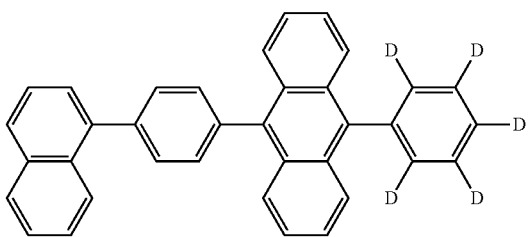
H29
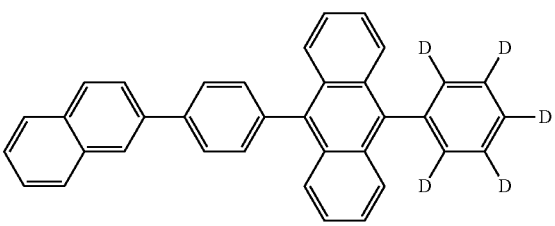
H30
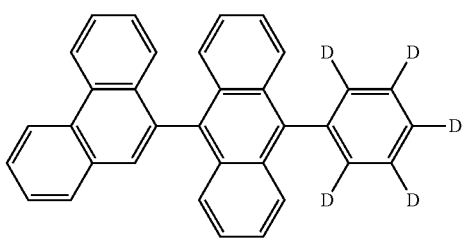

H31
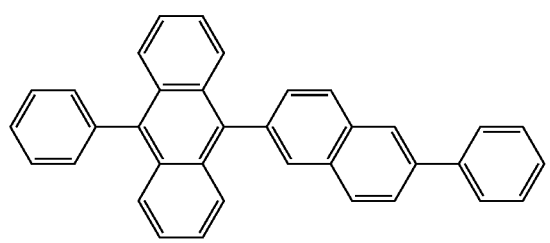
H32
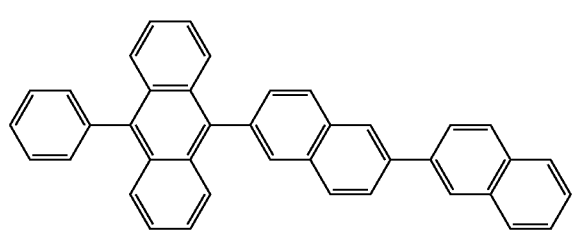
H33
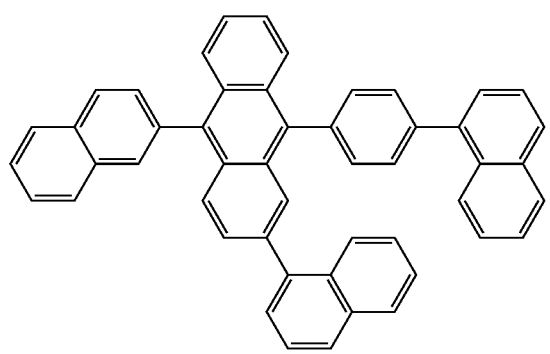
H34
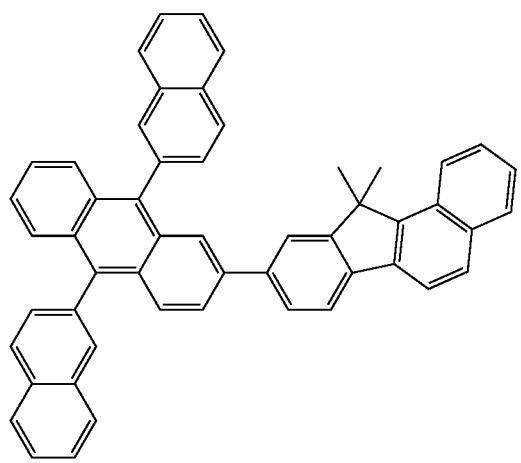
H35
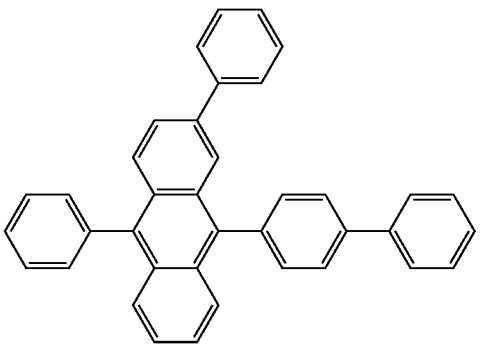
H36
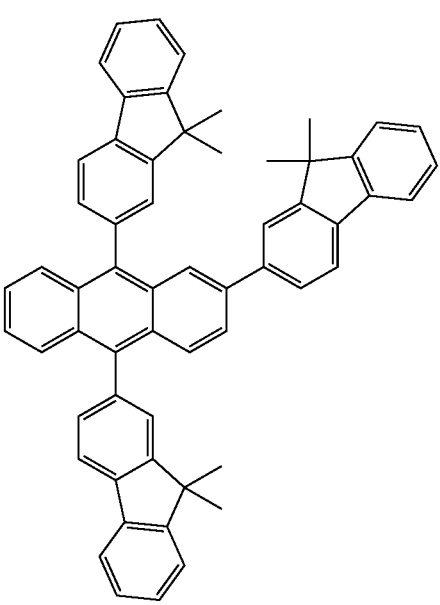
H37
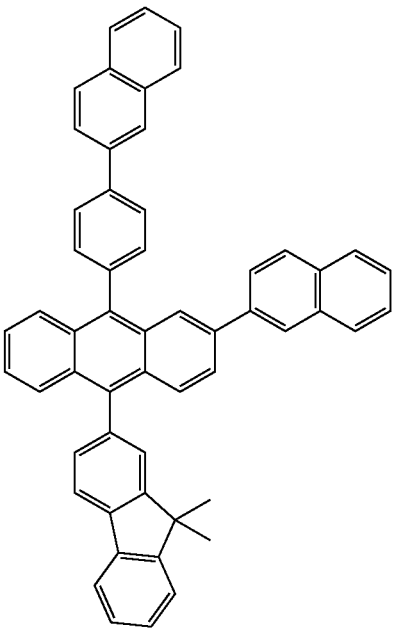

H38
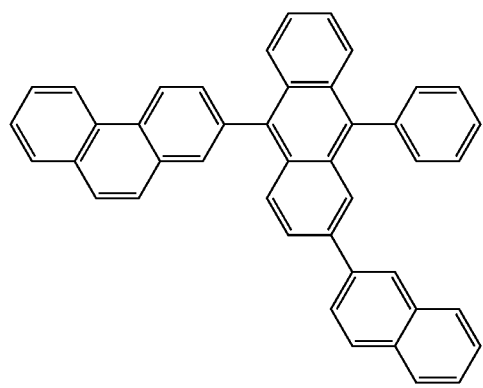
H39
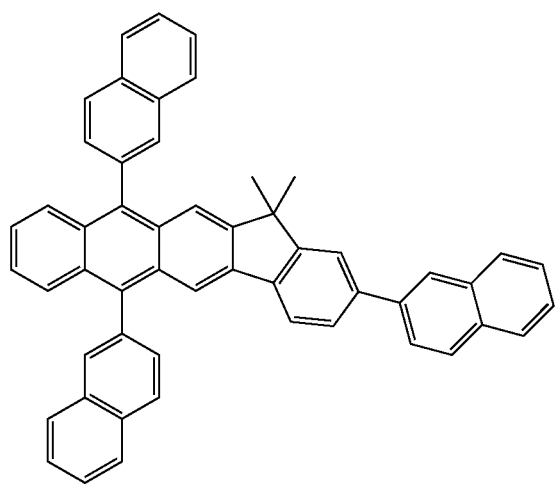
H40
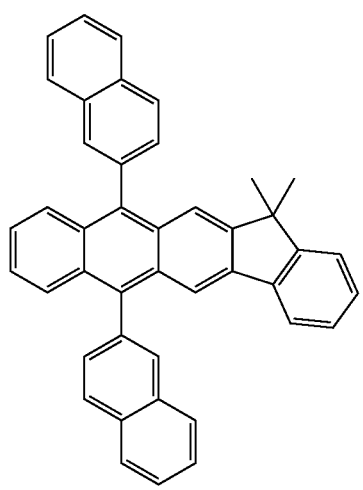
H41
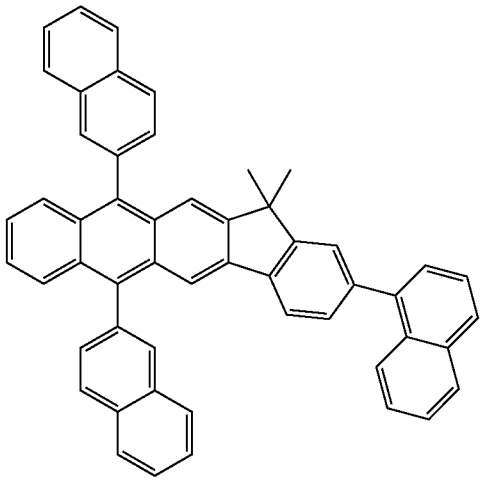
H42
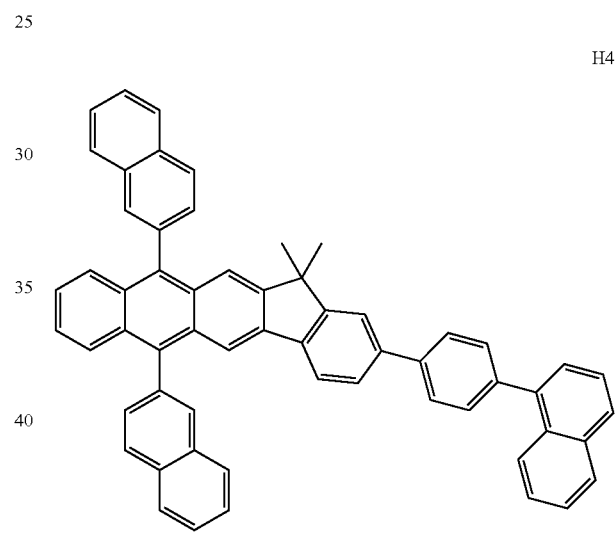
In an implementation, the host may include at least one of Compounds H43 to H49 below.
H43
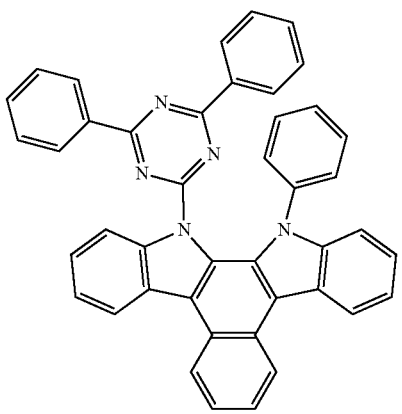

H44
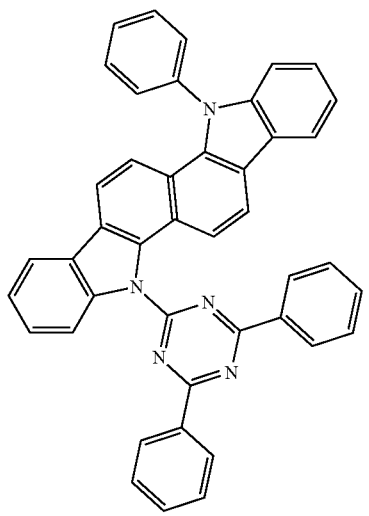

H45
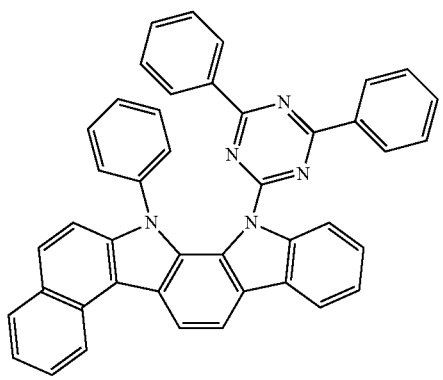

H46
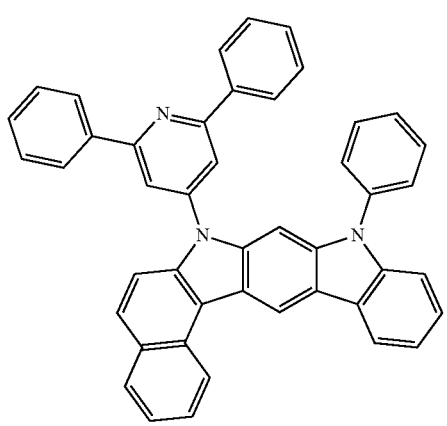

H47
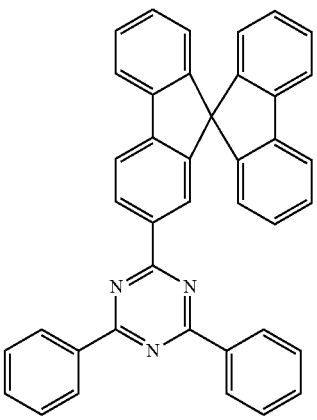

H48
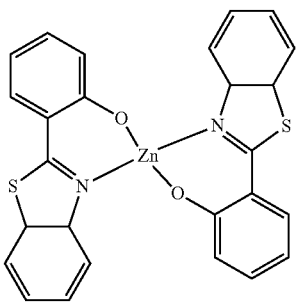

H49
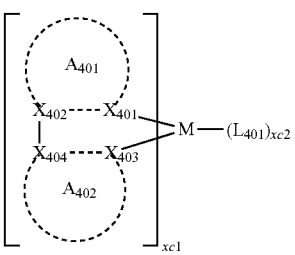

The dopant may include at least one selected from a fluorescent dopant and a phosphorescent dopant.

The phosphorescent dopant may include an organometallic complex represented by Formula 401 below.

<Formula 401>

$$\left[ \begin{array}{c} A_{401} \\ X_{402} \text{---} X_{401} \\ X_{404} \text{---} X_{403} \\ A_{402} \end{array} \right]_{xc1} M - (L_{401})_{xc2}$$

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may each independently be nitrogen or carbon;

rings $A_{401}$ and $A_{402}$ may each independently be selected from a substituted or unsubstituted benzene, a substituted or unsubstituted naphthalene, a substituted or unsubstituted fluorenene, a substituted or unsubstituted spiro-fluorenene, a substituted or unsubstituted indene, a substituted or unsubstituted pyrrol, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazol, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; and at least one substituent of the substituted benzene, substituted naphthalene, substituted fluorenene, substituted spiro-fluorenene, substituted indene, substituted pyrrol, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazol, substituted benzoimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_1$-$C_{60}$ alkenyl group, a $C_1$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$) and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$), $L_{401}$ may be an organic ligand;

xc1 may be 1, 2, or 3; and xc2 may be 0, 1, 2, or 3.

$Q_{401}$ to $Q_{407}$, $Q_{411}$ to $Q_{417}$, and $Q_{421}$ to $Q_{427}$ may be understood by referring to the descriptions of Q groups provided herein.

$L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propandionate, 2,2,6,6-tetramethyl-3,5-heptandionate, or hexafluoroacetonate), a carboxylic acid ligand (for example, picolinate, dimethyl-3-pyrazolecarboxylate, or benzoate), a carbon monooxide ligand, an isonitrile ligand, a cyano ligand, and a phosphorous ligand (for example, phosphine, and phosphaite).

When $A_{401}$ in Formula 401 has two or more substituents, the substituents of $A_{401}$ may bind to each other to form a saturated or unsaturated ring.

When $A_{401}$ in Formula 402 has two or more substituents, the substituents of $A_{402}$ may bind to each other to form a saturated or unsaturated ring.

When xc1 in Formula 401 is two or more, a plurality of ligands

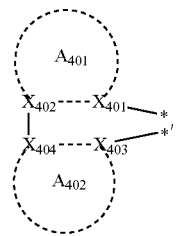

in Formula 401 may be identical or different. When xc1 in Formula 401 is two or more, $A_{401}$ and $A_{402}$ may be respectively directly connected to $A_{401}$ and $A_{402}$ of other neighboring ligands with or without a linker (for example, a $C_1$-$C_5$ alkylene, or —N(R')— (wherein R' may be a $C_1$-$C_{10}$ alkyl group or a $C_6$-$C_{20}$ aryl group) or —C(=O)—) therebetween.

The phosphorescent dopant may include at least one of Compounds PD1 to PD74 below.

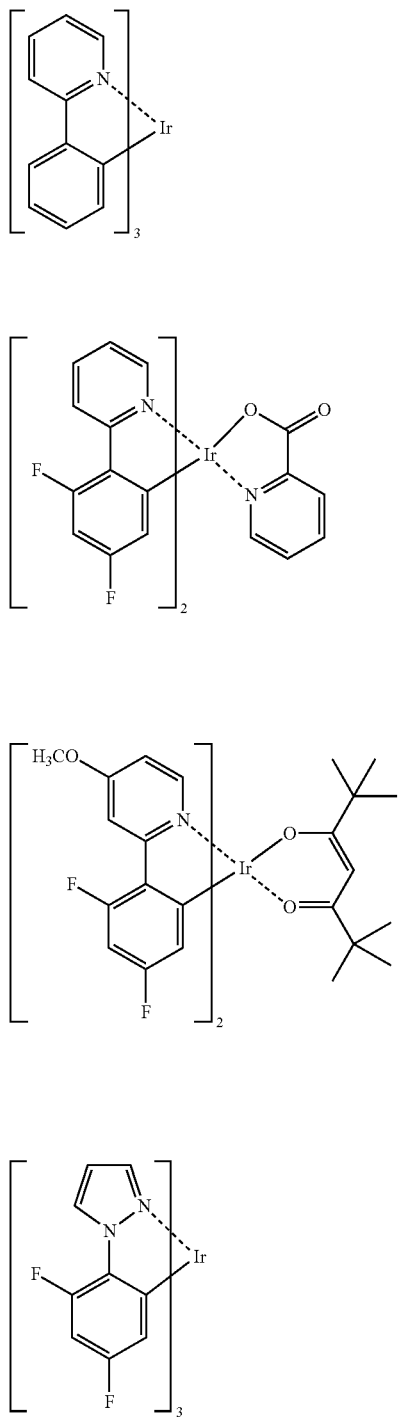

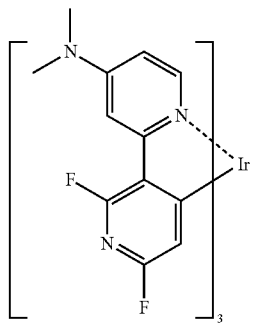

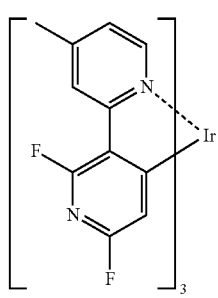

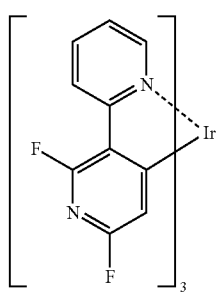

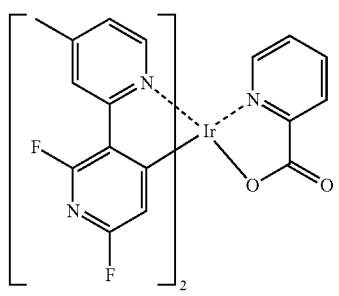

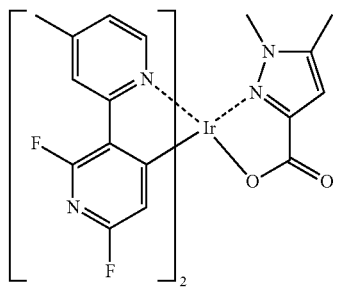

-continued
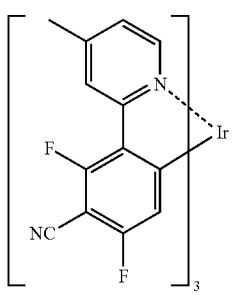
PD10
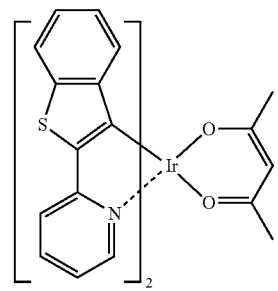
PD15
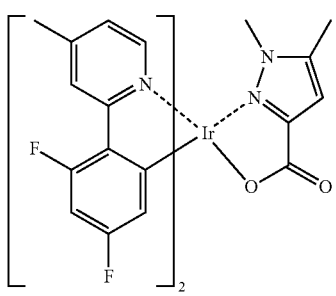
PD11
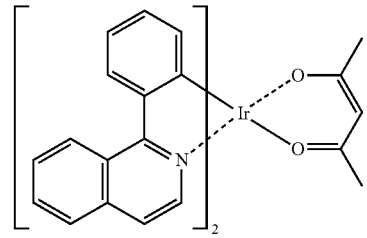
PD16
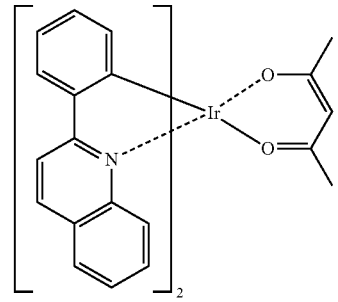
PD12
PD17
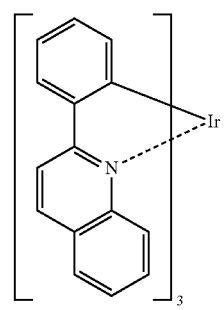
PD13
PD18
PD14
PD19
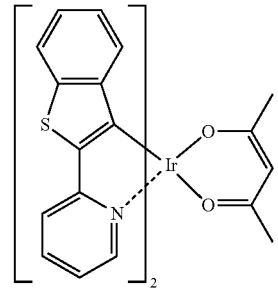

PD20 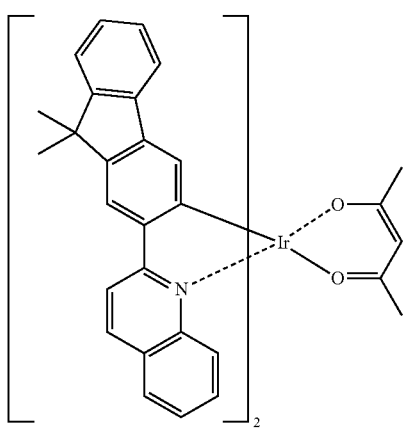
PD21 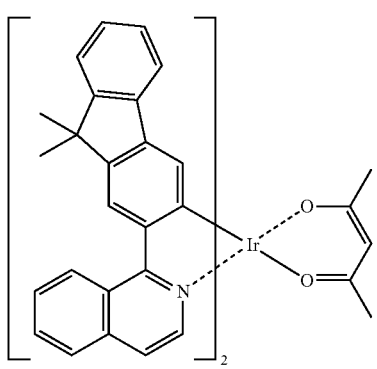
PD22 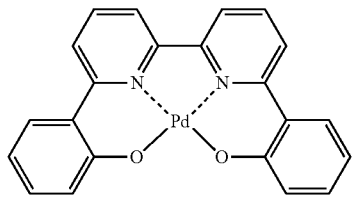
PD23 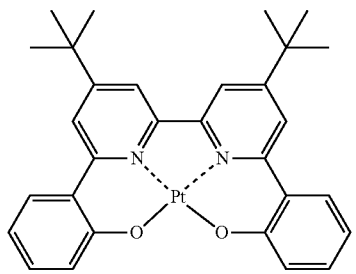
PD24 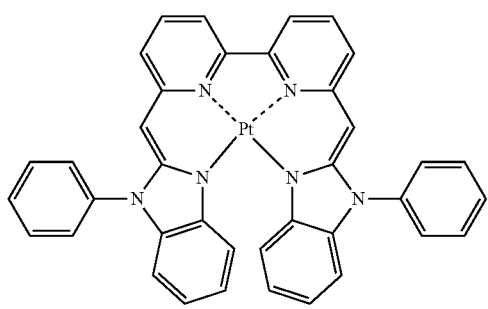
PD25 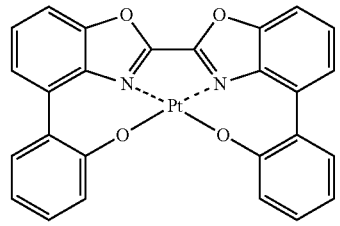
PD26 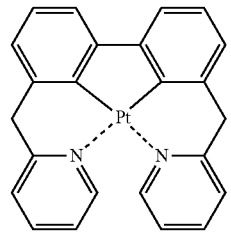
PD27 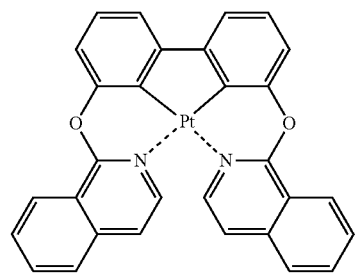
PD28 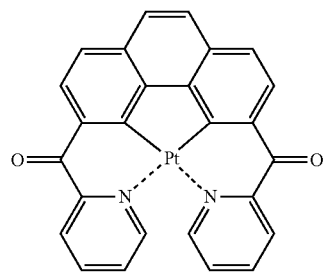
PD29 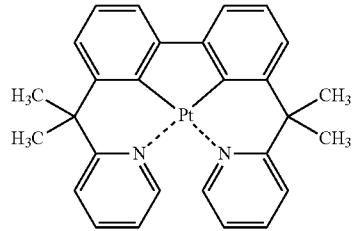
PD30 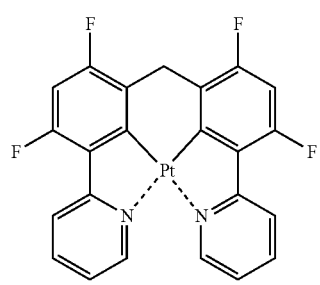

-continued
PD31 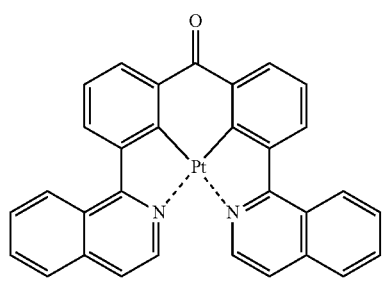
PD32 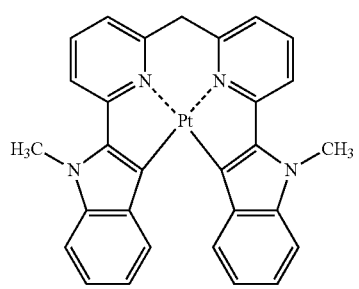
PD33 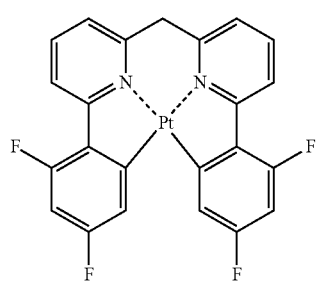
PD34 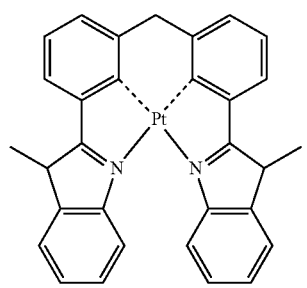
PD35 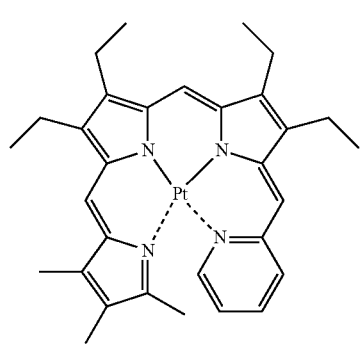
-continued
PD36 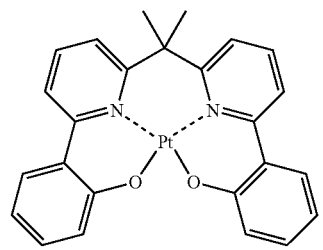
PD37 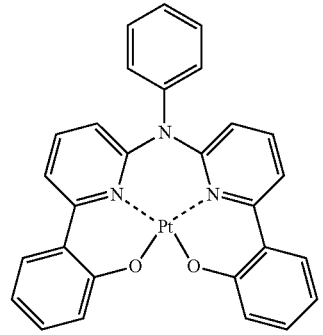
PD38 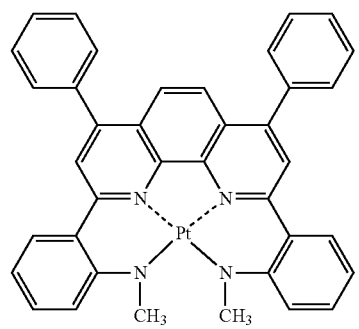
PD39 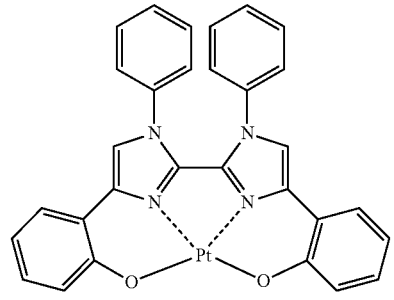
PD40 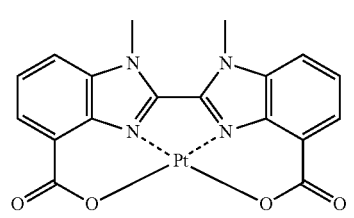
PD41

PD42 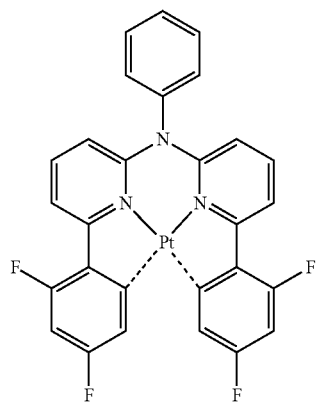
PD43 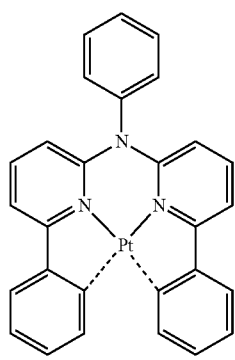
PD44 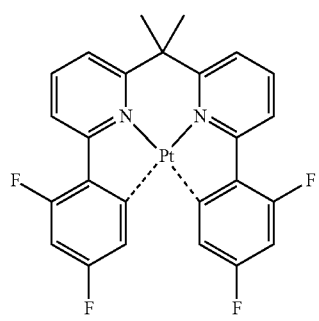
PD45 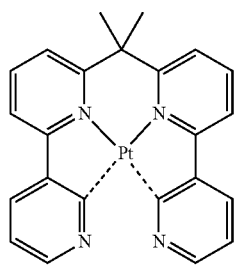
PD46 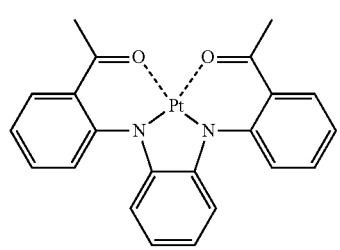
PD47 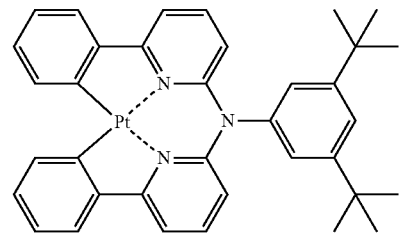
PD48 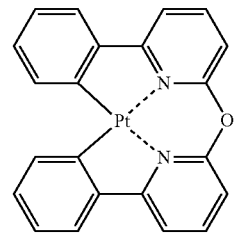
PD49 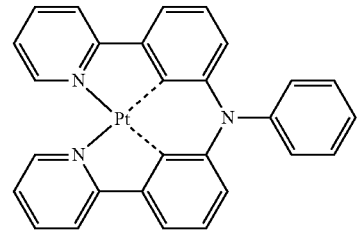
PD50 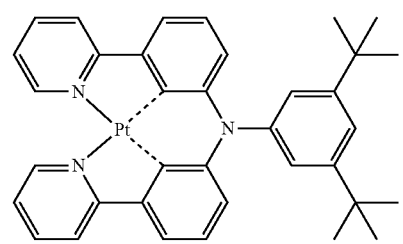
PD51 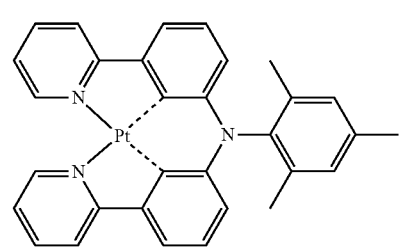
PD52 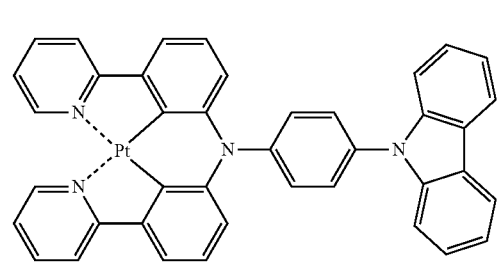

-continued
PD53
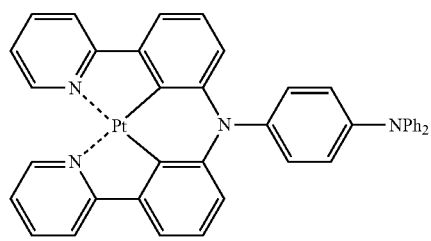
PD54
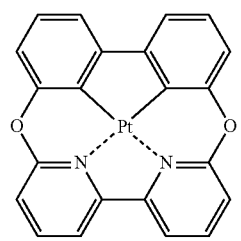
PD55
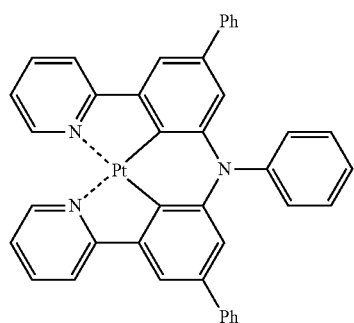
PD56
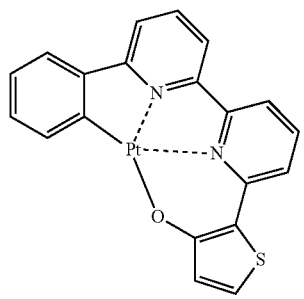
PD57
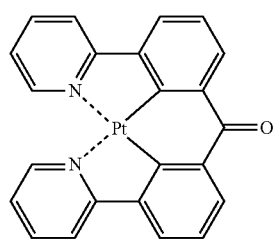
-continued
PD58
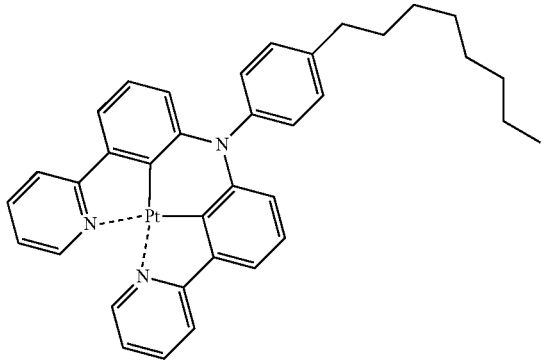
PD59
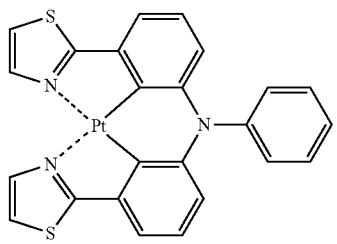
PD60
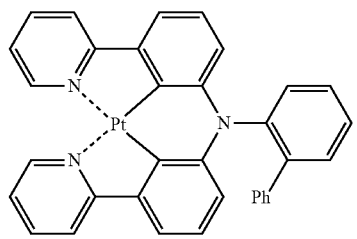
PD61
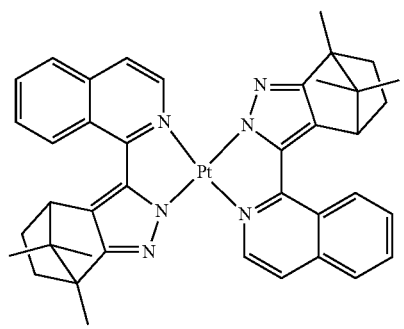
PD62
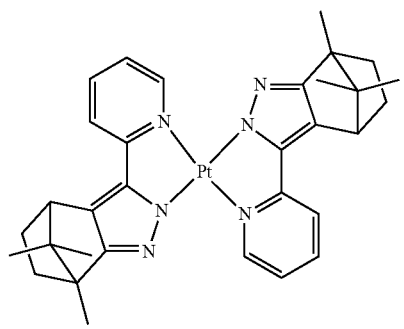

PD63 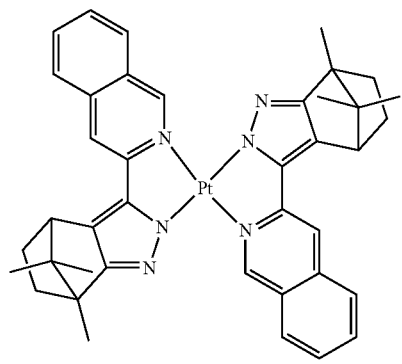
PD64 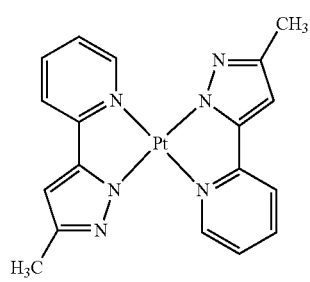
PD65 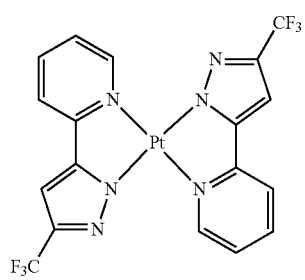
PD66 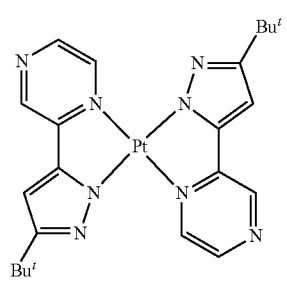
PD67 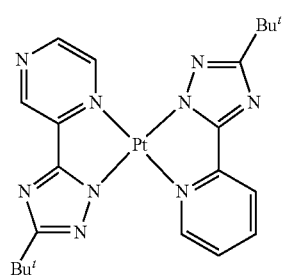
PD68 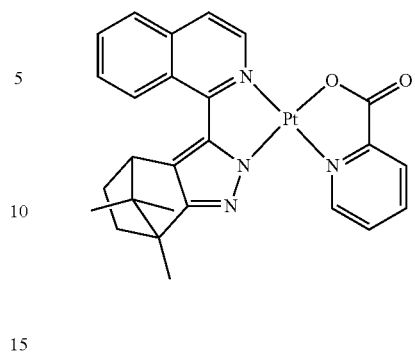
PD69 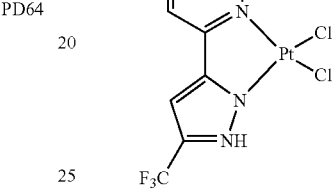
PD70 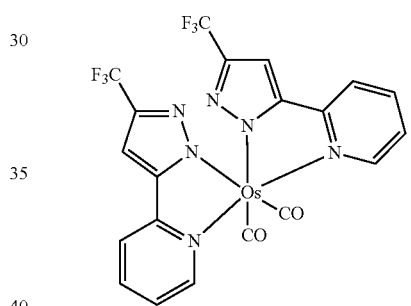
PD71 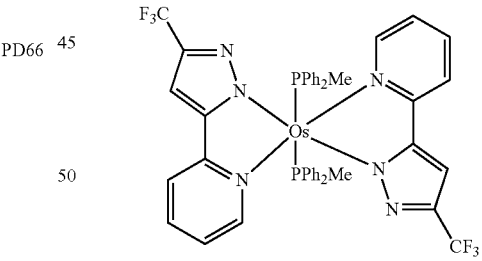
PD72 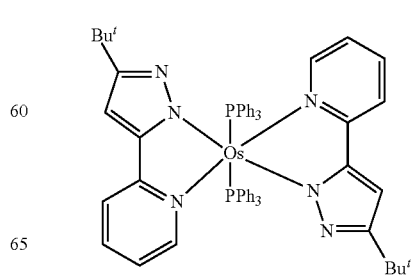

-continued
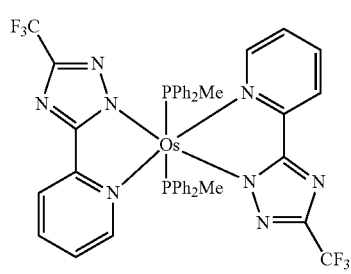
PD73
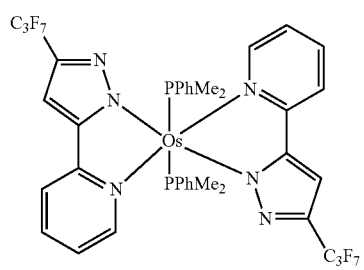
PD74
In some embodiments, the phosphorescent dopant may include PtOEP:
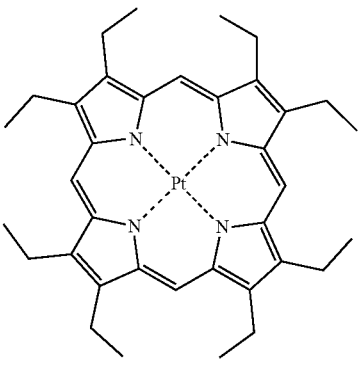
PtOEP
The fluorescent dopant may include at least one selected from DPAVBi, BDAVBi, TBPe, DCM, DCJTB, Coumarin 6, and C545T.
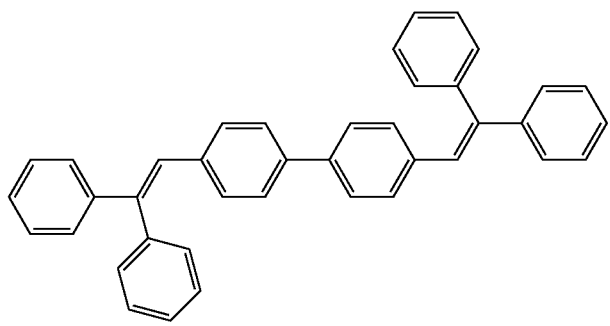
DPVBi
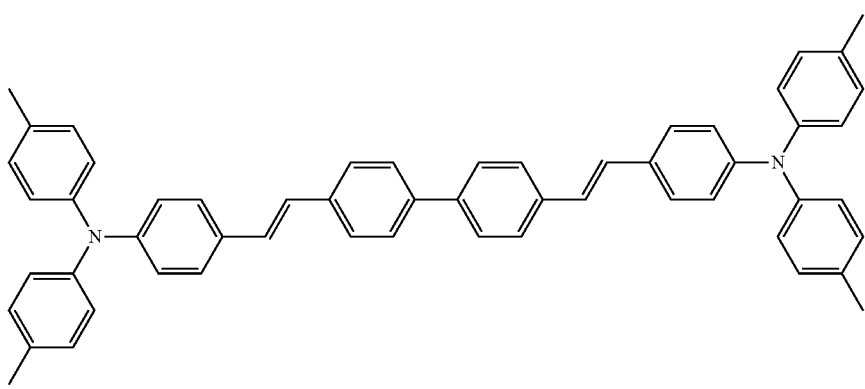
DPAVBi

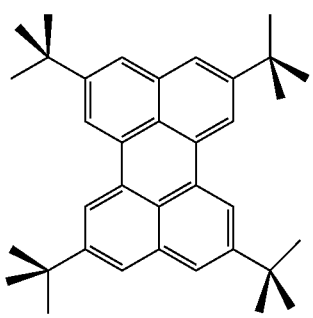
TBPe

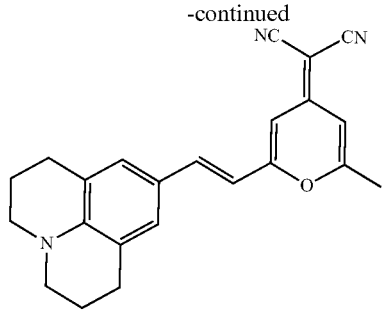
DCM

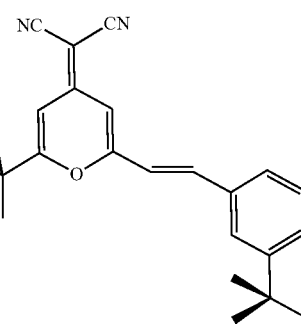
DCJTB

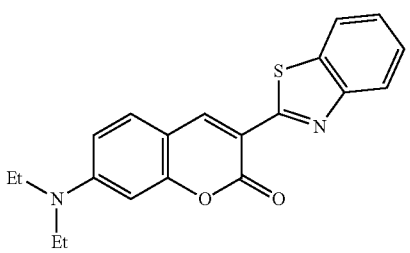
Coumarin 6

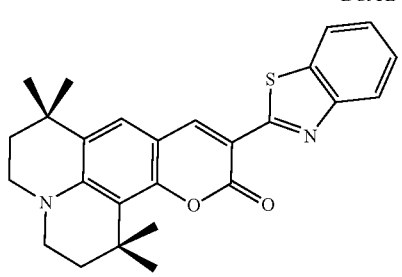
C545T

In some embodiments, the fluorescent dopant may include a compound represented by Formula 501 below.

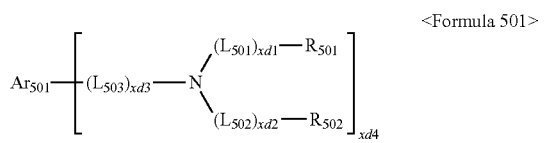
<Formula 501>

In Formula 501, $Ar_{501}$ may be selected from a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, monovalent non-aromatic condensed heteropolycyclic group, and —Si($Q_{501}$)($Q_{502}$)($Q_{503}$) ($Q_{501}$ to $Q_{503}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

Descriptions of $L_{501}$ to $L_{503}$ are the same as the descriptions provided herein in connection with $L_{301}$;

$R_{501}$ and $R_{502}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group;

xd1 to xd3 may each independently be selected from 0, 1, 2, and 3; and xd4 may be selected from 1, 2, 3, and 4.

The fluorescent dopant may include at least one of Compounds FD1 to FD9.
FD1
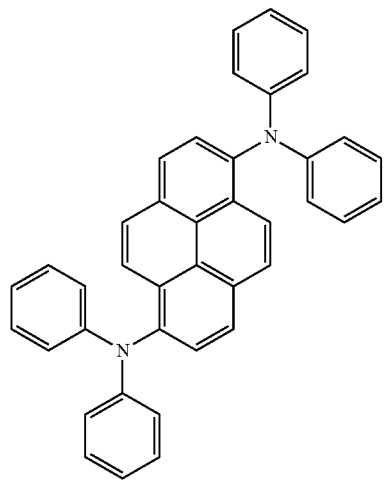
FD2
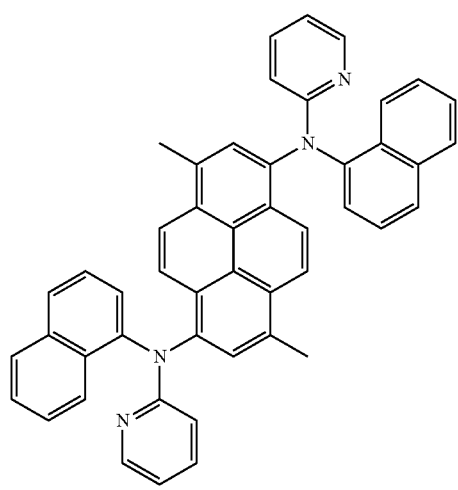
FD3
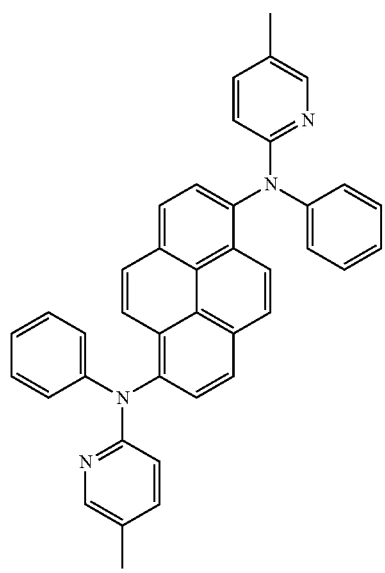
FD4
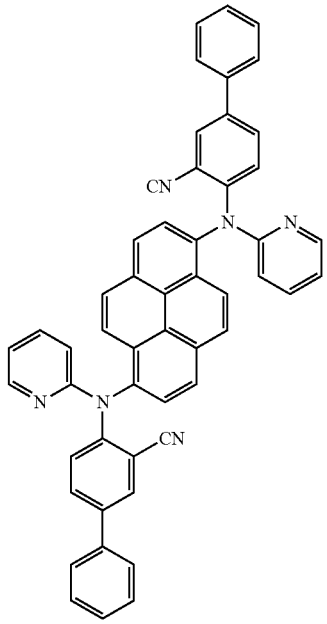
FD5
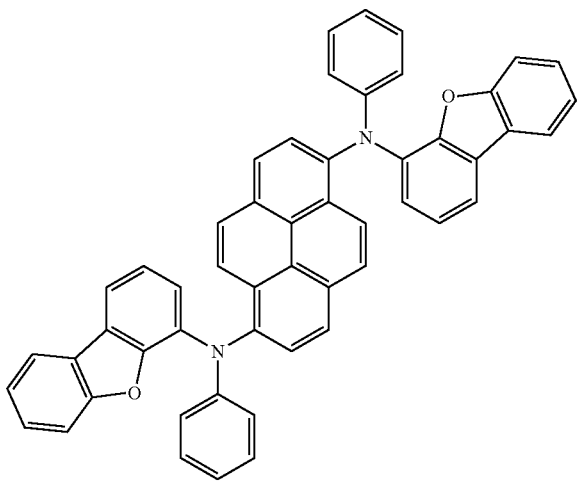
FD6

-continued

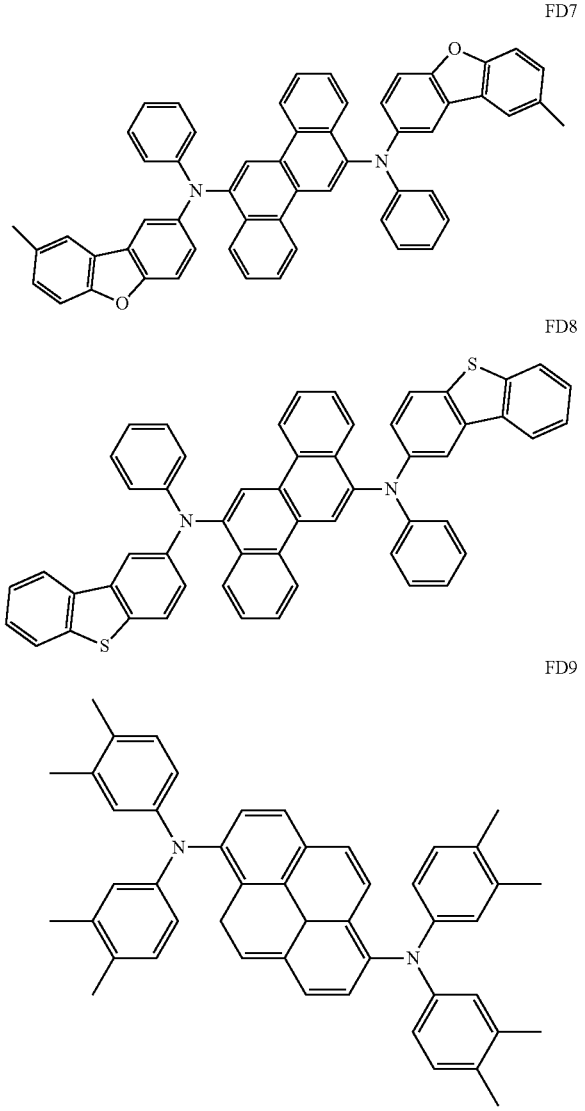

FD7

FD8

FD9

An amount of the dopant in the emission layer may be, e.g., about 0.01 to about 15 parts by weight, based on 100 parts by weight of the host.

A thickness of the emission layer may be in a range of about 100 Å to about 1,000 Å, e.g., about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer.

For example, the electron transport region may have a structure of electron transport layer/electron injection layer or a structure of hole blocking layer/electron transport layer/electron injection layer, wherein layers of each structure are sequentially stacked from the emission layer in the stated order.

According to an embodiment, the organic layer 150 of the organic light-emitting device may include an electron transport region disposed between the emission layer and the second electrode 190.

The electron transport region may include a hole blocking layer. The hole blocking layer may be formed, when the emission layer includes a phosphorescent dopant, to prevent diffusion of excitons or holes into an electron transport layer.

When the electron transport region includes a hole blocking layer, the hole blocking layer may be formed on the emission layer by using various methods, such as vacuum deposition, spin coating casting, a Langmuir-Blodgett (LB) method, ink-jet printing, laser-printing, or laser-induced thermal imaging. When the hole blocking layer is formed by vacuum deposition or spin coating, deposition and coating conditions for the hole blocking layer may be determined by referring to the deposition and coating conditions for the hole injection layer.

The hole blocking layer may include, for example, at least one of BCP and Bphen.

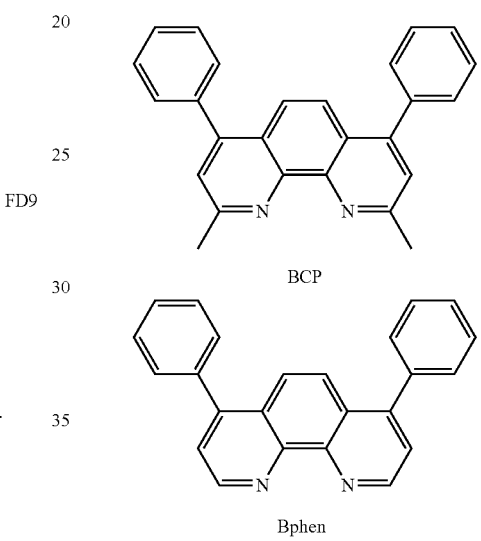

BCP

Bphen

A thickness of the hole blocking layer may be in a range of about 20 Å to about 1,000 Å, e.g., about 30 Å to about 300 Å. When the thickness of the hole blocking layer is within these ranges, the hole blocking layer may have excellent hole blocking characteristics without a substantial increase in driving voltage.

The electron transport region may include an electron transport layer. The electron transport layer may be formed on the emission layer or the hole blocking layer by using various methods, such as vacuum deposition, spin coating casting, a LB method, ink-jet printing, laser-printing, or laser-induced thermal imaging. When an electron transport layer is formed by vacuum deposition or spin coating, deposition and coating conditions for the electron transport layer may be the same as the deposition and coating conditions for the hole injection layer.

According to an embodiment, the organic layer 150 of the organic light-emitting device may include an electron transport region disposed between the emission layer and the second electrode 190. The electron transport region may include at least one selected from an electron transport layer and an electron injection layer.

The electron transport layer may further include at least one selected from BCP, Bphen, Alq$_3$, Balq, TAZ, and NTAZ.

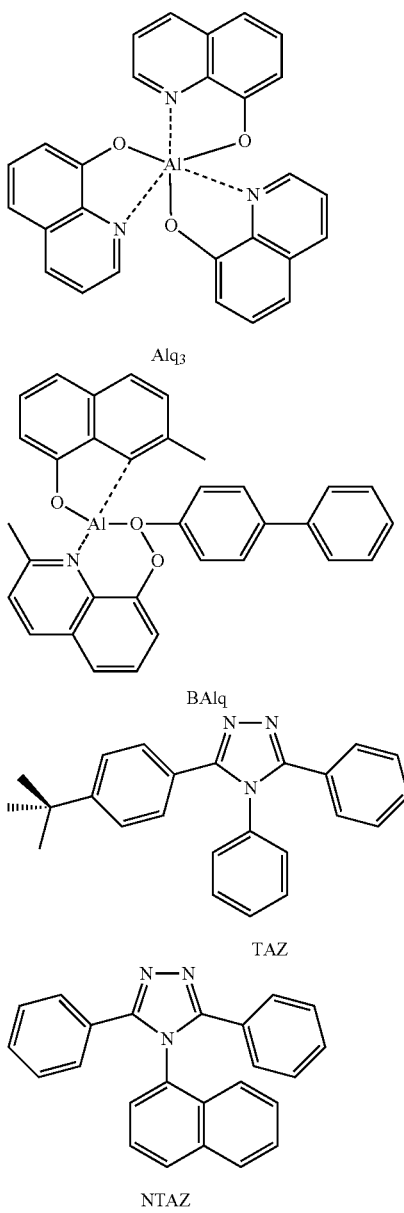

Alq3

BAlq

TAZ

NTAZ

In an implementation, the electron transport layer may include at least one compound selected from a compound represented by Formula 601 and a compound represented by Formula 602 illustrated below.

$Ar_{601}\text{-}[(L_{601})_{xe1}\text{-}E_{601}]_{xe2}$ <Formula 601>

In Formula 601, $Ar_{601}$ may be selected from a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, monovalent non-aromatic condensed heteropolycyclic group, and —Si($Q_{301}$)($Q_{302}$)($Q_{303}$) ($Q_{301}$ to $Q_{303}$ may be each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group);

descriptions of $L_{601}$ may be understood by referring to the descriptions provided in connection with $L_{301}$;

$E_{601}$ may be selected from a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3; and
xe2 may be selected from 1, 2, 3, and 4.

<Formula 602>

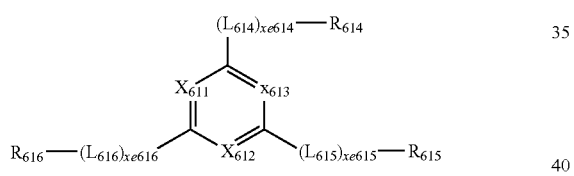

In Formula 602,
$X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, and at least one selected from $X_{611}$ to $X_{613}$ may be N;

$L_{611}$ to $L_{616}$ may be understood by referring to the description provided herein in connection with $L_{301}$;

$R_{611}$ and $R_{616}$ may each independently be selected from
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

The compound represented by Formula 601 and/or the compound represented by Formula 602 may each be selected from Compounds ET1 to ET15 illustrated below.

ET1

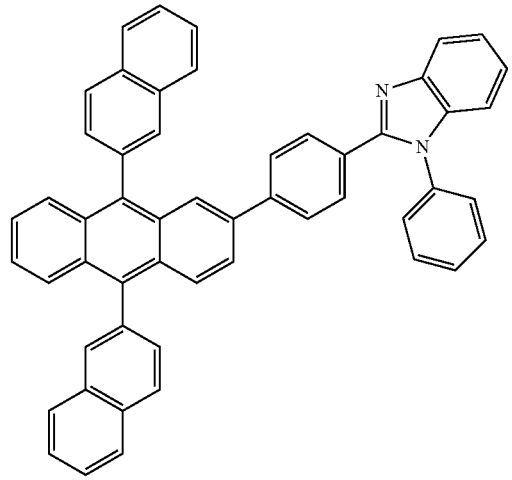

ET2

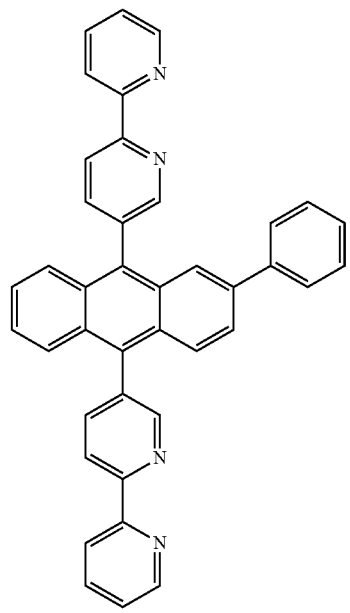

195
-continued
ET3
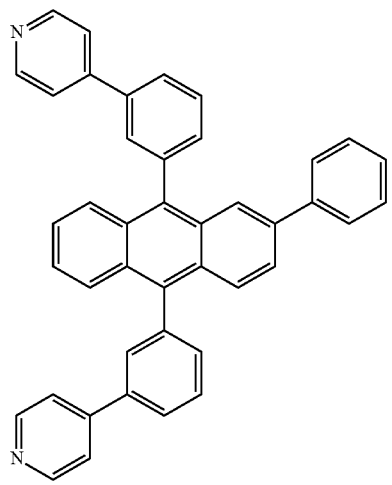
ET4
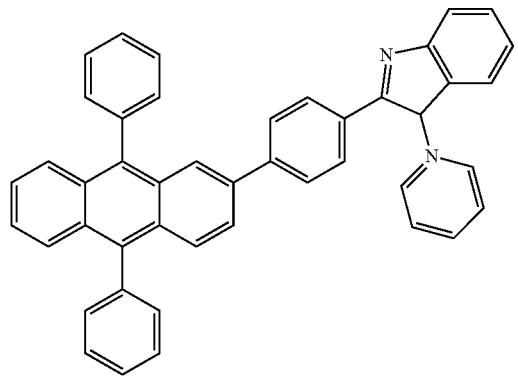
ET5
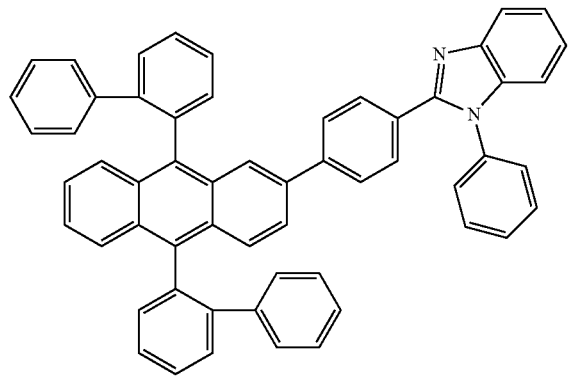
196
-continued
ET6
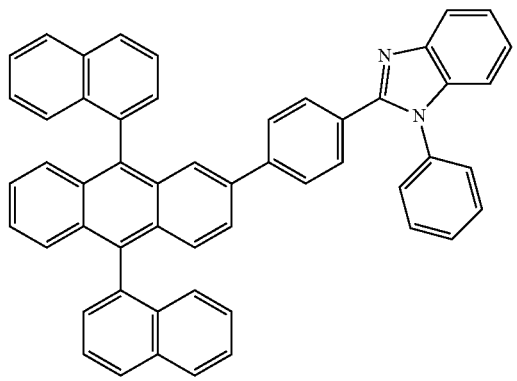
ET7
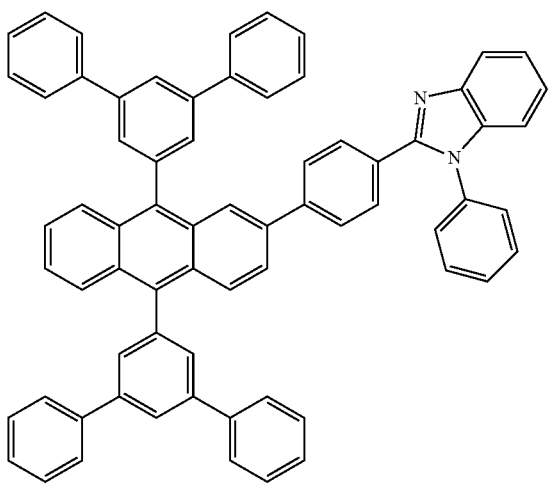
ET8
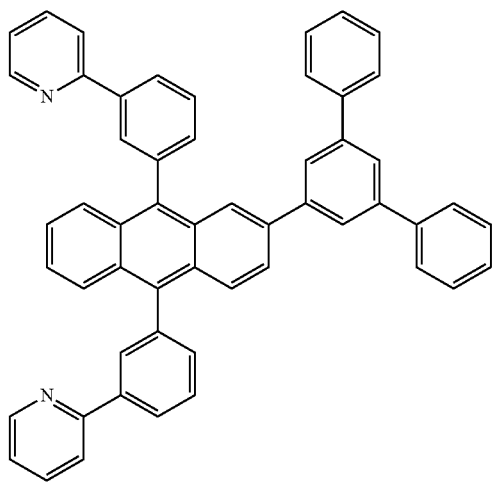

ET9
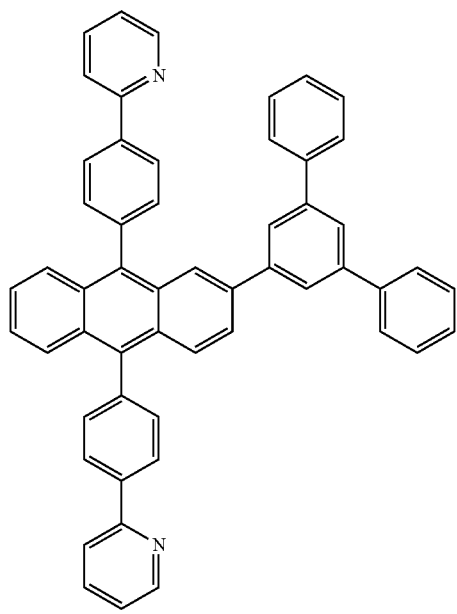
ET10
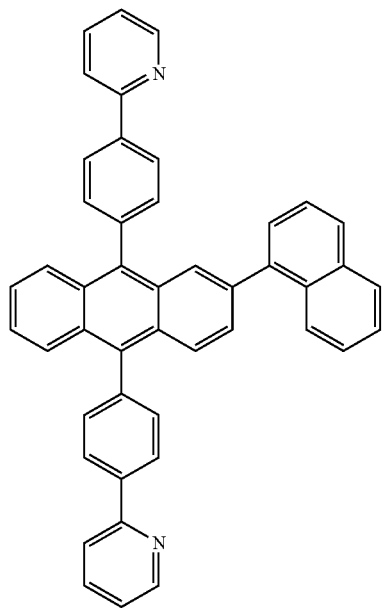
ET11
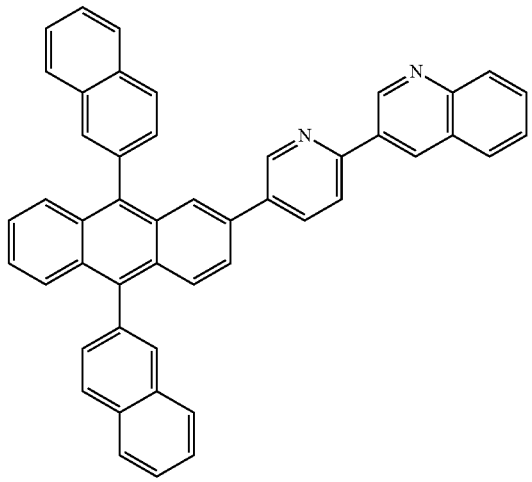
ET12
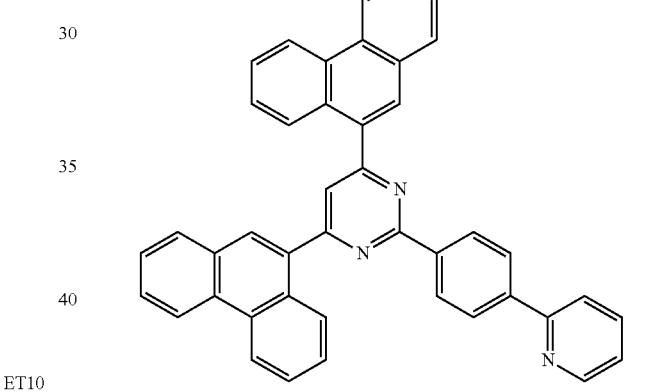
ET13
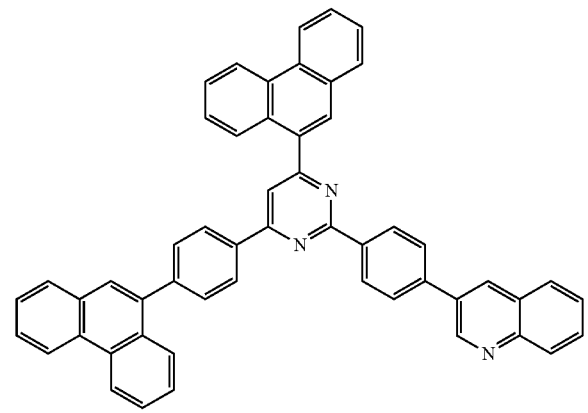

-continued

ET14

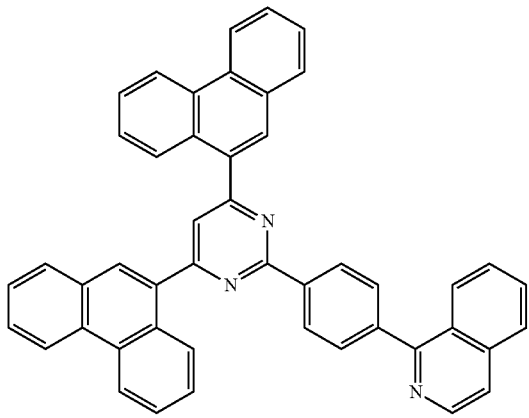

ET15

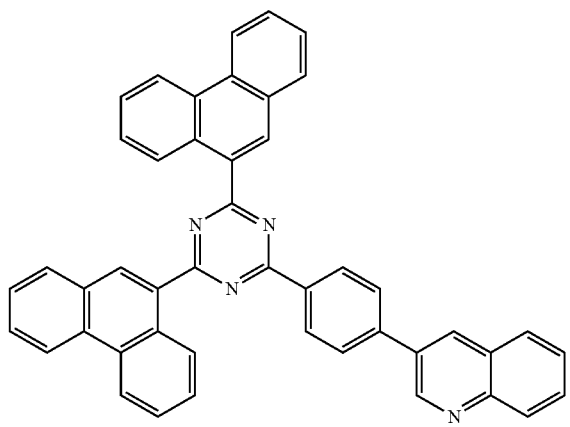

A thickness of the electron transport layer may be in a range of about 100 Å to about 1,000 Å, e.g., about 150 Å to about 500 Å. When the thickness of the electron transport layer is within the range described above, the electron transport layer may have satisfactory electron transport characteristics without a substantial increase in driving voltage.

In an implementation, the electron transport layer may further include, in addition to the materials described above, a metal-containing material.

The metal-containing material may include a Li complex. The Li complex may include, e.g., Compound ET-D1 (lithium quinolate, LiQ) or ET-D2.

ET-D1

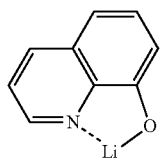

-continued

ET-D2

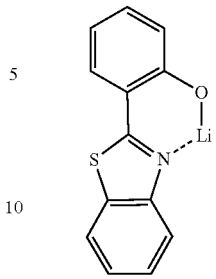

The electron transport region may include an electron injection layer that allows electrons to be easily provided from the second electrode 190.

The electron injection layer may be formed on the electron transport layer by using various methods, e.g., vacuum deposition, spin coating casting, a LB method, ink-jet printing, laser-printing, or laser-induced thermal imaging. When an electron injection layer is formed by vacuum deposition or spin coating, deposition and coating conditions for the electron injection layer may be the same as those for the hole injection layer.

The electron injection layer may include at least one selected from, LiF, NaCl, CsF, $Li_2O$, BaO, and LiQ.

A thickness of the electron injection layer may be in a range of about 1 Å to about 100 Å, e.g., about 3 Å to about 90 Å. When the thickness of the electron injection layer is within the range described above, the electron injection layer may have satisfactory electron injection characteristics without a substantial increase in driving voltage.

The second electrode 190 may be disposed on the organic layer 150 having such a structure. The second electrode 190 may be a cathode which is an electron injection electrode, and in this regard, a material for the second electrode 190 may be selected from metal, an alloy, an electrically conductive compound, and a mixture thereof, which have a relatively low work function. Examples of the material for the second electrode 190 may include lithium (Li), magnesium (Mg), aluminum (Al), aluminum-lithium (Al—Li), calcium (Ca), magnesium-indium (Mg—In), or magnesium-silver (Mg—Ag). In an implementation, the material for forming the second electrode 190 may be ITO or IZO. The second electrode 190 may be a reflective electrode, a semi-transmissive electrode, or a transmissive electrode.

Hereinbefore, the organic light-emitting device has been described with reference to FIG. 1.

A $C_1$-$C_{60}$ alkyl group used herein refers to a linear or branched aliphatic hydrocarbon monovalent group having 1 to 60 carbon atoms, and detailed examples thereof are a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group), and detailed examples thereof are a methoxy group, an ethoxy group, and an isopropyloxy group.

A $C_2$-$C_{60}$ alkenyl group used herein refers to a hydrocarbon group having at least one carbon double bond in the middle or at the terminal of the $C_2$-$C_{60}$ alkyl group, and detailed examples thereof are an ethenyl group, a prophenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group having one carbon triple bond in the middle or at the terminal of the $C_2$-$C_{60}$ alkyl group, and detailed examples thereof are an ethynyl group, and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group having at least one hetero atom selected from N, O, P, and S as a ring-forming atom and 1 to 10 carbon atoms, and detailed examples thereof are a tetrahydrofuranyl group, and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromacity, and detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group used herein refers to a monovalent group having a carboncyclic aromatic system that has at least one hetero atom selected from N, O, P, and S as a ring-forming atom, and 1 to 60 carbon atoms. A $C_1$-$C_{60}$ heteroarylene group used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

A monovalent non-aromatic condensed polycyclic group used herein refers to a monovalent group (for example, having 8 to 60 carbon atoms) that has two or more rings condensed to each other, only carbon atoms as a ring forming atom, and non-aromacity in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a momovalent group (for example, having 2 to 60 carbon atoms) that has two or more rings condensed to each other, has a heteroatom selected from N, O P, and S, other than carbon atoms, as a ring forming atom, and has non-aromacity in the entire molecular structure. An example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

at least one substituent of the substituted $C_6$-$C_{20}$ aromatic ring, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted a divalent non-aromatic condensed polycyclic group, substituted a divalent non-aromatic condensed heteropolycyclic group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_1$-$C_{60}$ alkenyl group, a $C_1$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), and —B($Q_{24}$)($Q_{25}$); and —Si($Q_{31}$)($Q_{32}$)($Q_{33}$), and —B($Q_{34}$)($Q_{35}$);

$Q_{11}$ to $Q_{15}$, $Q_{21}$ to $Q_{25}$, and $Q_{31}$ to $Q_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The term "Ph" used herein refers to a phenyl group, the term "Me" used herein refers to a methyl group, the term "Et" used herein refers to an ethyl group, and the term "ter-Bu" or "Bu$^t$" used herein refers to a tert-butyl group.

Hereinafter, an organic light-emitting device according to an embodiment will be described in detail with reference to Synthesis Examples and Examples. The wording "B was used instead of A" used in describing Synthesis Examples means that a molar equivalent of A was identical to a molar equivalent of B.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1

Synthesis of Compound 3

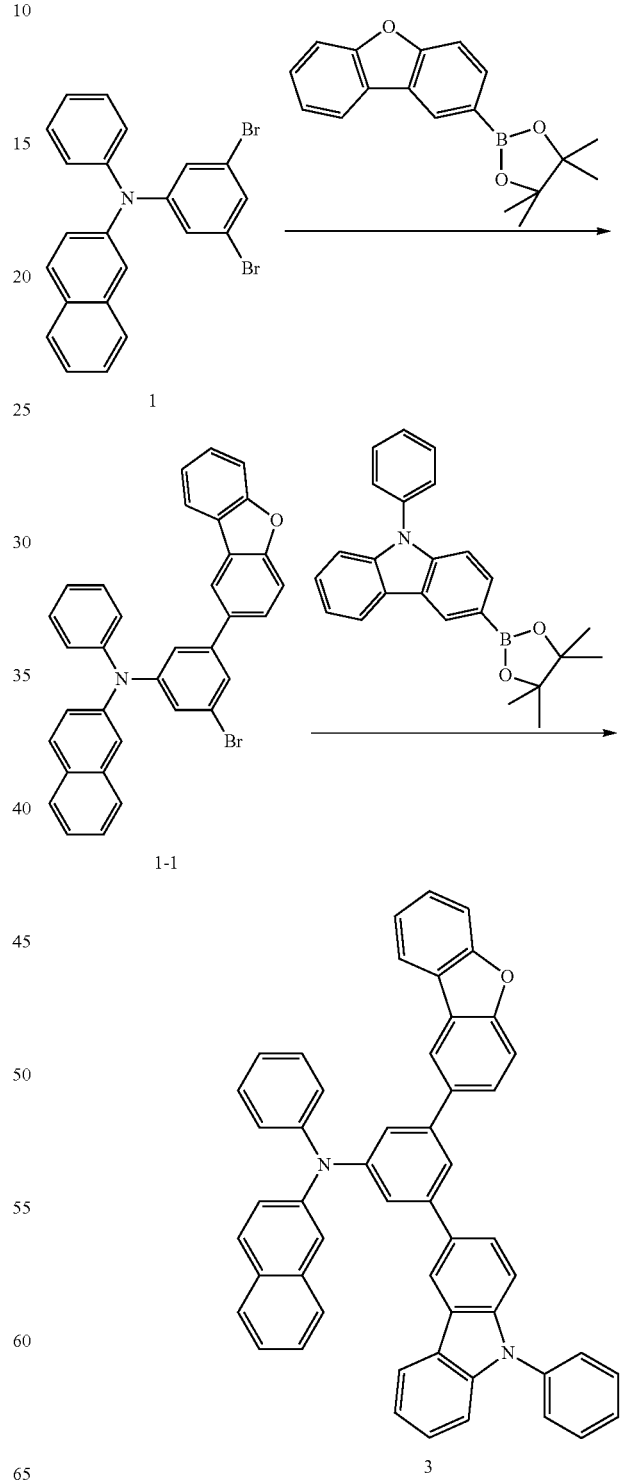

205

Synthesis of Intermediate 1-1

10 g of Starting Material 1 was diluted in 150 ml of THF, and then the temperature was decreased to −78° C. At −78° C., n-BuLi(2.5 M, 14.7 ml) was slowly added dropwise thereto. One hour after the addition, 3.8 g of 2-(dibenzo[b,d]furan-2-yl)-4,4,5,5,-tetramethyl-1,3,2-dioxaborane was slowly added thereto. Three minutes after the addition, the temperature was slowly raised to ambient temperature, and then, the result was stirred for 6 hours. The reaction was quenched by using a saturated ammonium chloride aqueous solution, and an organic layer was separated therefrom, and then, dried using an anhydrous magnesium sulfate and subjected to concentration under reduced pressure. The residual was separation-purified by silica gel column chromatography to obtain Intermediate 1-1 (9.9 g, yield: 78%).

Synthesis of Compound 3

Compound 3 (yield: 91%) was prepared in the same manner used to synthesize Intermediate 1-1, except that 3 g of Intermediate 1-1 was used instead of Starting Material 1 and 4.5 g of 2-(9-phenyl-9H-carbazole-2-yl)-4,4,5,5-tetramethyl-1,3,2-dioxaborane was used instead of 3.8 g of 2-(dibenzo[b,d]furan-2-yl)-4,4,5,5,-tetramethyl-1,3,2-dioxaborane.

Synthesis Example 2

Synthesis of Compound 21

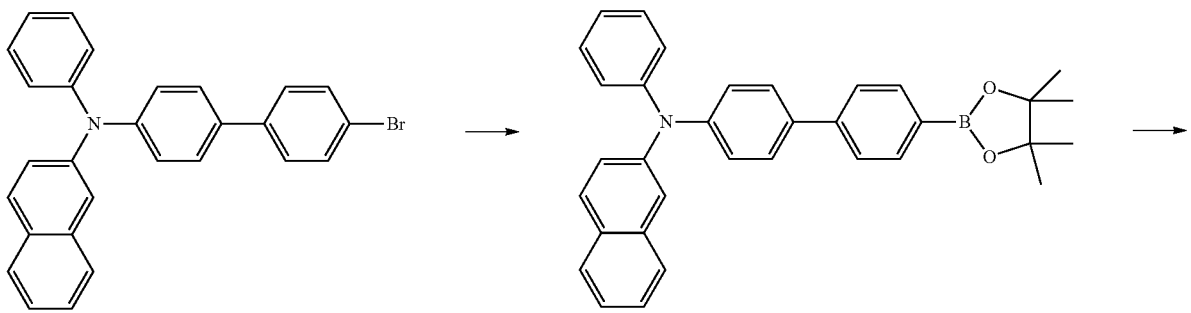

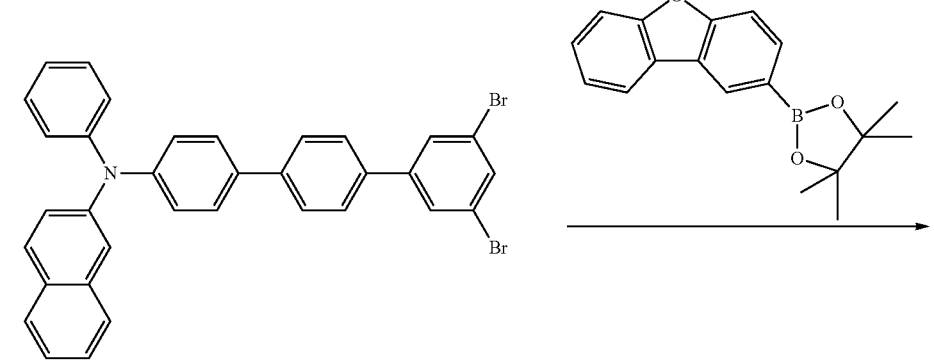

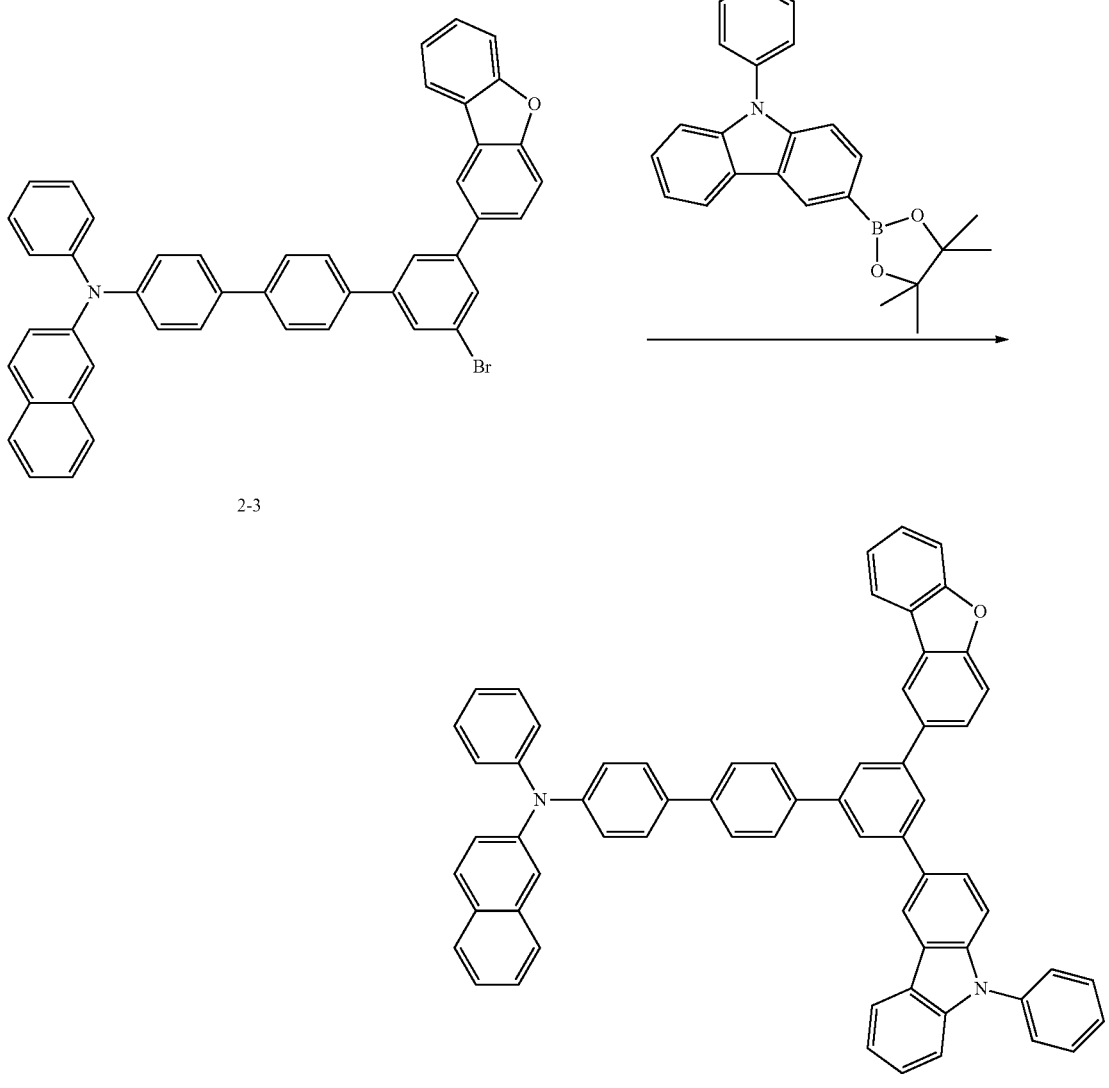

Synthesis of Intermediate 2-1

10 g of Starting Material 2 was diluted in 150 ml of THF, and then the temperature was decreased to −78° C. At −78° C., n-BuLi(2.5 M, 14.7 ml) was slowly added dropwise thereto. One hour after the addition, 3 g of 2-isopropoxy-4,4,5,5-tetramethyl-1.3.2-diaoxaborane was slowly added thereto. Three minutes after the addition, the temperature was slowly raised to ambient temperature, and then, the result was stirred for 6 hours. The reaction was quenched by using a saturated ammonium chloride aqueous solution, and an organic layer was separated therefrom, and then, dried using an anhydrous magnesium sulfate and subjected to concentration under reduced pressure. The residual was separation-purified by silica gel column chromatography to obtain Intermediate 2-1.

Synthesis of Intermediate 2-2

9.9 g of Intermediate 2-1 and 4.8 g of 1,3,5-tribromoa benzene were diluted in 120 ml of THF, and then, 1.5 g of pd(pph$_3$)$_4$ and 11 g of potassiumcarbonate were added thereto, and the result was stirred at a temperature of 60° C. 12 hours after the stirring, the temperature was decreased to ambient temperature, and then, an extraction process was performed thereon three times by using ethyl acetate. A separated organic layer was dried by using anhydrous magnesium sulfate and and distilled under reduced pressure, and the residual was separation-purified by silica gel column chromatography to obtain Intermediate 2-2.

Synthesis of Intermediate 2-3

Intermediate 2-3 was obtained in the same manner as used to synthesize Intermediate 1-1, except that 3 g of Intermediate 2-2 was used instead of Starting Material 2, and 3.8 g of 2-(dibenzo[b,d]furan-2-yl)-4,4,5,5,-tetramethyl-1,3,2-dioxaborane was used instead of 2-isopropoxy-4,4,5,5-tetramethyl-1.3.2-diaoxaborane.

Synthesis of Compound 21
Compound 21 (yield: 90.1%) was obtained in the same manner as used to synthesize Intermediate 1-1, except that 3 g of Intermediate 2-3 was used instead of Starting Material 2, and 4.5 g of 2-(9-phenyl-9H-carbazole-2-yl)-4,4,5,5-tetramethyl-1,3,2-dioxaborane was used instead of 2-isopropoxy-4,4,5,5-tetramethyl-1.3.2-diaoxaborane.
Synthesis Example 3
Synthesis of Compound 29
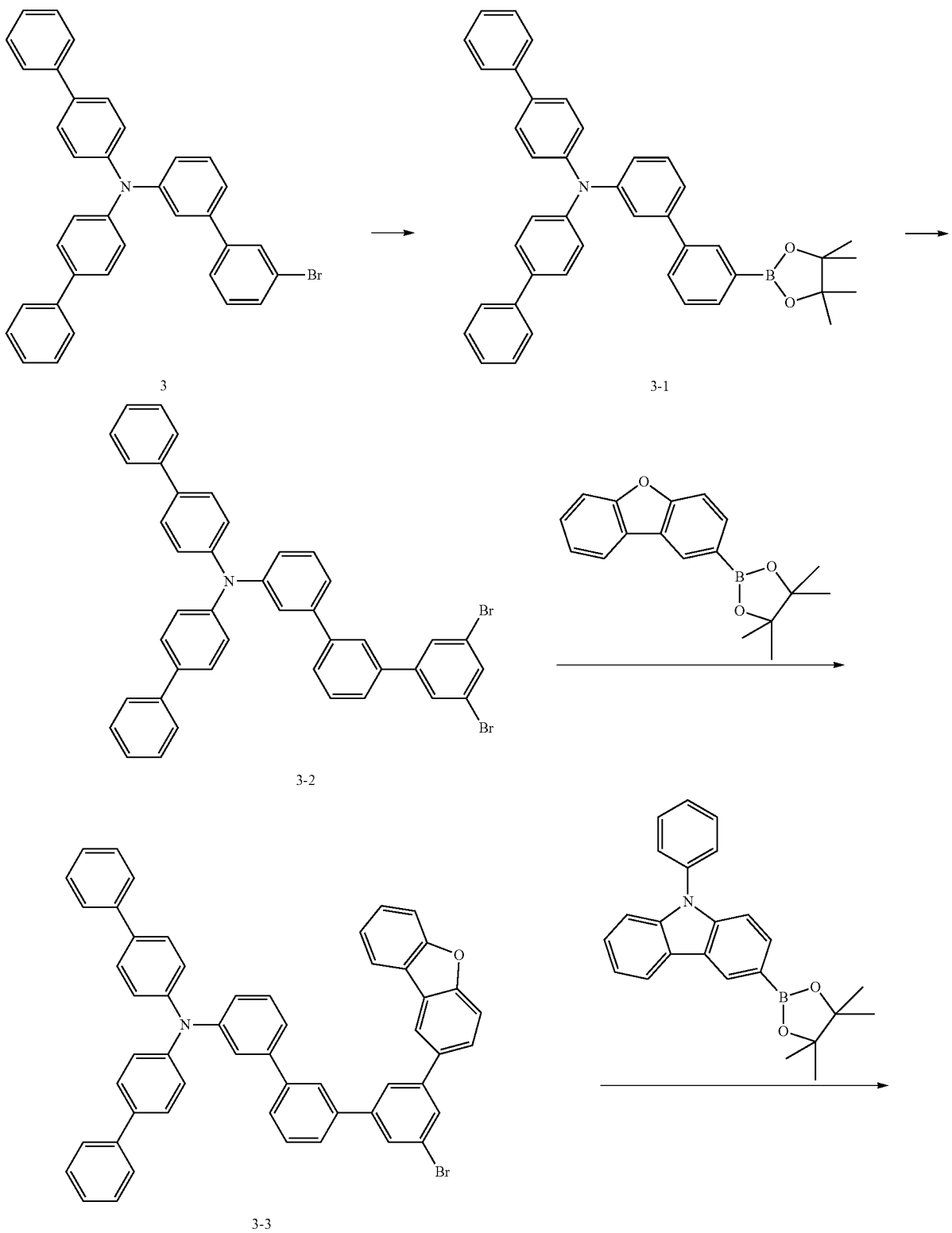 [SMILES: Brc1cccc(-c2cccc(N(c3ccc(-c4ccccc4)cc3)c3ccc(-c4ccccc4)cc3)c2)c1 ; CC1(C)OB(c2cccc(-c3cccc(N(c4ccc(-c5ccccc5)cc4)c4ccc(-c5ccccc5)cc4)c3)c2)OC1(C)C ; Brc1cc(Br)cc(-c2cccc(-c3cccc(N(c4ccc(-c5ccccc5)cc4)c4ccc(-c5ccccc5)cc4)c3)c2)c1 ; CC1(C)OB(c2ccc3oc4ccccc4c3c2)OC1(C)C ; Brc1cc(-c2cccc(-c3cccc(N(c4ccc(-c5ccccc5)cc4)c4ccc(-c5ccccc5)cc4)c3)c2)cc(-c2ccc3oc4ccccc4c3c2)c1 ; CC1(C)OB(c2ccc3c(c2)c2ccccc2n3-c2ccccc2)OC1(C)C]

-continued

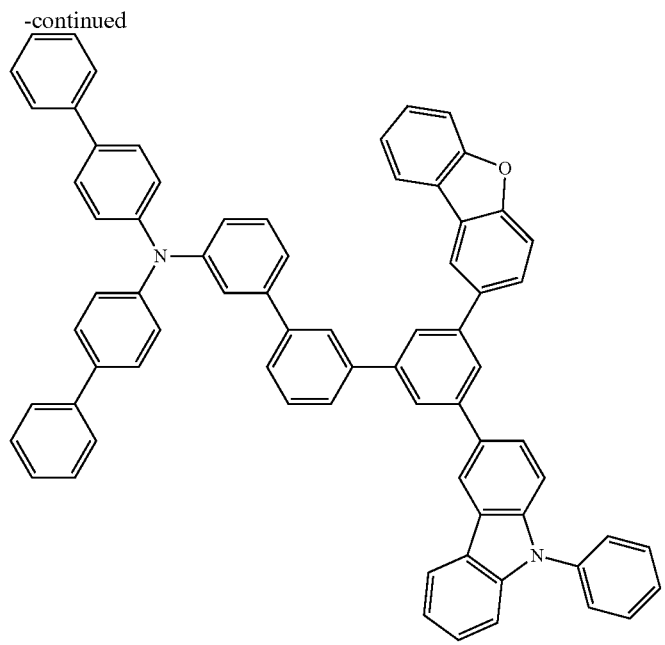
29

Synthesis of Intermediate 3-1

Intermediate 3-1 was synthesized in the same manner as used in synthesizing Intermediate 2-1, except that Starting Material 3 was used instead of Starting Material 2.

Synthesis of Intermediate 3-2

Intermediate 3-2 was synthesized in the same manner as in synthesizing Intermediate 2-2, except that Intermediate 3-1 was used instead of Intermediate 2-1.

Synthesis of Intermediate 3-3

Intermediate 3-3 was synthesized in the same manner as in synthesizing Intermediate 2-3, except that Intermediate 3-2 was used instead of Intermediate 2-2.

Synthesis of Compound 29

Compound 29 (yield: 90.2%) was synthesized in the same manner as used to synthesize Compound 21, except that Intermediate 3-3 was used instead of Intermediate 2-3.

Synthesis Example 4

Synthesis of Compound 40

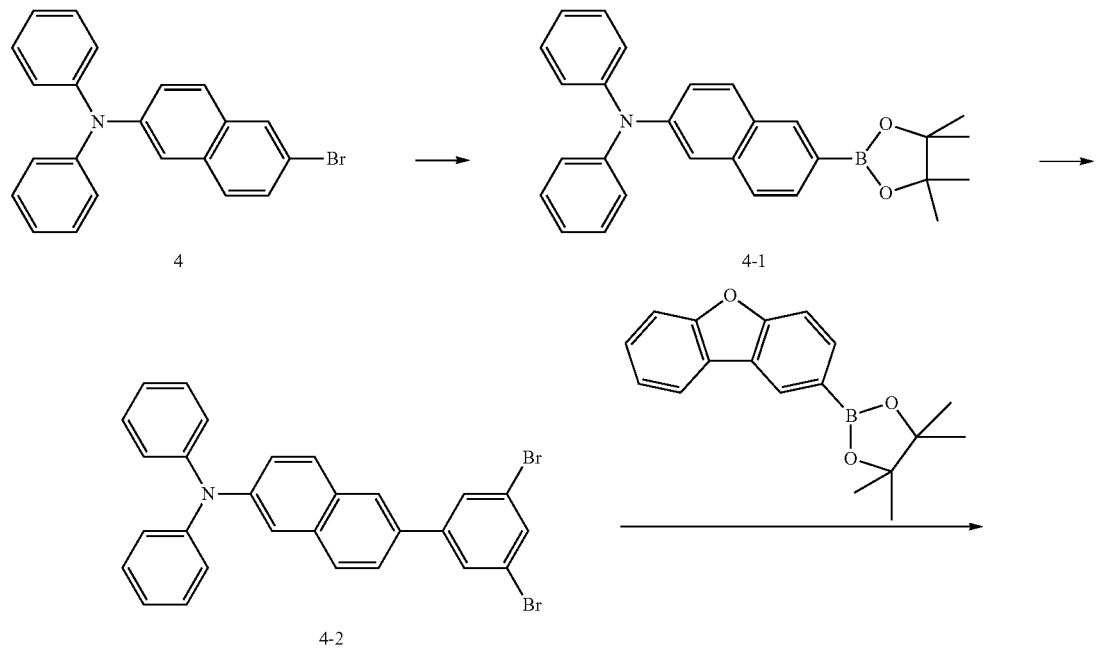

-continued

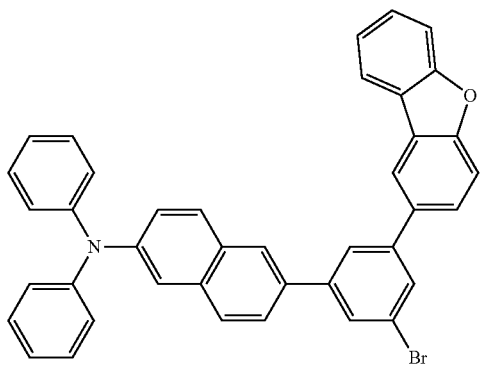
4-3

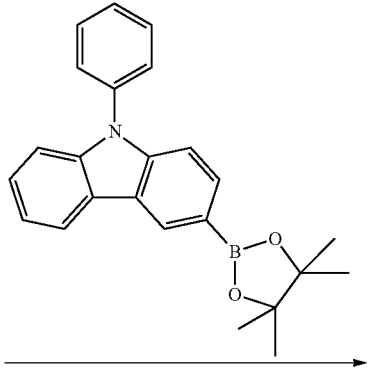

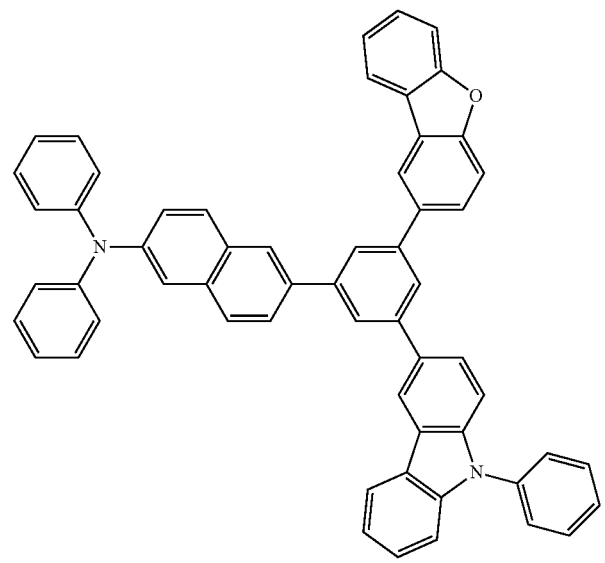
40

Synthesis of Intermediate 4-1

Intermediate 4-1 was synthesized in the same manner as used in synthesizing Intermediate 2-1, except that Starting Material 4 was used instead of Starting Material 2.

Synthesis of Intermediate 4-2

Intermediate 4-2 was synthesized in the same manner as in synthesizing Intermediate 2-2, except that Intermediate 4-1 was used instead of Intermediate 2-1.

Synthesis of Intermediate 4-3

Intermediate 4-3 was synthesized in the same manner as in synthesizing Intermediate 2-3, except that Intermediate 4-2 was used instead of Intermediate 2-2.

Synthesis of Compound 40

Compound 40 (yield: 86.6%) was synthesized in the same manner as used to synthesize Compound 21, except that Intermediate 4-3 was used instead of Intermediate 2-3.

Synthesis Example 5

Synthesis of Compound 49

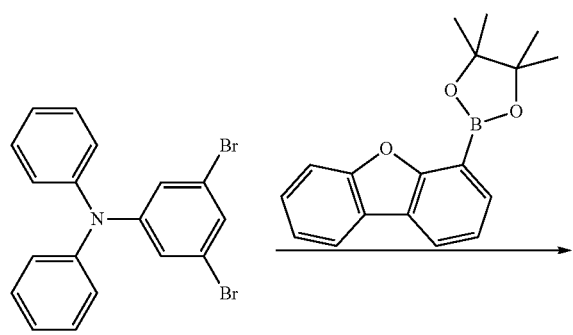

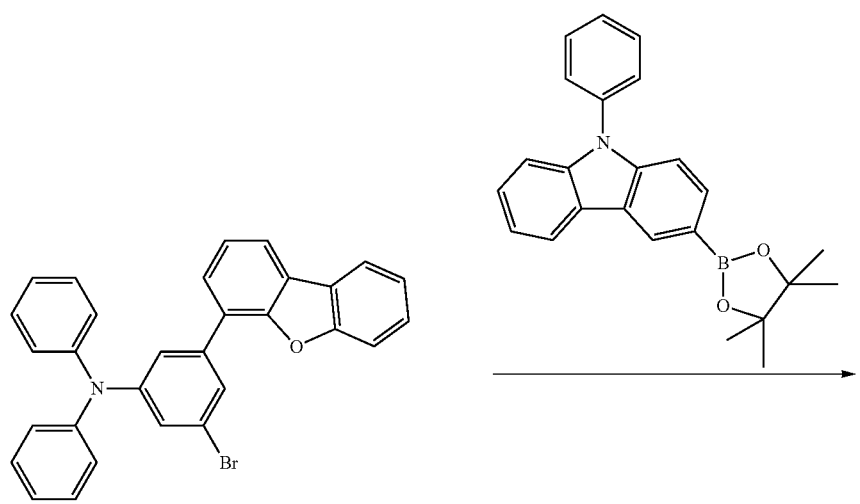

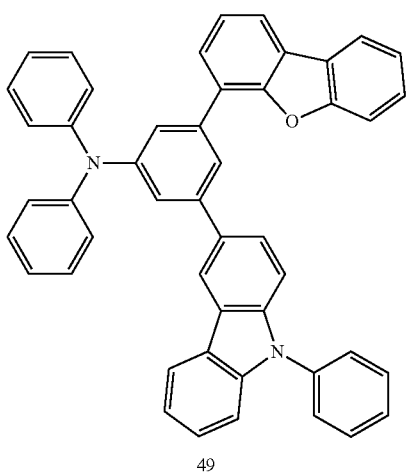

Synthesis of Intermediate 5-1

Intermediate 5-1 was prepared in the same manner as used to synthesize Intermediate 1-1, except that Starting Material 5 was used instead of Starting Material 1, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 49

Compound 49 (yield: 85.1%) was synthesized in the same manner as used to synthesize Compound 3, except that Intermediate 5-1 was used instead of Intermediate 1-1.

Synthesis Example 6
Synthesis of Compound 56
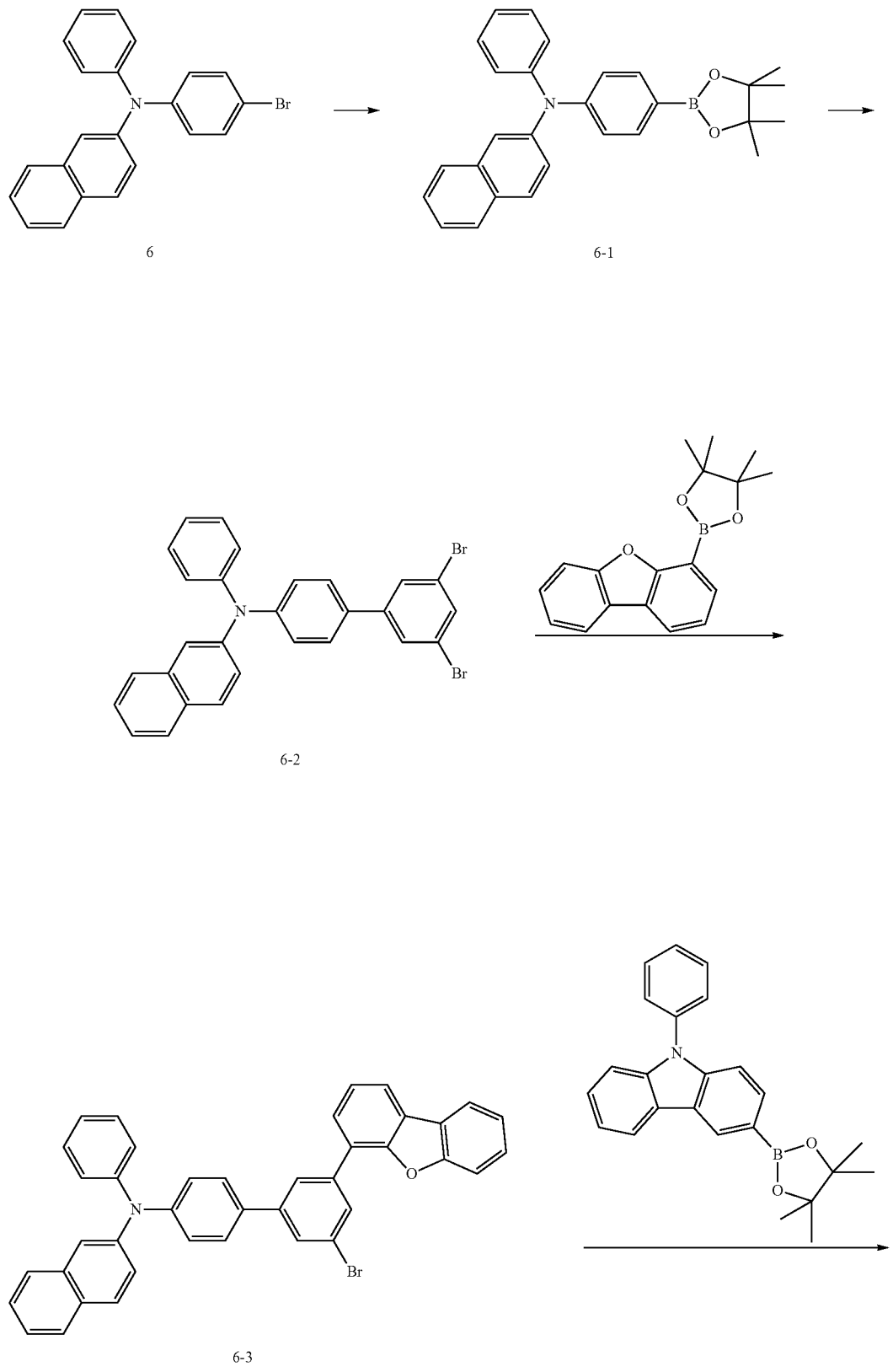

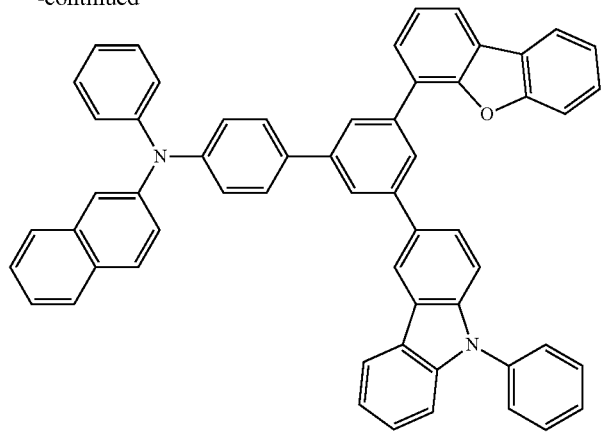

56

Synthesis of Intermediate 6-1

Intermediate 6-1 was synthesized in the same manner as used in synthesizing Intermediate 2-1, except that Starting Material 6 was used instead of Starting Material 2.

Synthesis of Intermediate 6-2

Intermediate 6-2 was synthesized in the same manner as in synthesizing Intermediate 2-2, except that Intermediate 6-1 was used instead of Intermediate 2-1.

Synthesis of Intermediate 6-3

Intermediate 6-3 was prepared in the same manner as used to synthesize Intermediate 2-3, except that Intermediate 6-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 56

Compound 56 (yield: 88.5%) was synthesized in the same manner as used to synthesize Compound 21, except that Intermediate 6-3 was used instead of Intermediate 2-3.

Synthesis Example 7

Synthesis of Compound 57

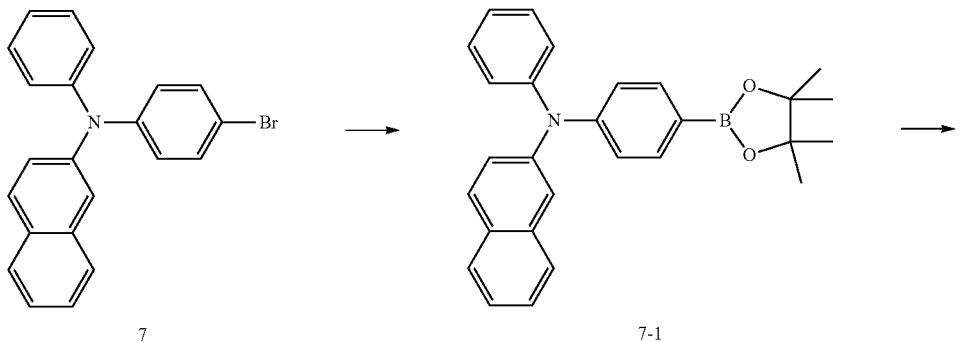

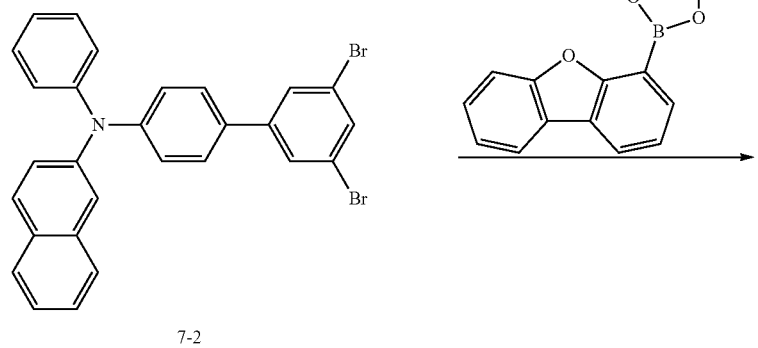

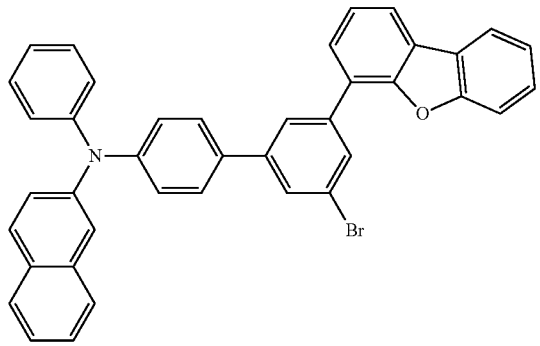

7-3

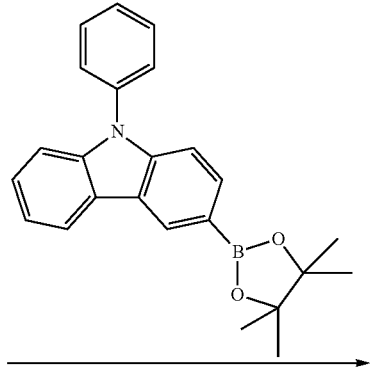

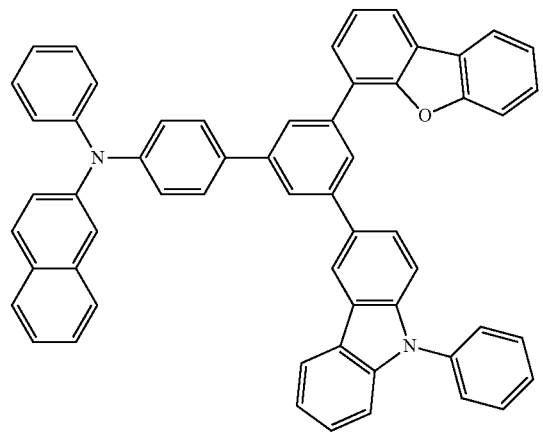

57

Synthesis of Intermediate 7-1

Intermediate 7-1 was synthesized in the same manner as used in synthesizing Intermediate 2-1, except that Starting Material 7 was used instead of Starting Material 2.

Synthesis of Intermediate 7-2

Intermediate 7-2 was synthesized in the same manner as in synthesizing Intermediate 2-2, except that Intermediate 7-1 was used instead of Intermediate 2-1.

Synthesis of Intermediate 7-3

Intermediate 7-3 was prepared in the same manner as used to synthesize Intermediate 2-3, except that Intermediate 7-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 57

Compound 57 (yield: 92.4%) was synthesized in the same manner as used to synthesize Compound 21, except that Intermediate 7-3 was used instead of Intermediate 2-3.

Synthesis Example 8
Synthesis of Compound 59
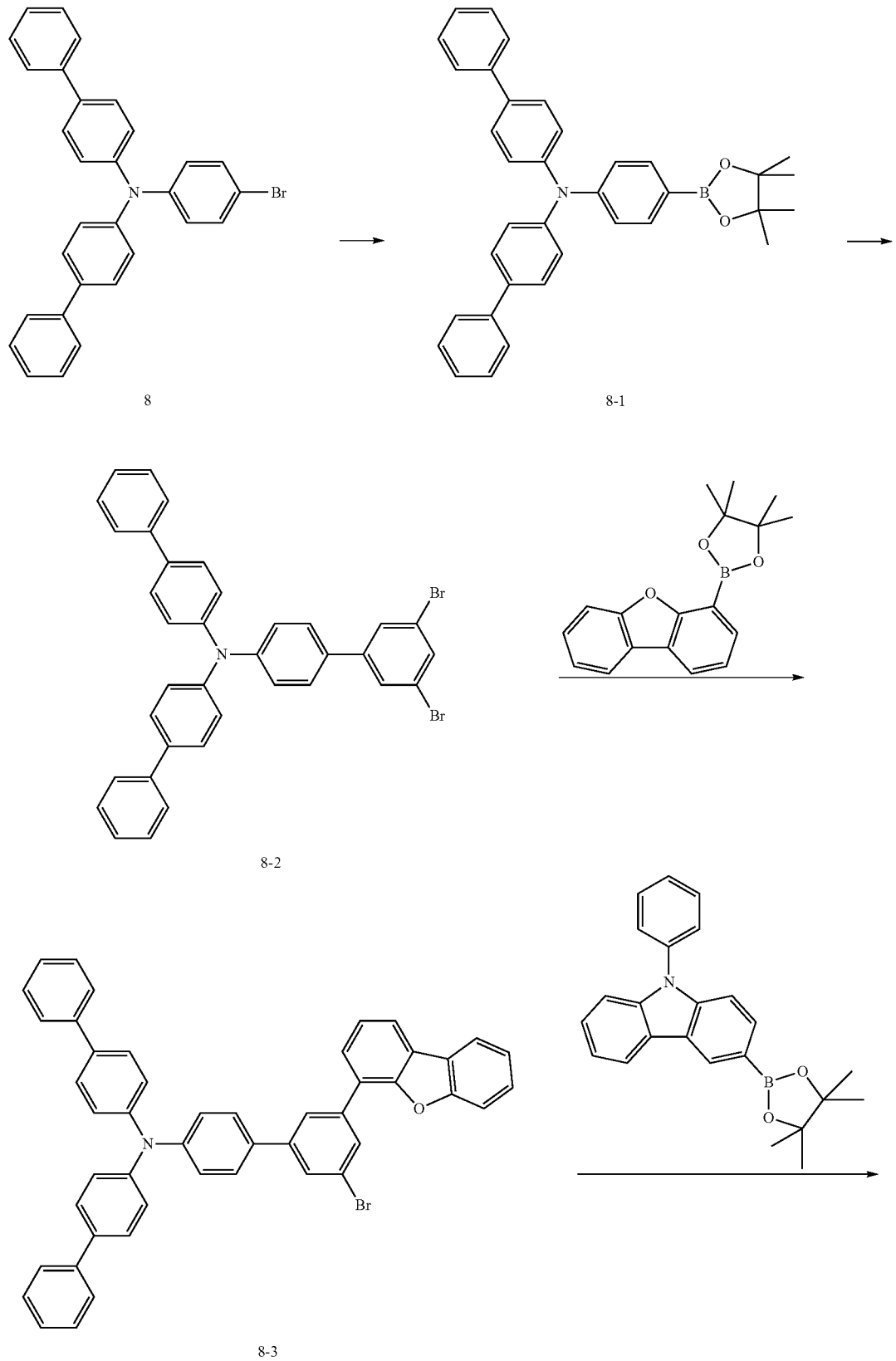

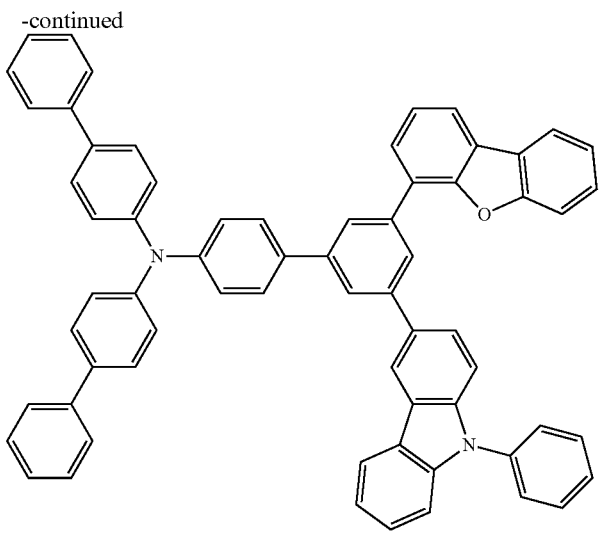

59

Synthesis of Intermediate 8-1

Intermediate 8-1 was synthesized in the same manner as used in synthesizing Intermediate 2-1, except that Starting Material 8 was used instead of Starting Material 2.

Synthesis of Intermediate 8-2

Intermediate 8-2 was synthesized in the same manner as in synthesizing Intermediate 2-2, except that Intermediate 8-1 was used instead of Intermediate 2-1.

Synthesis of Intermediate 8-3

Intermediate 8-3 was prepared in the same manner as used to synthesize Intermediate 2-3, except that Intermediate 8-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 59

Compound 59 (yield: 87.4%) was synthesized in the same manner as used to synthesize Compound 21, except that Intermediate 8-3 was used instead of Intermediate 2-3.

Synthesis Example 9

Synthesis of Compound 62

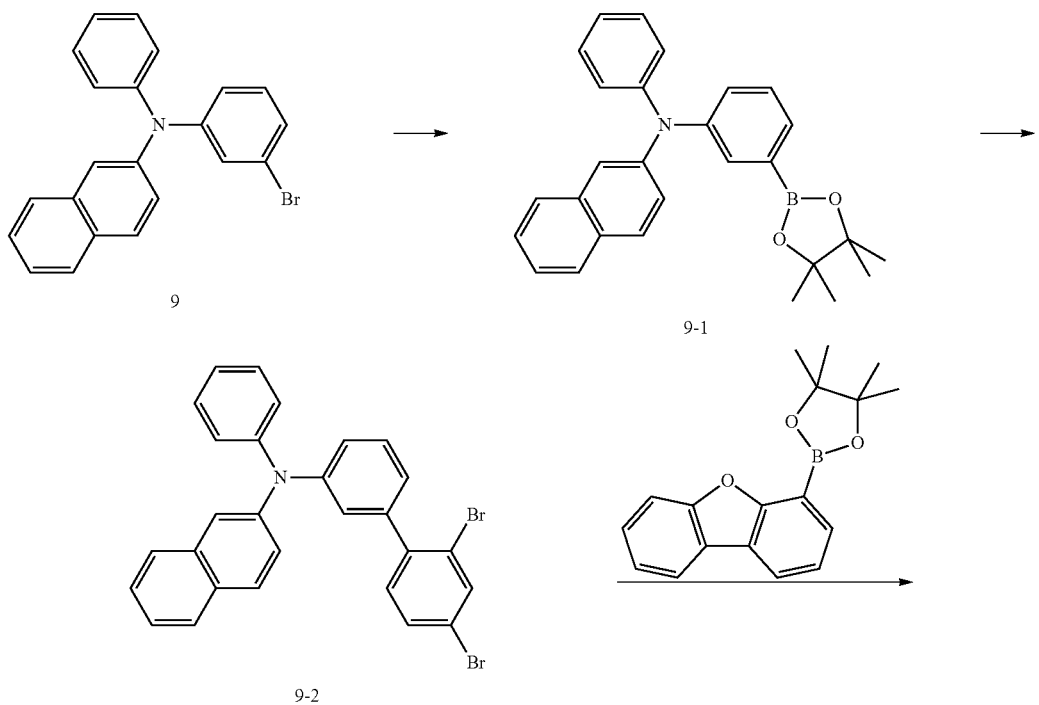

-continued

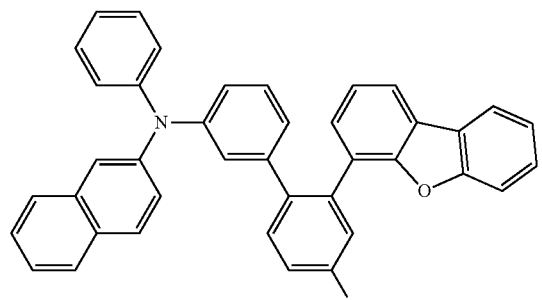
9-3

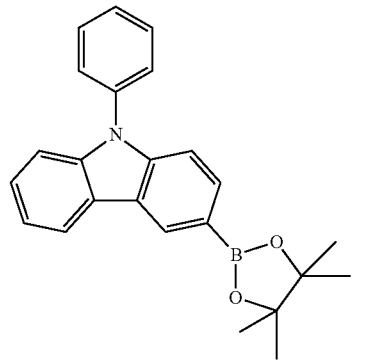

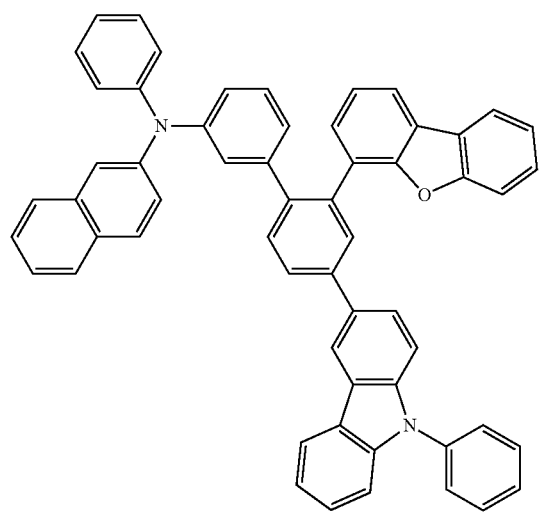
62

Synthesis of Intermediate 9-1

Intermediate 9-1 was synthesized in the same manner as used in synthesizing Intermediate 2-1, except that Starting Material 9 was used instead of Starting Material 2.

Synthesis of Intermediate 9-2

Intermediate 9-2 was synthesized in the same manner as in synthesizing Intermediate 2-2, except that Intermediate 9-1 was used instead of Intermediate 2-1, and 1,2,4-tribromobenzene was used instead of 1,3,5-tribromobenzene.

Synthesis of Intermediate 9-3

Intermediate 9-3 was prepared in the same manner as used to synthesize Intermediate 2-3, except that Intermediate 9-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 62

Compound 62 (yield: 88.6%) was synthesized in the same manner as used to synthesize Compound 21, except that Intermediate 9-3 was used instead of Intermediate 2-3.

Synthesis Example 10
Synthesis of Compound 63
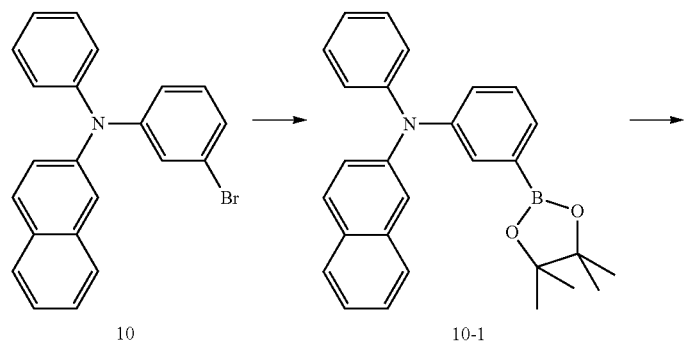
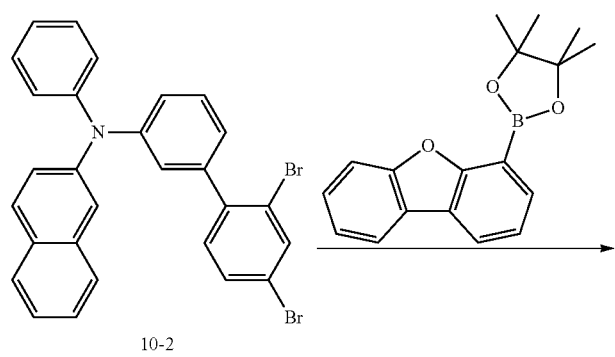
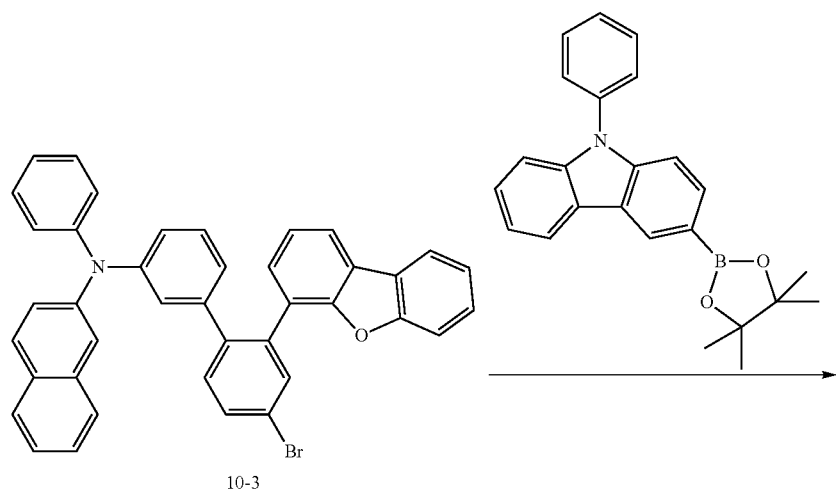

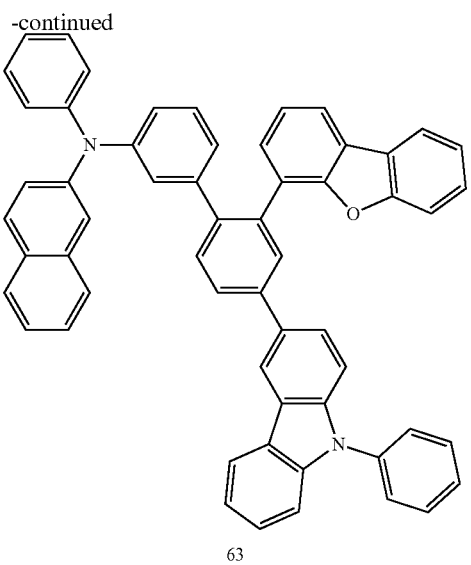

63

Synthesis of Intermediate 10-1

Intermediate 10-1 was synthesized in the same manner as used in synthesizing Intermediate 2-1, except that Starting Material 10 was used instead of Starting Material 2.

Synthesis of Intermediate 10-2

Intermediate 10-2 was synthesized in the same manner as in synthesizing Intermediate 2-2, except that Intermediate 10-1 was used instead of Intermediate 2-1, and 1,2,4-tribromobenzene was used instead of 1,3,5-tribromobenzene.

Synthesis of Intermediate 10-3

Intermediate 10-3 was prepared in the same manner as used to synthesize Intermediate 2-3, except that Intermediate 10-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 63

Compound 63 (yield: 85.1%) was synthesized in the same manner as used to synthesize Compound 21, except that Intermediate 10-3 was used instead of Intermediate 2-3.

Synthesis Example 11

Synthesis of Compound 70

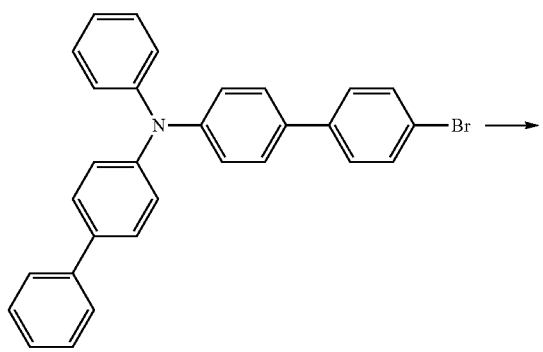

11

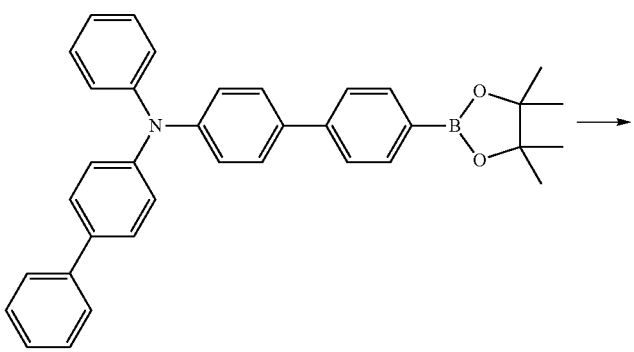
11-1
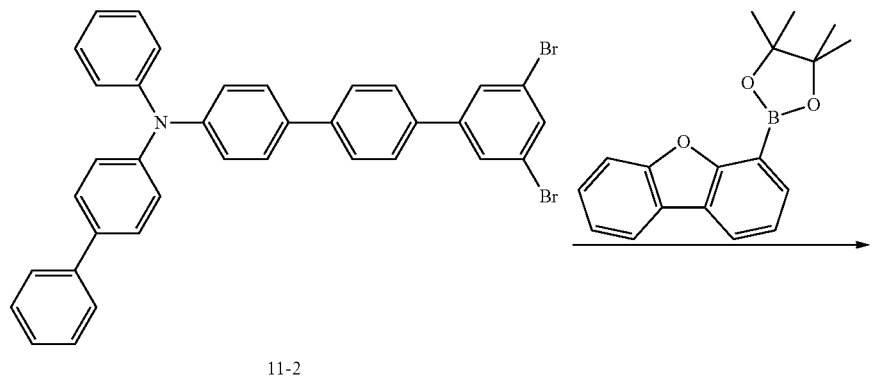
11-2
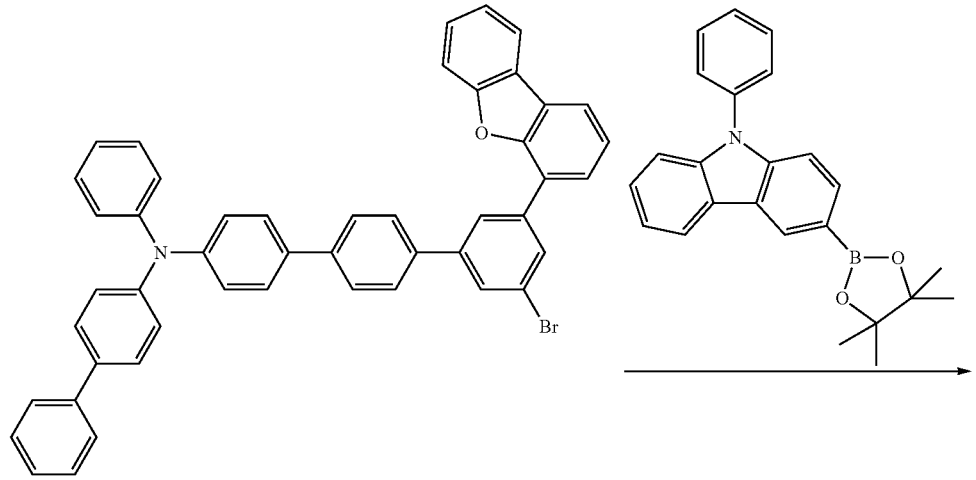
11-3

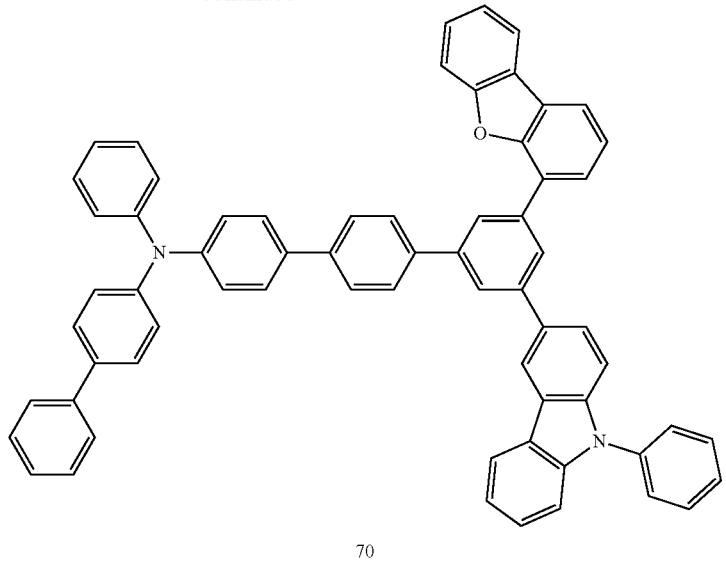 [SMILES: c1ccc(-c2ccc(N(c3ccccc3)c3ccc(-c4ccc(-c5cc(-c6ccc7c(c6)c6ccccc6n7-c6ccccc6)cc(-c6cccc7c6oc6ccccc67)c5)cc4)cc3)cc2)cc1]

70

Synthesis of Intermediate 11-1

Intermediate 11-1 was synthesized in the same manner as used in synthesizing Intermediate 2-1, except that Starting Material 11 was used instead of Starting Material 2.

Synthesis of Intermediate 11-2

Intermediate 11-2 was synthesized in the same manner as in synthesizing Intermediate 2-2, except that Intermediate 11-1 was used instead of Intermediate 2-1.

Synthesis of Intermediate 11-3

Intermediate 11-3 was prepared in the same manner as used to synthesize Intermediate 2-3, except that Intermediate 11-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 70

Compound 70 (yield: 90.2%) was synthesized in the same manner as used to synthesize Compound 21, except that Intermediate 11-3 was used instead of Intermediate 2-3.

Synthesis Example 12

Synthesis of Compound 74

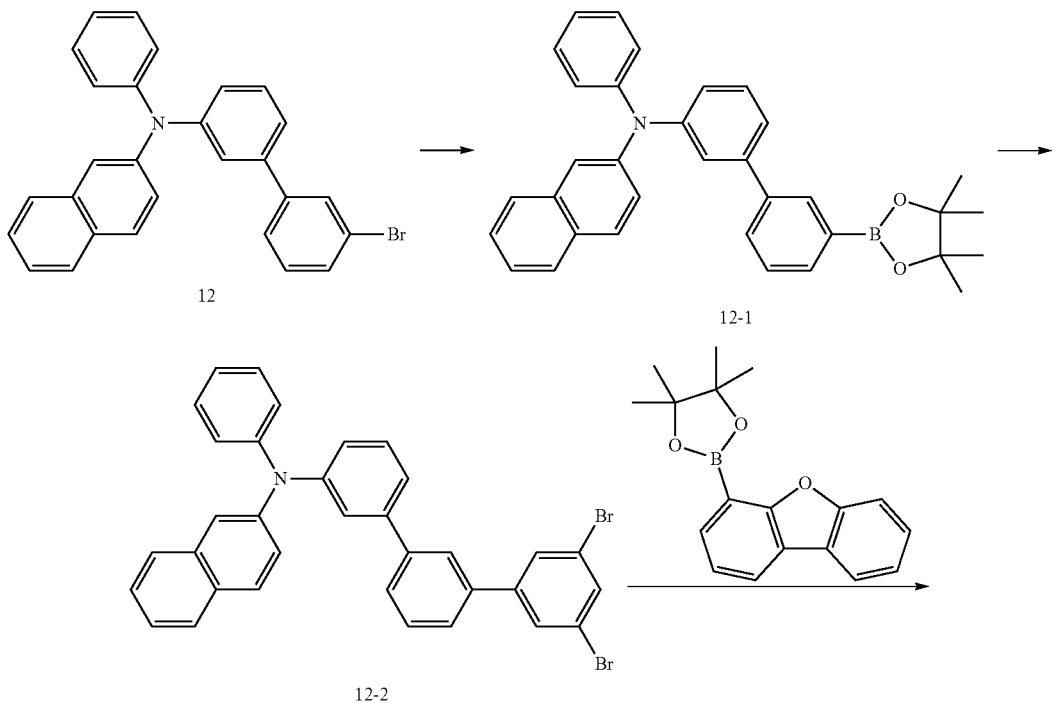

-continued

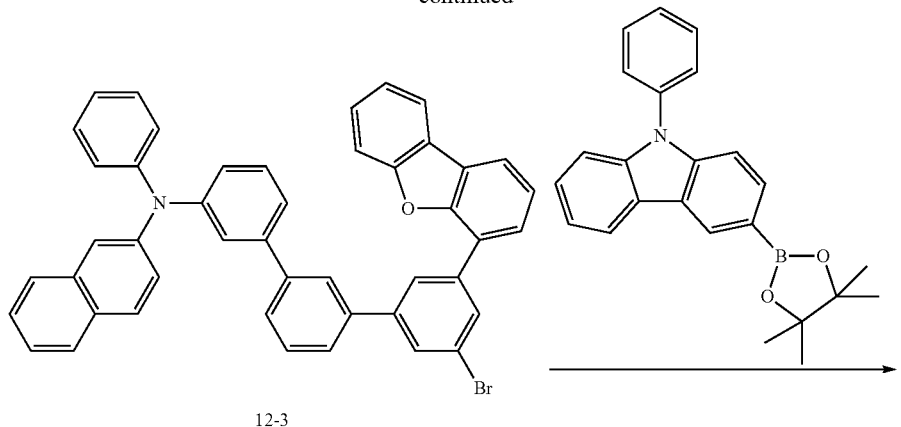

12-3

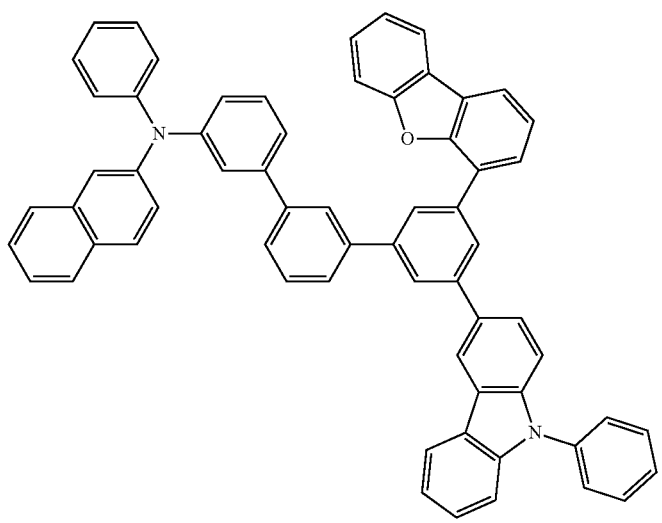

74

Synthesis of Intermediate 12-1

Intermediate 12-1 was synthesized in the same manner as used in synthesizing Intermediate 2-1, except that Starting Material 12 was used instead of Starting Material 2.

Synthesis of Intermediate 12-2

Intermediate 12-2 was synthesized in the same manner as in synthesizing Intermediate 2-2, except that Intermediate 12-1 was used instead of Intermediate 2-1.

Synthesis of Intermediate 12-3

Intermediate 12-3 was prepared in the same manner as used to synthesize Intermediate 2-3, except that Intermediate 12-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 74

Compound 74 (yield: 85.4%) was synthesized in the same manner as used to synthesize Compound 21, except that Intermediate 12-3 was used instead of Intermediate 2-3.

Synthesis Example 13
Synthesis of Compound 78
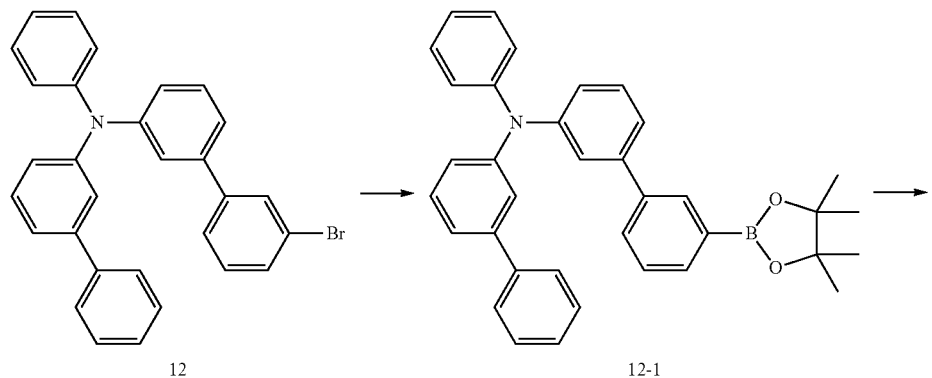
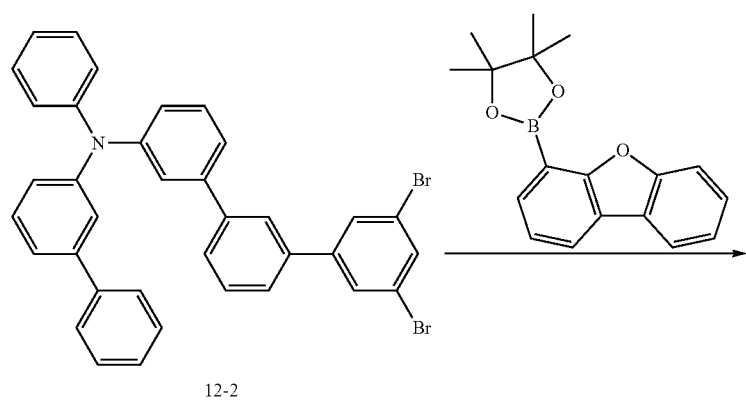
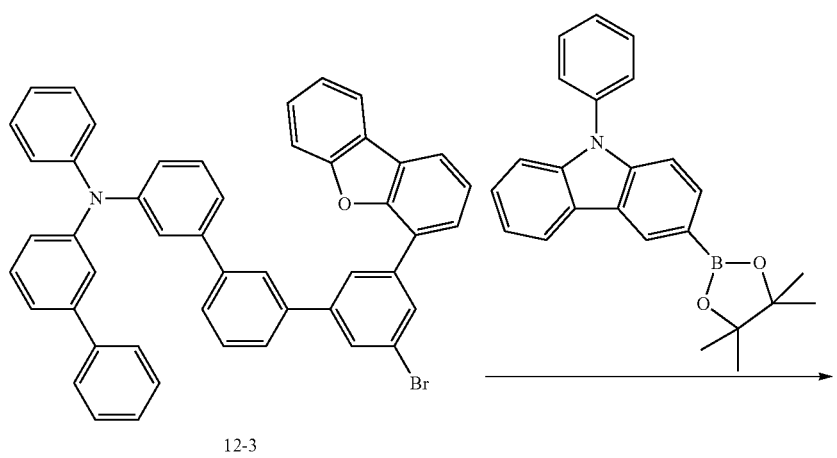

-continued

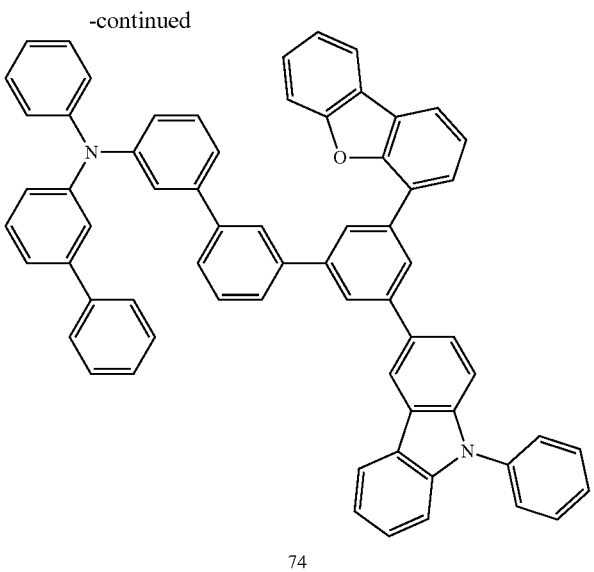

74

Synthesis of Intermediate 13-1

Intermediate 13-1 was synthesized in the same manner as used in synthesizing Intermediate 2-1, except that Starting Material 13 was used instead of Starting Material 2.

Synthesis of Intermediate 13-2

Intermediate 13-2 was synthesized in the same manner as in synthesizing Intermediate 2-2, except that Intermediate 13-1 was used instead of Intermediate 2-1.

Synthesis of Intermediate 13-3

Intermediate 13-3 was prepared in the same manner as used to synthesize Intermediate 2-3, except that Intermediate 13-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 78

Compound 78 (yield: 90.8%) was synthesized in the same manner as used to synthesize Compound 21, except that Intermediate 13-3 was used instead of Intermediate 2-3.

Synthesis Example 14

Synthesis of Compound 85

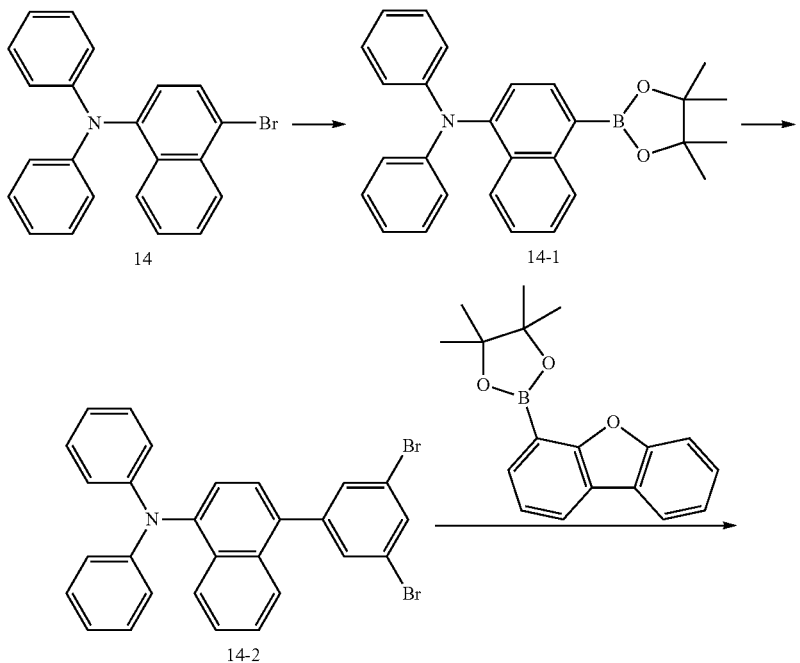

-continued

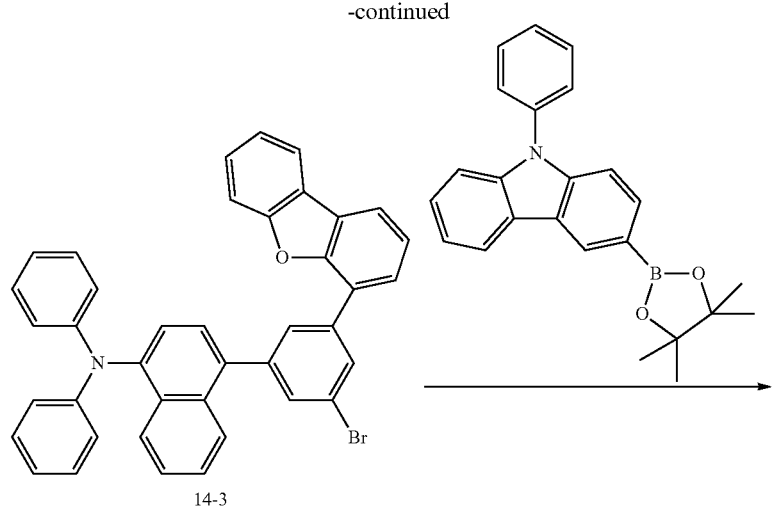

14-3

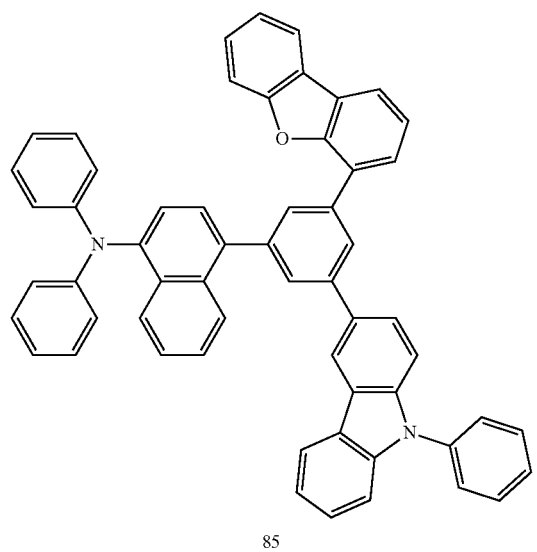

85

Synthesis of Intermediate 14-1

Intermediate 14-1 was synthesized in the same manner as used in synthesizing Intermediate 2-1, except that Starting Material 14 was used instead of Starting Material 2.

Synthesis of Intermediate 14-2

Intermediate 14-2 was synthesized in the same manner as in synthesizing Intermediate 2-2, except that Intermediate 14-1 was used instead of Intermediate 2-1.

Synthesis of Intermediate 14-3

Intermediate 14-3 was prepared in the same manner as used to synthesize Intermediate 2-3, except that Intermediate 14-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 85

Compound 85 (yield: 86.1%) was synthesized in the same manner as used to synthesize Compound 21, except that Intermediate 14-3 was used instead of Intermediate 2-3.

Synthesis Example 15
Synthesis of Compound 89
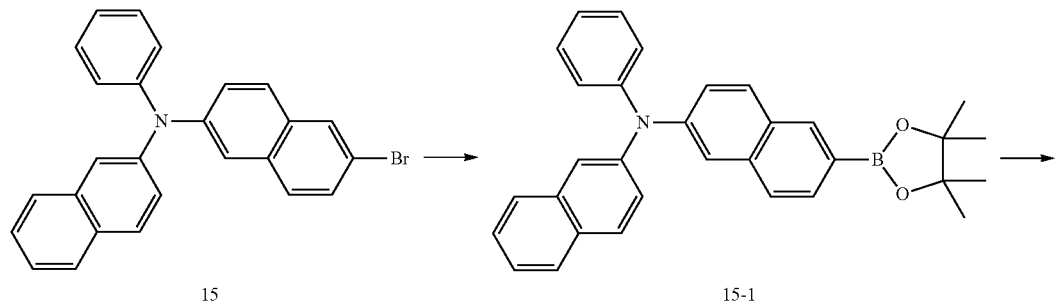
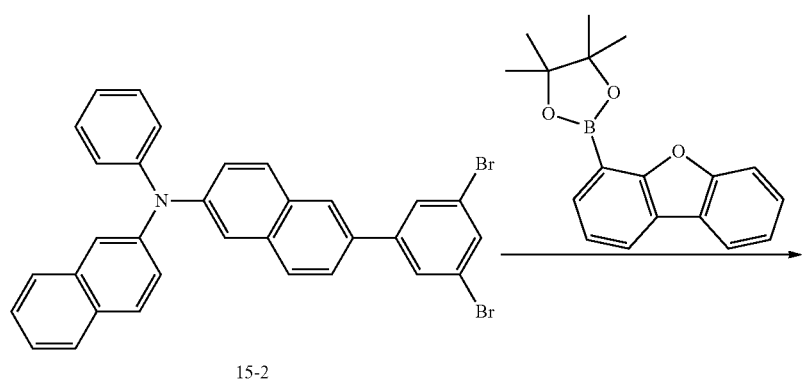
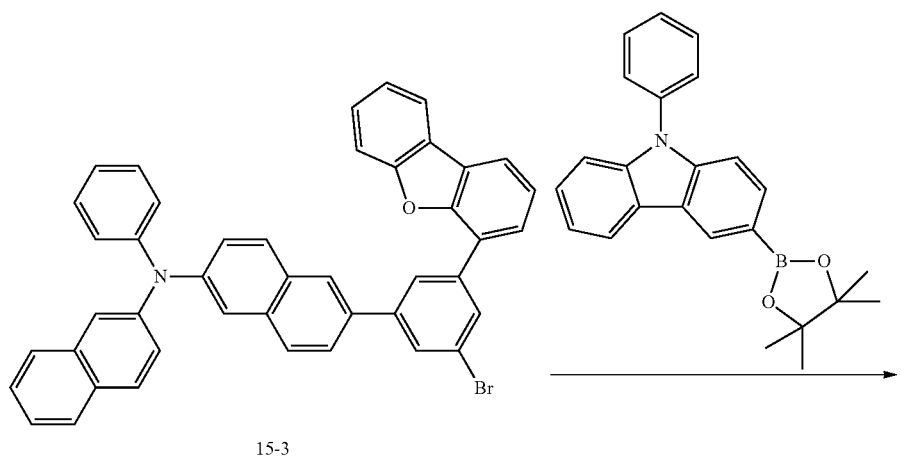

-continued

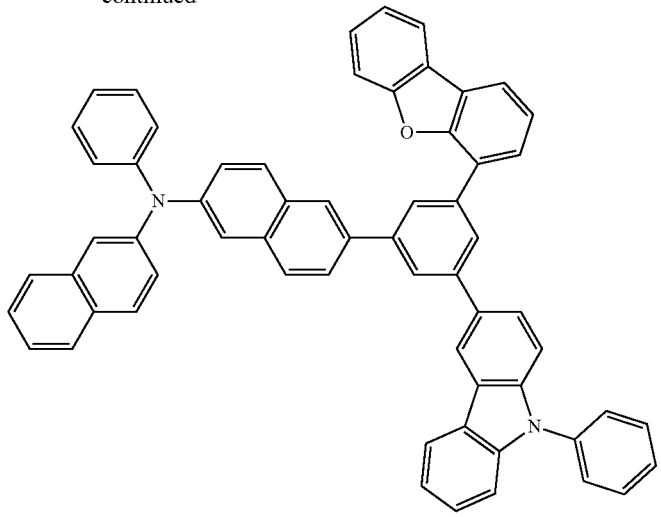

89

Synthesis of Intermediate 15-1

Intermediate 15-1 was synthesized in the same manner as used in synthesizing Intermediate 2-1, except that Starting Material 15 was used instead of Starting Material 2.

Synthesis of Intermediate 15-2

Intermediate 15-2 was synthesized in the same manner as in synthesizing Intermediate 2-2, except that Intermediate 15-1 was used instead of Intermediate 2-1.

Synthesis of Intermediate 15-3

Intermediate 15-3 was prepared in the same manner as used to synthesize Intermediate 2-3, except that Intermediate 15-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 89

Compound 89 (yield: 90.1%) was synthesized in the same manner as used to synthesize Compound 21, except that Intermediate 15-3 was used instead of Intermediate 2-3.

Synthesis Example 16

Synthesis of Compound 90

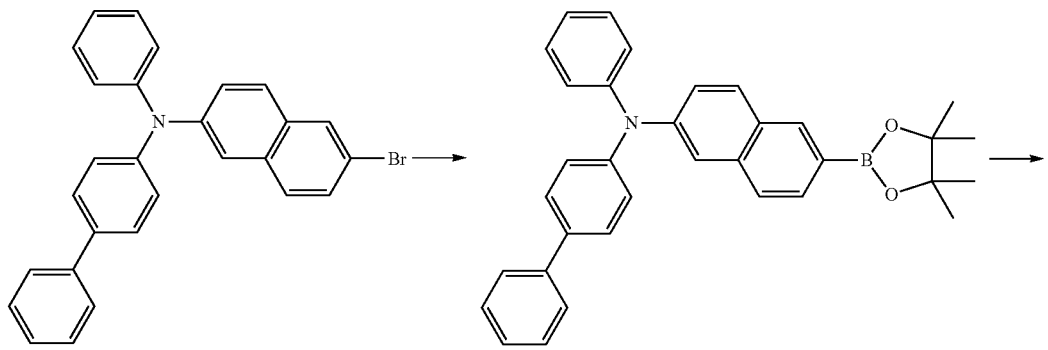

16                                    16-1

-continued

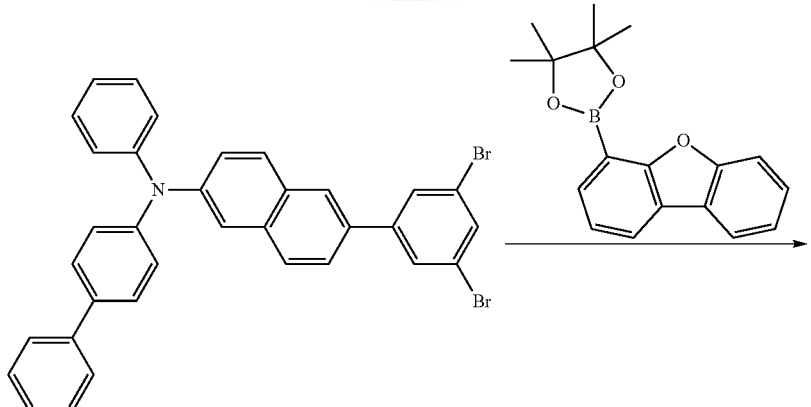

16-2

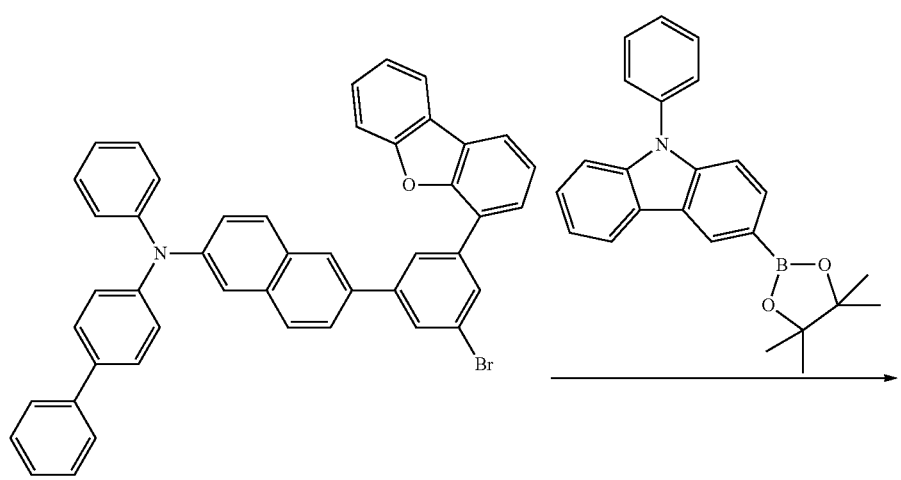

16-3

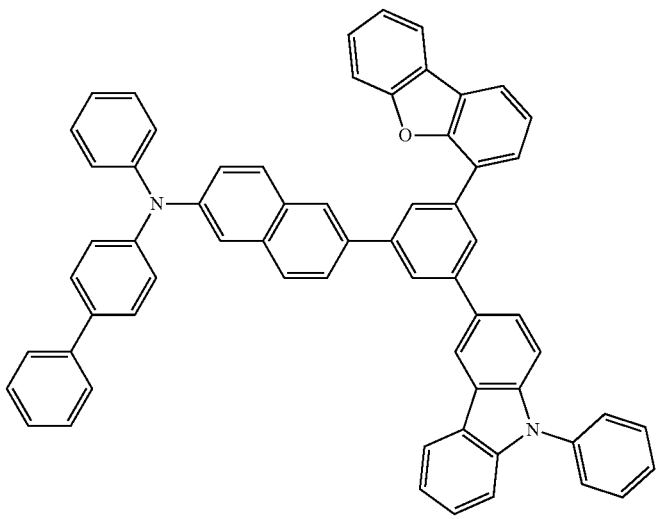

90

Synthesis of Intermediate 16-1

Intermediate 16-1 was synthesized in the same manner as used in synthesizing Intermediate 2-1, except that Starting Material 16 was used instead of Starting Material 2.

Synthesis of Intermediate 16-2

Intermediate 16-2 was synthesized in the same manner as in synthesizing Intermediate 2-2, except that Intermediate 16-1 was used instead of Intermediate 2-1.

Synthesis of Intermediate 16-3

Intermediate 16-3 was prepared in the same manner as used to synthesize Intermediate 2-3, except that Intermediate 16-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 90

Compound 90 (yield: 84.7%) was synthesized in the same manner as used to synthesize Compound 21, except that Intermediate 16-3 was used instead of Intermediate 2-3.

Synthesis Example 17

Synthesis of Compound 98

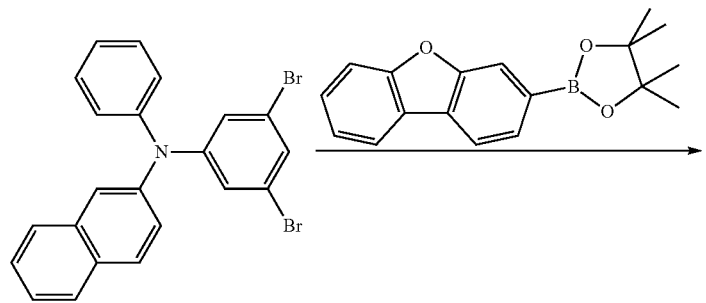

17

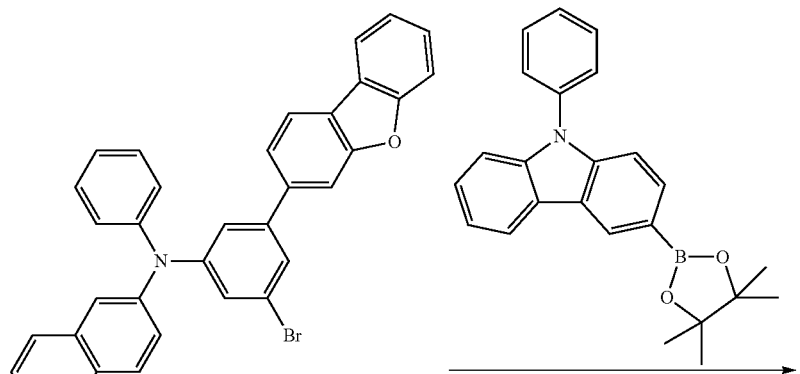

17-1

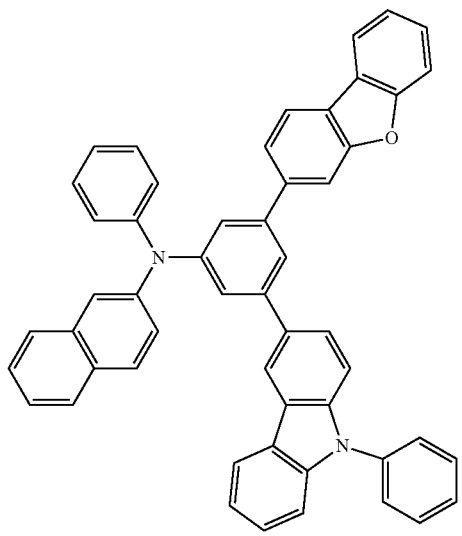

98

253
Synthesis of Intermediate 17-1

Intermediate 17-1 was prepared in the same manner as used to synthesize Intermediate 1-1, except that Starting Material 17 was used instead of Starting Material 1, and 2-(dibenzo[b,d]furan-3-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

254
Synthesis of Compound 98

Compound 98 (yield: 87.2%) was synthesized in the same manner as used to synthesize Compound 3, except that Intermediate 17-1 was used instead of Intermediate 1-1.

Synthesis Example 18

Compound 102

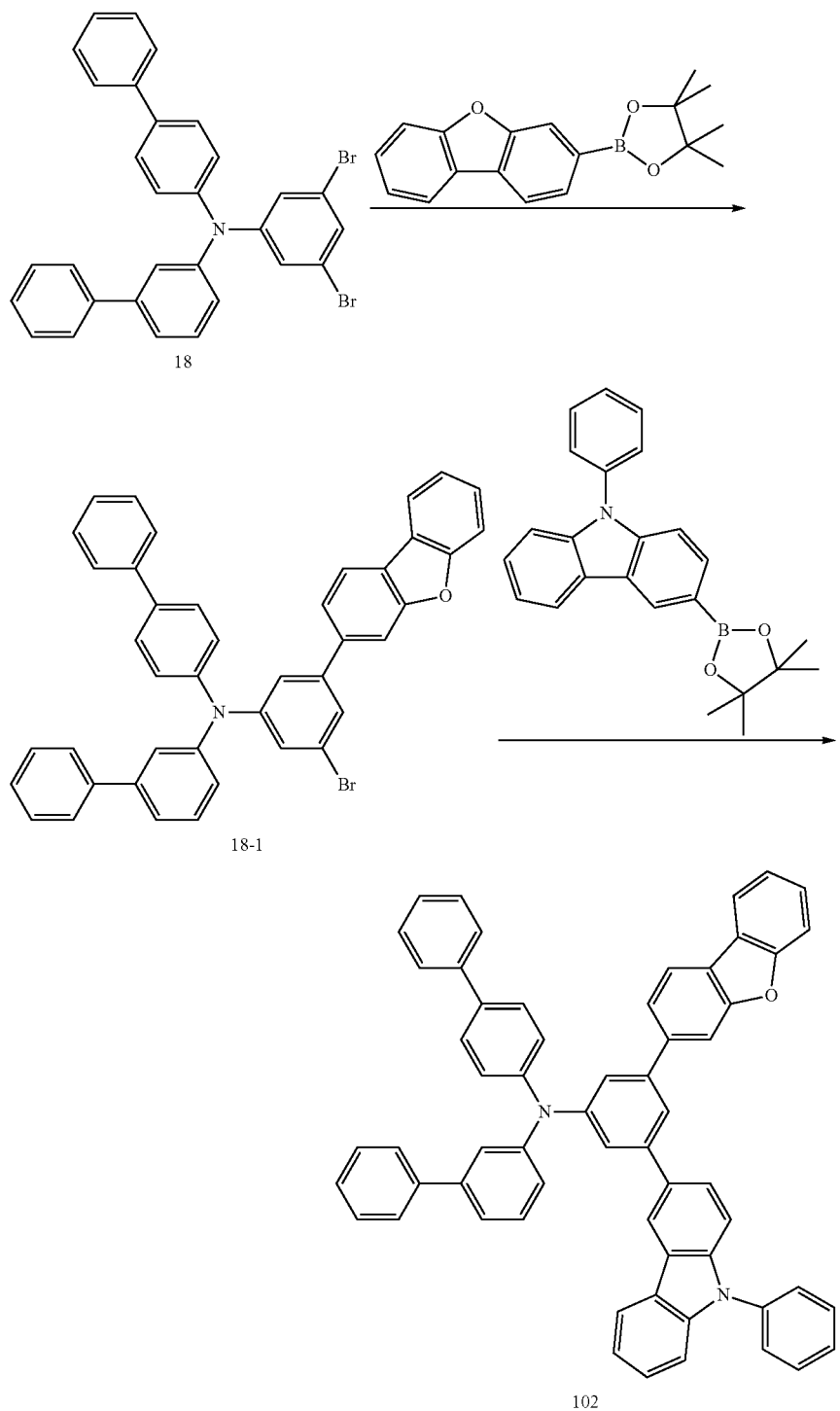

Synthesis of Intermediate 18-1

Intermediate 18-1 was prepared in the same manner as used to synthesize Intermediate 1-1, except that Starting Material 18 was used instead of Starting Material 1, and 2-(dibenzo[b,d]furan-3-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 102

Compound 102 (yield: 90.6%) was synthesized in the same manner as used to synthesize Compound 3, except that Intermediate 18-1 was used instead of Intermediate 1-1.

Synthesis Example 19

Synthesis of Compound 230

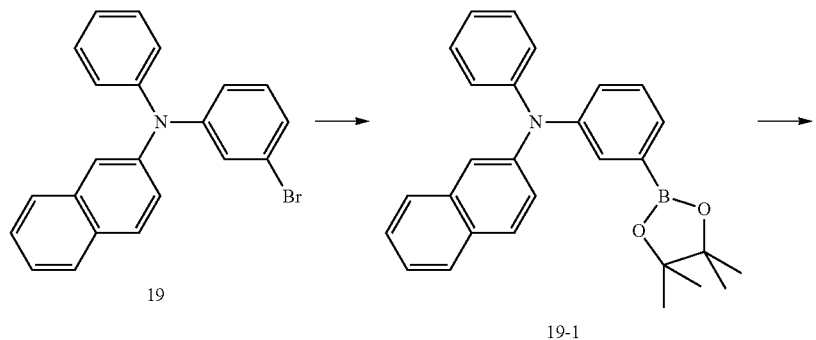

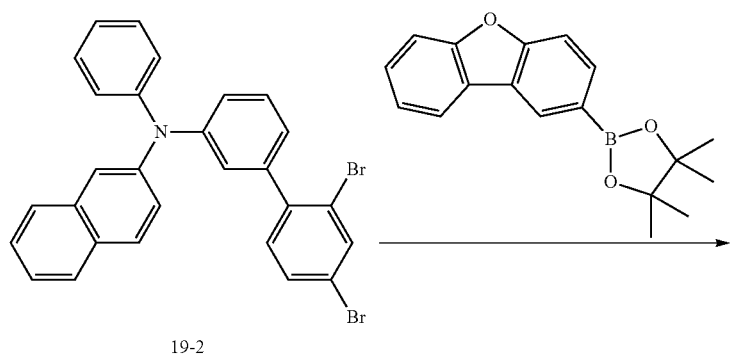

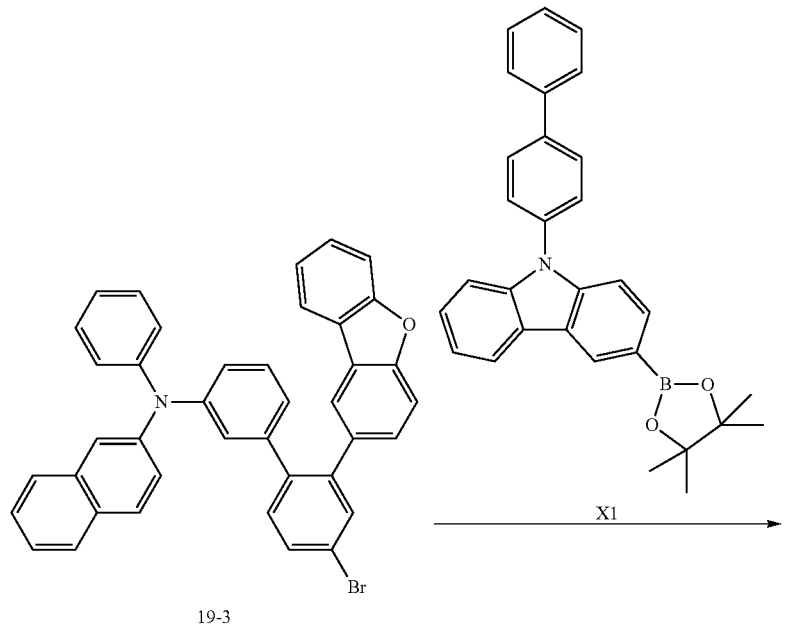

-continued

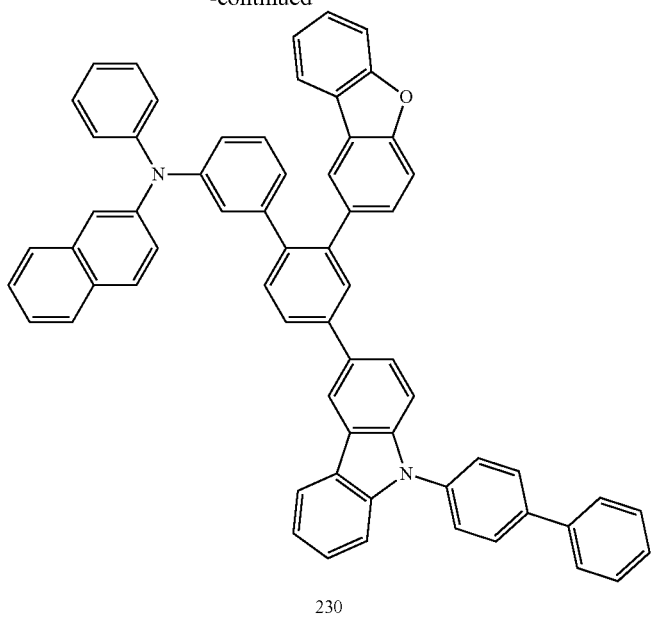

230

Synthesis of Intermediate 19-1

Intermediate 19-1 was synthesized in the same manner as used in synthesizing Intermediate 2-1, except that Starting Material 19 was used instead of Starting Material 2.

Synthesis of Intermediate 19-2

Intermediate 19-2 was synthesized in the same manner as in synthesizing Intermediate 2-2, except that Intermediate 19-1 was used instead of Intermediate 2-1, and 1,2,4-tribromobenzene was used instead of 1,3,5-tribromobenzene.

Synthesis of Intermediate 19-3

Intermediate 19-3 was synthesized in the same manner as in synthesizing Intermediate 2-3, except that Intermediate 19-2 was used instead of Intermediate 2-2.

Synthesis of Compound 230

Compound 230 (yield: 79%) was synthesized in the same manner as used to synthesize Compound 21, except that Intermediate 19-3 was used instead of Intermediate 2-3, and Compound X1 was used instead of 2-(9-phenyl-9H-carbazole-2-yl)-4,4,5,5-tetramethyl-1,3,2-dioxaborane.

Synthesis Example 20

Synthesis of Compound 244

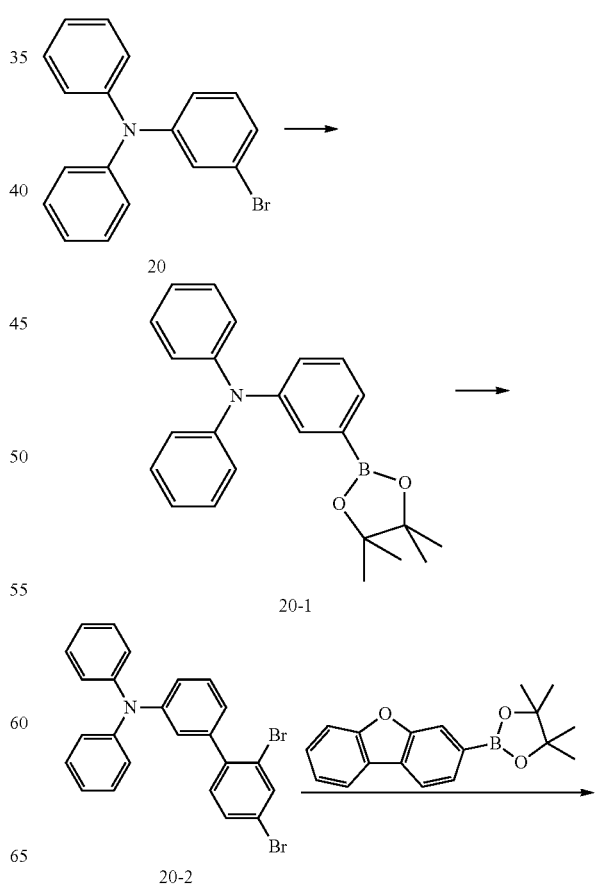

-continued

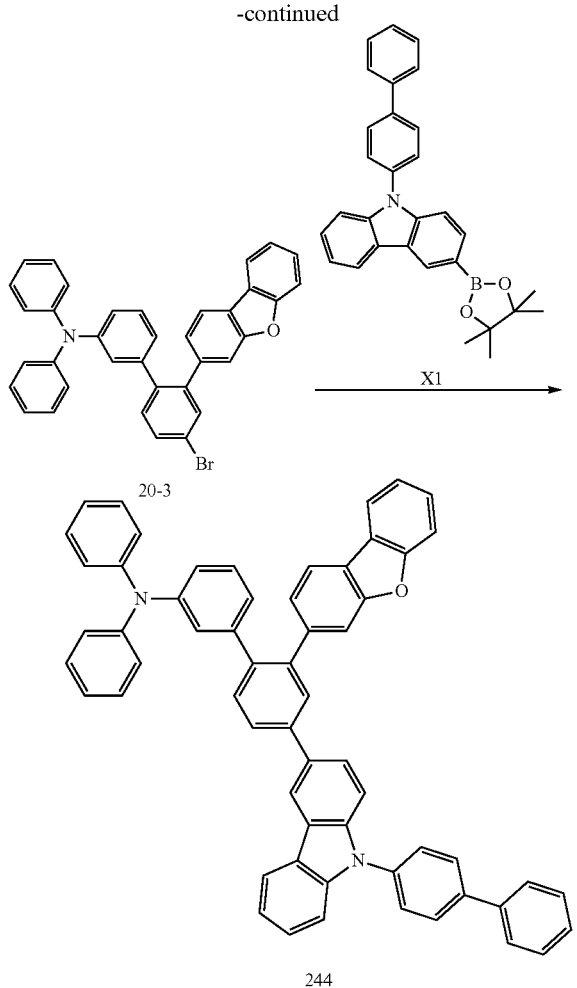

Synthesis of Intermediate 20-1

Intermediate 20-1 was synthesized in the same manner as used in synthesizing Intermediate 2-1, except that Starting Material 20 was used instead of Starting Material 2.

Synthesis of Intermediate 20-2

Intermediate 20-2 was synthesized in the same manner as in synthesizing Intermediate 2-2, except that Intermediate 20-1 was used instead of Intermediate 2-1, and 1,2,4-tribromobenzene was used instead of 1,3,5-tribromobenzene.

Synthesis of Intermediate 20-3

Intermediate 20-3 was prepared in the same manner as used to synthesize Intermediate 2-3, except that Intermediate 20-2 was used instead of Intermediate 2-2, and 2-(dibenzo[b,d]furan-3-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 244

Compound 244 (yield: 81%) was synthesized in the same manner as used to synthesize Compound 21, except that Intermediate 20-3 was used instead of Intermediate 2-3, and Compound X1 was used instead of 2-(9-phenyl-9H-carbazole-2-yl)-4,4,5,5-tetramethyl-1,3,2-dioxaborane.

Synthesis Example 21

Synthesis of Compound 271

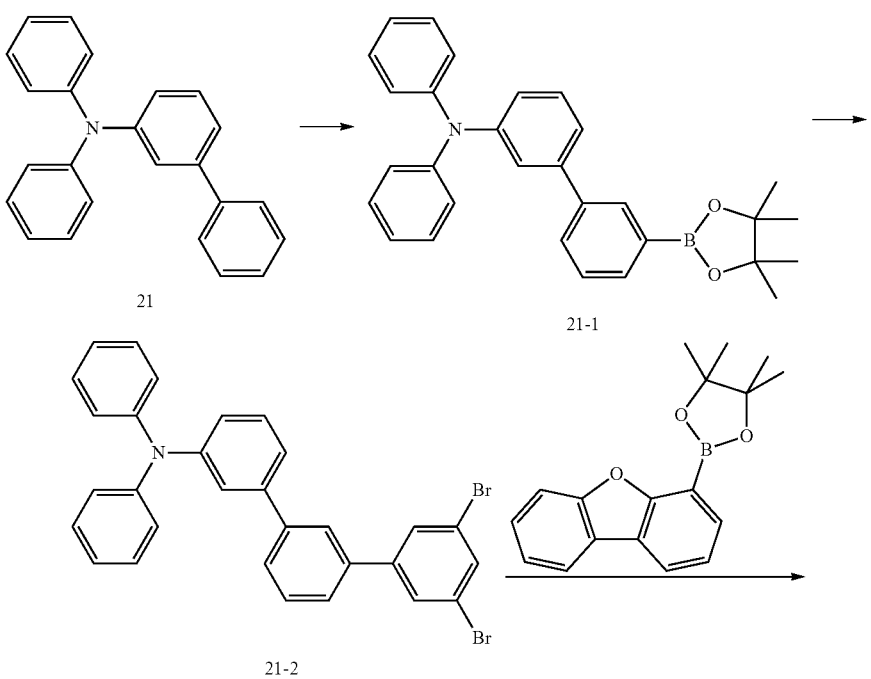

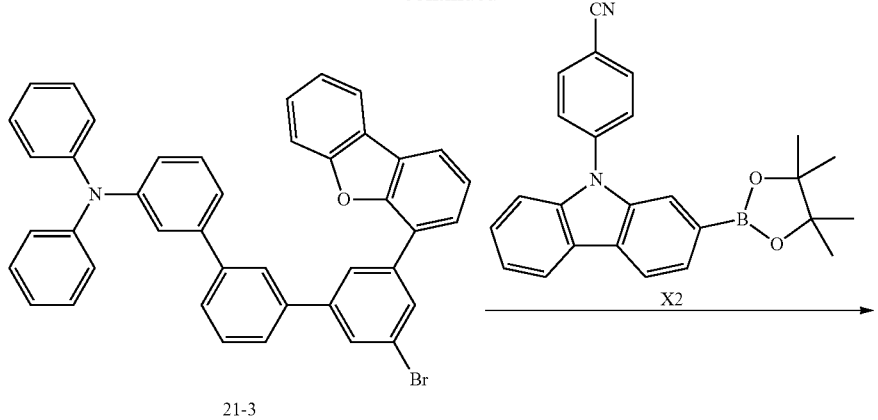

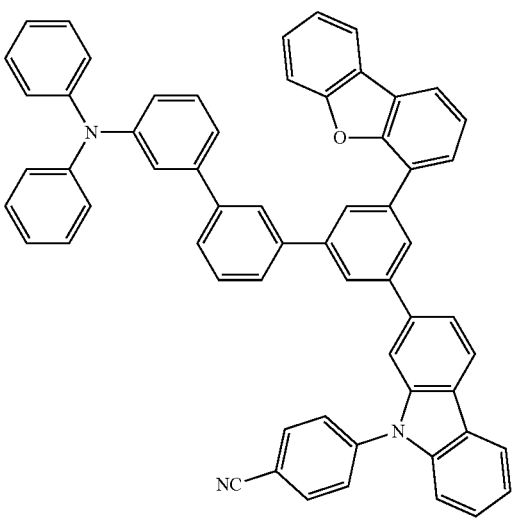

Synthesis of Intermediate 21-1

Intermediate 20-1 was synthesized in the same manner as used in synthesizing Intermediate 2-1, except that Starting Material 21 was used instead of Starting Material 2.

Synthesis of Intermediate 21-2

Intermediate 21-2 was synthesized in the same manner as in synthesizing Intermediate 2-2, except that Intermediate 21-1 was used instead of Intermediate 2-1, and 1,2,4-tribromobenzene was used instead of 1,3,5-tribromobenzene.

Synthesis of Intermediate 21-3

Intermediate 21-3 was prepared in the same manner as used to synthesize Intermediate 2-3, except that Intermediate 21-2 was used instead of Intermediate 2-2, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 271

Compound 271 (yield: 83%) was synthesized in the same manner as used to synthesize Compound 21, except that Intermediate 21-3 was used instead of Intermediate 2-3, and Compound X2 was used instead of 2-(9-phenyl-9H-carbazole-2-yl)-4,4,5,5-tetramethyl-1,3,2-dioxaborane.

Synthesis Example 22
Synthesis of Compound 289
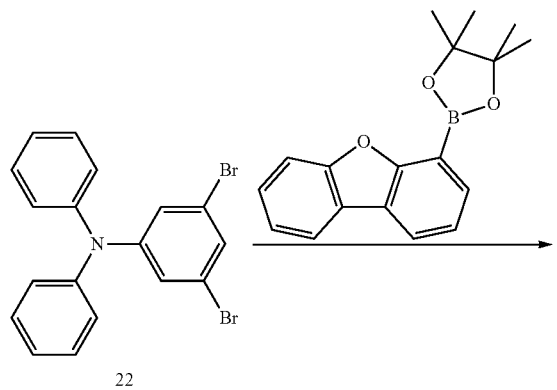
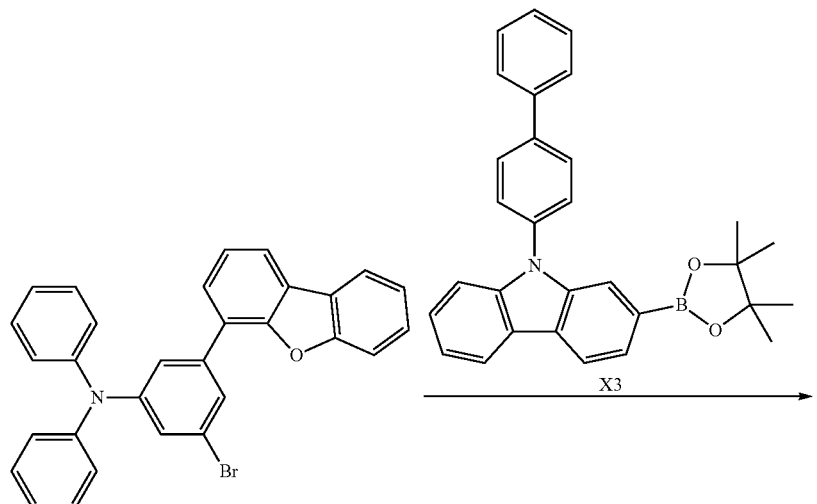
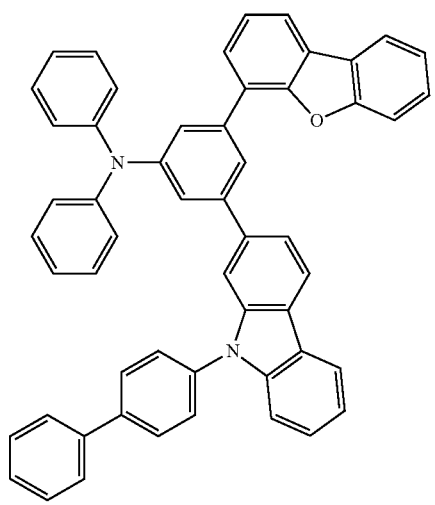

265

Synthesis of Intermediate 22-1

Intermediate 22-1 was prepared in the same manner as used to synthesize Intermediate 1-1, except that Starting Material 22 was used instead of Starting Material 1, and 2-(dibenzo[b,d]furan-4-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

266

Synthesis of Compound 289

Compound 289 (yield: 87%) was synthesized in the same manner as used to synthesize Compound 3, except that Intermediate 22-1 was used instead of Intermediate 1-1, and Compound X3 was used instead of 2-(9-phenyl-9H-carbazole-2-yl)-4,4,5,5-tetramethyl-1,3,2-dioxaborane.

Synthesis Example 23

Synthesis of Compound 299

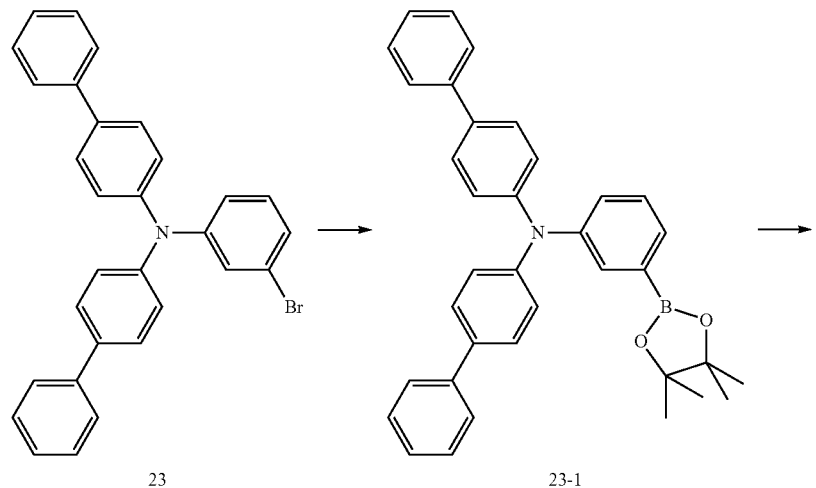

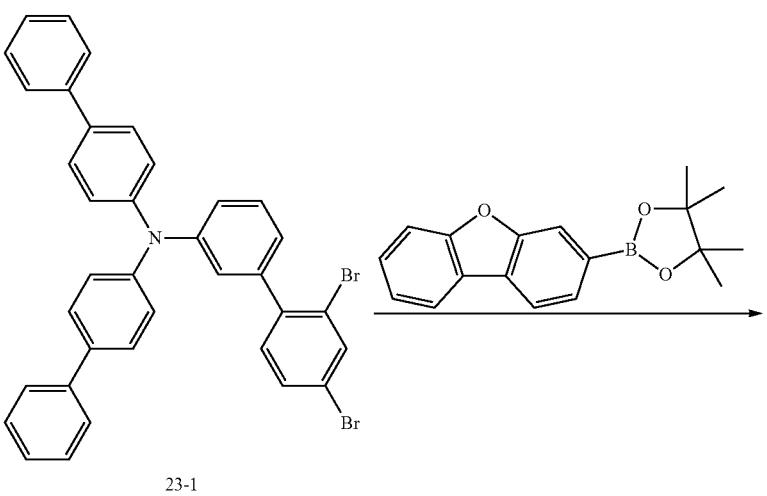

-continued

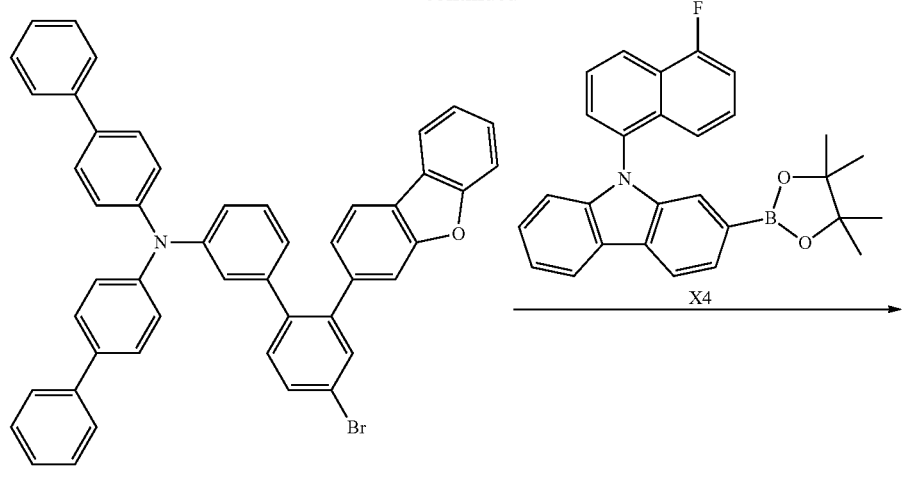

23-3

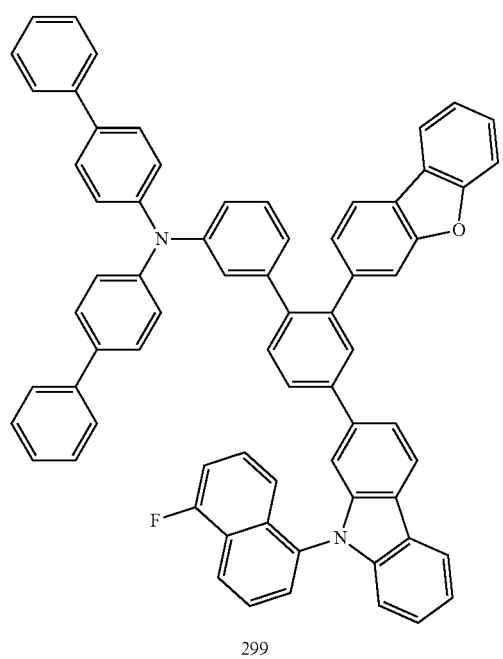 [SMILES: Fc1cccc2c(-n3c4ccccc4c4ccc(-c5ccc(-c6cccc(N(c7ccc(-c8ccccc8)cc7)c7ccc(-c8ccccc8)cc7)c6)c(-c6ccc7c(c6)oc6ccccc67)c5)cc43)cccc12]

299

Synthesis of Intermediate 23-1

Intermediate 23-1 was synthesized in the same manner as used in synthesizing Intermediate 2-1, except that Starting Material 23 was used instead of Starting Material 2.

Synthesis of Intermediate 23-2

Intermediate 23-2 was synthesized in the same manner as in synthesizing Intermediate 2-2, except that Intermediate 23-1 was used instead of Intermediate 2-1, and 1,2,4-tribromobenzene was used instead of 1,3,5-tribromobenzene.

Synthesis of Intermediate 23-3

Intermediate 23-3 was prepared in the same manner as used to synthesize Intermediate 2-3, except that Intermediate 23-2 was used instead of Intermediate 2-2, and 2-(dibenzo[b,d]furan-3-yl)-4,4,5,5,-tetramethyl-1,3,2-dioxaborane was used instead of 2-(dibenzo[b,d]furan-2-yl)-4,4,5,5,-tetramethyl-1,3,2-dioxaborane.

Synthesis of Compound 299

Compound 299 (yield: 71%) was synthesized in the same manner as used to synthesize Compound 21, except that Intermediate 23-3 was used instead of Intermediate 2-3, and Compound X4 was used instead of 2-(9-phenyl-9H-carbazole-2-yl)-4,4,5,5-tetramethyl-1,3,2-dioxaborane.

The compounds synthesized according to Synthesis Examples 1-23 were confirmed by $^1$H NMR and MS/FAB. Results thereof are shown in Table 1 below.

TABLE 1

| Compound | $^1$H NMR (CDCl$_3$, 400 MHz) | MS/FAB found | MS/FAB calc. |
|---|---|---|---|
| Compound 3 | 8.21 (d, 1H), 8.03 (s, 1H), 7.95 (t, 1H), 7.91 (d, 1H), 7.84 (d, 1H), 7.77 (d, 1H), 7.64 (d.1H), 7.53 (m, 2H), 7.32 (m, 1H), 7.26 (m, 2H), 7.05 (m, 2H), 6.83 (t, 1H), 6.64 (m, 2H), 6.32 (m, 1H), 5.85 (m, 1H), 3.21 (t, 1H) | 702.23 | 702.86 |
| Compound 21 | 8.21 (d, 1H), 8.09 (s, 1H), 7.87 (t, 2H), 7.81 (m, 1H), 7.74 (m, 1H), 7.61 (m, 1H), 7.56 (m, 3H), 7.39 (m, 3H), 7.23 (m, 5H), 7.15 (m, 2H), 7.02 (t, 1H), 6.94 (t, 1H), 6.74 (m, 1H), 6.62 (m, 1H), 6.45 (m, 1H), 6.23 (m, 2H), 5.87 (m, 2H), 3.16 (m, 2H) | 854.32 | 855.05 |
| Compound 29 | 8.22 (d, 1H), 8.02 (s, 1H), 7.75 (t, 1H), 7.54 (m, 1H), 7.35 (m, 4H), 7.09 (m, 5H), 6.91 (m, 1H), 6.74 (m, 2H), 6.2 (m, 2H), 5.8 (m, 2H), 3.21 (m, 2H) | 957.15 | 956.38 |
| Compound 40 | 8.210 (d, 1H), 8.07 (s, 1H), 7.91 (t, 1H), 7.83 (m, 3H), 7.62 (m, 3H), 7.57 (t, 1H), 7.51 (m, 5H), 7.32 (m, 5H), 7.23 (m, 1H), 7.03 (m, 5H), 6.93 (m, 1H), 6.64 (m, 2H), 6.32 (d, 2H), 6.22 (d, 1H), 6.12 (m, 5H), 3.84 (s, 1H), 3.67 (d, 1H) | 778.95 | 778.30 |
| Compound 49 | 8.27 (d, 1H), 8.10 (s, 1H), 7.97 (t, 1H), 7.90 (d, 1H), 7.81 (d, 1H), 7.68 (m, 3H)7.57 (d, 1H), 7.53 (t, 1H), 7.48 (m, 5H), 7.25 (m, 7H), 7.28 (m, 1H), 7.05 (m, 4H), 6.95 (d, 2H), 6.62 (m, 2H), 6.23 (m, 4H) | 639.23 | 639.78 |
| Compound 56 | 8.25 (d, 1H), 8.14 (s, 1H), 8.08 (t, 1H)7.98 (t, 1H), 7.89 (d, 1H), 7.88 (s, 1H), 7.84 (m, 2H), 7.79 (t, 1H), 7.77 (d, 1H), 7.74 (t, 1H), 7.72 (d, 1H), 7.55 (m, 7H), 7.31 (m, 5H), 7.19 (d, 1H), 7.13 (m, 1H), 7.04 (m, 2H), 6.63 (t, 1H), 6.58 (m, 2H), 6.24 (m, 2H) | 778.30 | 778.95 |
| Compound 57 | 8.24 (d, 1H), 8.14 (s, 1H), 8.08 (t, 1H), 7.82 (m, 6H), 7.59 (d, 1H), 7.49 (m, 7H), 7.30 (m, 3H), 7.19 (d, 1H), 7.30 (m, 4H), 6.87 (m, 3H), 6.65 (t, 2H), 6.15 (m, 2H) | 728.23 | 728.89 |
| Compound 59 | 8.24 (d, 1H), 8.14 (s, 1H), 8.08 (t, 1H), 7.98 (t, 1H), 7.89 (d, 1H), 7.84 (t, 1H), 7.74 (m, 3H), 7.45 (m, 12H), 7.32 (m, 6H), 7.19 (d, 1H), 6.82 (m, 4H), 6.66 (m, 2H) | 880.37 | 881.09 |
| Compound 62 | 8.23 (d, 1H), 8.13 (s, 1H), 7.95 (t, 1H), 7.92 (d, 1H), 7.88 (d, 1H), 7.83 (t, 2H), 7.74 (d, 1H), 7.71 (s, 1H), 7.66 (m, 12H), 7.31 (m, 7H), 7.09 (m, 4H), 7.00 (s, 1H), 6.66 (t, 1H), 6.20 (m, 3H) | 778.24 | 778.95 |
| Compound 63 | 8.23 (d, 1H), 8.13 (s, 1H), 7.94 (t, 1H), 7.91 (d, 1H), 7.88 (d, 1H), 7.73 (t, 2H), 7.54 (d, 1H), 7.70 (s, 1H), 7.62 (m, 12H), 7.29 (m, 7H), 7.01 (m, 4H), 6.92 (s, 1H), 6.61 (t, 1H), 6.24 (m, 3H) | 778.28 | 778.95 |
| Compound 70 | 8.24 (d, 1H), 8.14 (s, 1H), 8.08 (s, 1H), 7.89 (d, 1H), 7.82 (m, 3H), 7.74 (m, 2H), 7.65 (m, 2H), 6.55 (m, 14H), 7.2 (m, 4H), 7.19 (d, 1H), 7.06 (t, 1H), 6.84 (m, 2H), 6.65 (s, 1H), 6.21 (m, 2H) | 880.31 | 881.09 |
| Compound 74 | 8.22 (d, 1H), 8.13 (s, 1H), 8.05 (s, 1H), 7.91 (d, 1H), 7.81 (m, 3H), 7.74 (d, 1H), 7.59 (m, 2H), 7.50 (m, 6H), 7.09 (m, 4H), 6.97 (s, 1H), 6.75 (d, 1H), 6.64 (t, 1H), 6.41 (d, 1H), 6.18 (m, 2H), 5.82 (m, 2H), 3.15 (d, 1H) | 854.33 | 855.05 |
| Compound 78 | 8.22 (d, 1H), 8.12 (s, 1H), 8.02 (s, 1H), 7.89 (d, 1H), 7.80 (m, 3H), 7.69 (d, 1H), 7.54 (m, 2H), 7.47 (m, 6H), 7.09 (m, 4H), 6.91 (s, 1H), 6.82 (d, 1H), 6.74 (t, 1H), 6.52 (d, 1H), 6.24 (m, 2H), 5.71 (m, 2H), 3.17 (d, 1H) | 880.32 | 881.09 |
| Compound 85 | 8.22 (d, 1H), 8.17 (s, 1H), 8.14 (s, 1H), 8.02 (d, 1H), 7.84 (m, 6H), 7.78 (d, 1H), 7.74 (d, 1H), 7.66 (t, 1H), 7.57 (d, 1H), 7.51 (m, 6H), 7.43 (d, 1H), 7.35 (t, 1H), 7.27 (m, 3H), 7.19 (d, 1H), 7.01 (m, 5H), 6.63 (m, 2H), 6.05 (m, 4H) | 778.29 | 778.95 |
| Compound 89 | 8.22 (d, 1H), 8.10 (s, 1H), 7.92 (s, 1H), 7.91 (d, 1H), 7.88 (m, 2H), 7.86 (d, 2H), 7.84 (d, 2H), 7.82 (m, 2H), 7.80 (d, 1H), 7.72 (m, 2H), 7.51 (m, 12H), 7.31 (m, 6H), 7.19 (d, 1H), 7.16 (d, 1H), 7.07 (m, 3H), 6.98 (d, 1H), 6.65 (t, 1H), 6.37 (d, 1H), 6.25 (m, 1H), 3.89 (s, 1H) | 828.21 | 829.01 |
| Compound 90 | 8.89 (d, 1H), 8.61 (s, 1H), 8.46 (s, 1H), 8.21 (m, 2H), 7.90 (m, 3H), 7.77 (m, 4H), 7.52 (m, 6H), 7.32 (m, 6H), 7.21 (d, 1H), 7.05 (m, 4H), 6.89 (m, 4H), 6.65 (m, 2H), 6.16 (m, 4H) | 841.82 | 842.03 |
| Compound 98 | 8.23 (d, 1H), 8.15 (s, 1H), 8.06 (s, 1H), 7.94 (d, 1H), 7.86 (d, 1H), 7.84 (s, 1H), 7.80 (s, 1H), 7.69 (m, 2H), 7.57 (d, 1H), 7.55 (t, 1H), 7.51 (m, 4H), 7.47 (m, 4H), 7.38 (m, 5H), 7.29 (m, 2H), 7.20 (m, 2H), 7.08 (m, 2H), 6.98 (s, 1H), 6.85 (m, 2H), 6.67 (t, 1H), 6.27 (d, 2H) | 702.67 | 702.86 |
| Compound 102 | 8.24 (d, 1H), 8.15 (s, 1H), 8.06 (s, 1H), 7.97 (d, 1H), 7.84 (d, 1H), 7.71 (s, 1H), 7.69 (m, 2H), 7.56 (m, 4H), 7.50 (m, 4H), 7.48 (m, 6H), 7.45 (m, 4H), 7.38 (m, 6H), 7.30 (m, 3H), 7.23 (t, 1H), 7.19 (m, 4H), 7.04 (t, 1H), 6.98 (s, 1H), 6.93 (s, 1H), 6.84 (s, 1H), 6.61 (m, 2H), 5.98 (d, 1H) | 804.40 | 804.99 |
| Compound 230 | 8.24 (d, 1H), 8.14 (s, 1H), 8.06 (s, 1H), 7.92 (d, 1H), 7.84 (s, 1H), 7.76 (s, 1H), 7.61 (m, 2H), 7.55 (d, 1H), 7.53 (t, 1H), 7.51 (m, 4H), 7.41 (m, 9H), 7.28 (m, 2H), 7.20 (m, 2H), 7.06 (m, 2H), 6.95 (s, 1H), 6.84 (m, 2H), 6.66 (t, 1H), 6.36 (d, 2H) | 855.33 | 855.05 |
| Compound 244 | 8.24 (d, 1H), 8.13 (s, 1H), 8.08 (t, 1H), 7.86 (t, 1H), 7.88 (d, 1H), 7.83 (t, 1H), 7.74 (m, 3H), 7.41 (m, 11H), 7.31 (m, 6H), 7.21 (d, 1H), 6.79 (m, 4H), 6.55 (m, 2H) | 855.31 | 855.05 |

TABLE 1-continued

| Compound | $^{1}$H NMR (CDCl$_3$, 400 MHz) | MS/FAB found | MS/FAB calc. |
|---|---|---|---|
| Compound 271 | 8.23 (d, 1H), 8.14 (s, 1H), 8.07 (s, 1H), 7.89 (d, 1H), 7.81 (m, 3H), 7.74 (m, 2H), 7.65 (m, 2H), 6.49 (m, 14H), 7.12 (m, 4H), 7.18 (d, 1H), 7.06 (t, 1H), 6.83 (m, 2H), 6.61 (s, 1H), 6.20 (m, 2H) | 830.31 | 830.00 |
| Compound 289 | 8.23 (d, 1H), 8.13 (s, 1H), 7.94 (t, 1H), 7.91 (d, 1H), 7.88 (d, 1H), 7.83 (t, 2H), 7.71 (d, 1H), 7.68 (s, 1H), 7.62 (m, 6H), 7.29 (m, 3H), 7.10 (m, 4H), 7.04 (s, 1H), 6.63 (t, 1H), 6.17 (m, 2H) | 728.28 | 728.89 |
| Compound 299 | 8.23 (d, 1H), 8.13 (s, 1H), 8.07 (s, 1H), 7.89 (d, 1H), 7.86 (m, 3H), 7.84 (m, 2H), 7.69 (m, 2H), 7.49 (m, 12H), 7.11 (m, 6H), 7.18 (d, 1H), 7.05 (t, 1H), 6.61 (s, 1H), 6.20 (m, 2H) | 948.36 | 948.15 |

Example 1

An ITO glass substrate (a product of Corning Co., Ltd) having a sheet resistance of 15 Ω/cm$^2$ and thickness of 1,200 Å was cut to a size of 50 mm×50 mm×0.7 mm, and then, sonicated by using isopropyl alcohol and pure water each for 5 minutes, and cleaned by the exposure to ultraviolet rays for 30 minutes, and then ozone, and the ITO glass substrate was mounted on a vacuum deposition apparatus.

2-TNATA was deposited on the ITO anode substrate to form an hole injection layer having a thickness of 600 Å, and then, Compound 3 was deposited on the hole injection layer to form a hole transport layer having a thickness of 300 Å.

9,10-di(naphthalen-2-yl)anthracene (ADN) (as a host) and N,N,N',N'-tetraphenyl-pyrene-1,6-diamine (TPD) (as a dopant) were co-deposited on the hole transport layer at a weight ratio of 98:2 to form an emission layer having a thickness of 300 Å.

Thereafter, Alq$_3$ was deposited on the emission layer to form an electron transport layer having a thickness of 300 Å, and LiF was deposited on the electron transport layer to form an electron injection layer having a thickness of 10 Å, and Al was deposited on the electron injection layer to form a cathode having a thickness of 3,000 Å, thereby completing the manufacture of an organic light-emitting device.

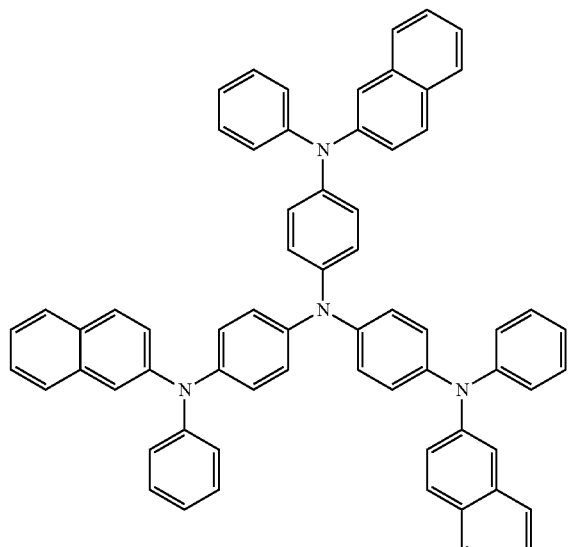

2-TNATA

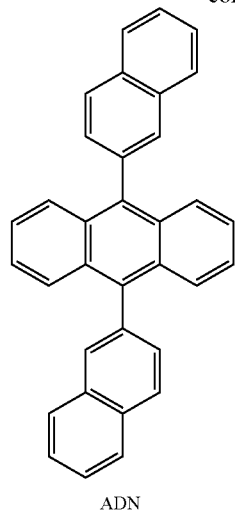

ADN

TPD

Example 2

An organic light-emitting device was manufactured in the same manner as in Example 1, except that in forming the hole transport layer, Compound 21 was used instead of Compound 3.

Example 3

An organic light-emitting device was manufactured in the same manner as in Example 1, except that in forming the hole transport layer, Compound 29 was used instead of Compound 3.

Example 4

An organic light-emitting device was manufactured in the same manner as in Example 1, except that in forming the hole transport layer, Compound 40 was used instead of Compound 3.

Example 5

An organic light-emitting device was manufactured in the same manner as in Example 1, except that in forming the hole transport layer, Compound 49 was used instead of Compound 3.

Example 6

An organic light-emitting device was manufactured in the same manner as in Example 1, except that in forming the hole transport layer, Compound 56 was used instead of Compound 3.

Example 7

An organic light-emitting device was manufactured in the same manner as in Example 1, except that in forming the hole transport layer, Compound 57 was used instead of Compound 3.

Example 8

An organic light-emitting device was manufactured in the same manner as in Example 1, except that in forming the hole transport layer, Compound 59 was used instead of Compound 3.

Example 9

An organic light-emitting device was manufactured in the same manner as in Example 1, except that in forming the hole transport layer, Compound 62 was used instead of Compound 3.

Example 10

An organic light-emitting device was manufactured in the same manner as in Example 1, except that in forming the hole transport layer, Compound 63 was used instead of Compound 3.

Example 11

An organic light-emitting device was manufactured in the same manner as in Example 1, except that in foaming the hole transport layer, Compound 70 was used instead of Compound 3.

Example 12

An organic light-emitting device was manufactured in the same manner as in Example 1, except that in forming the hole transport layer, Compound 74 was used instead of Compound 3.

Example 13

An organic light-emitting device was manufactured in the same manner as in Example 1, except that in forming the hole transport layer, Compound 78 was used instead of Compound 3.

Example 14

An organic light-emitting device was manufactured in the same manner as in Example 1, except that in forming the hole transport layer, Compound 85 was used instead of Compound 3.

Example 15

An organic light-emitting device was manufactured in the same manner as in Example 1, except that in forming the hole transport layer, Compound 89 was used instead of Compound 3.

Example 16

An organic light-emitting device was manufactured in the same manner as in Example 1, except that in forming the hole transport layer, Compound 90 was used instead of Compound 3.

Example 17

An organic light-emitting device was manufactured in the same manner as in Example 1, except that in forming the hole transport layer, Compound 98 was used instead of Compound 3.

Example 18

An organic light-emitting device was manufactured in the same manner as in Example 1, except that in forming the hole transport layer, Compound 102 was used instead of Compound 3.

Example 19

An organic light-emitting device was manufactured in the same manner as in Example 1, except that in forming the hole transport layer, Compound 230 was used instead of Compound 3.

Example 20

An organic light-emitting device was manufactured in the same manner as in Example 1, except that in forming the hole transport layer, Compound 244 was used instead of Compound 3.

Example 21

An organic light-emitting device was manufactured in the same manner as in Example 1, except that in forming the hole transport layer, Compound 271 was used instead of Compound 3.

Example 22

An organic light-emitting device was manufactured in the same manner as in Example 1, except that in forming the hole transport layer, Compound 289 was used instead of Compound 3.

Example 23

An organic light-emitting device was manufactured in the same manner as in Example 1, except that in forming the hole transport layer, Compound 299 was used instead of Compound 3.

Comparative Example 1

An organic light-emitting device was manufactured in the same manner as in Example 1, except that in forming the hole transport layer, NPB was used instead of Compound 3.

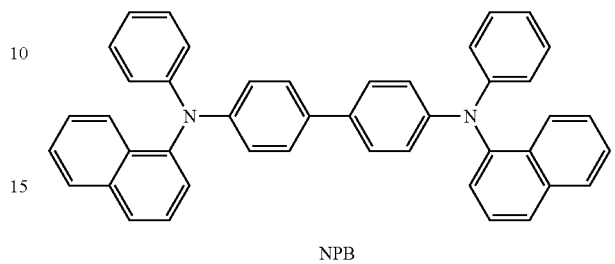

NPB

Evaluation Example 1

The driving voltage, current density, brightness, efficiency, and half-lifespan of the organic light-emitting devices manufactured according to Examples 1 to 23 and Comparative Example 1 were measured by using Kethley SMU 236 and a brightness photometer PR650, and results thereof are shown in Table 2. The half-lifespan is a period of time that lapses until the brightness of the organic light-emitting device was 50% of initial brightness.

TABLE 2

| | Hole transport layer Material | Driving voltage (V) | Current density (mA/cm$^2$) | Brightness (cd/m$^2$) | Efficiency (cd/A) | Emission color | Half lifespan (hr @100 mA/cm$^2$) |
|---|---|---|---|---|---|---|---|
| Example 1 | Compound 3 | 5.38 | 50 | 3580 | 6.16 | Blue | 345 |
| Example 2 | Compound 21 | 5.55 | 50 | 3895 | 6.17 | Blue | 328 |
| Example 3 | Compound 29 | 5.80 | 50 | 3342 | 6.26 | Blue | 312 |
| Example 4 | Compound 40 | 5.45 | 50 | 3568 | 6.19 | Blue | 320 |
| Example 5 | Compound 49 | 5.74 | 50 | 3680 | 6.42 | Blue | 345 |
| Example 6 | Compound 56 | 5.32 | 50 | 3670 | 6.22 | Blue | 325 |
| Example 7 | Compound 57 | 5.23 | 50 | 3220 | 6.44 | Blue | 335 |
| Example 8 | Compound 59 | 5.40 | 50 | 3450 | 6.50 | Blue | 340 |
| Example 9 | Compound 62 | 5.12 | 50 | 3330 | 6.56 | Blue | 355 |
| Example 10 | Compound 63 | 5.20 | 50 | 3230 | 6.66 | Blue | 330 |
| Example 11 | Compound 70 | 5.21 | 50 | 3320 | 6.44 | Blue | 350 |
| Example 12 | Compound 74 | 5.15 | 50 | 3575 | 6.43 | Blue | 340 |
| Example 13 | Compound 78 | 5.51 | 50 | 3470 | 6.44 | Blue | 355 |
| Example 14 | Compound 85 | 5.23 | 50 | 3348 | 6.50 | Blue | 320 |
| Example 15 | Compound 89 | 5.43 | 50 | 3670 | 6.44 | Blue | 335 |
| Example 16 | Compound 90 | 5.51 | 50 | 3215 | 6.43 | Blue | 354 |
| Example 17 | Compound 98 | 5.60 | 50 | 3200 | 6.40 | Blue | 338 |
| Example 18 | Compound 102 | 5.15 | 50 | 3290 | 6.58 | Blue | 350 |
| Example 19 | Compound 230 | 5.80 | 50 | 3790 | 6.42 | Blue | 345 |
| Example 20 | Compound 244 | 5.57 | 50 | 3200 | 6.40 | Blue | 340 |
| Example 21 | Compound 271 | 5.61 | 50 | 3220 | 6.44 | Blue | 370 |
| Example 22 | Compound 289 | 5.70 | 50 | 3215 | 6.50 | Blue | 340 |
| Example 23 | Compound 299 | 5.55 | 50 | 3200 | 6.50 | Blue | 350 |
| Comparative Example 1 | NPB | 7.01 | 50 | 2645 | 5.29 | Blue | 358 |

From Table 2, it may be that the organic light-emitting devices manufactured according to Examples 1 to 23 have higher driving voltage, higher brightness, higher efficiency, and longer half-lifespan than the organic light-emitting device manufactured according to Comparative Example 1.

An organic light-emitting device including the amine-based compound according to an embodiment may have a low driving voltage, high efficiency, high brightness, and long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. An amine-based compound represented by Formula 1 below:

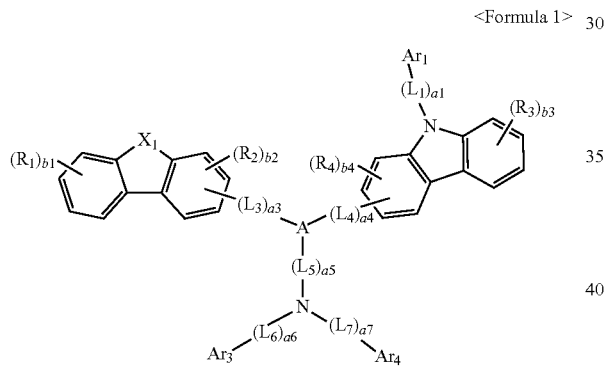

<Formula 1> wherein in Formula 1,
A is a substituted or unsubstituted $C_6$-$C_{20}$ aromatic ring;
$X_1$ is selected from N-$(L_2)_{a2}$-$(Ar_2)$, an oxygen atom (O), and a sulfur atom (S);
$L_1$ to $L_7$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;
a1 to a7 are each independently an integer selected from 0 to 3;
$Ar_1$ and $Ar_2$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted heteroaryl group, a substituted or unsubstituted monovalent non-aromatic condensed polycyclic group, and a substituted or unsubstituted monovalent non-aromatic condensed heteropolycyclic group;
$Ar_3$ and $Ar_4$ are each independently selected from:
a phenyl group, a pentalenyl group, an indenyl group, a naphthyl group, an azulenyl group, a heptalenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group; and
a phenyl group, a pentalenyl group, an indenyl group, a naphthyl group, an azulenyl group, a heptalenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, an imidazopyrimidinyl group, —Si($Q_{31}$)($Q_{32}$)($Q_{33}$), and —B($Q_{34}$)($Q_{35}$), in which $Q_{31}$ to $Q_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —B($Q_4$)($Q_5$);

b1 and b3 are each independently an integer selected from 0 to 4, b2 and b4 are each independently an integer selected from 0 to 3; and at least one substituent of the substituted $C_6$-$C_{20}$ aromatic ring, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted a divalent non-aromatic condensed polycyclic group, substituted a divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), and —B($Q_{14}$)($Q_{15}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{31}$)($Q_{32}$)($Q_{33}$), and —B($Q_{34}$)($Q_{35}$), each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), and —B($Q_{24}$)($Q_{25}$);

wherein $Q_1$ to $Q_5$, $Q_{10}$ to $Q_{15}$, $Q_{21}$ to $Q_{25}$ and $Q_{31}$ to $Q_{35}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

2. The amine-based compound as claimed in claim 1, wherein A is selected from a substituted or unsubstituted a benzene group, a substituted or unsubstituted a naphthalene group, a substituted or unsubstituted an anthracene group, a substituted or unsubstituted a pyrene group, a substituted or unsubstituted a phenanthrene group, a substituted or unsubstituted a chrysene group, and a substituted or unsubstituted triphenylene group.

3. The amine-based compound as claimed in claim 1, wherein A is a group represented by one of the following Formulae 2-1 to 2-19:

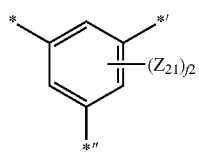

Formula 2-1

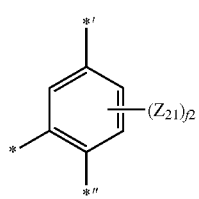

Formula 2-2

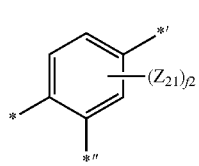

Formula 2-3

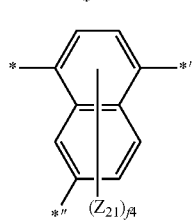

Formula 2-4

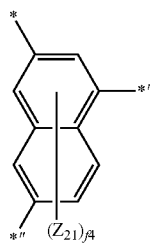

Formula 2-5

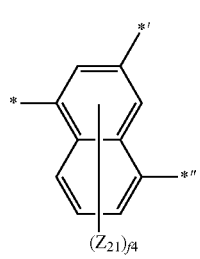

Formula 2-6

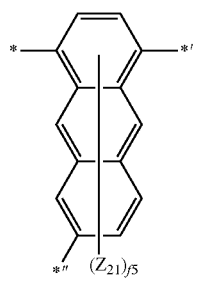

Formula 2-7

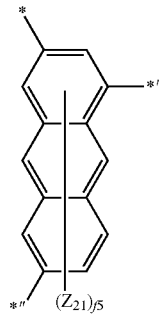

Formula 2-8

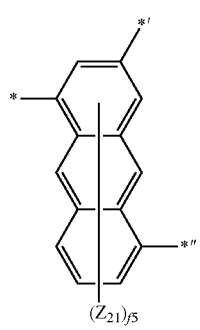

Formula 2-9

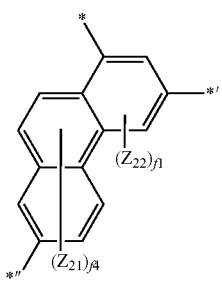
Formula 2-10
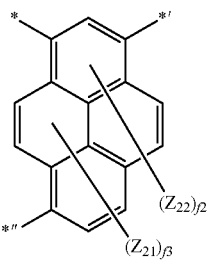
Formula 2-15
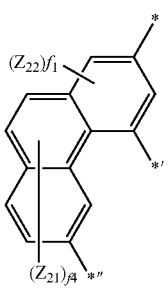
Formula 2-11
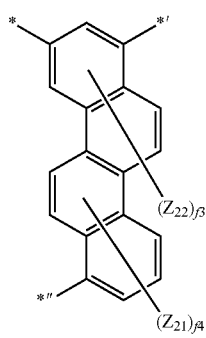
Formula 2-16
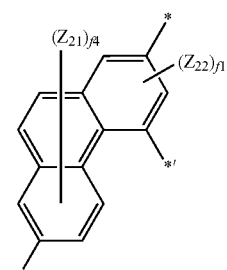
Formula 2-12
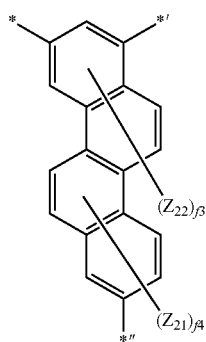
Formula 2-17
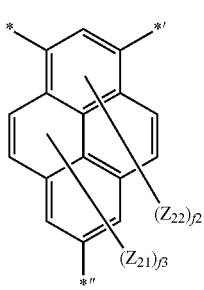
Formula 2-13
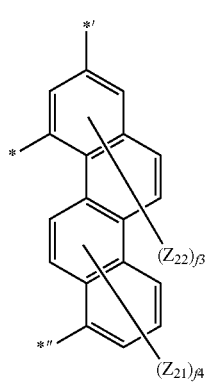
Formula 2-18
Formula 2-14

-continued

Formula 2-19

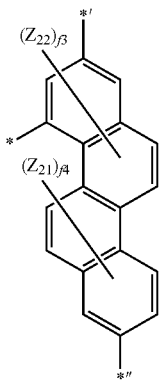

wherein, in Formulae 2-1 to 2-19, $Z_{21}$ and $Z_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

f1 is 1 or 2, f2 is an integer selected from 1 to 3, f3 is an integer selected from 1 to 4, f4 is an integer selected from 1 to 5, and f5 is an integer selected from 1 to 7;

* and *' indicate binding sites to neighboring atoms, and *'' indicates a binding site to $L_5$ in -$(L_5)_{a5}$- or to N.

4. The amine-based compound as claimed in claim 1, wherein $X_1$ is O or S.

5. The amine-based compound as claimed in claim 1, wherein $L_1$ to $L_7$ are each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a phenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a furinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a furinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a pherylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

6. The amine-based compound as claimed in claim 1, wherein $L_1$ to $L_7$ are each independently a group represented by one of the following Formulae 3-1 to 3-33 below:

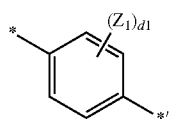

Formula 3-1

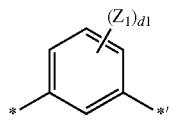

Formula 3-2

Formula 3-3

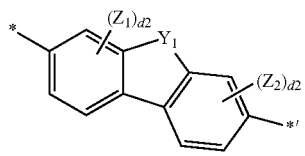

Formula 3-4

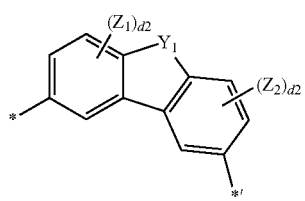

Formula 3-5

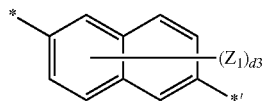

Formula 3-6

-continued

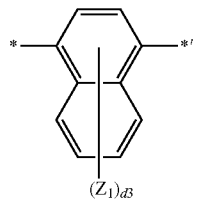

Formula 3-7

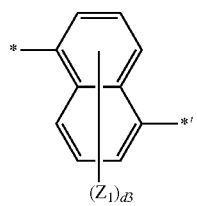

Formula 3-8

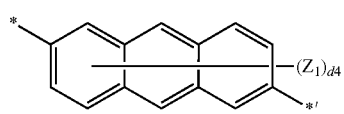

Formula 3-9

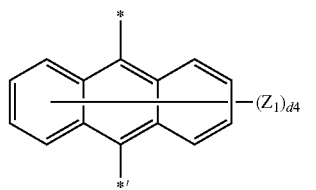

Formula 3-10

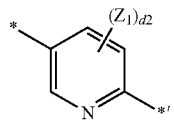

Formula 3-11

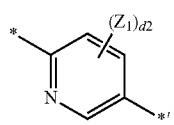

Formula 3-12

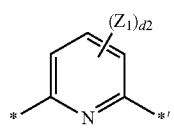

Formula 3-13

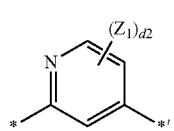

Formula 3-14

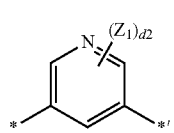

Formula 3-15

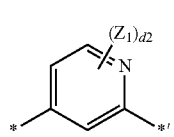

Formula 3-16

-continued

Formula 3-17
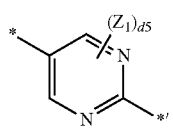

Formula 3-18
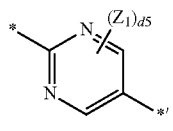

Formula 3-19
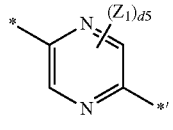

Formula 3-20

Formula 3-21

Formula 3-22
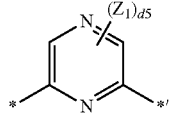

Formula 3-23
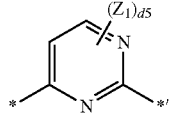

Formula 3-24

Formula 3-25
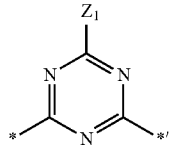

Formula 3-26
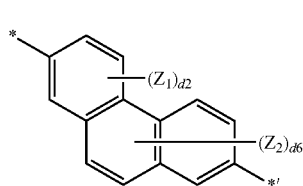

Formula 3-27
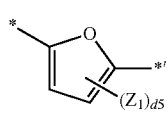

Formula 3-28
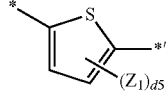

Formula 3-29
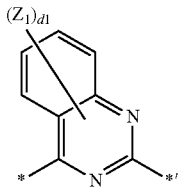

Formula 3-30
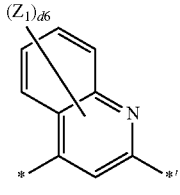

Formula 3-31
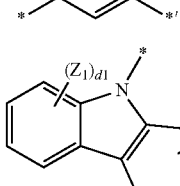

Formula 3-32
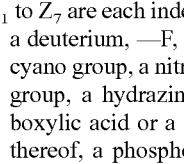

Formula 3-33
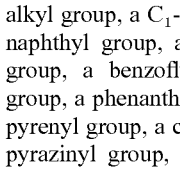

wherein, in Formulae 3-1 to 3-33, $Y_1$ is O, S, $C(Z_3)(Z_4)$, $N(Z_5)$, or $Si(Z_6)(Z_7)$;

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 is an integer selected from 1, 2, 3, and 4, d2 is an integer selected from 1, 2, and 3, d3 is an integer selected from 1, 2, 3, 4, 5, and 6, d4 is an integer selected from 1, 2, 3, 4, 5, 6, 7, and 8, d5 is 1 or 2, and d6 is an integer selected from 1, 2, 3, 4, and 5, and * and *' indicate binding sites to neighboring atoms.

7. The amine-based compound as claimed in claim 1, wherein:

a1, a2, a5, a6, and a7 are each independently 0, 1, 2, or 3, and a3 and a4 are each independently 0 or 1.

8. The amine-based compound as claimed in claim 1, wherein *-(L$_1$)$_{a1}$-*', *-(L$_2$)$_{a2}$-*', *-(L$_3$)$_{a3}$-*', *-(L$_4$)$_{a4}$-*', *-(L$_5$)$_{a5}$-*', *-(L$_6$)$_{a6}$-*, and *-(L$_7$)$_{a7}$-* are each independently a single bond or a group represented by one of the following Formulae 4-1 to 4-27:

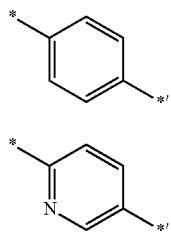
Formula 4-1

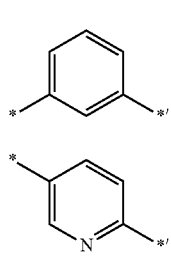
Formula 4-2

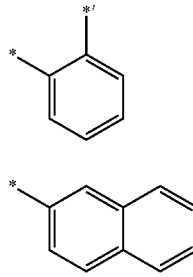
Formula 4-3

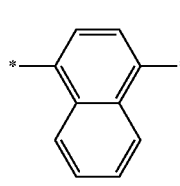
Formula 4-4

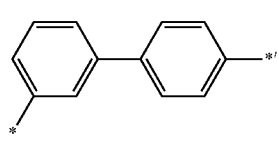
Formula 4-5

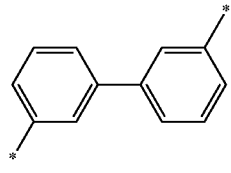
Formula 4-6

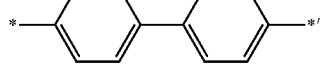
Formula 4-7

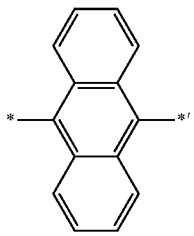
Formula 4-8

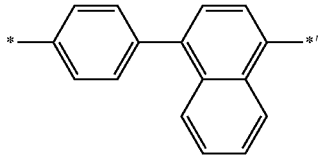
Formula 4-9

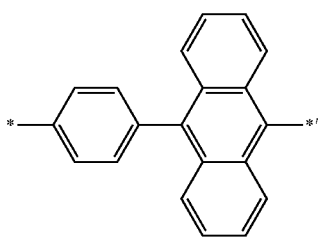
Formula 4-10

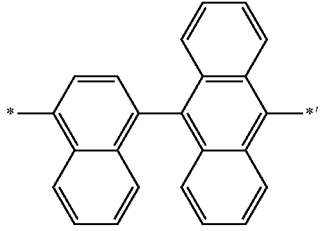
Formula 4-11

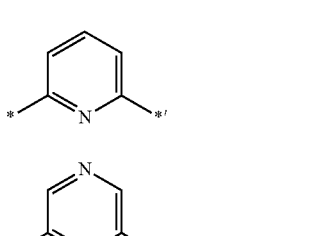
Formula 4-12

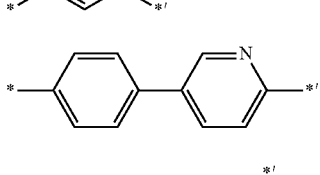
Formula 4-13

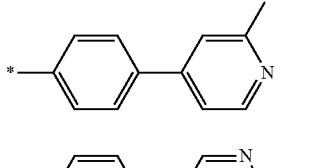
Formula 4-14

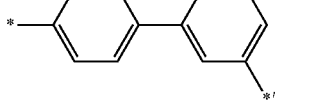
Formula 4-15

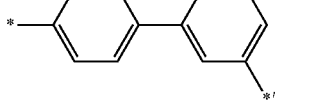
Formula 4-16

Formula 4-17

Formula 4-18

Formula 4-19

-continued

Formula 4-20
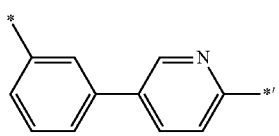

Formula 4-21
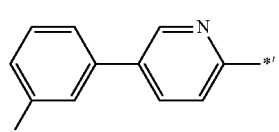

Formula 4-22
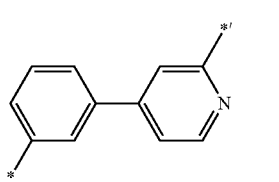

Formula 4-23
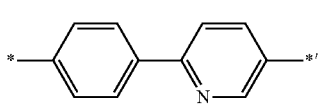

Formula 4-24
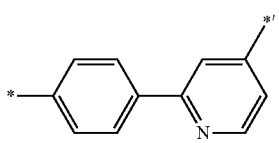

Formula 4-25
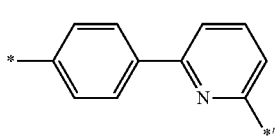

Formula 4-26
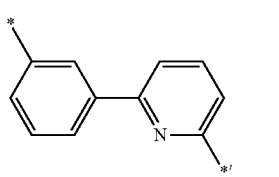

Formula 4-27
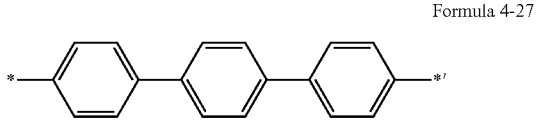

wherein * and *' indicate binding sites to neighboring atoms.

9. The amine-based compound as claimed in claim 1, wherein $Ar_1$ and $Ar_2$ are each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzofuranyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, an imidazopyrimidinyl group, —Si($Q_{31}$)($Q_{32}$)($Q_{33}$), and —B($Q_{34}$)($Q_{35}$), wherein $Q_{31}$ to $Q_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

10. The amine-based compound as claimed in claim 1, wherein $Ar_1$ and $Ar_2$ are each independently a group represented by one of the following Formulae 5-1 to 5-16:

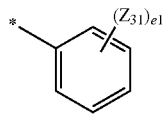

Formula 5-1

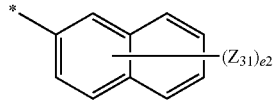

Formula 5-2

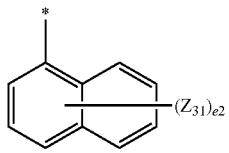

Formula 5-3

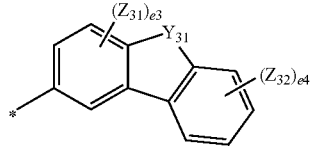

Formula 5-4

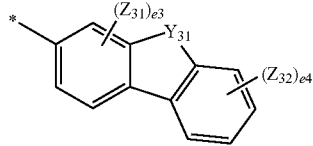

Formula 5-5

-continued

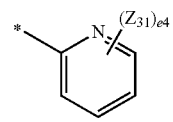

Formula 5-6

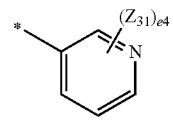

Formula 5-7

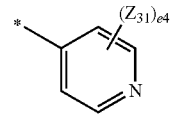

Formula 5-8

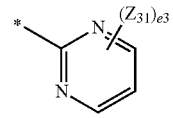

Formula 5-9

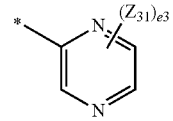

Formula 5-10

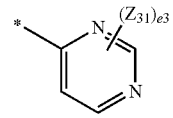

Formula 5-11

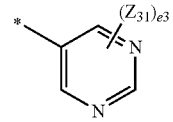

Formula 5-12

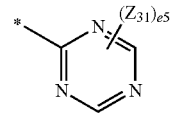

Formula 5-13

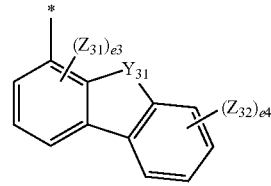

Formula 5-14

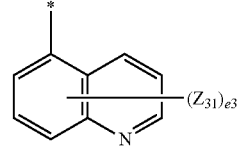

Formula 5-15

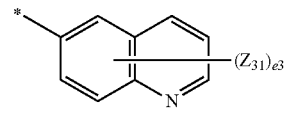

Formula 5-16 wherein, in Formulae 5-1 to 5-16, $Y_{31}$ is $C(Z_{33})(Z_{34})$ or $N(Z_{35})$;

$Z_{31}$ to $Z_{35}$ are each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group, and a dibenzocarbazolyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a benzocarbazolyl group, a dibenzocarbazolyl group, —Si$(Q_{31})(Q_{32})(Q_{33})$, and —B$(Q_{34})(Q_{35})$, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, and a naphthyl group;

$Q_{31}$ to $Q_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, 'a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and e1 is an integer of 1 to 5; e2 is an integer of 1 to 7; e3 is an integer of 1 to 3; e4 is an integer of 1 to 4; e5 is 1 or 2; and * indicates a binding site to a neighboring atom.

11. The amine-based compound as claimed in claim 1, wherein $Ar_1$ and $Ar_2$ are each independently a group represented by one of the following Formulae 6-1 to 6-24:

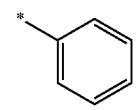

Formula 6-1

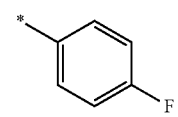

Formula 6-2

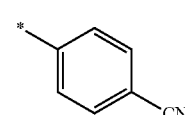

Formula 6-3

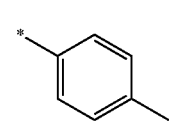

Formula 6-4

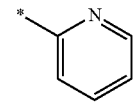

Formula 6-5

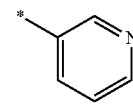

Formula 6-6

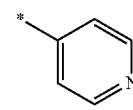

Formula 6-7

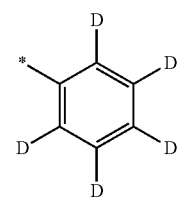

Formula 6-8

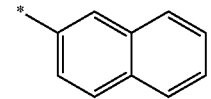

Formula 6-9

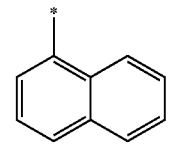

Formula 6-10

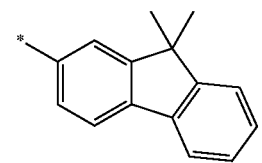

Formula 6-11

299
-continued

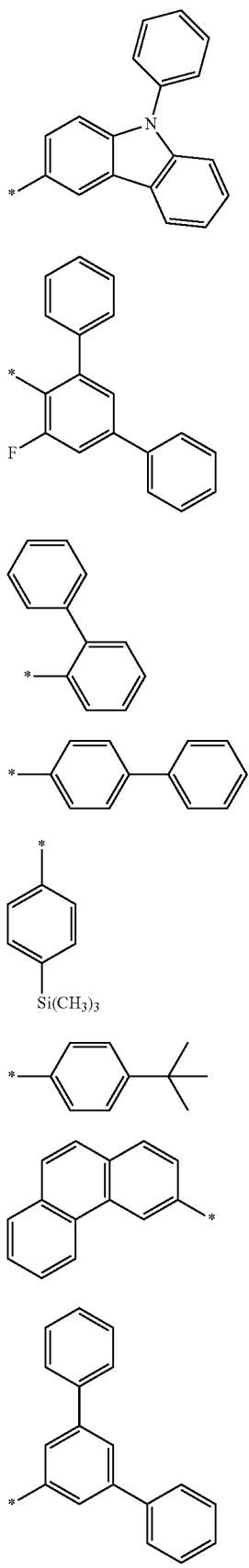

300
-continued

Formula 6-12

Formula 6-13

Formula 6-14

Formula 6-15

Formula 6-16

Formula 6-17

Formula 6-18

Formula 6-19

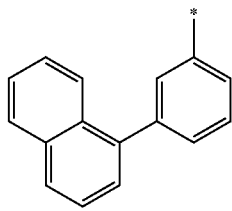

Formula 6-20

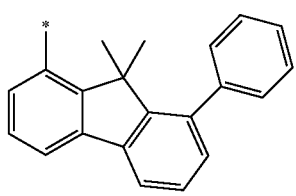

Formula 6-21

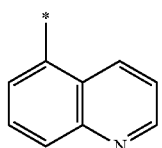

Formula 6-22

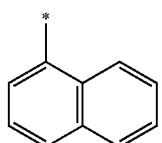

Formula 6-23

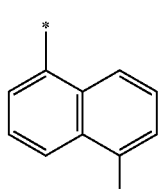

Formula 6-24 wherein, in Formulae 6-1 to 6-24, * indicates a binding site to a neighboring atom.

12. The amine-based compound as claimed in claim 1, wherein $R_1$ to $R_4$ are each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —Si($Q_{31}$)($Q_{32}$)($Q_{33}$); and —Si($Q_1$)($Q_2$)($Q_3$);

wherein $Q_1$ to $Q_3$ and $Q_{31}$ to $Q_{33}$ are each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

13. The amine-based compound as claimed in claim 1, wherein $R_1$ to $R_4$ are each independently selected from:

a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one selected from —F, a cyano group, a nitro group, a phenyl group, a naphthyl group, a pyridinyl group, a pyrimidinyl group, a triazinyl group, and —Si($Q_{33}$)($Q_{34}$)($Q_{35}$); and —Si($Q_1$)($Q_2$)($Q_3$);

wherein $Q_1$ to $Q_3$ and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

14. The amine-based compound as claimed in claim 1, wherein the amine-based compound represented by Formula 1 is represented by one of the following Formulae 1A to 1F:

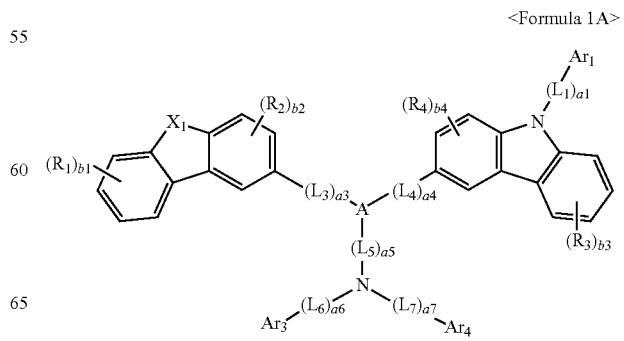

<Formula 1A>

<Formula 1B>

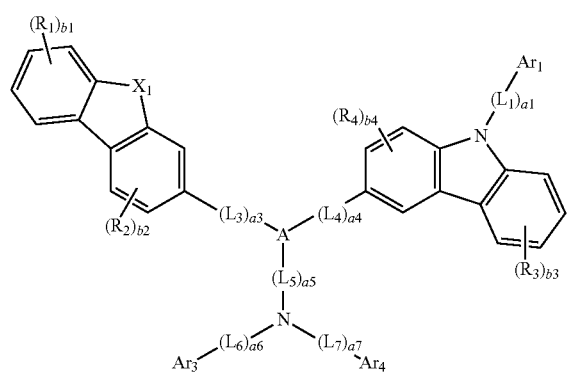

<Formula 1C>

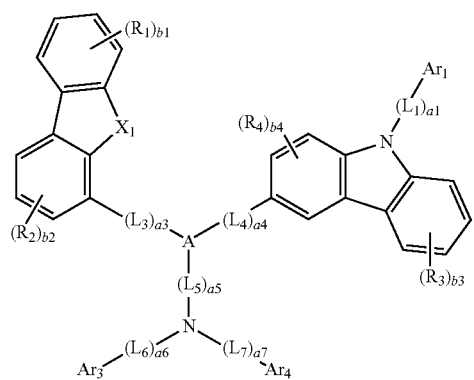

<Formula 1D>

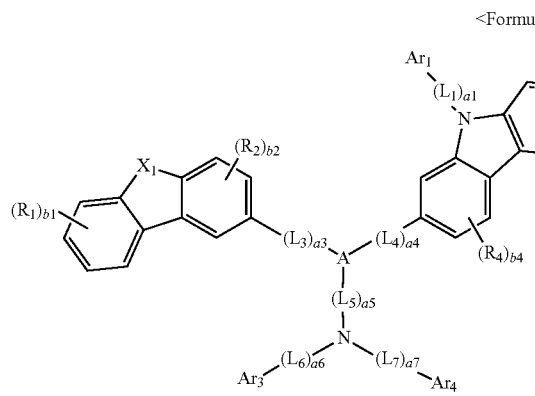

<Formula 1E>

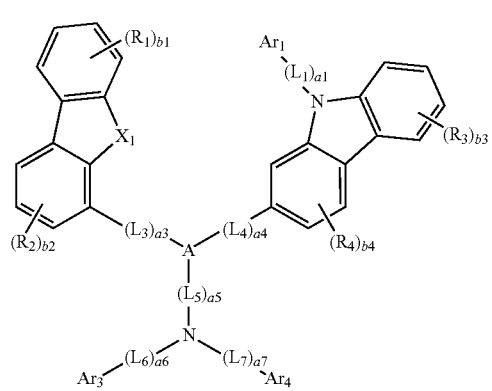

<Formula 1F>

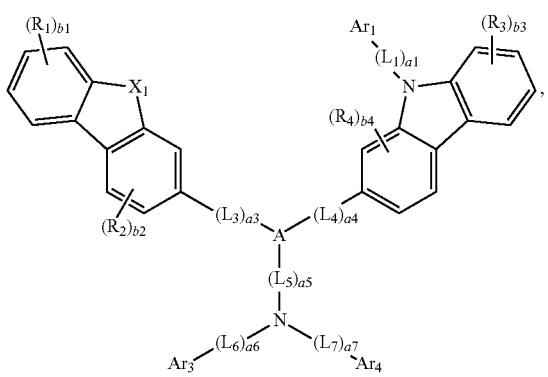

and
wherein, in Formulae 1A to 1f, $X_1$, A, $L_1$ to $L_7$, a1 to a7, $Ar_1$ to $Ar_4$, $R_1$ to $R_4$, and b1 to b4 are defined the same as $X_1$, A, $L_1$ to $L_7$, a1 to a7, $Ar_1$ to $Ar_4$, $R_1$ to $R_4$, and b1 to b4 of Formula 1.

15. The amine-based compound as claimed in claim 1, wherein the amine-based compound represented by Formula 1 is represented by one of the following Formulae 1A-1, 1A-2, 1B-1, 1B-2, 1C-1, 1C-2, 1D-1, 1D-2, 1E-1, 1E-2, 1F-1, and 1F-2, <Formula 1A-1>

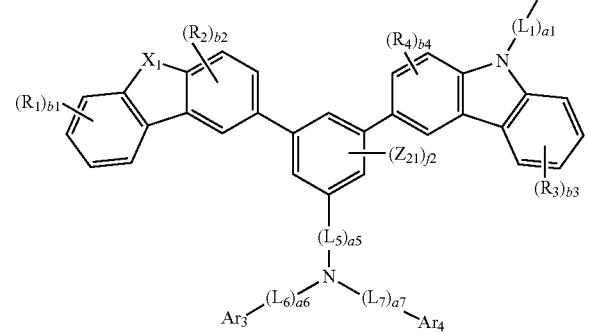

<Formula 1A-2>

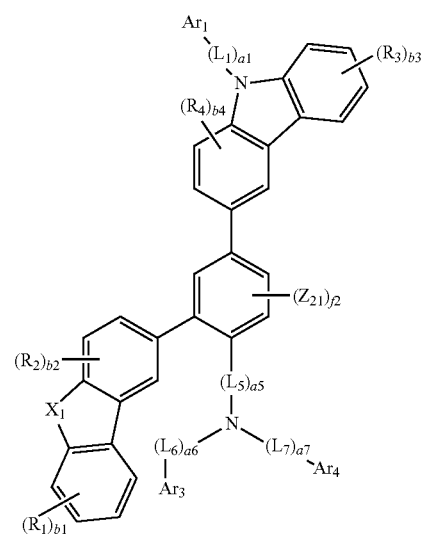

<Formula 1B-1>
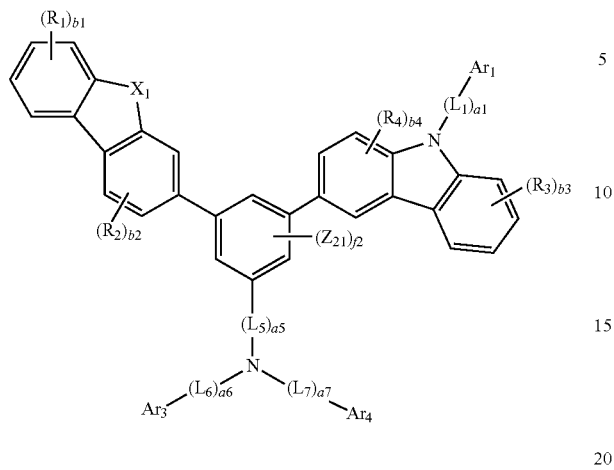
<Formula 1C-2>
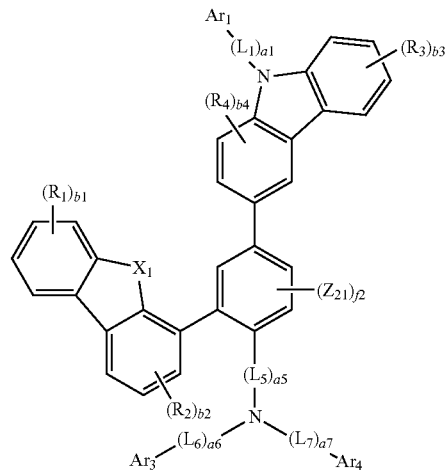
<Formula 1B-2>
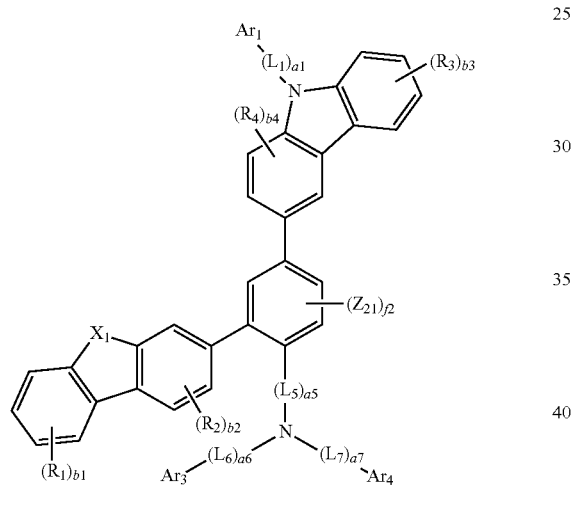
<Formula 1D-1>
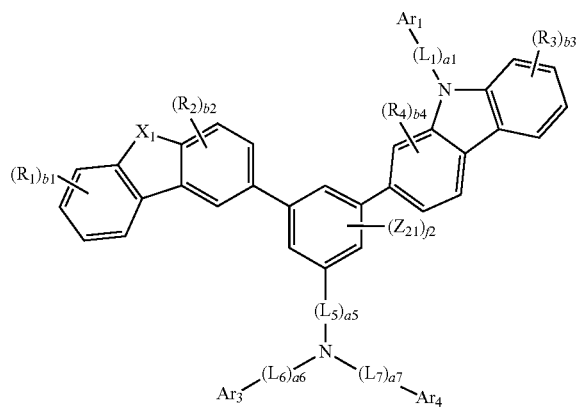
<Formula 1C-1>
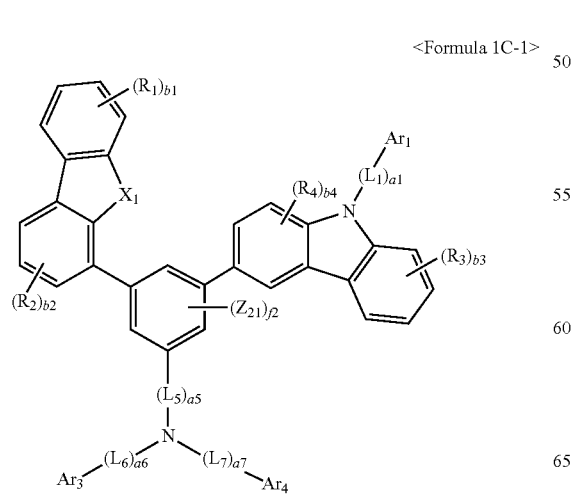
<Formula 1D-2>
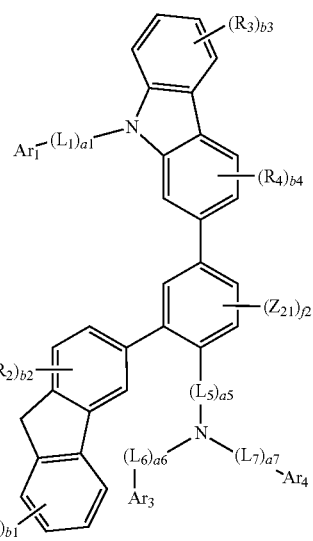

-continued

<Formula 1E-1>

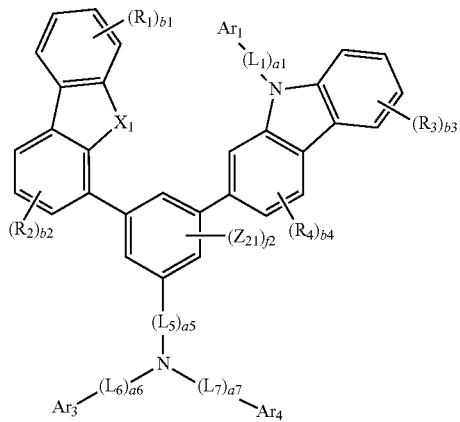

<Formula 1E-2>

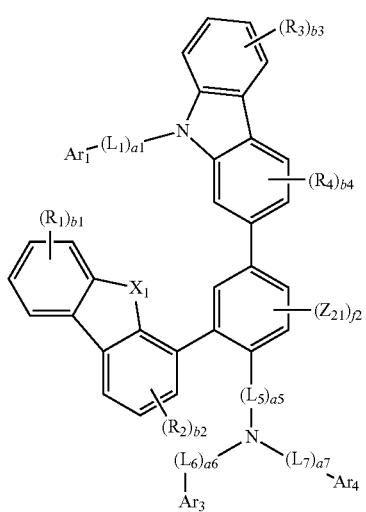

<Formula 1F-1>

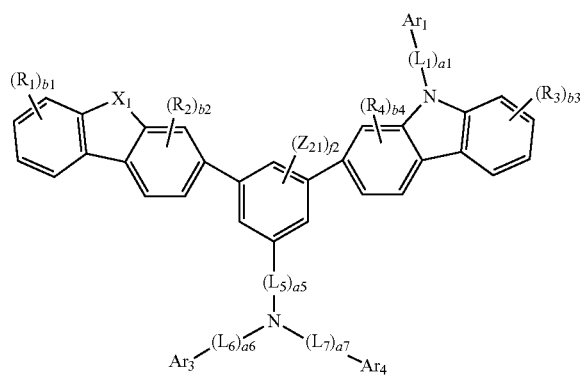

-continued

<Formula 1F-2>

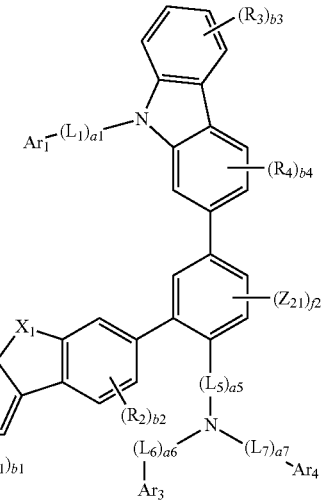

wherein in Formulae 1A-1, 1A-2, 1B-1, 1B-2, 1C-1, 1C-2, 1D-1, 1D-2, 1E-1, 1E-2, 1F-1, and 1F-2, $Z_{21}$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

f2 is an integer selected from 0 to 3;

$X_1$ is O or S;

$L_1$, $L_5$, $L_6$, and $L_7$ are each independently selected from:
a phenylene group, a naphthylene group, a pyridinylene group, a pyrimidinylene group, and a triazinylene group; and
a phenylene group, a naphthylene group, a pyridinylene group, a pyrimidinylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a1 is 0 or 1, a5, a6, and a7 are each independently an integer selected from 0 to 3;

Ar$_1$ and Ar$_2$ are each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, —Si(Q$_{31}$)(Q$_{32}$)(Q$_{33}$), and —B(Q$_{34}$)(Q$_{35}$), in which Q$_{31}$ to Q$_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

Ar$_3$ and Ar$_4$ are each independently selected from:

a phenyl group, a naphthyl group, a phenanthrenyl group, an anthracenyl group, a pyrenyl group, and a chrysenyl group; and a phenyl group, a naphthyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a phenanthrenyl group, an anthracenyl group, a pyrenyl group, a chrysenyl group, —Si(Q$_{31}$)(Q$_{32}$)(Q$_{33}$), and —B(Q$_{34}$)(Q$_{35}$), in which Q$_{31}$ to Q$_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

R$_1$ to R$_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, and a substituted or unsubstituted $C_1$-$C_{20}$ alkoxy group;

b1 and b3 are each independently an integer selected from 0 to 4, and b2 and b4 are each independently an integer selected from 0 to 3.

16. The amine-based compound as claimed in claim 1, wherein the amine-based compound represented by Formula 1 is one of the following Compounds 1 to 300:

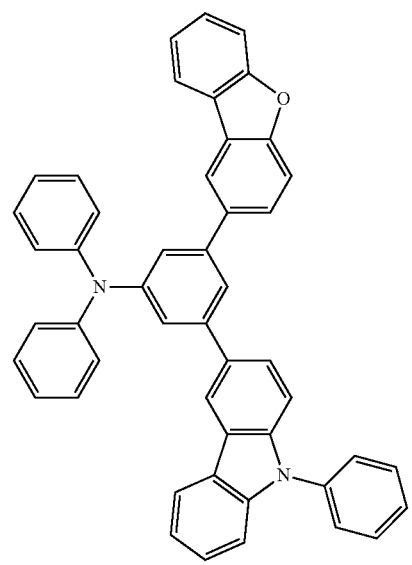

1

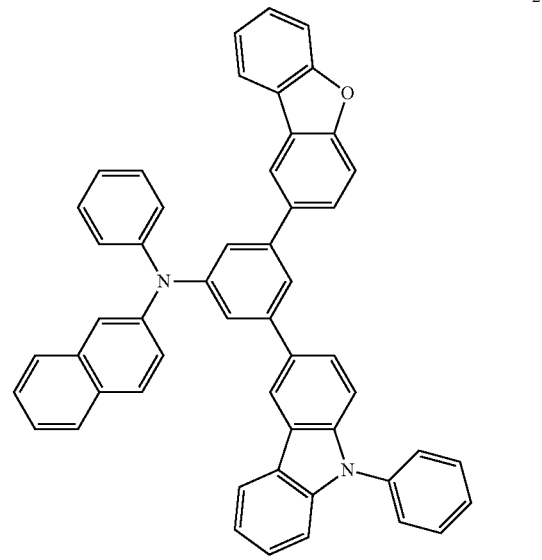

2

311
-continued
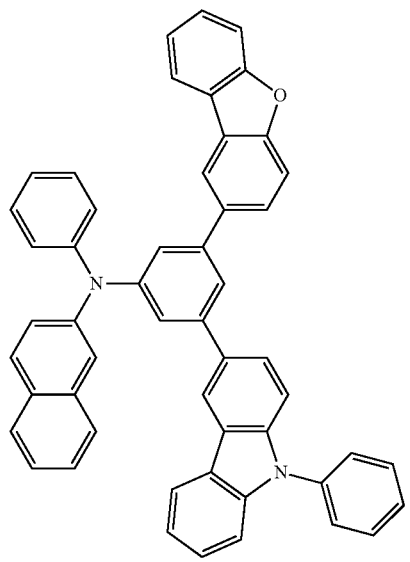
3
312
-continued
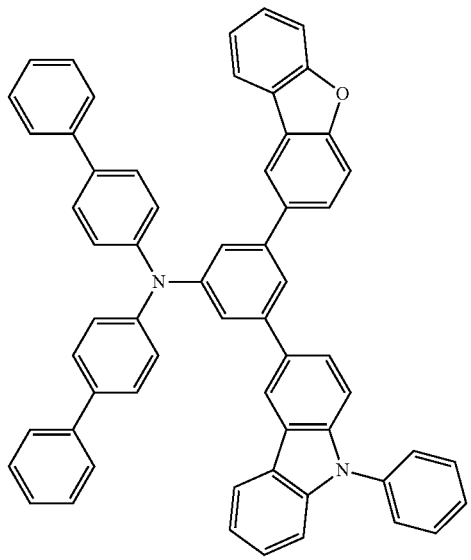
5
4
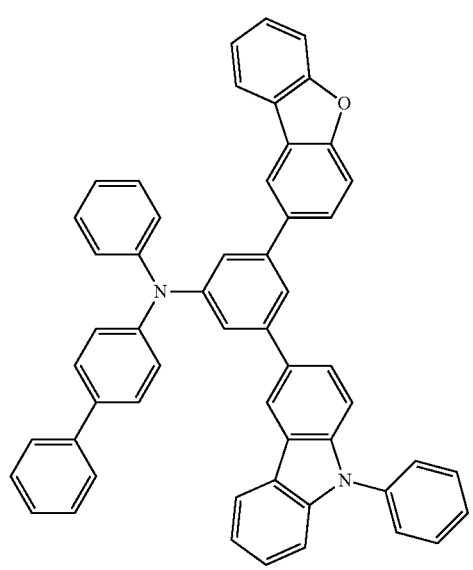
6
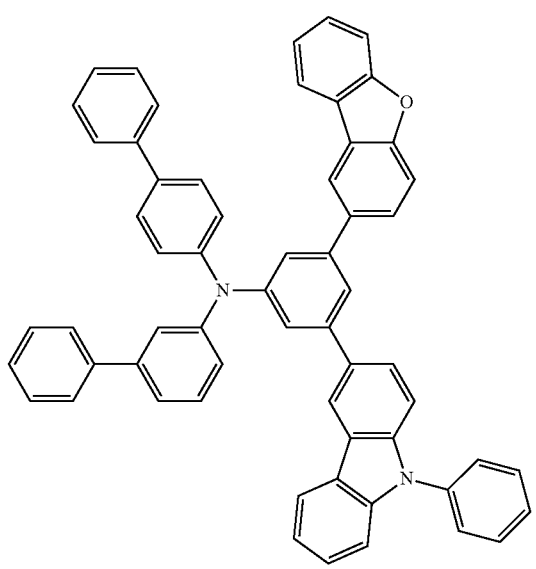

313
-continued
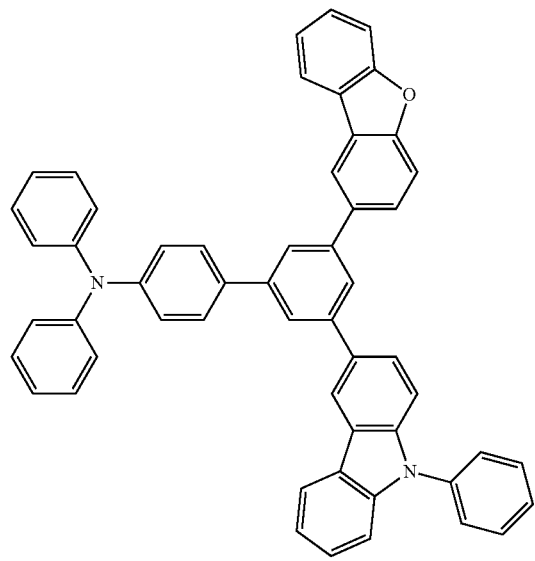
7
314
-continued
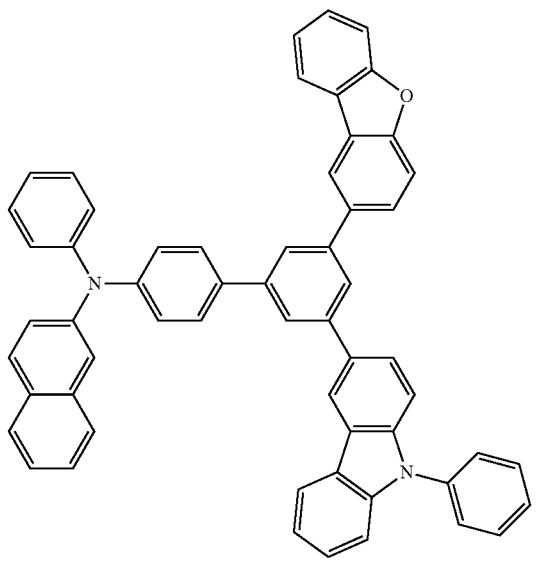
9
8
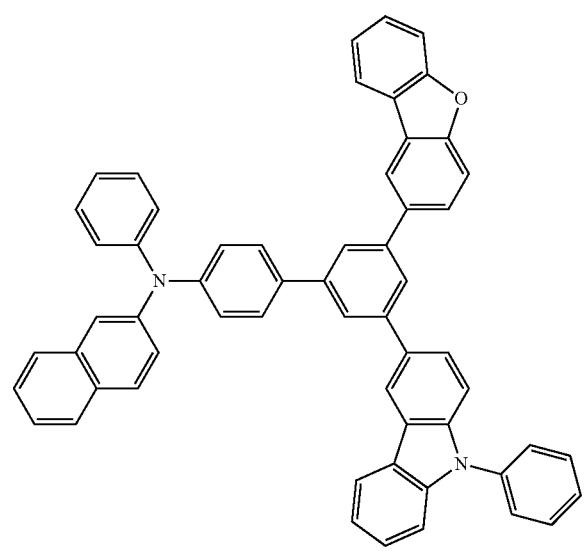
10
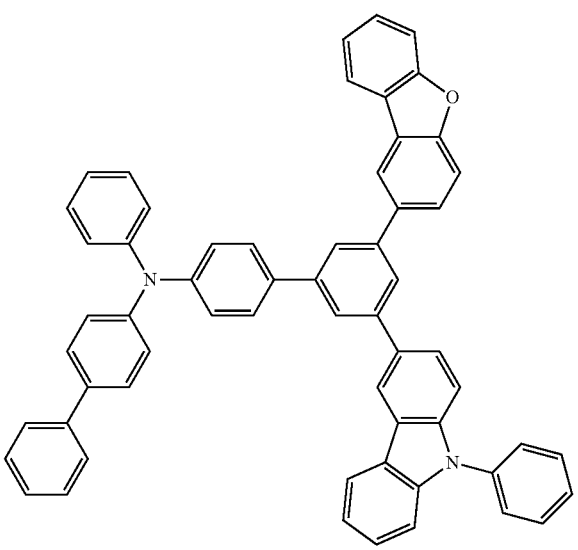

315
-continued
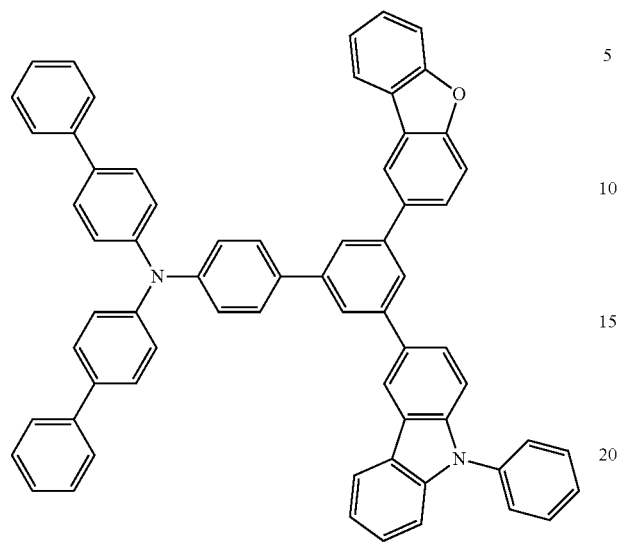
11
316
-continued
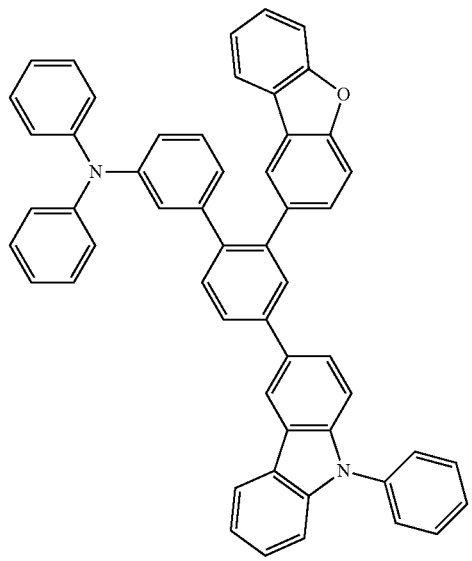
13
12
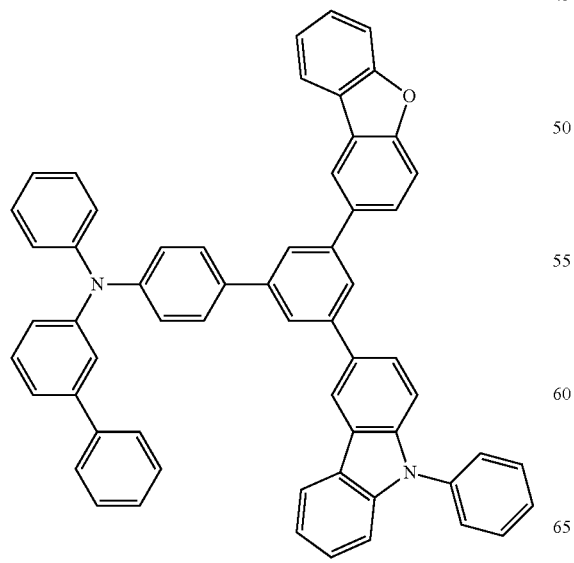
14
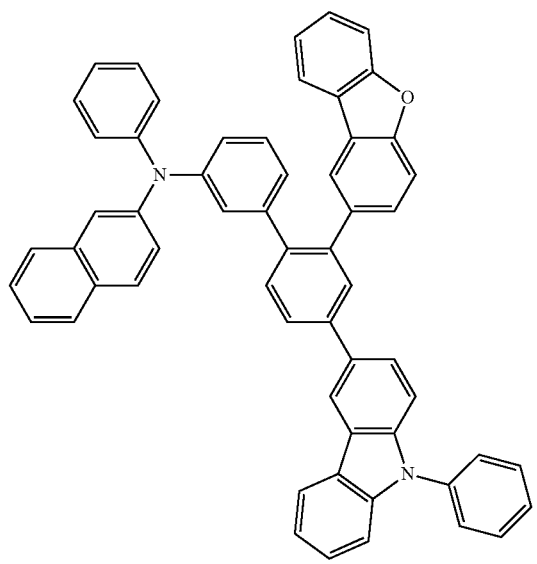

317
-continued
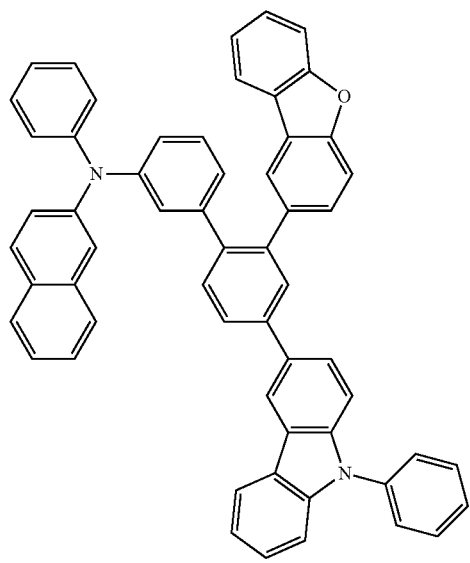
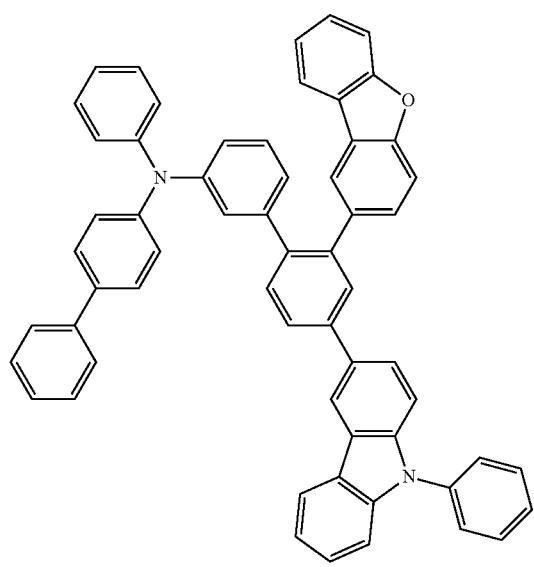
318
-continued
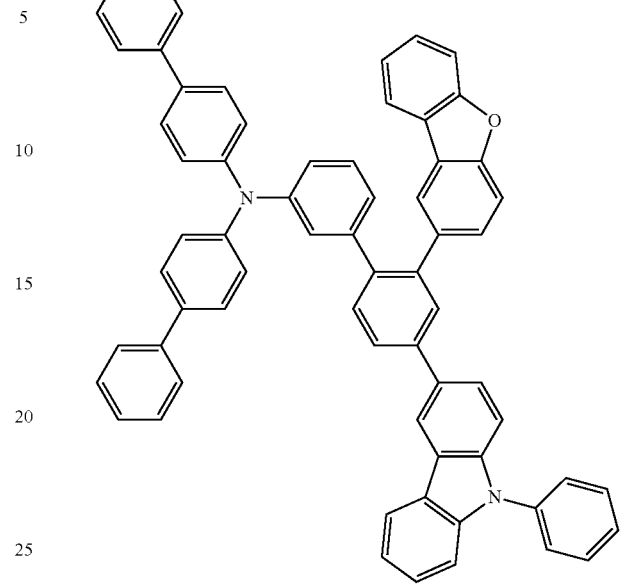
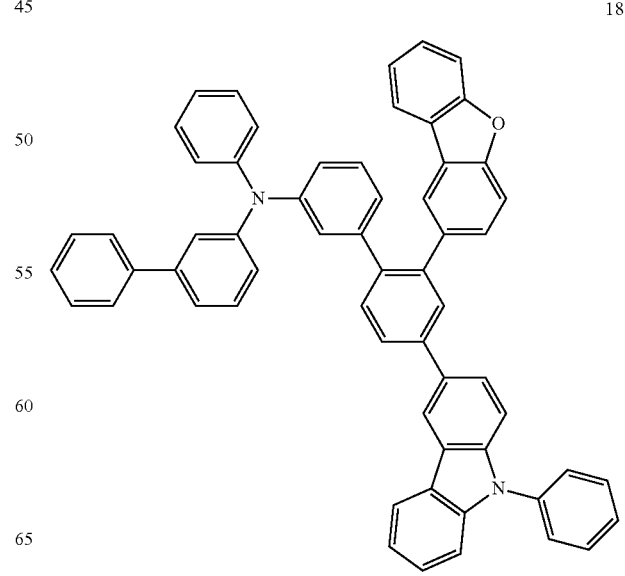

319
-continued
19
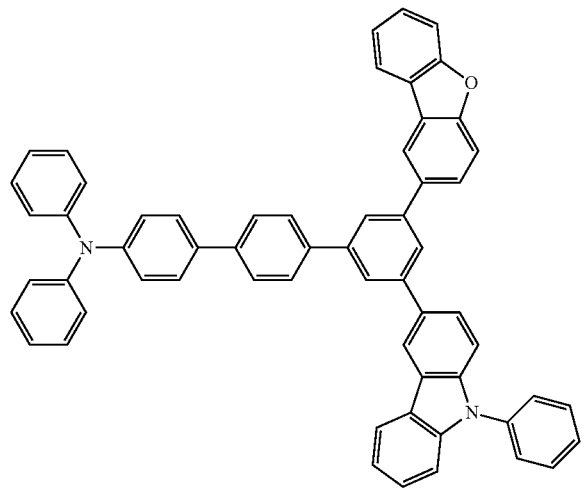
20
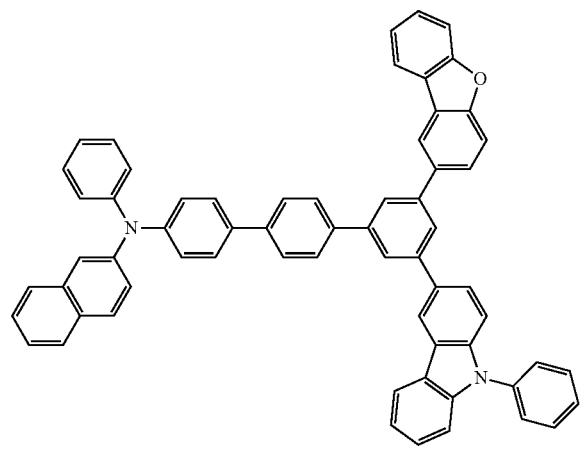
21
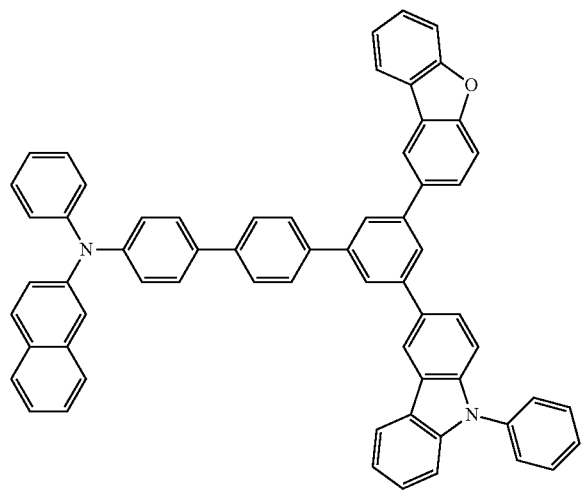
320
-continued
22
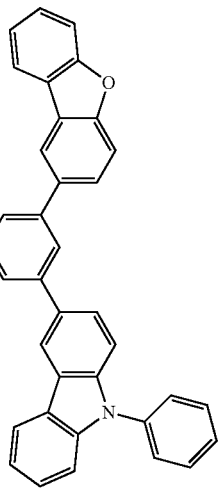
23
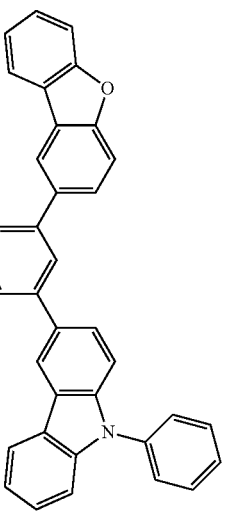
24
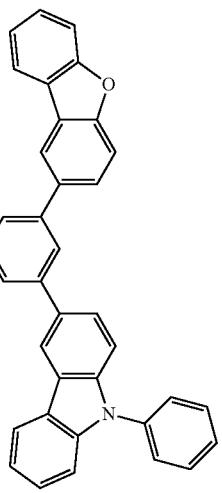

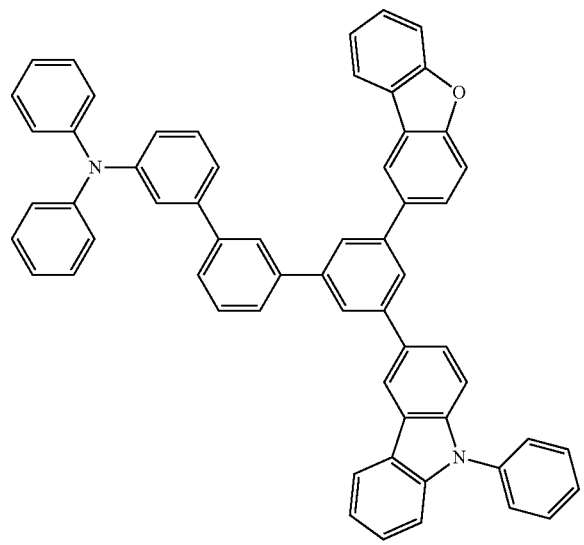
25
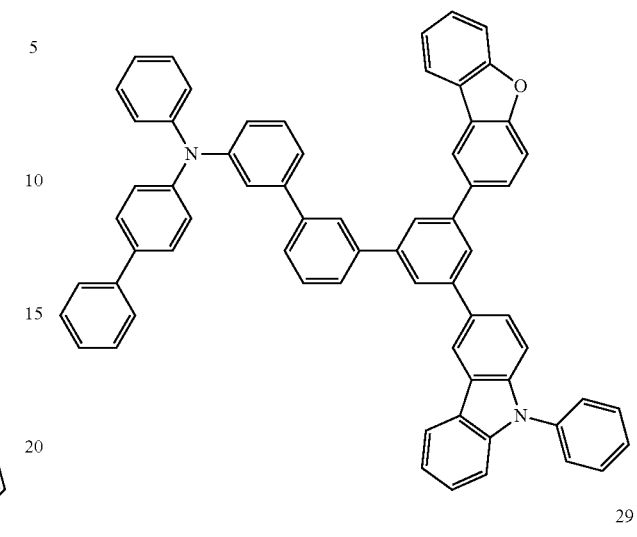
28
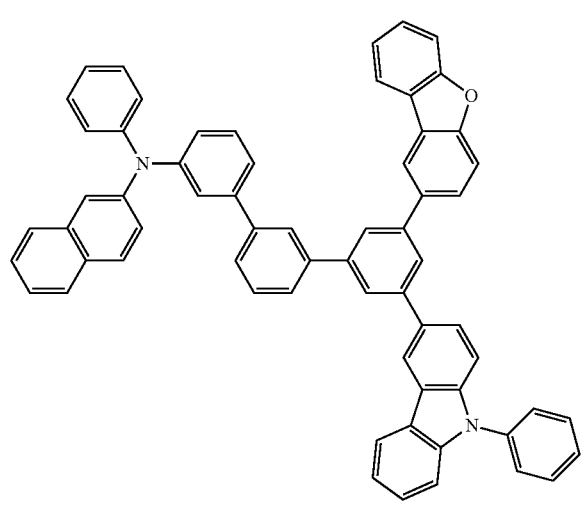
26
29
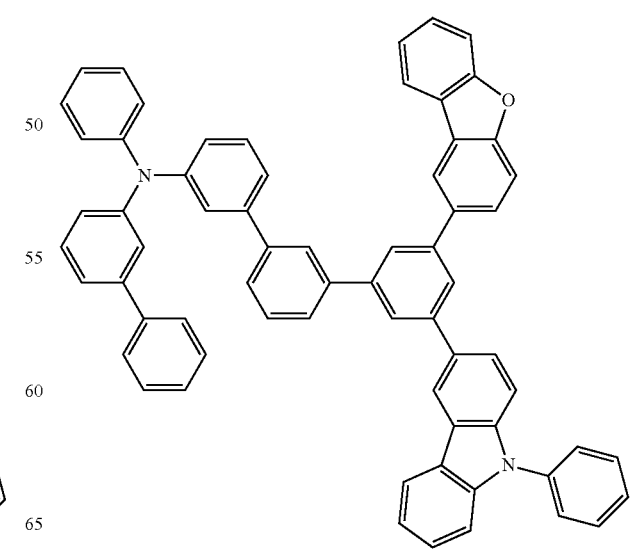
27
30

323
-continued
31
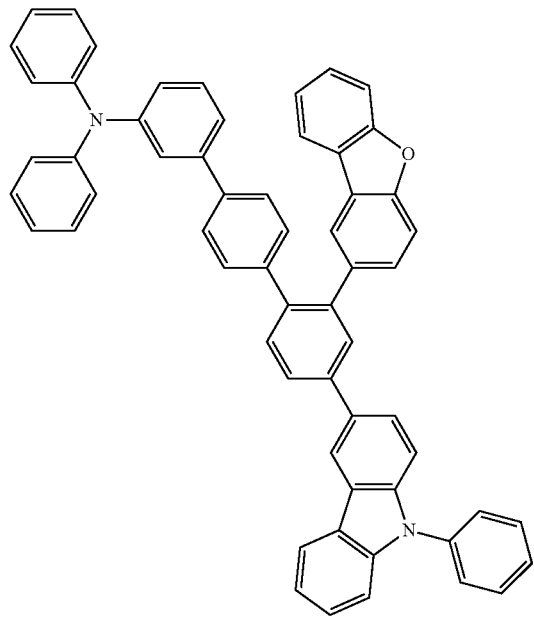
32
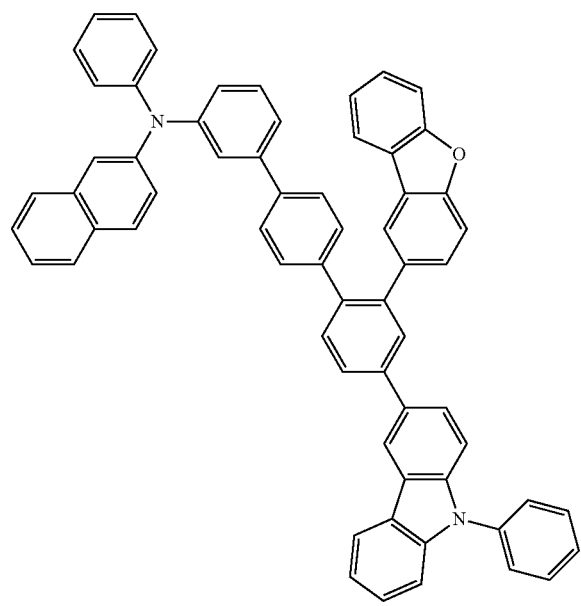
324
-continued
33
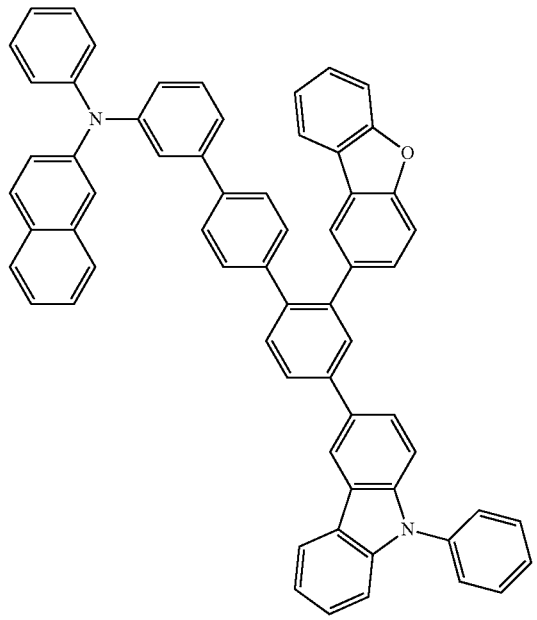
34
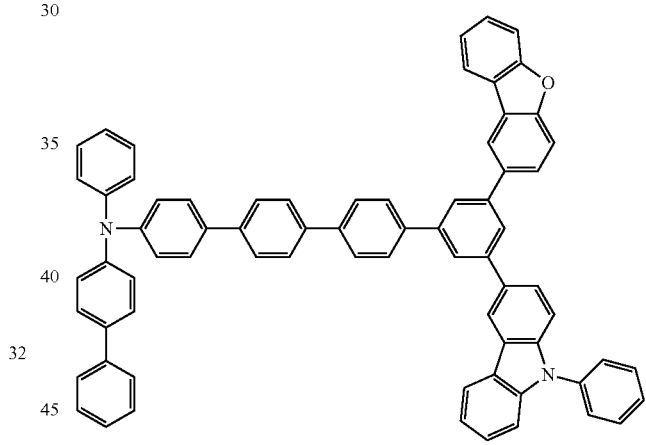
35
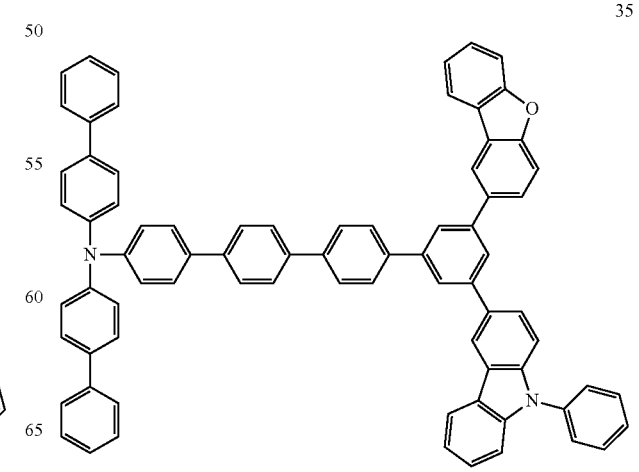

36
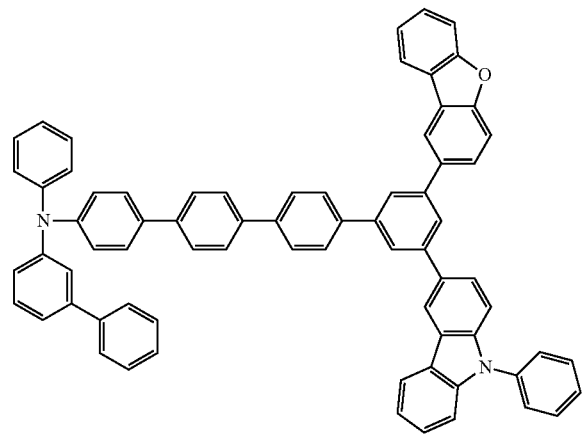
37
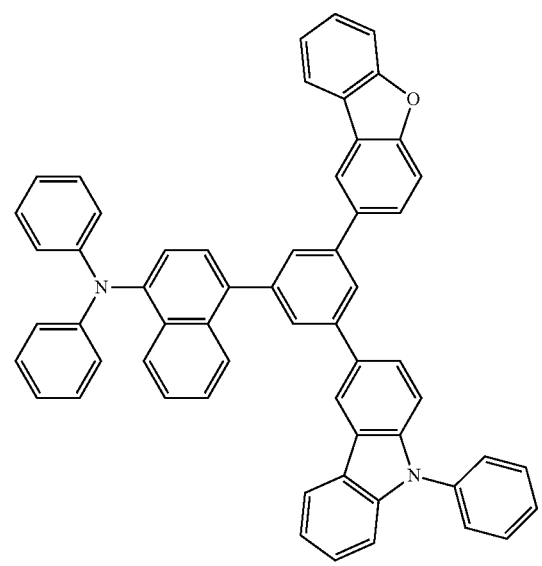
38
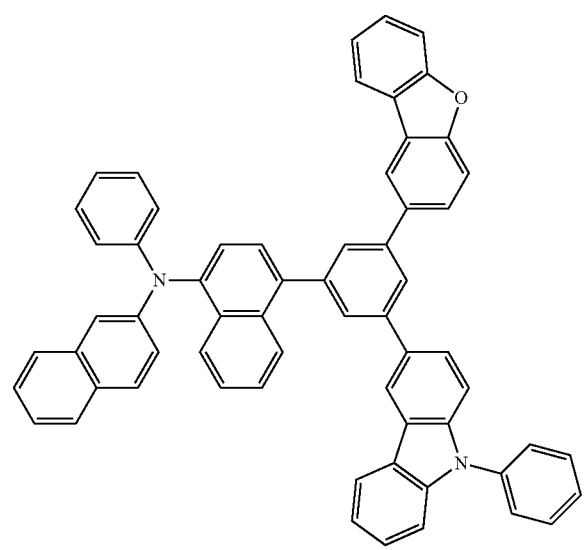
39
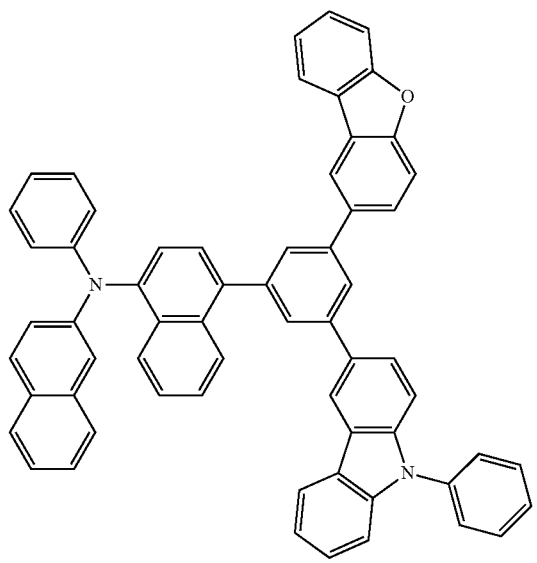
40
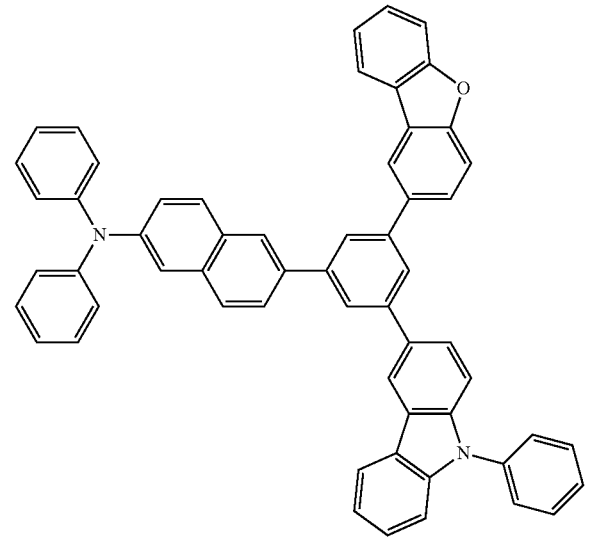
41
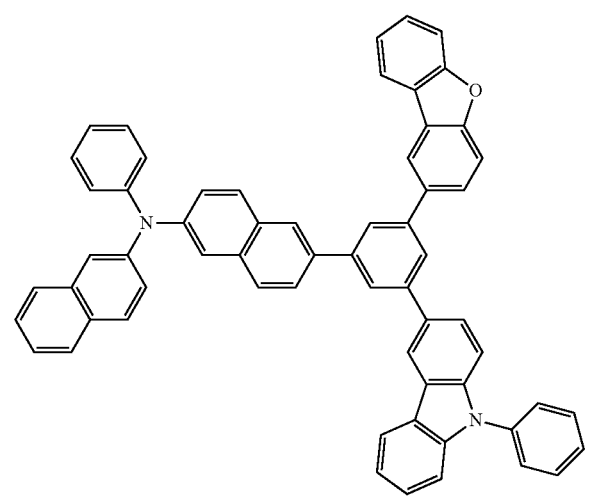

327
-continued
42
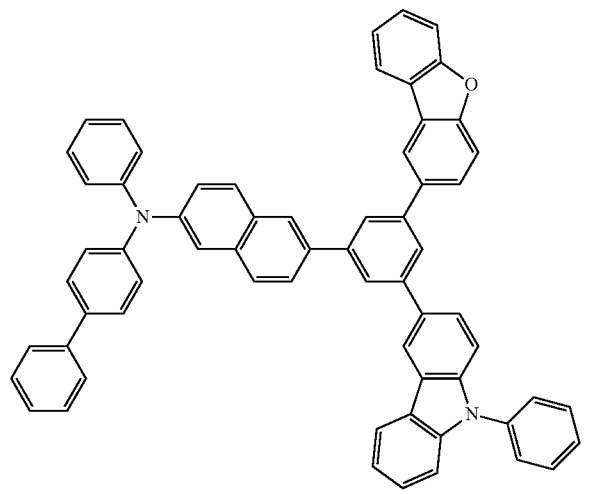
43
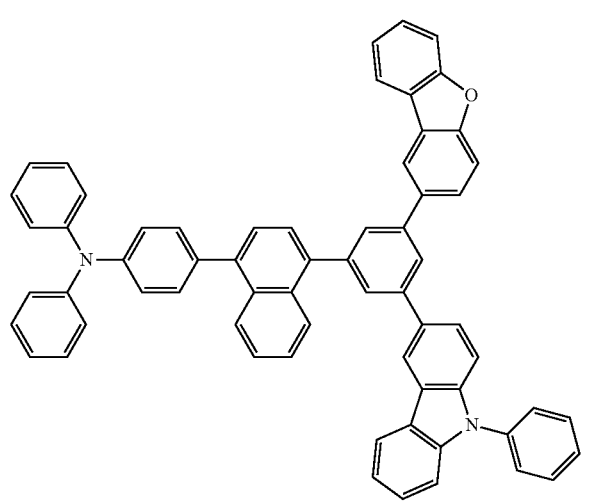
44
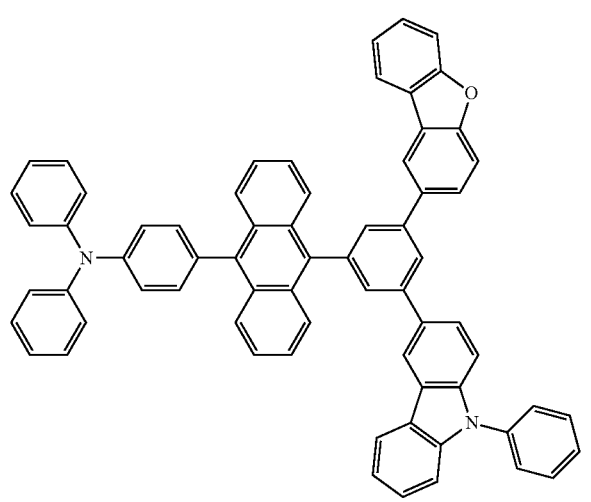
328
-continued
45
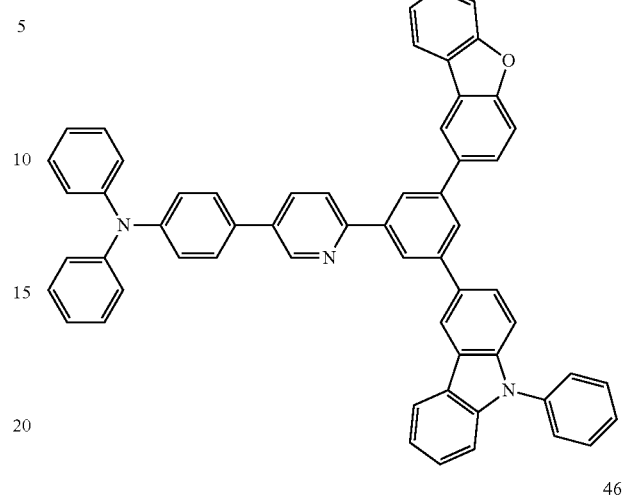
46
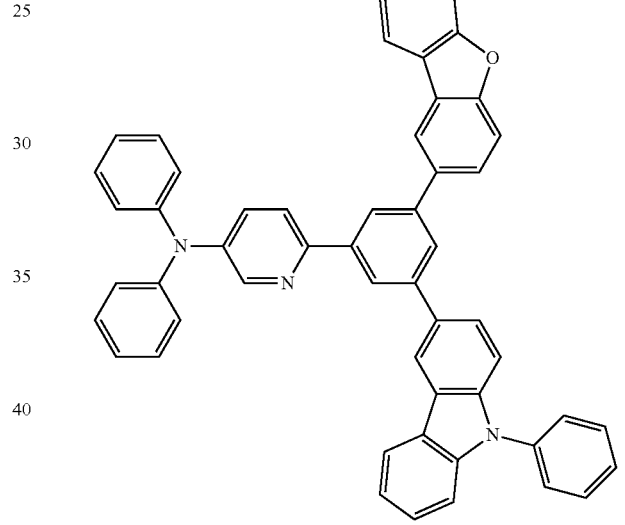
47
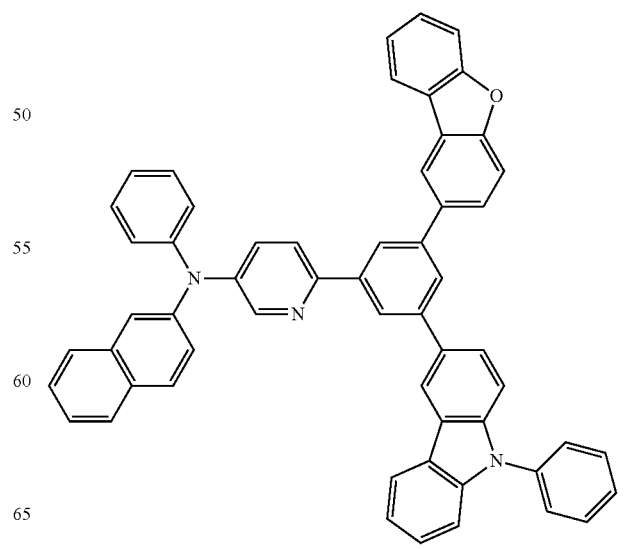

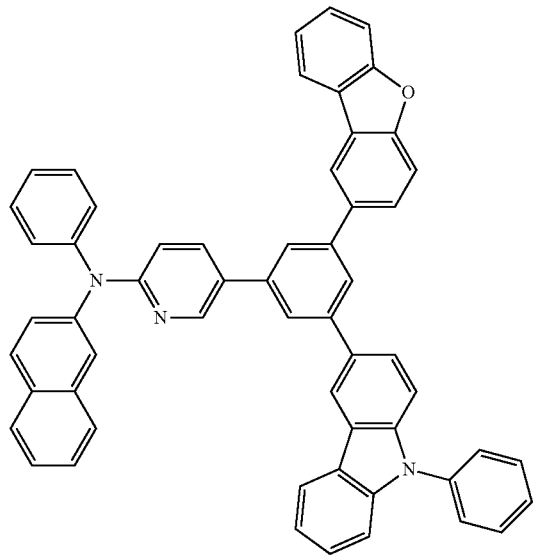
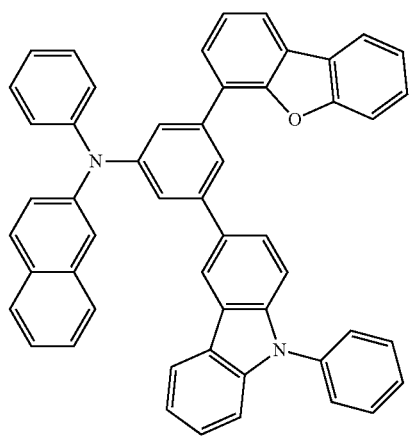
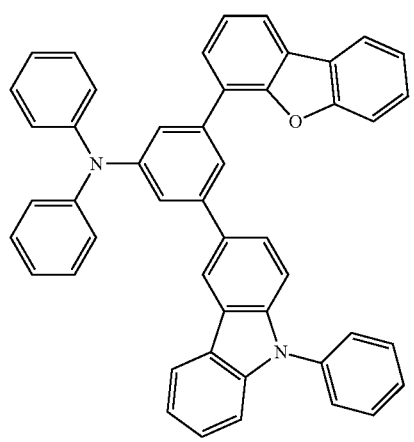
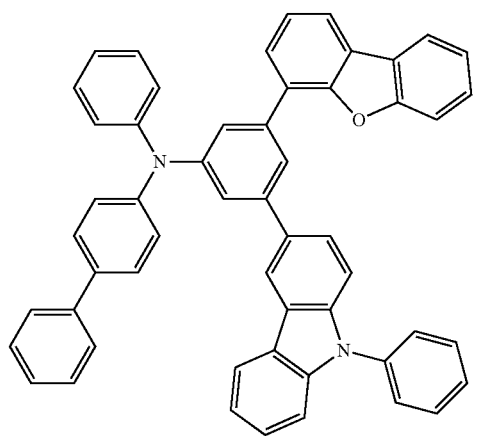

54
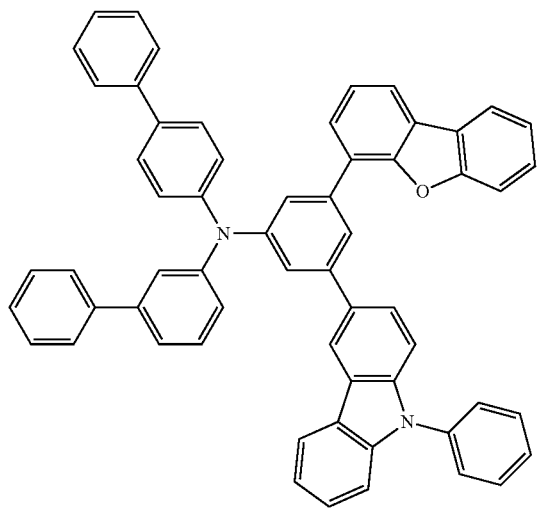
55
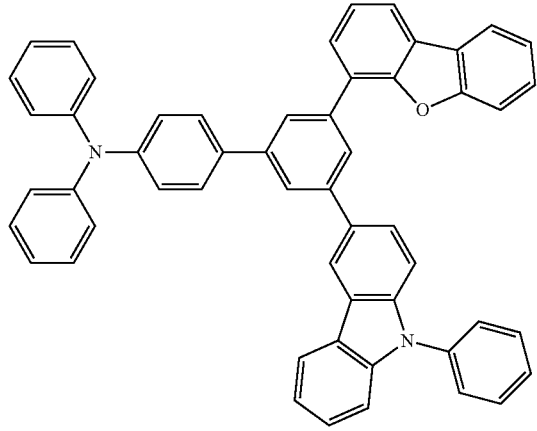
56
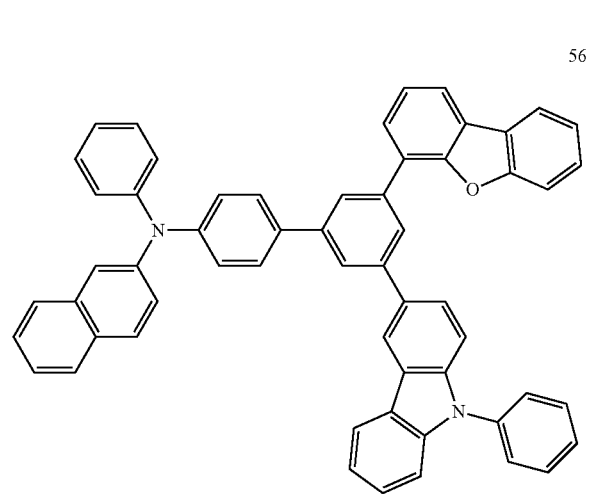
57
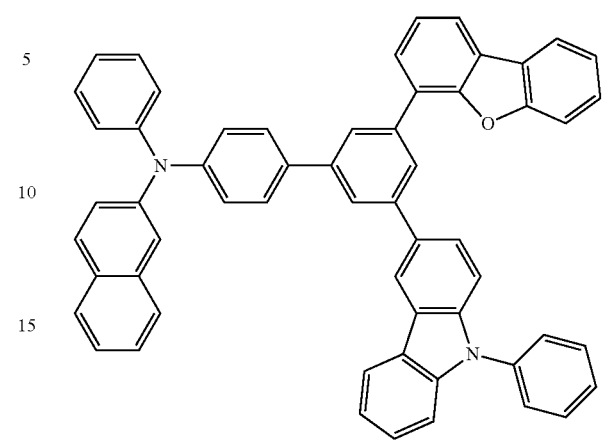
58
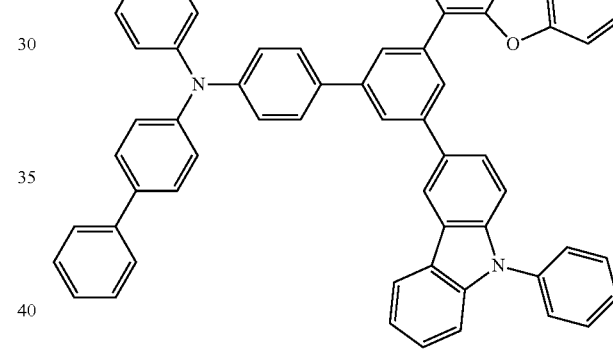
59
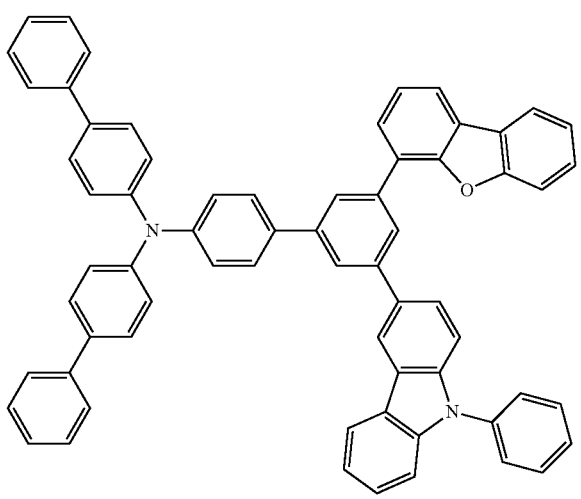

333
-continued
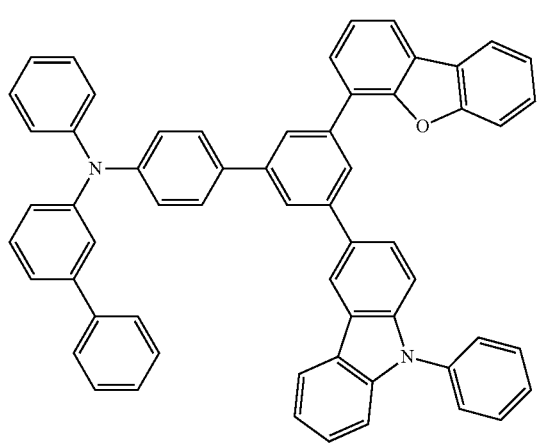
60
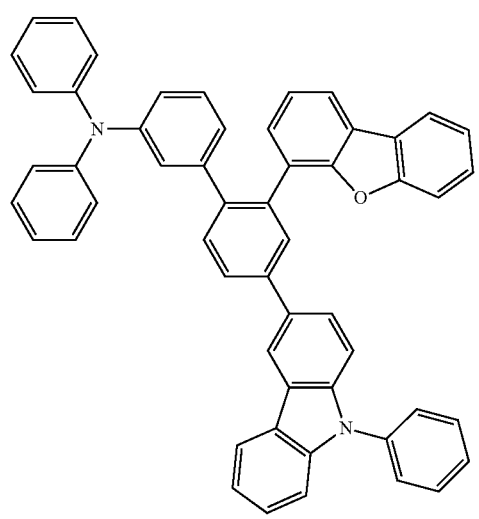
61
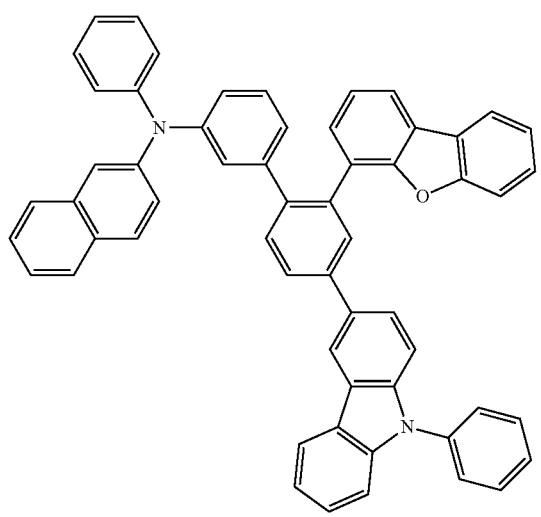
62
334
-continued
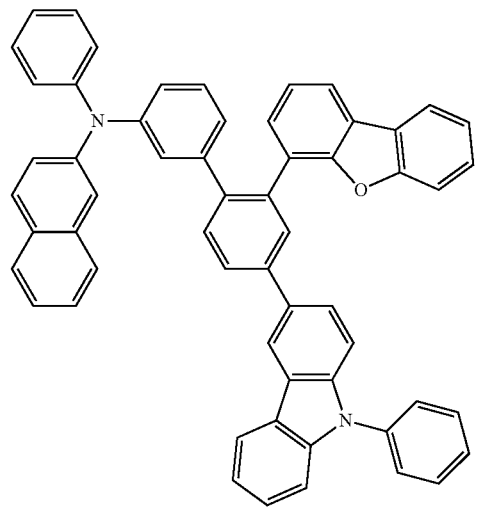
63
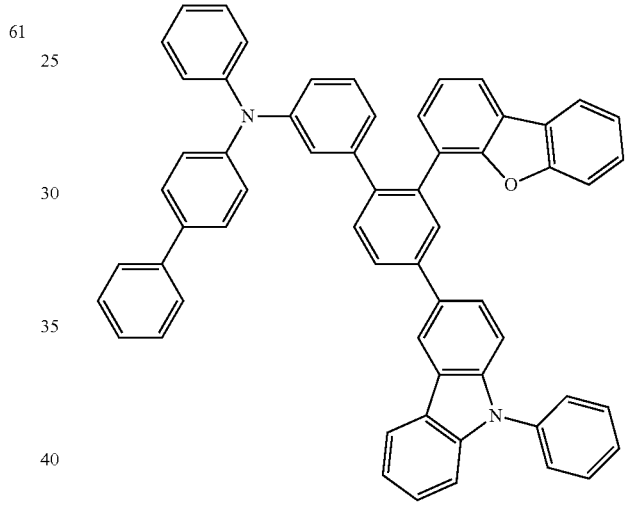
64
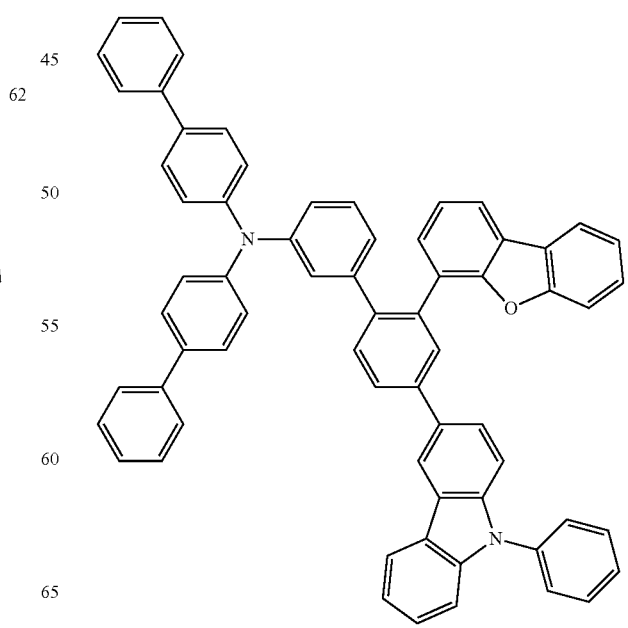
65

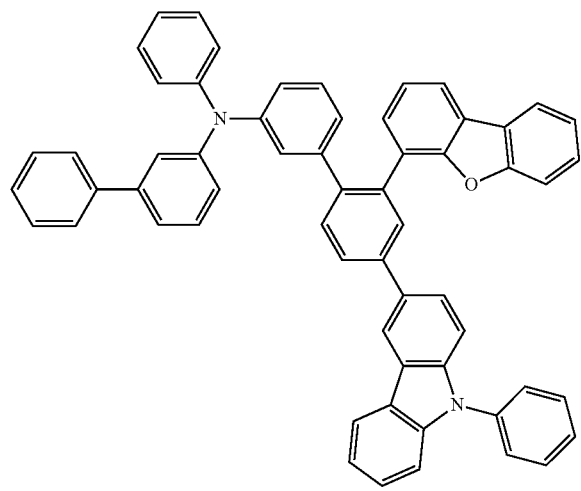
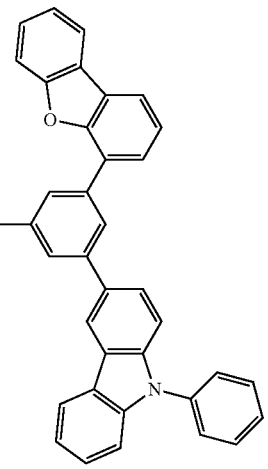
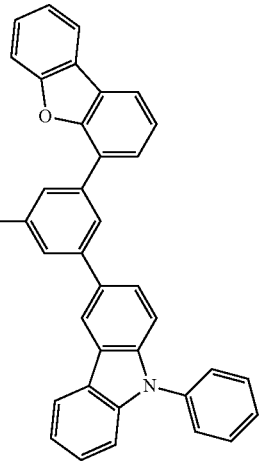
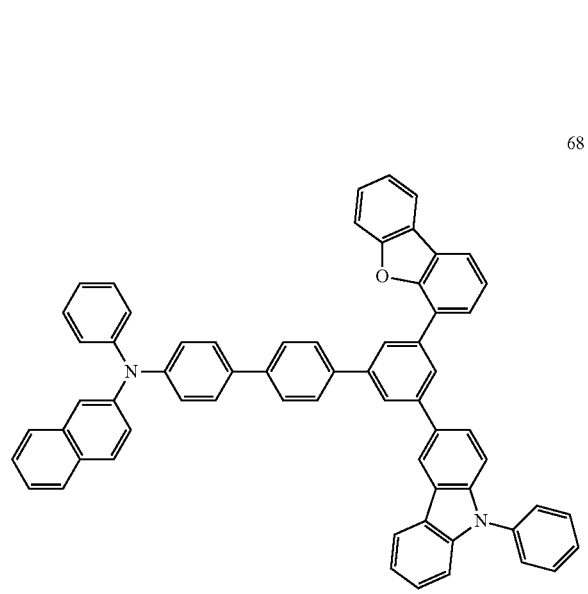
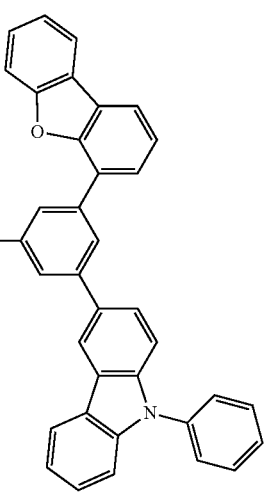

337
-continued
72
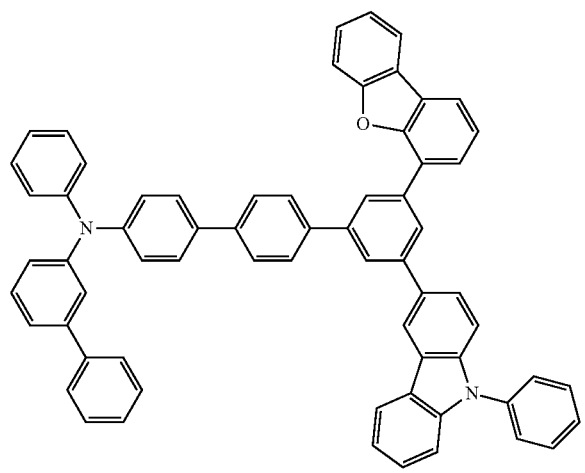
73
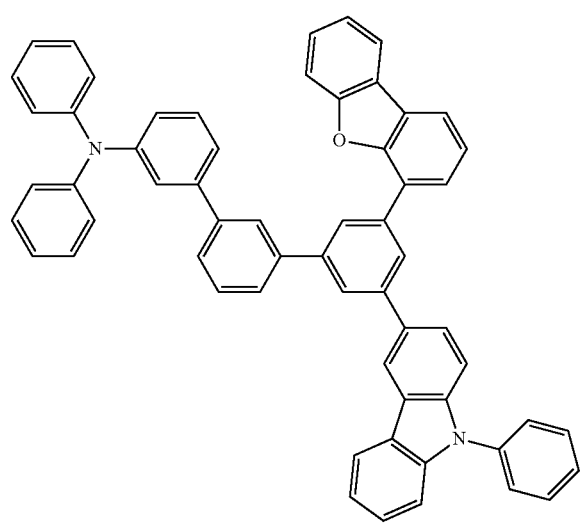
74
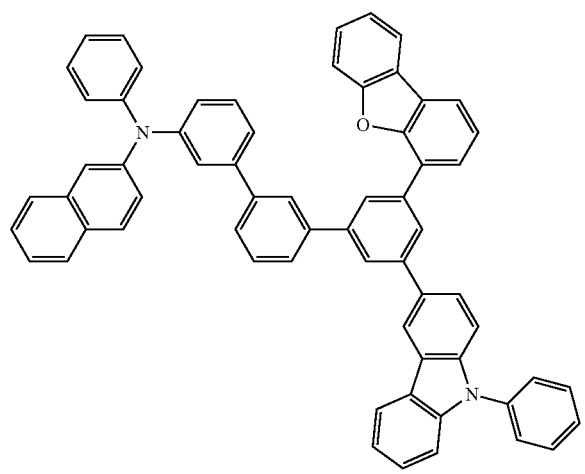
338
-continued
75
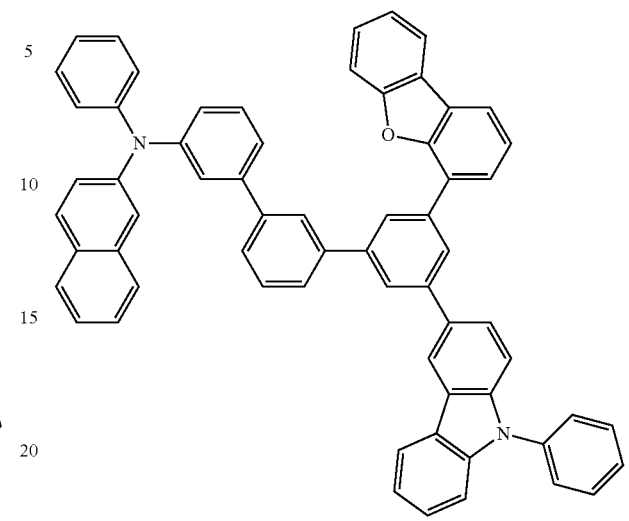
76
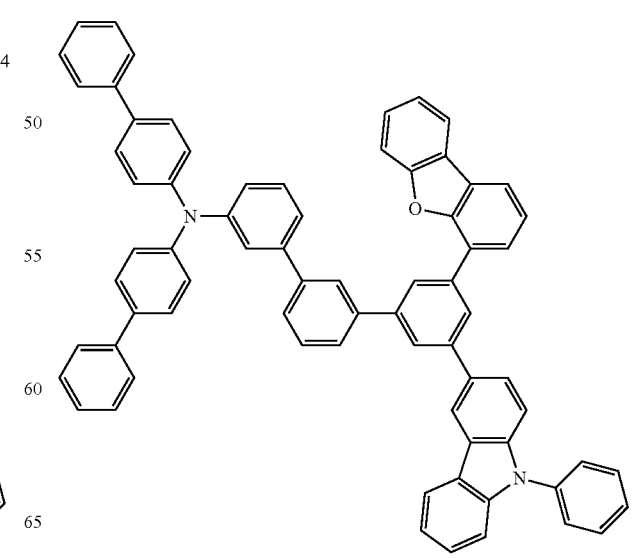
77

339
78
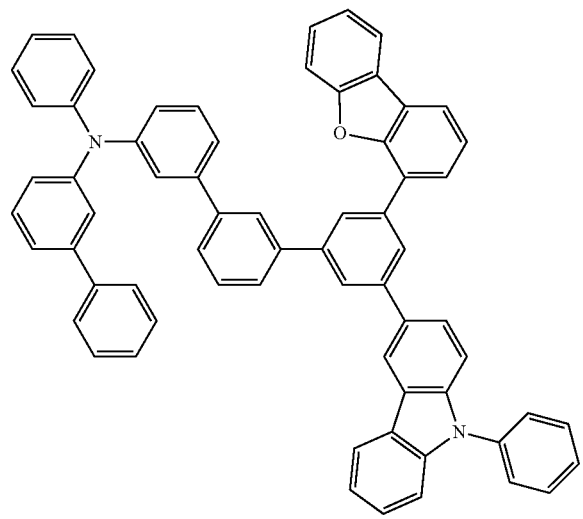
340
80
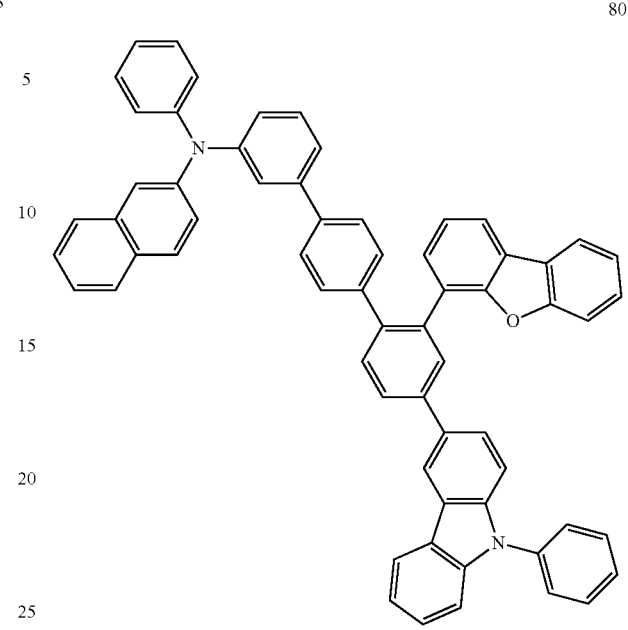
79
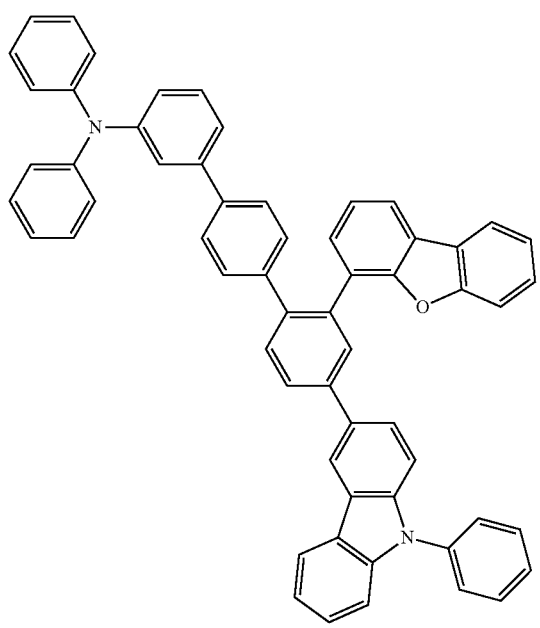
81
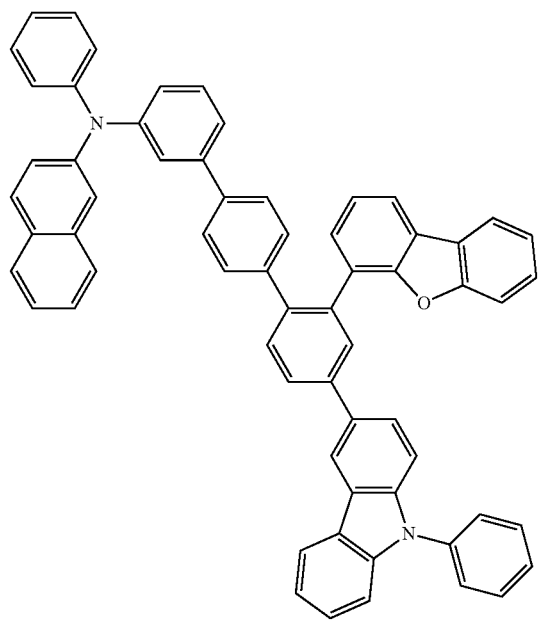

82
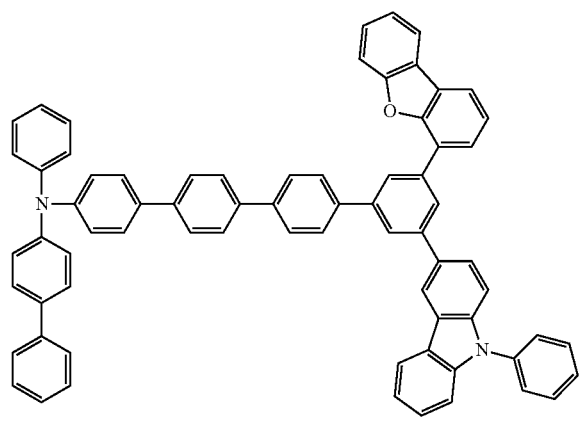
83
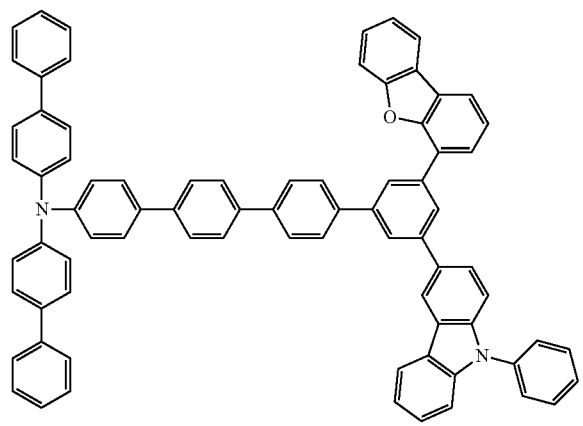
84
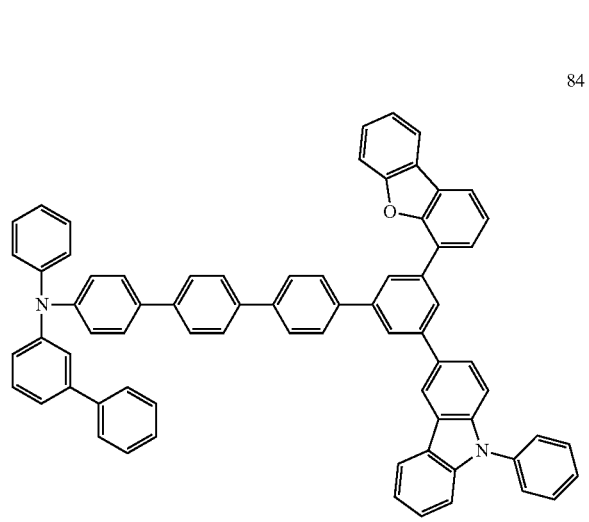
85
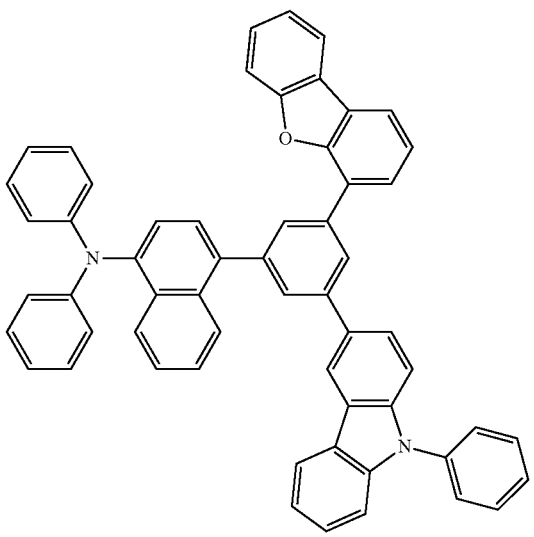
86
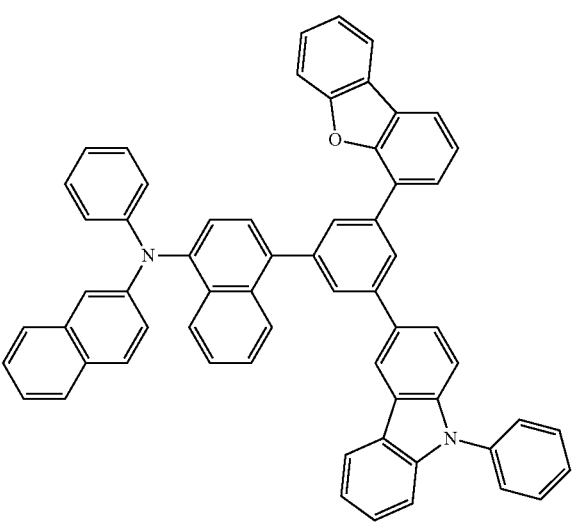
87
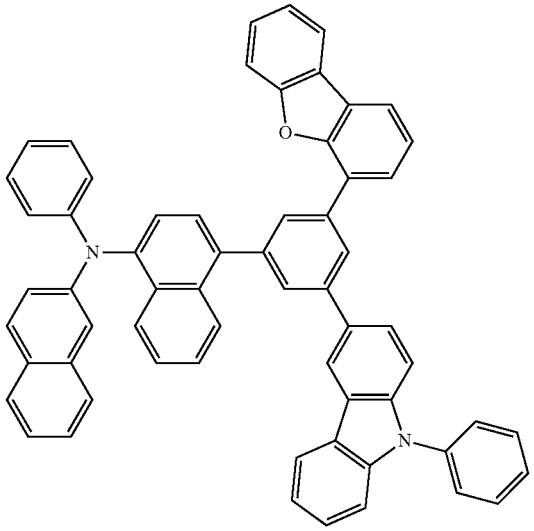

88
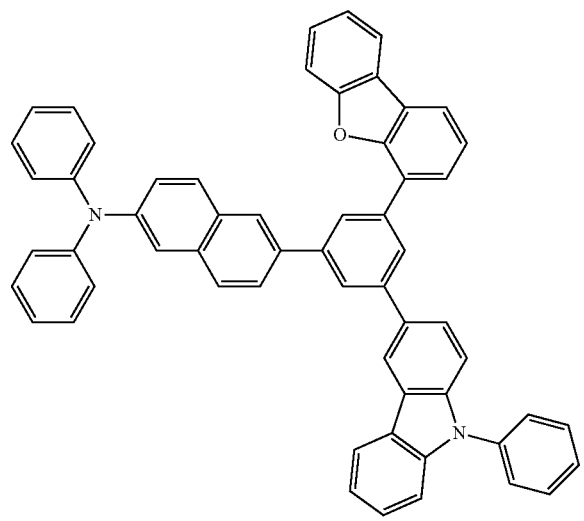
89
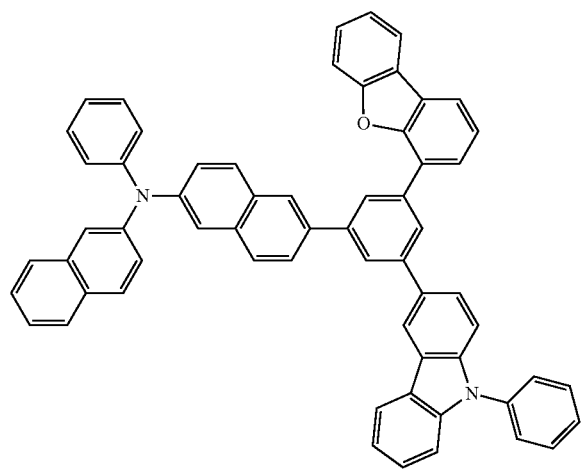
90
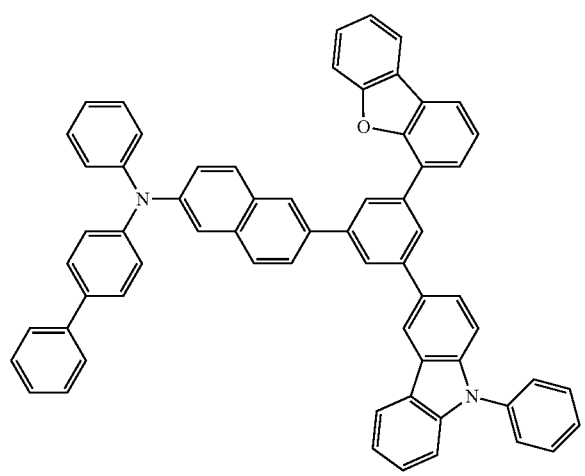
91
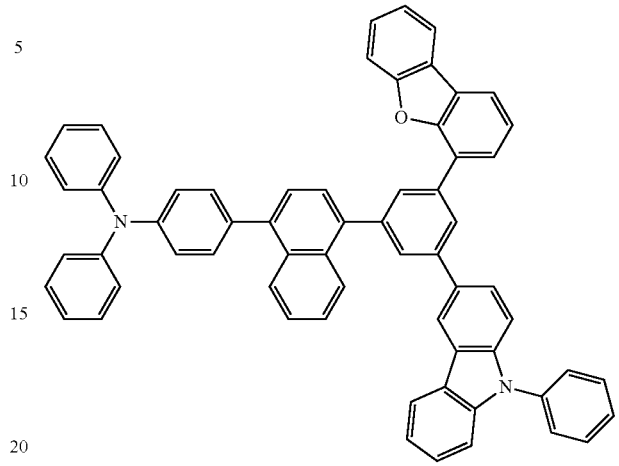
92
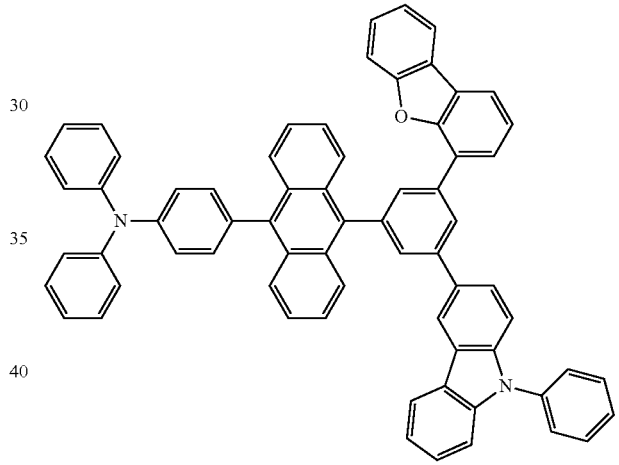
93
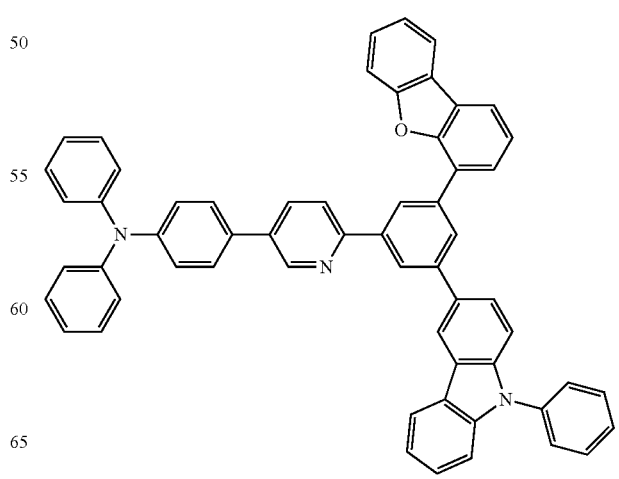

94
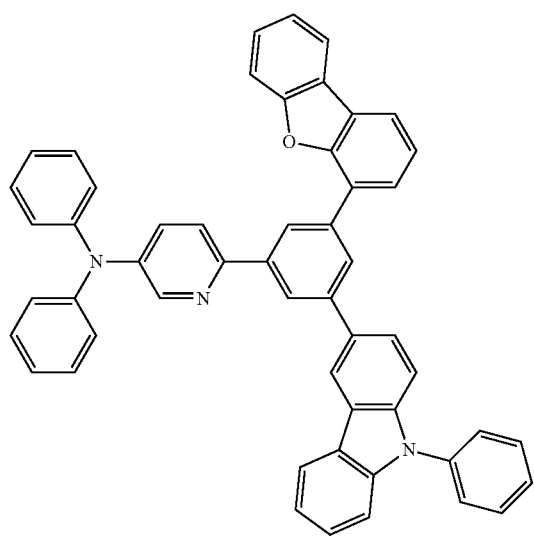
95
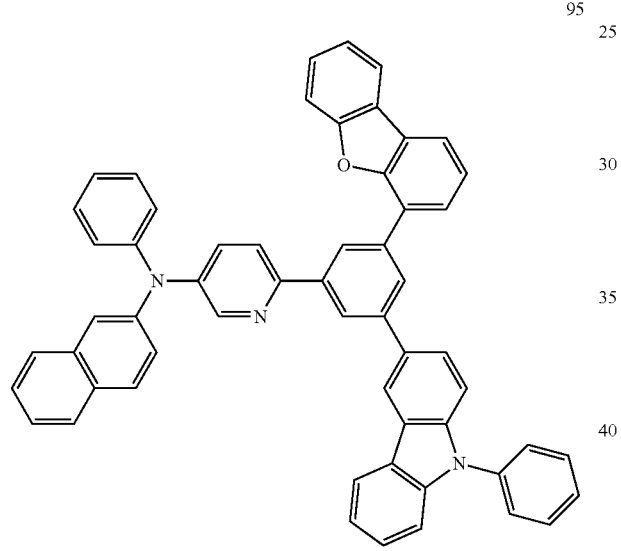
96
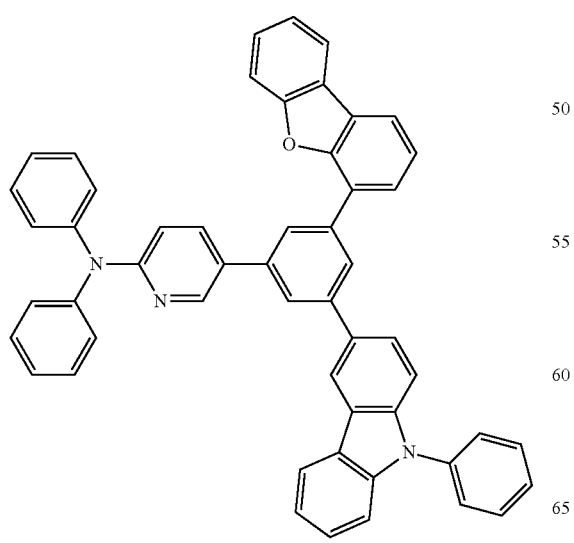
97
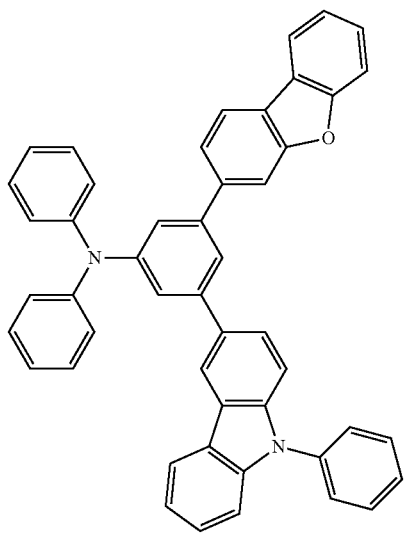
98
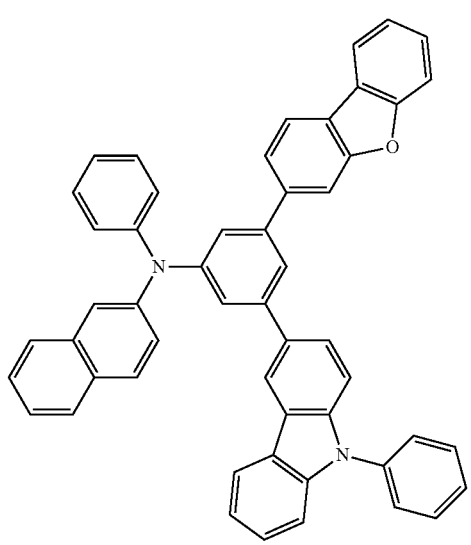
99
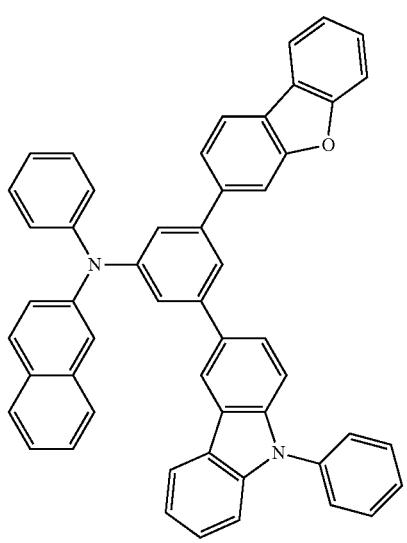

100
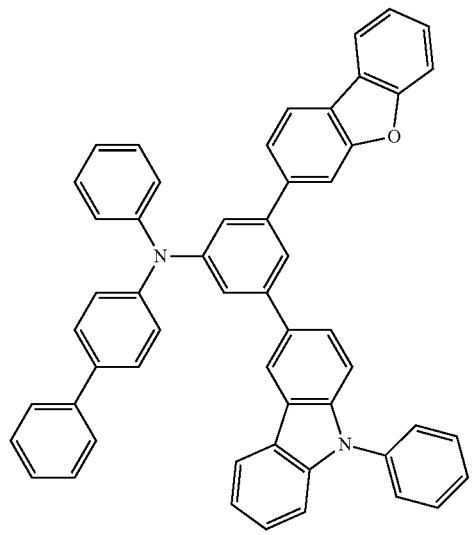
101
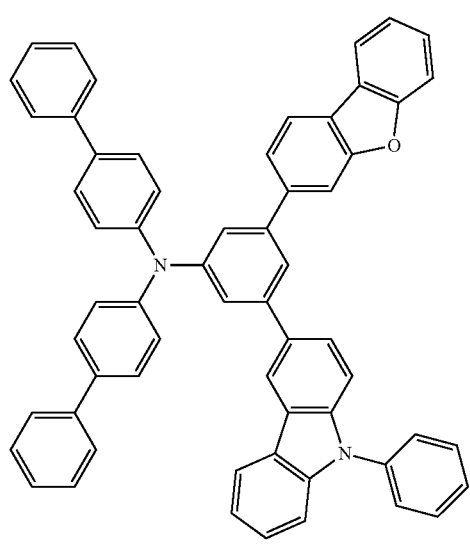
102
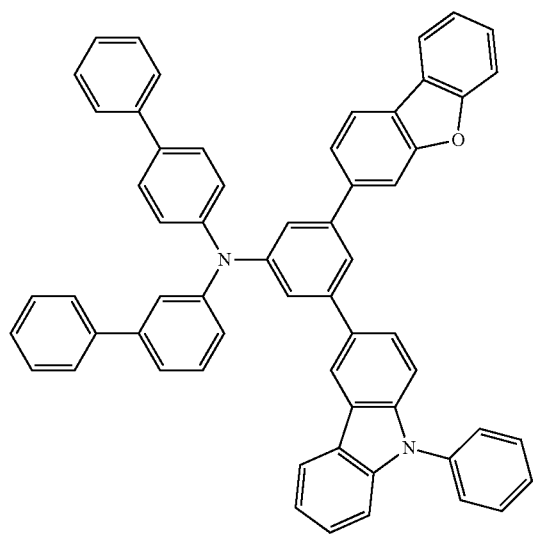
103
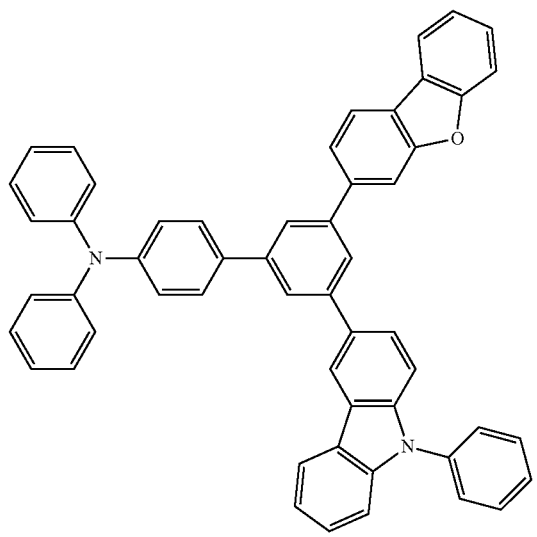
104
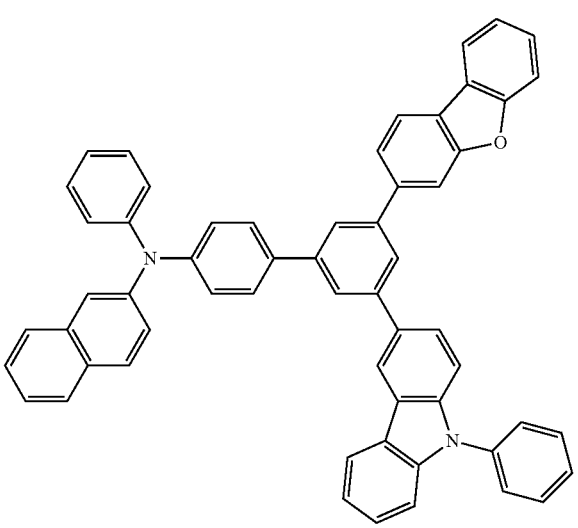
105
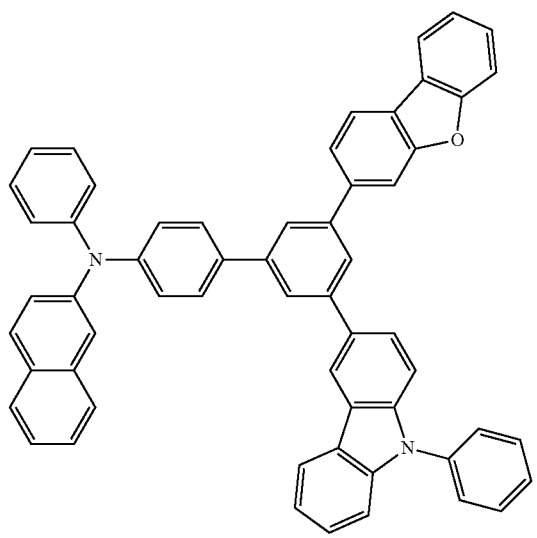

106
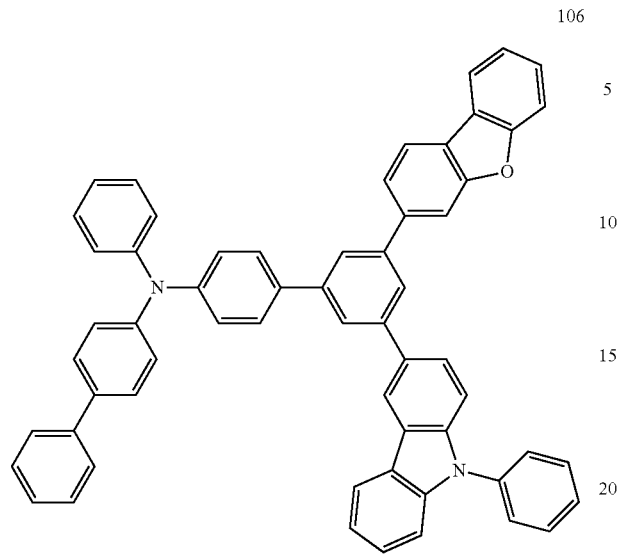
107
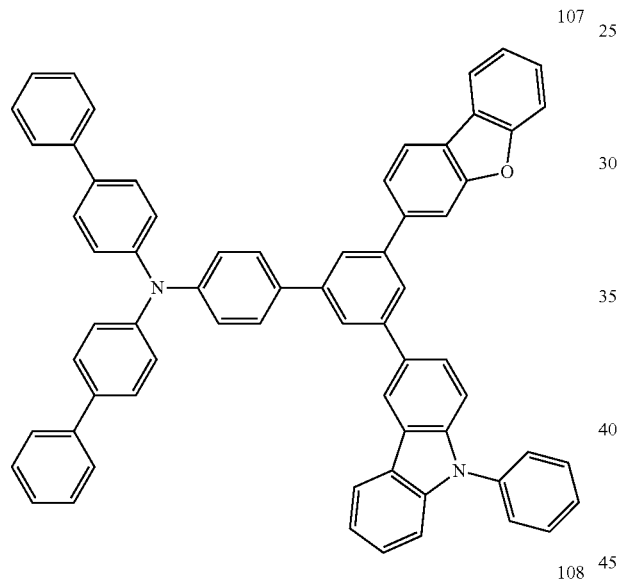
108
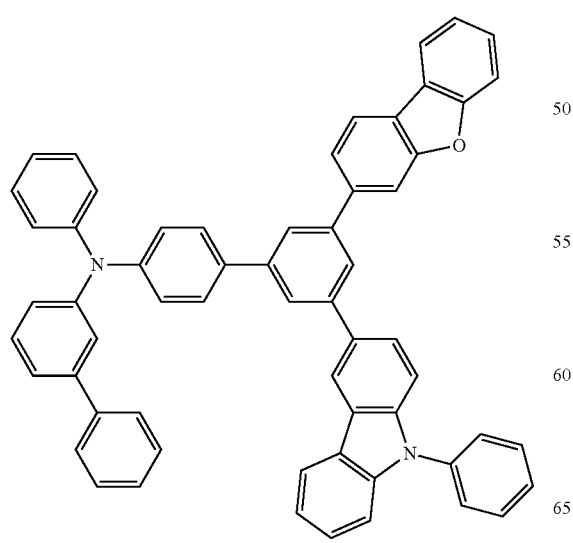
109
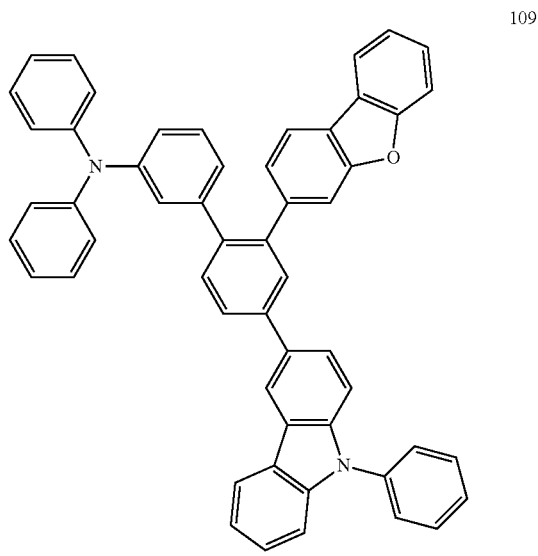
110
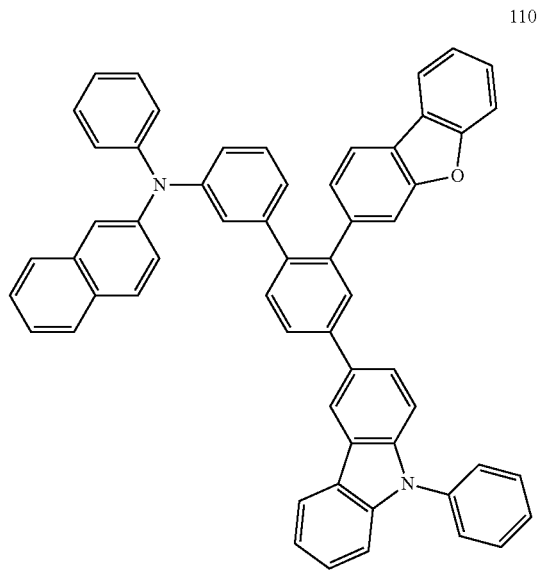
111
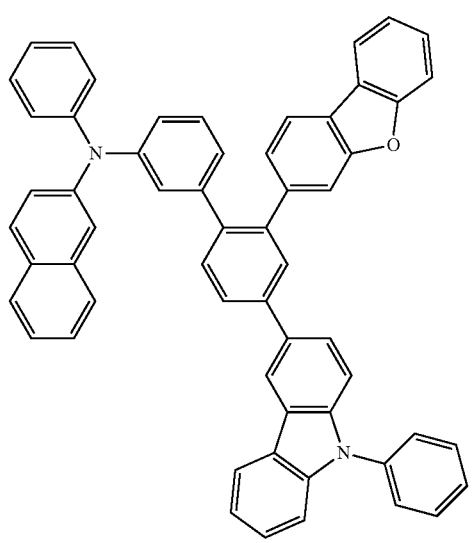

351
-continued
112
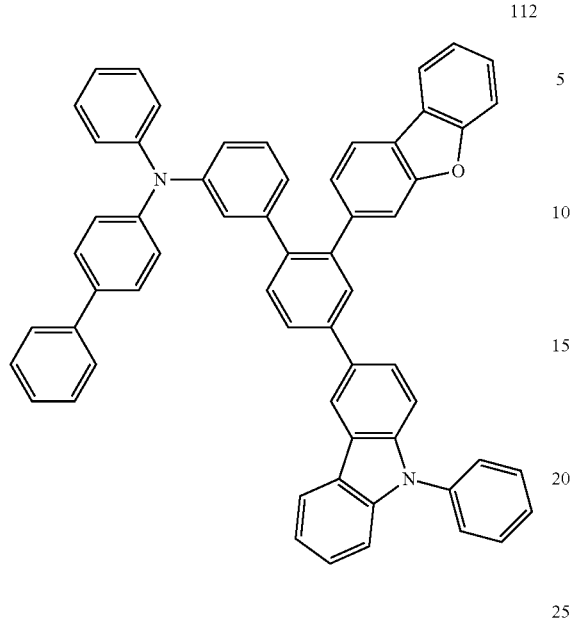
113
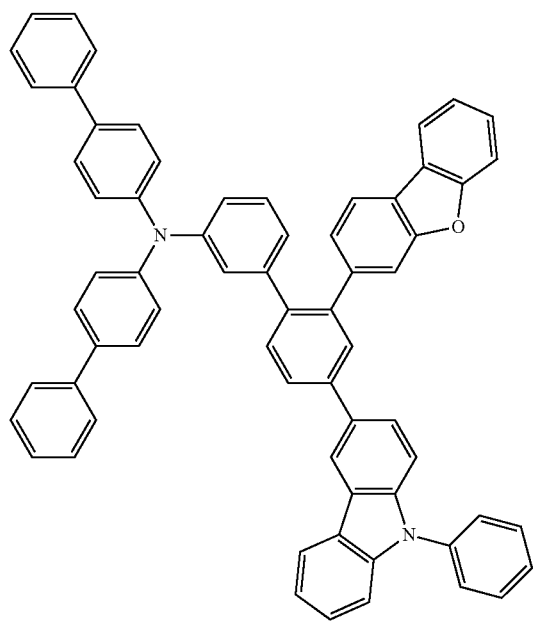
352
-continued
114
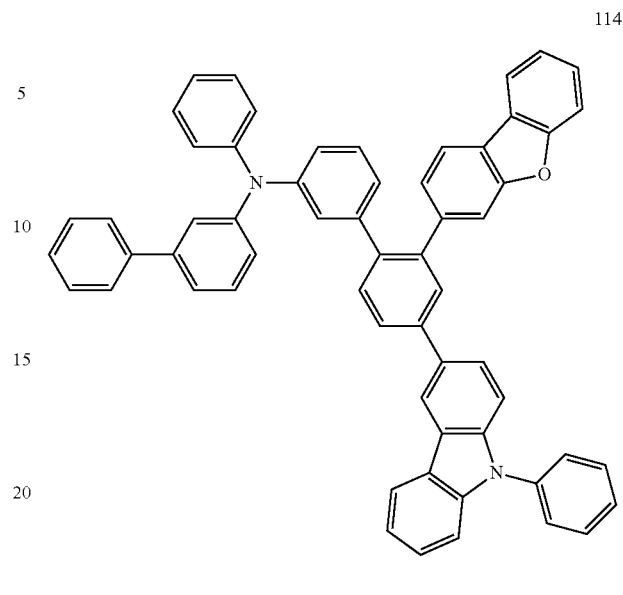
115
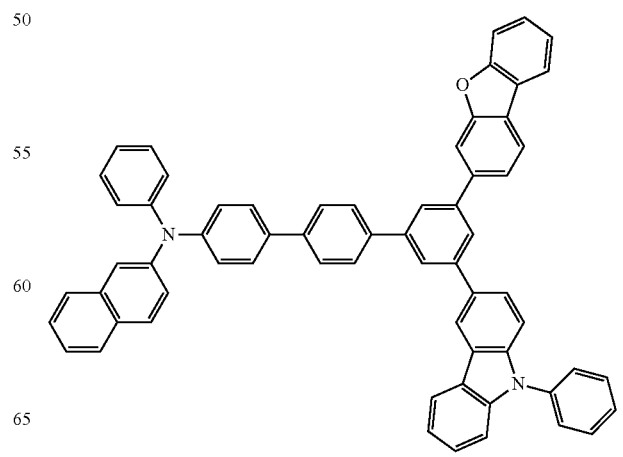
116

117
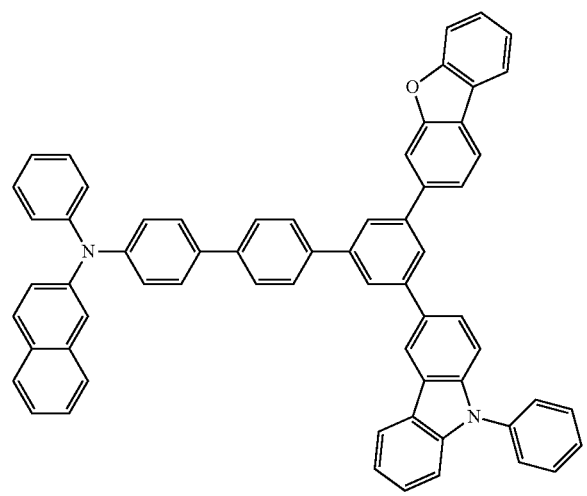
120
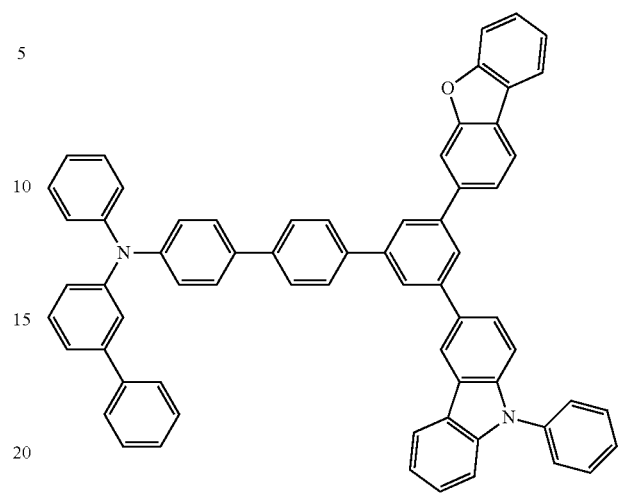
118
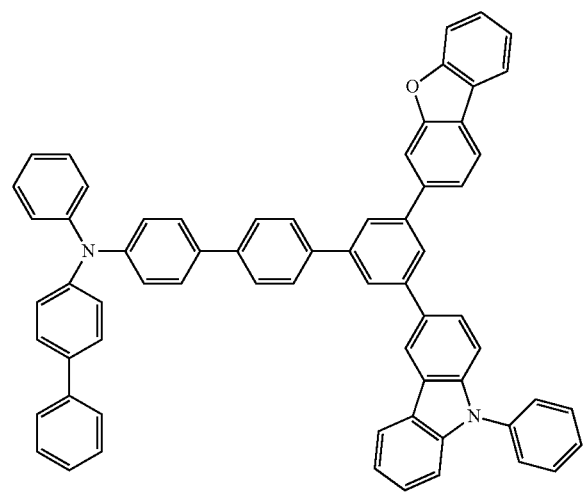
121
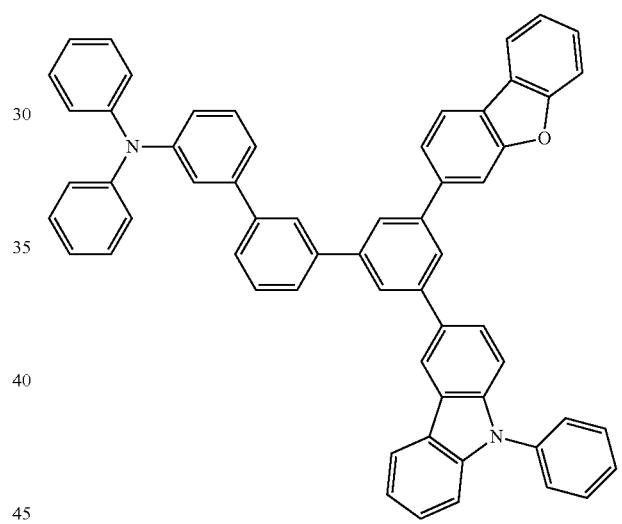
119
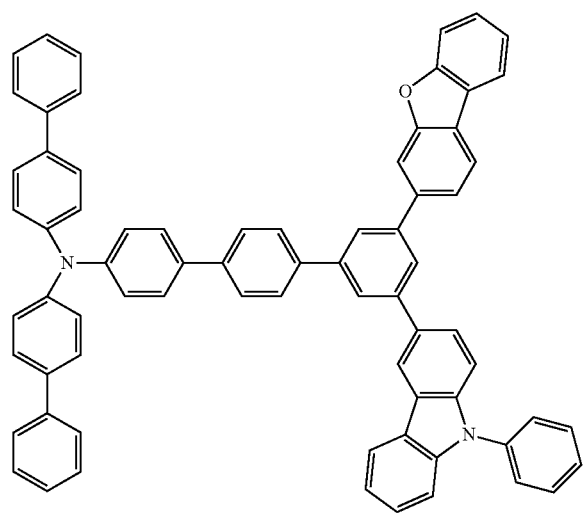
122
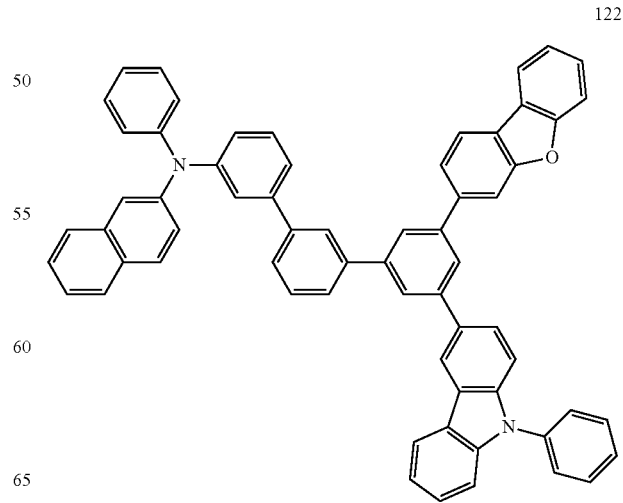

355
-continued
123
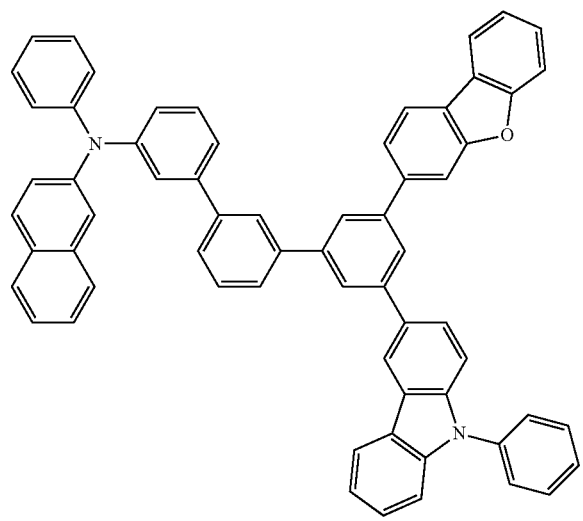
124
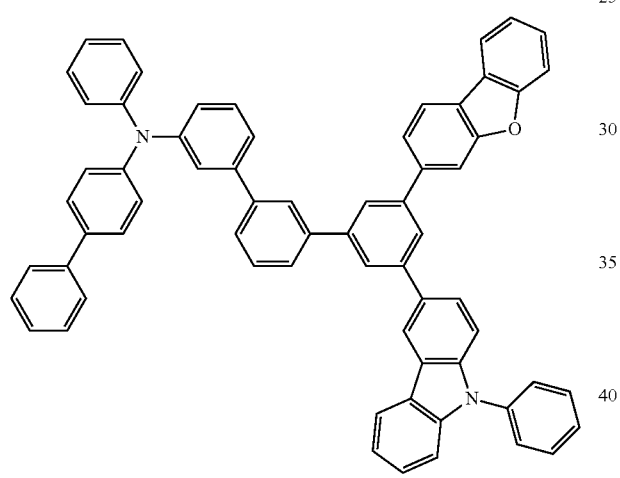
125
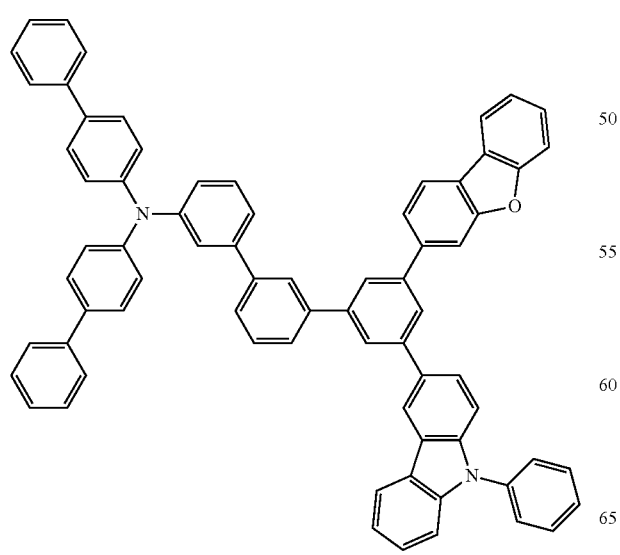
356
-continued
126
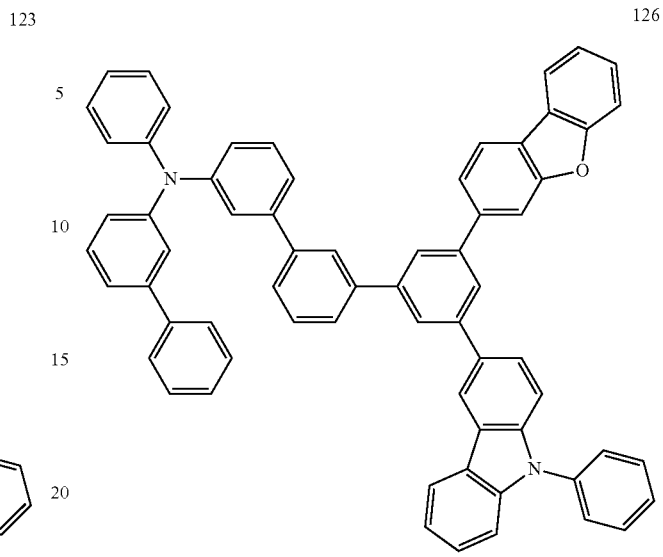
127
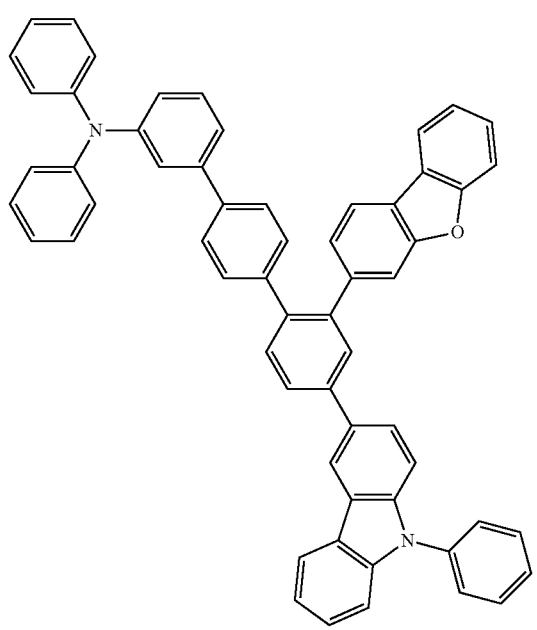

-continued
128
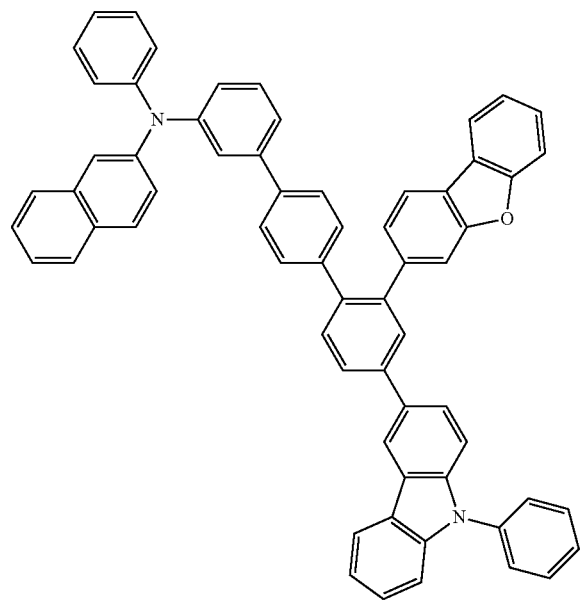
129
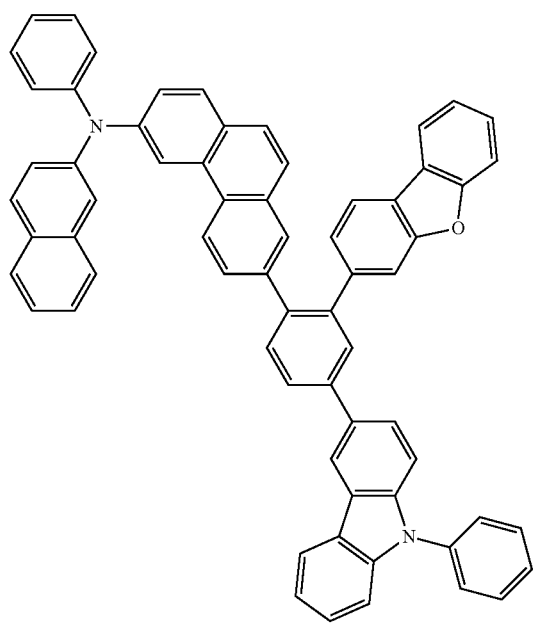
130
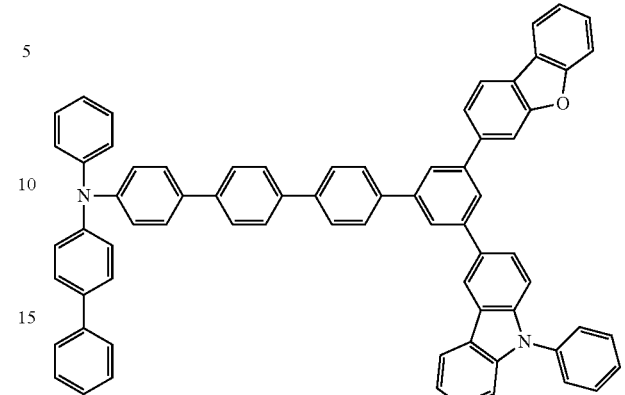
131
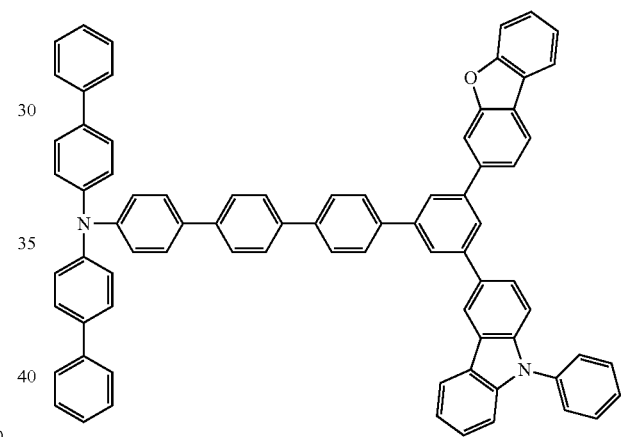
132

-continued
133
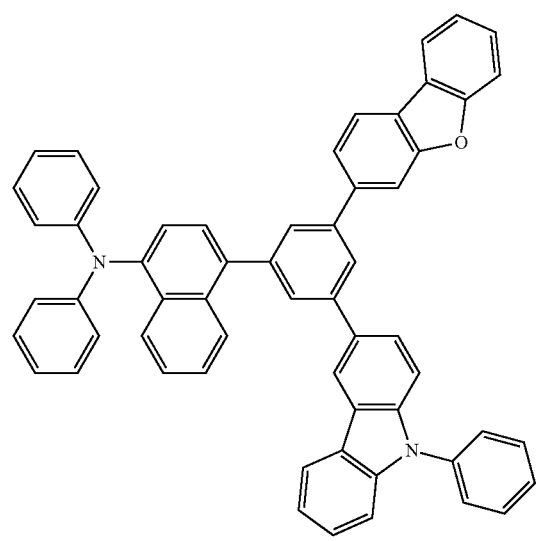
134
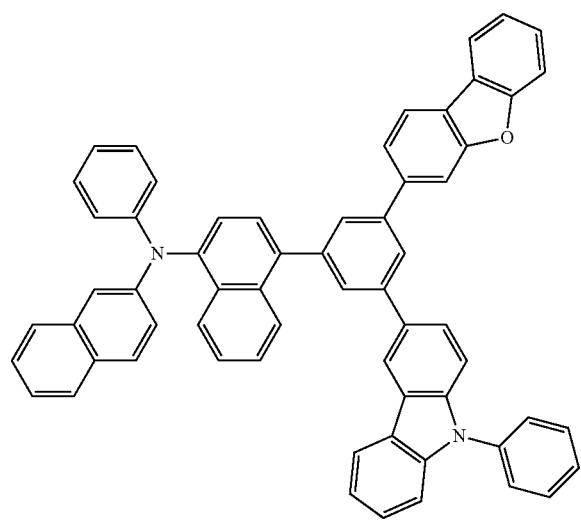
135
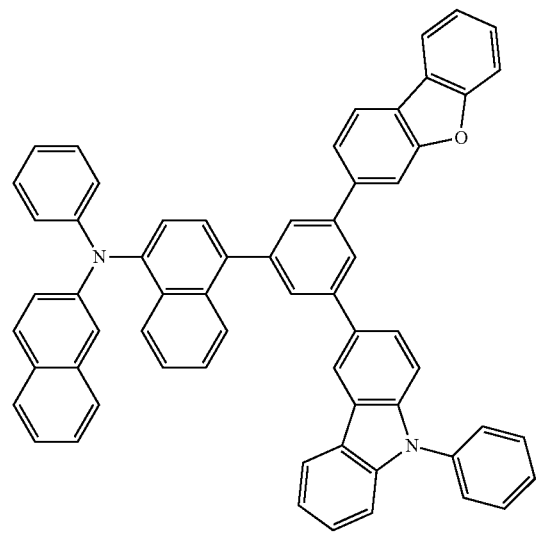
-continued
136
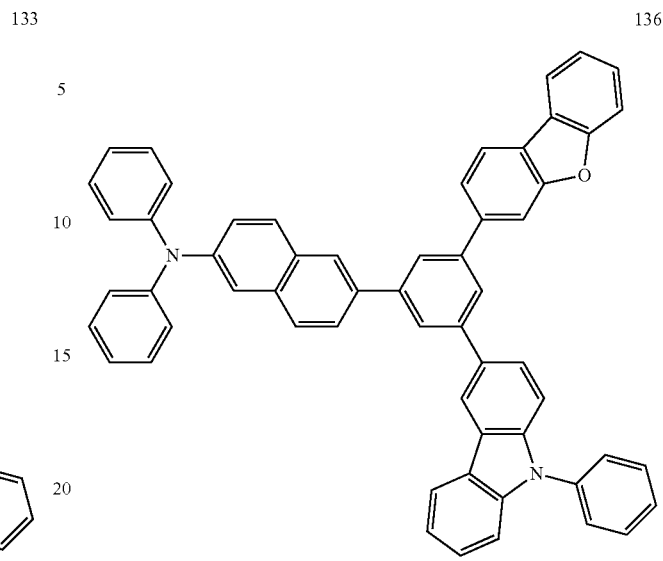
137
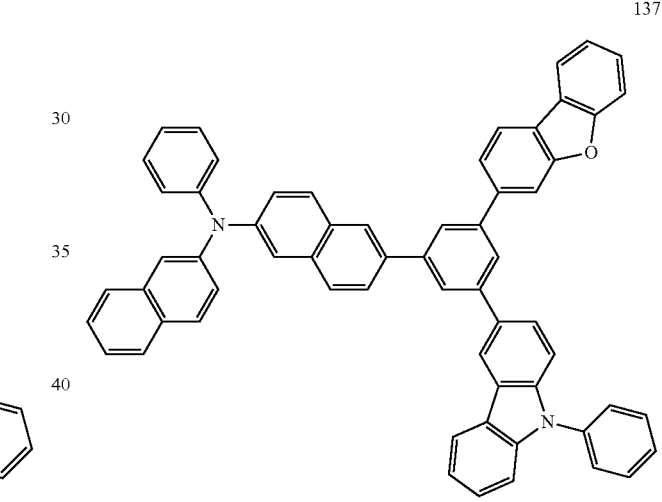
138
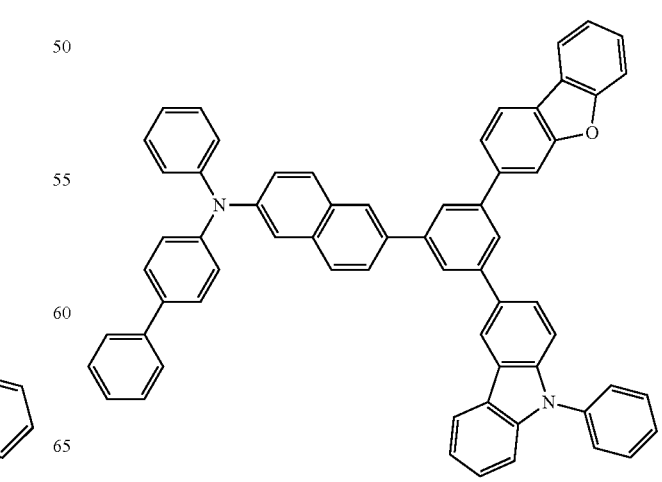

139
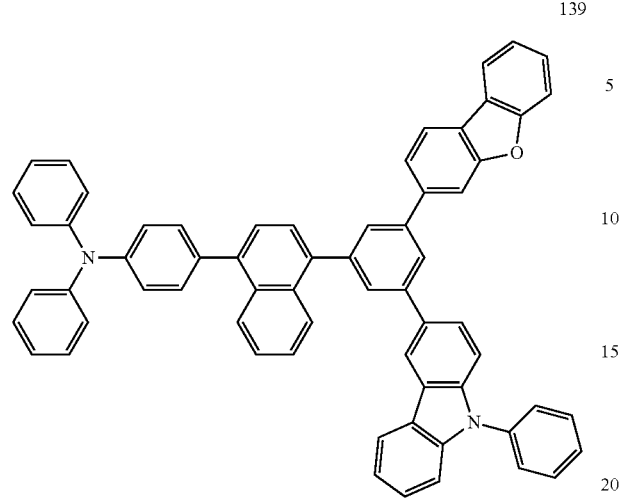
140
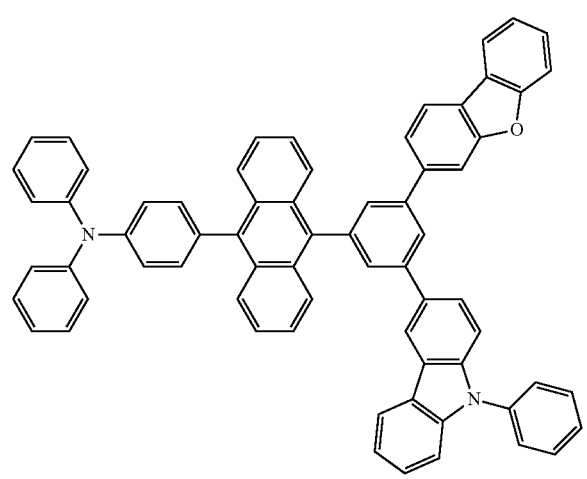
141
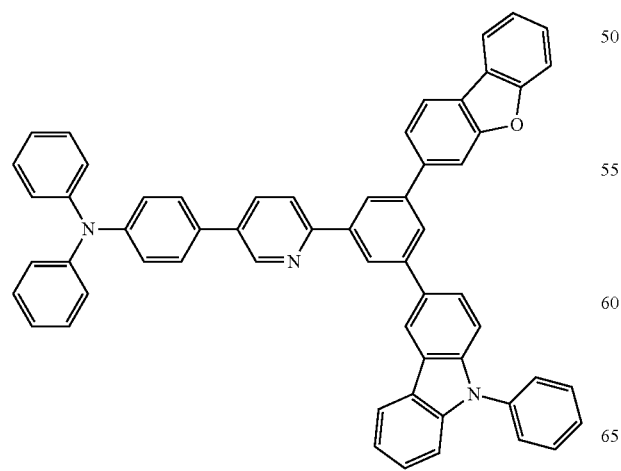
142
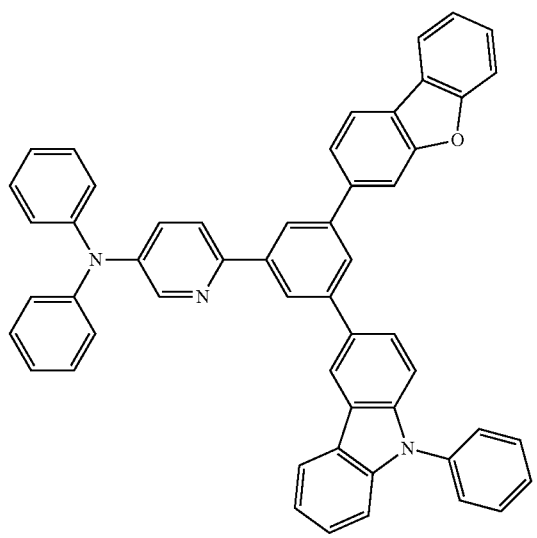
143
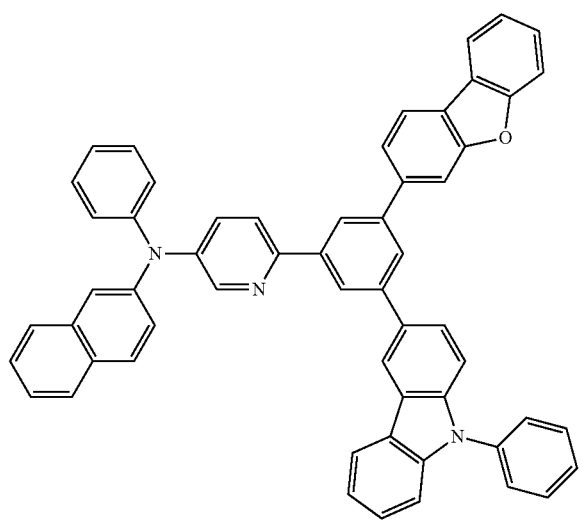
144
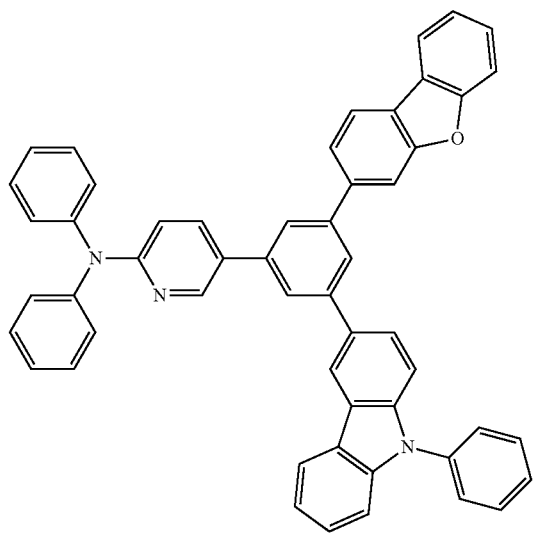

363
-continued
145
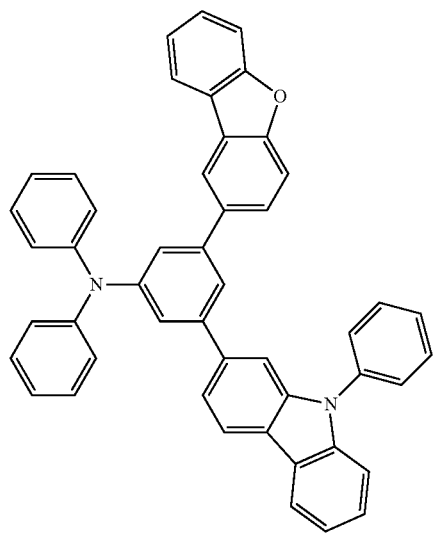
146
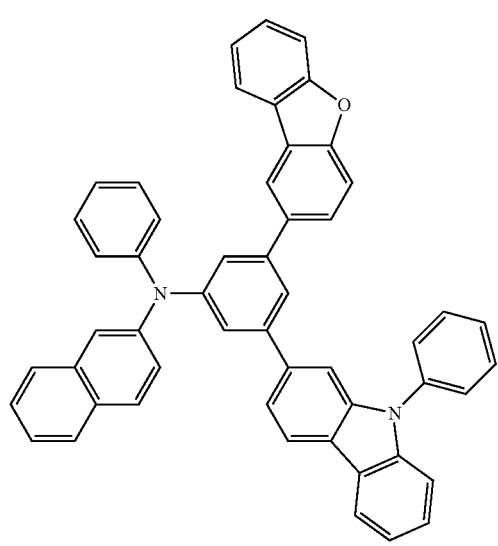
147
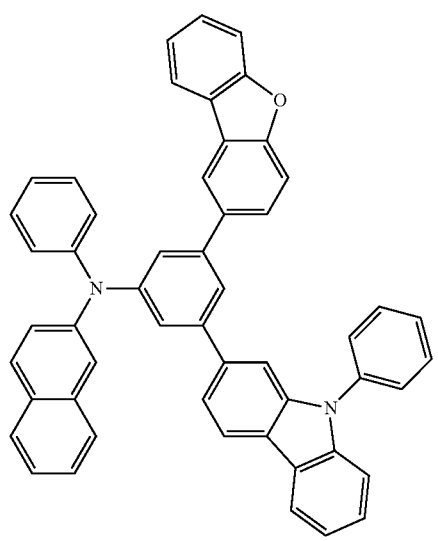
364
-continued
148
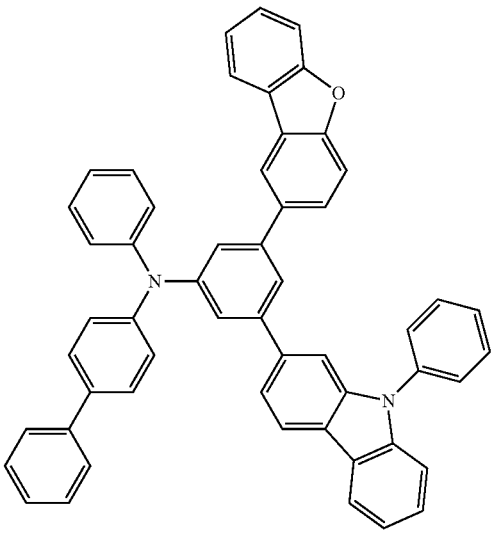
149
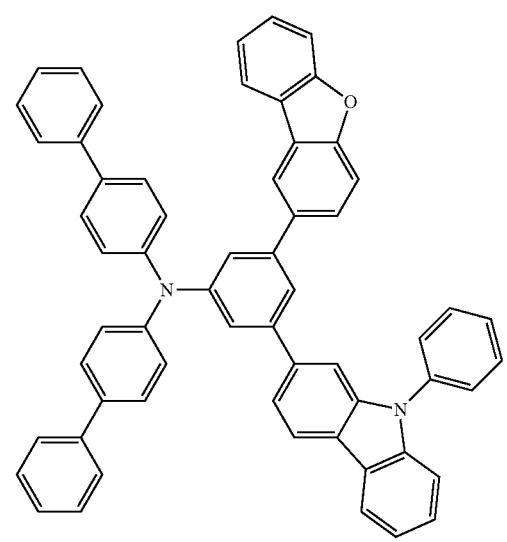
150
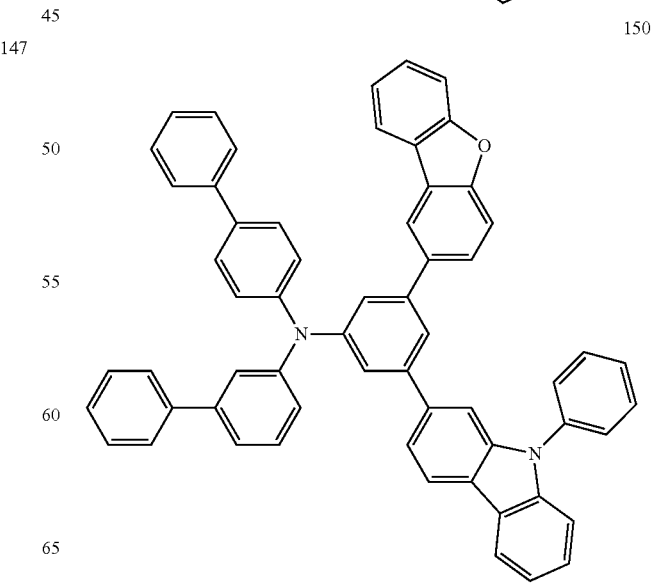

-continued
151
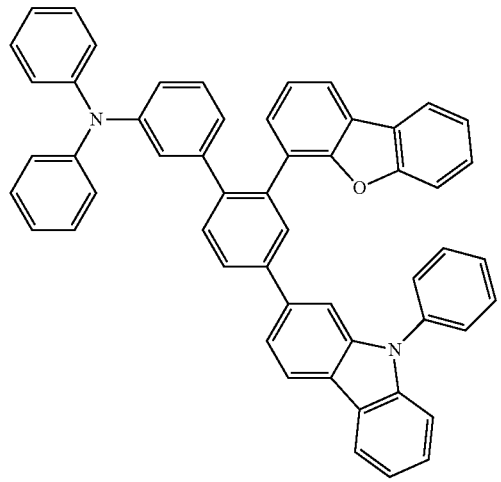
152
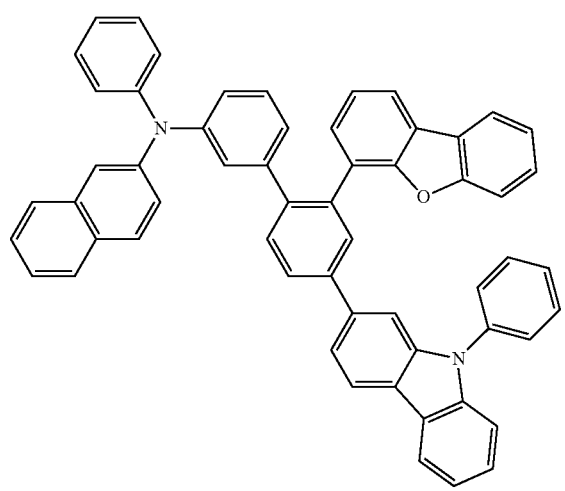
153
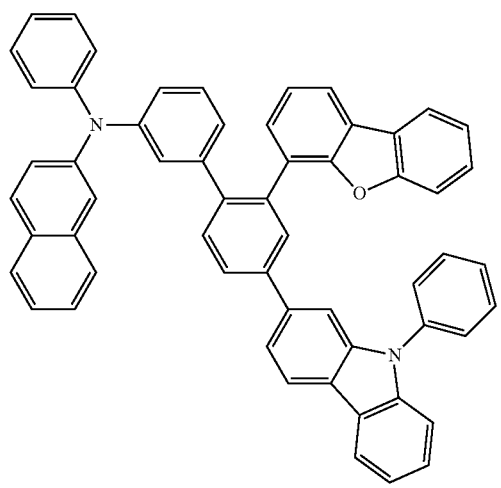
-continued
154
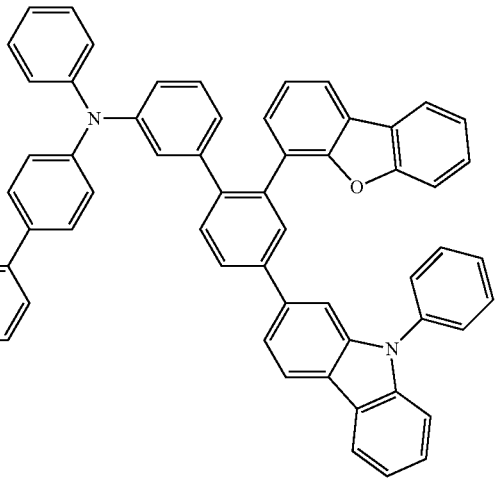
155
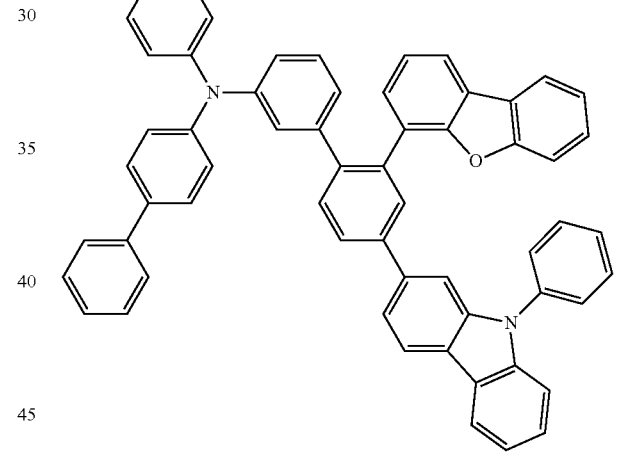
156
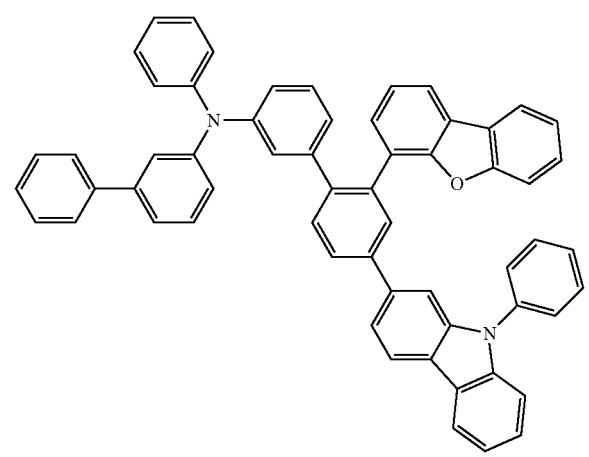

157
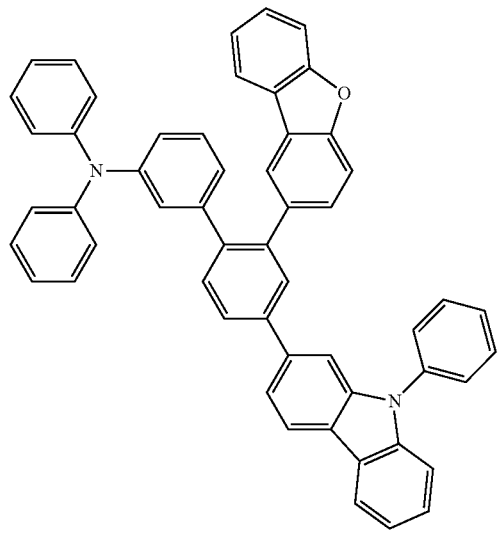
158
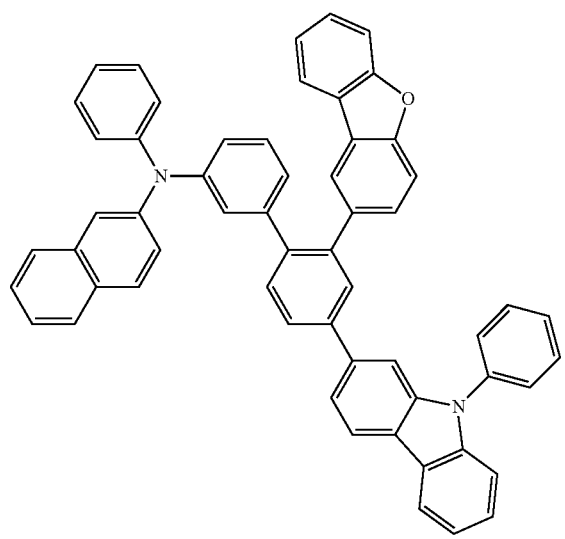
159
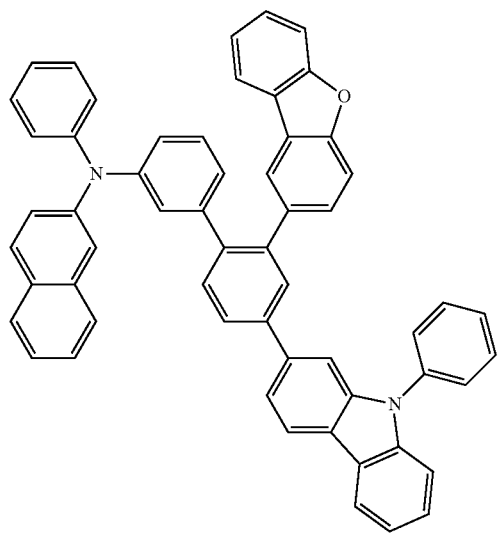
160
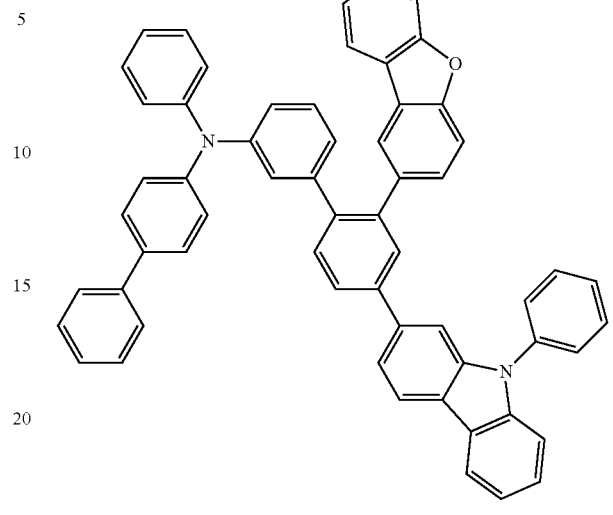
161
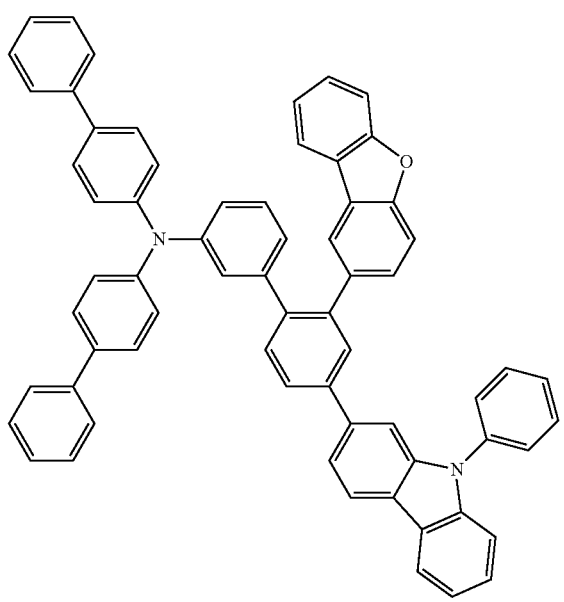

-continued
162
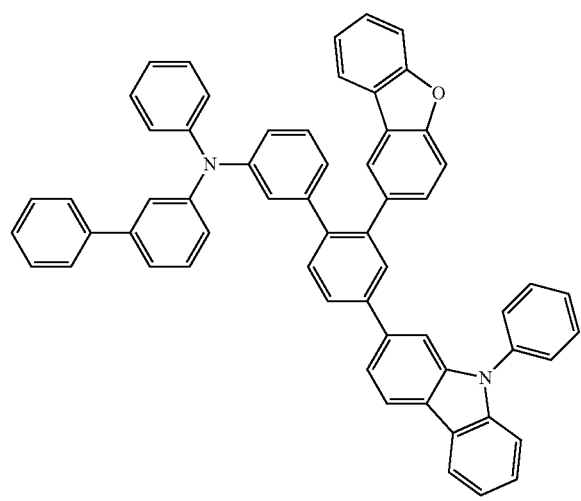
163
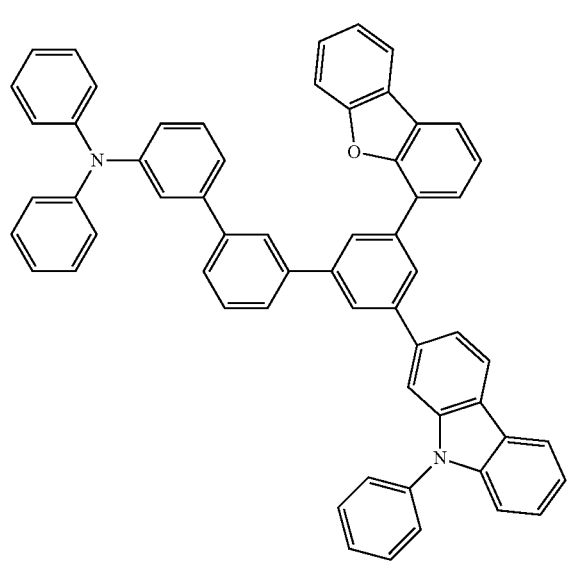
-continued
165
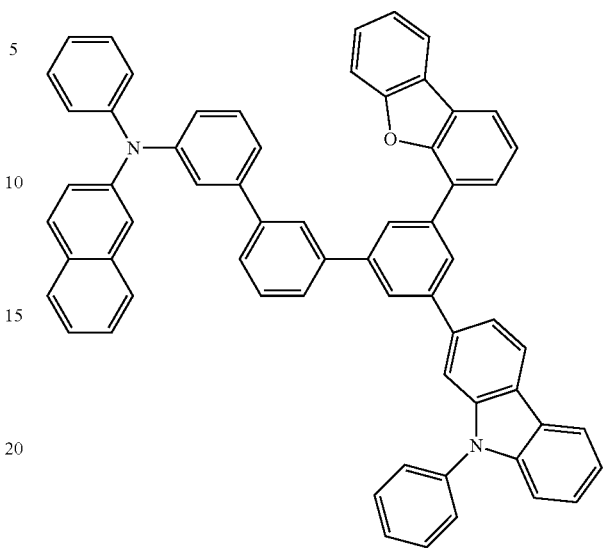
166
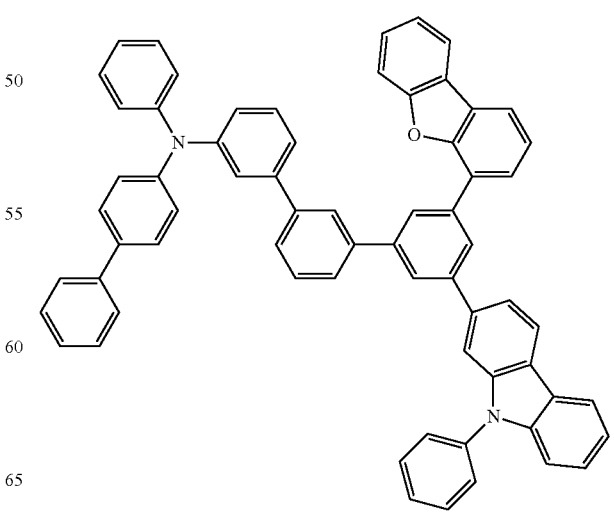
164
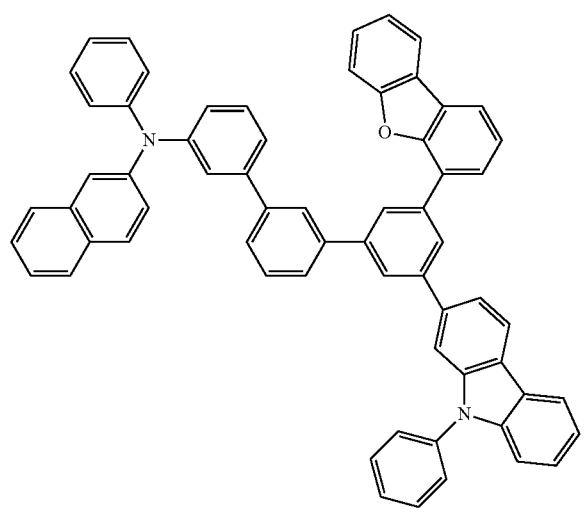

167
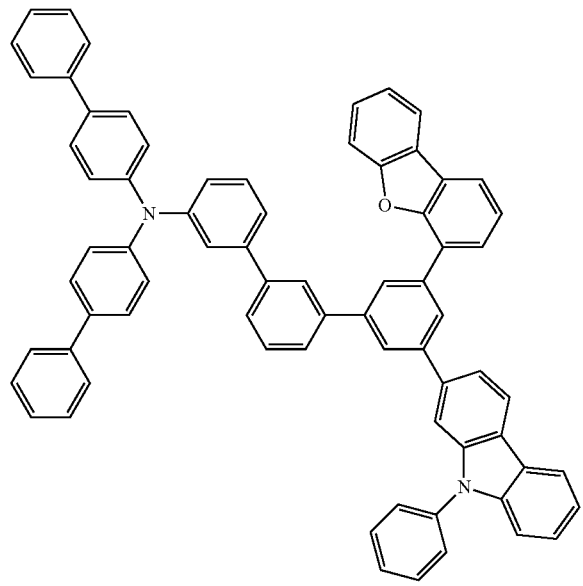
168
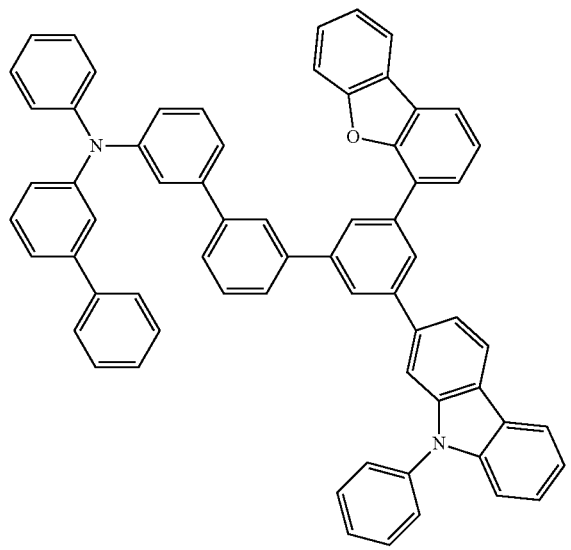
169
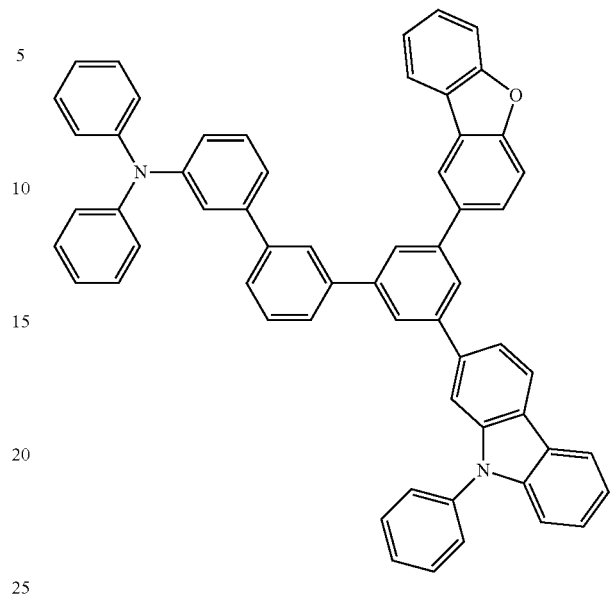
170
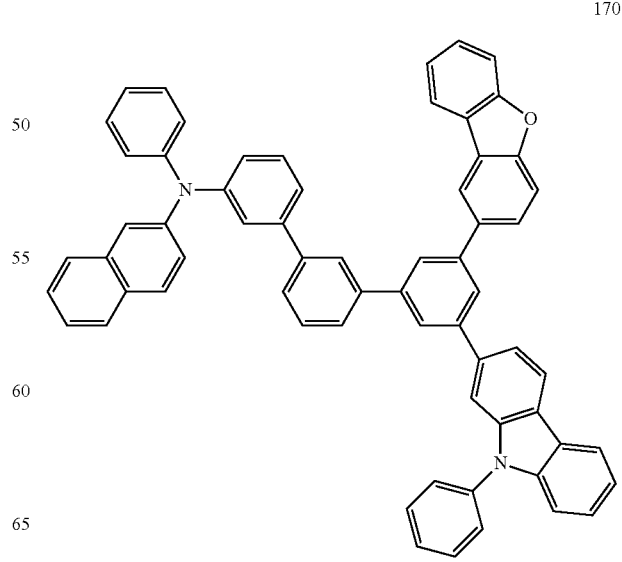

373
-continued
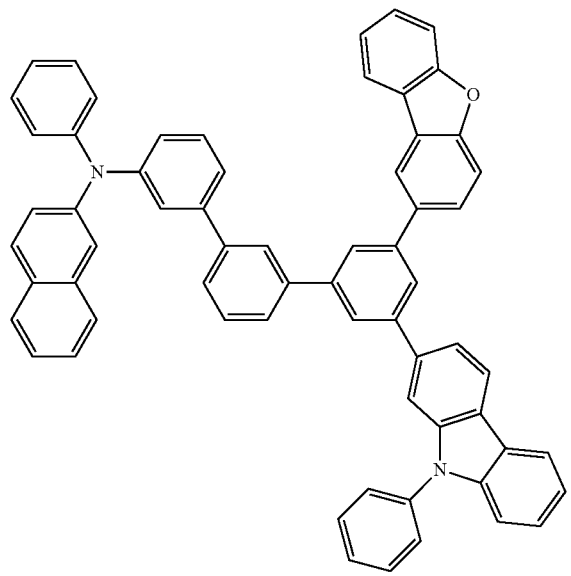
171
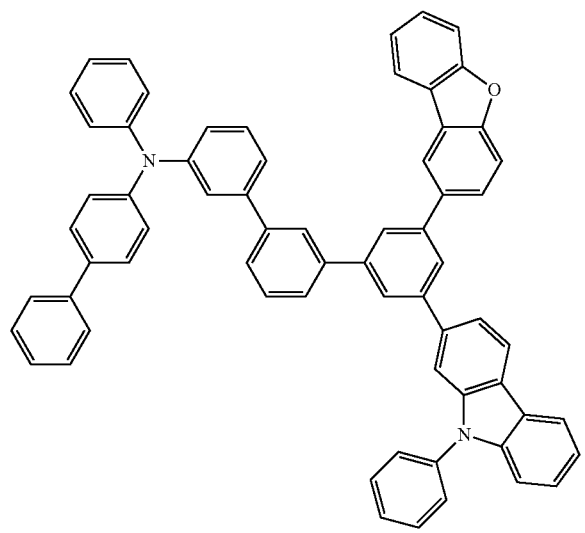
172
374
-continued
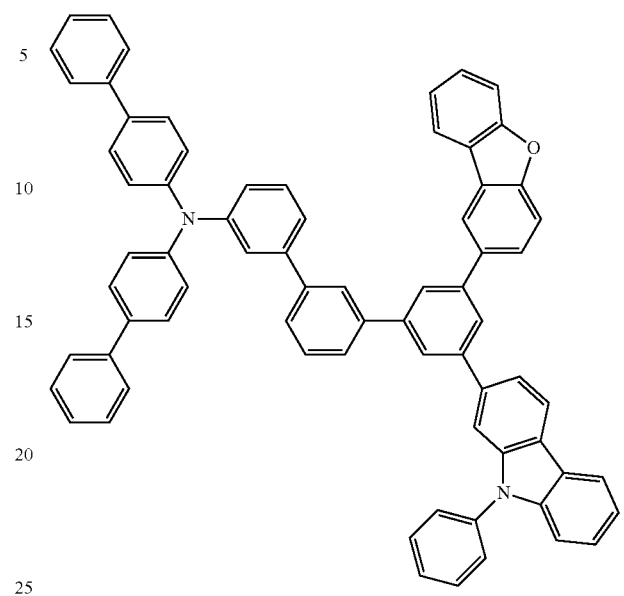
173
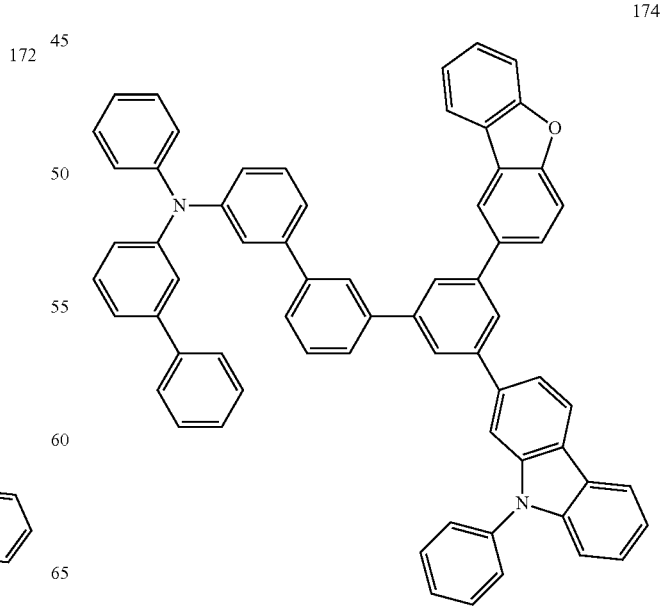
174

175
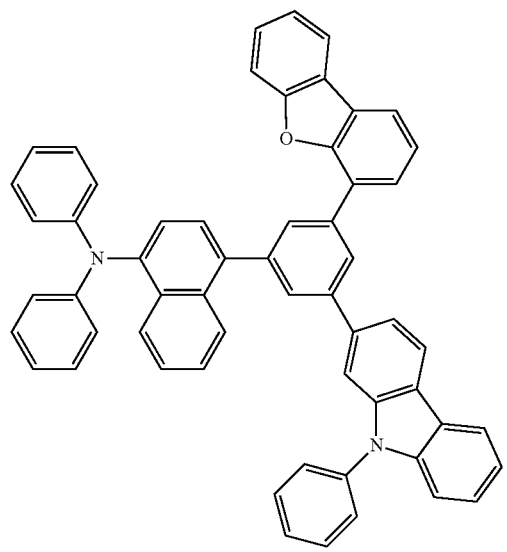
176
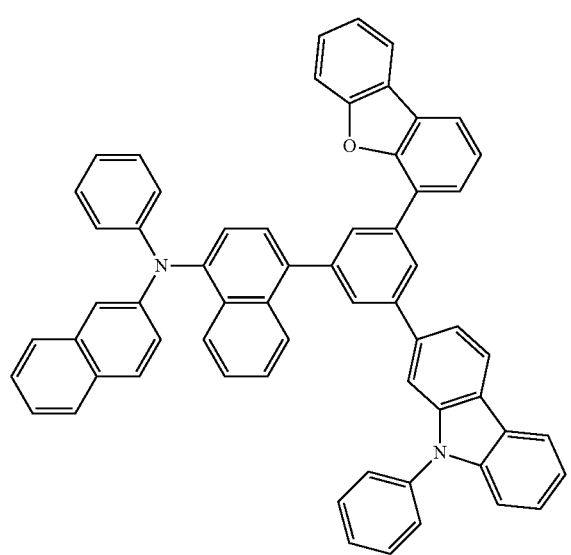
177
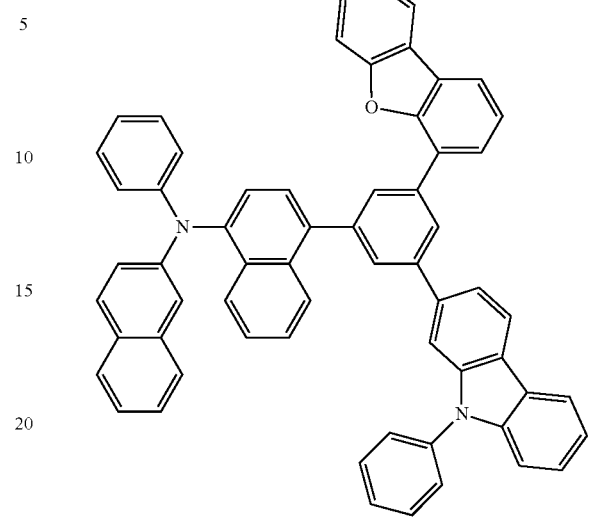
178
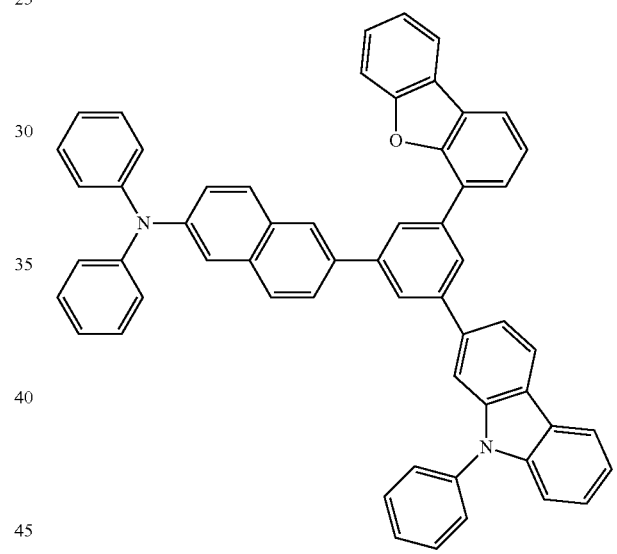
179

377
-continued
180
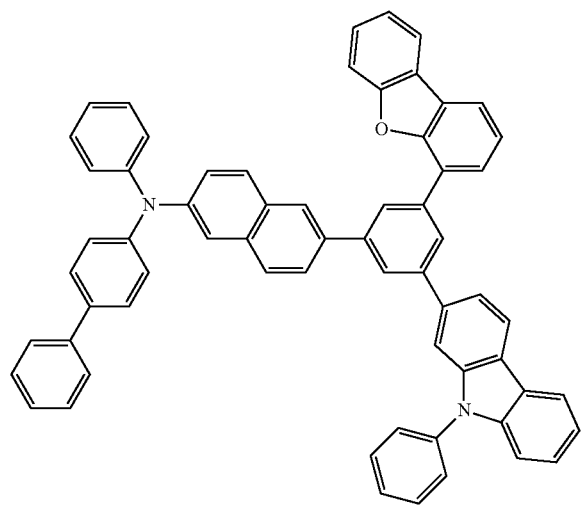
181
182
-continued
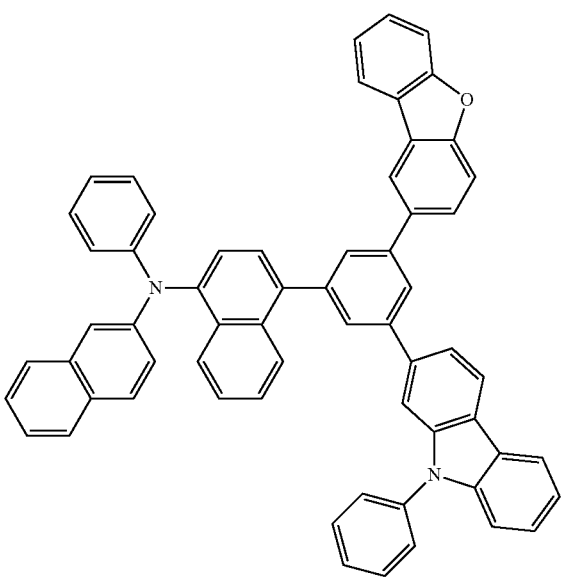
183
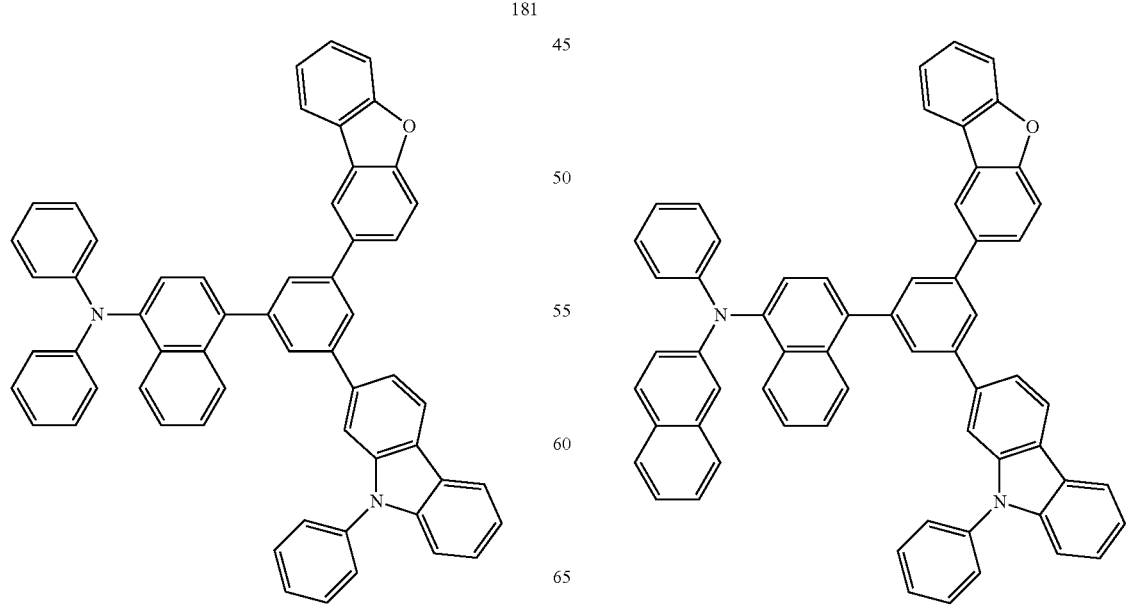

184
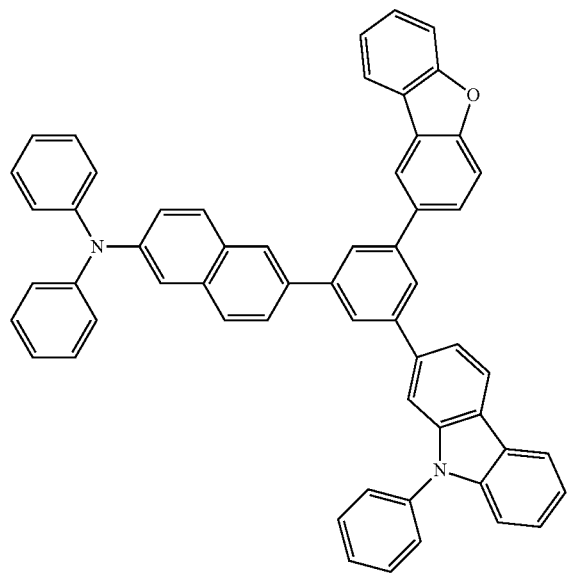
185
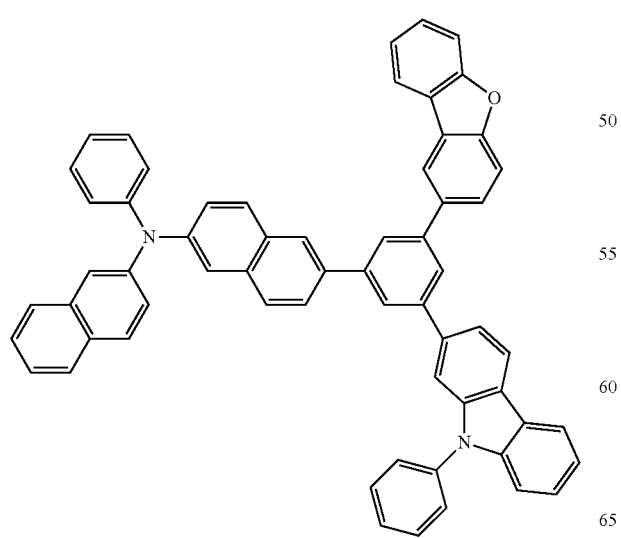
186
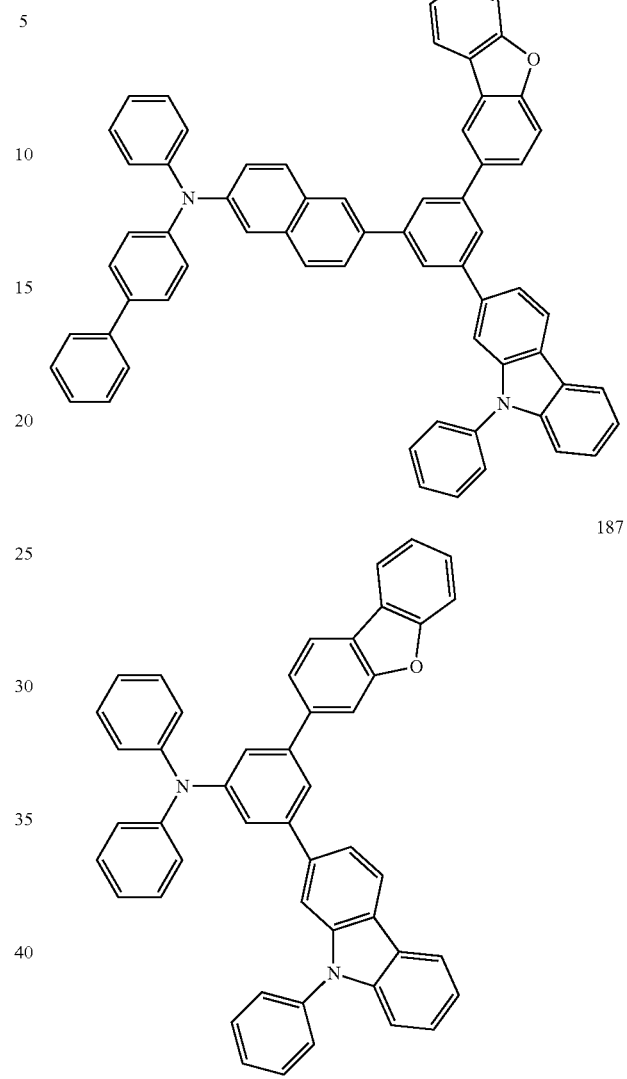
187
188

189
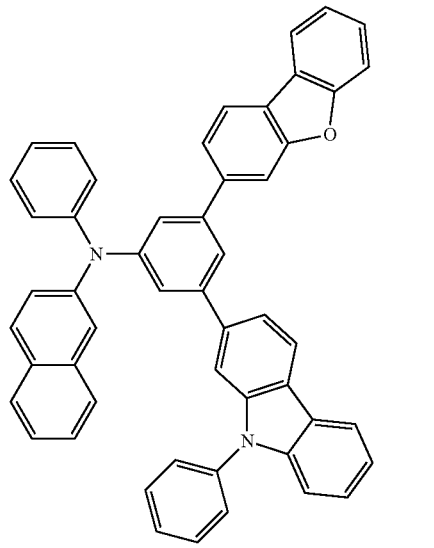
190
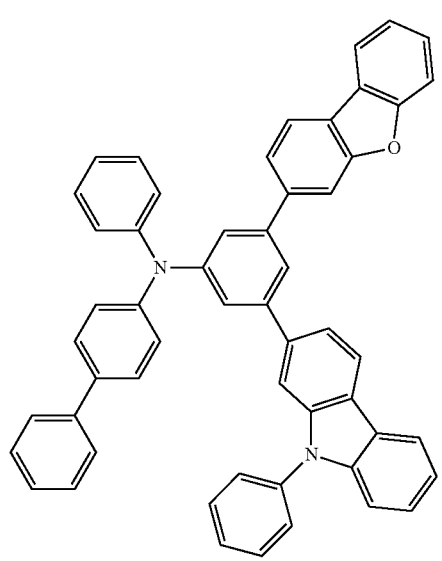
191
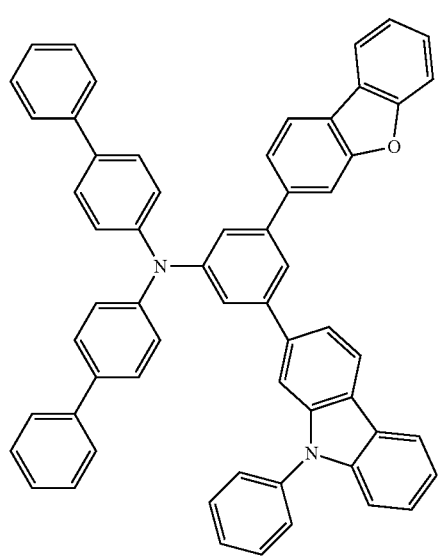
192
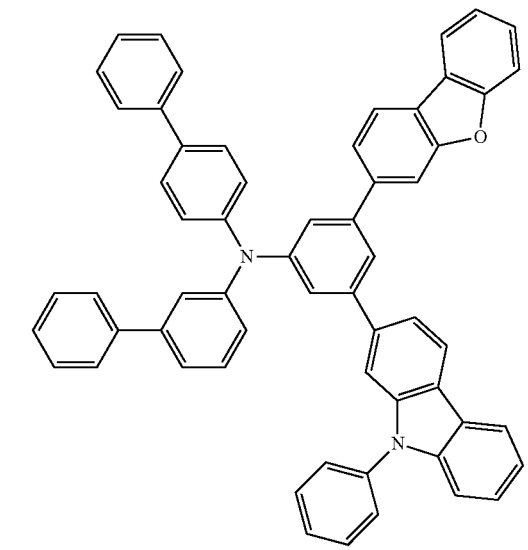
193
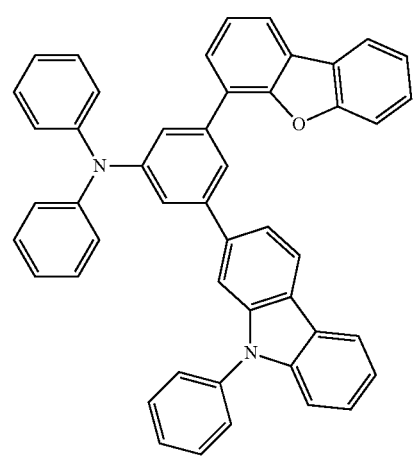
194
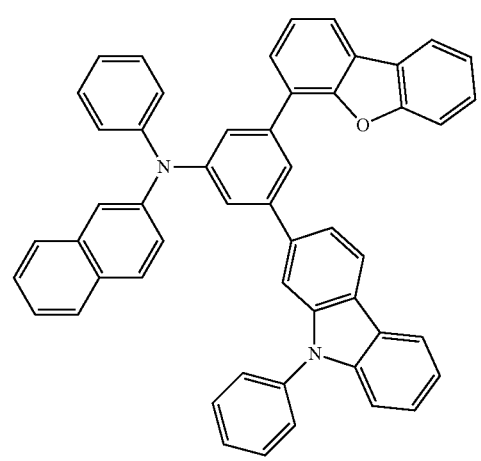

-continued
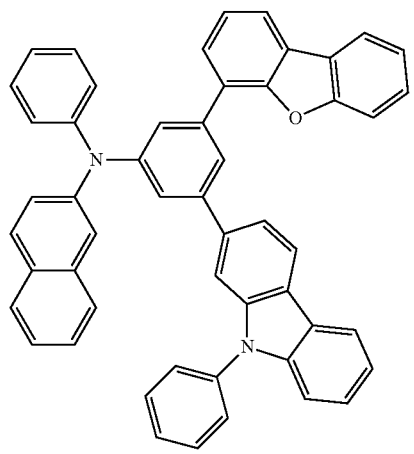
195
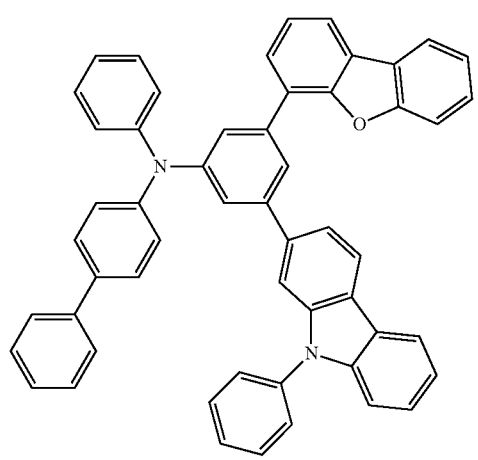
196
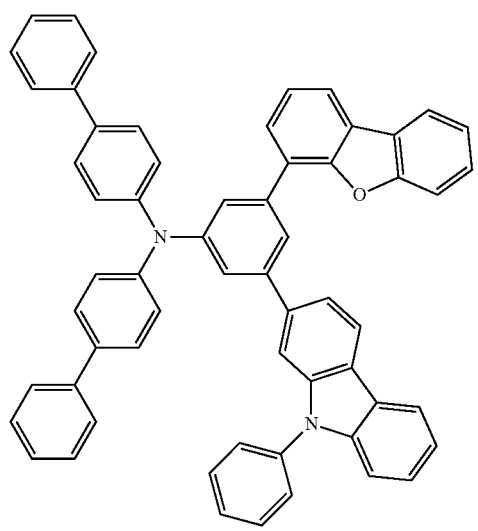
197
-continued
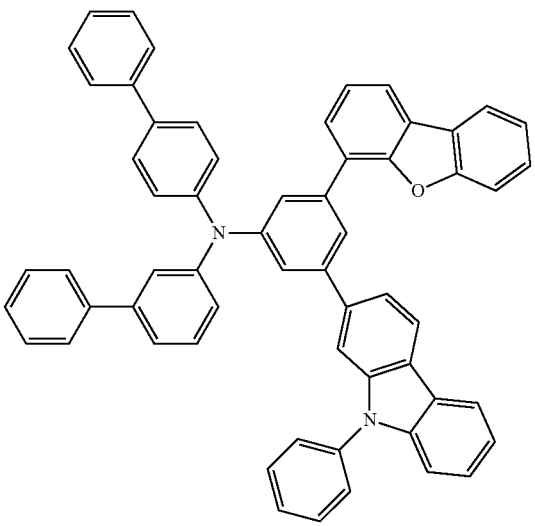
198
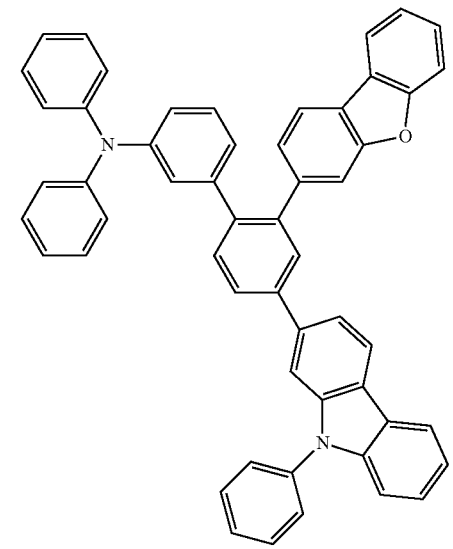
199
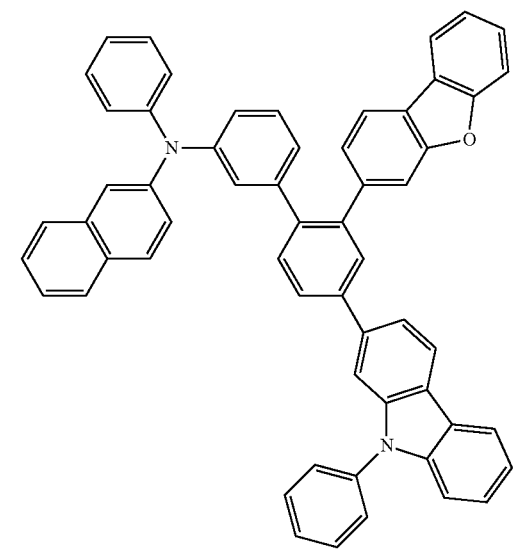
200

385
-continued
201
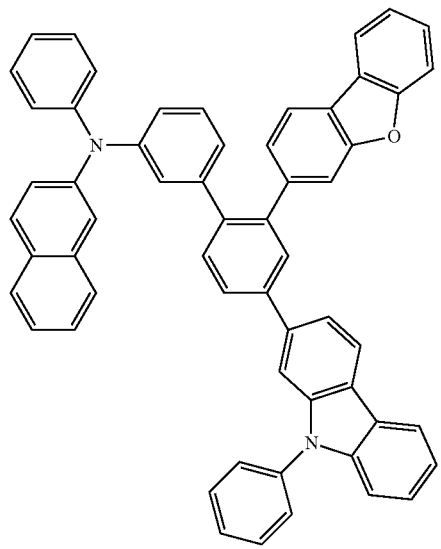
202
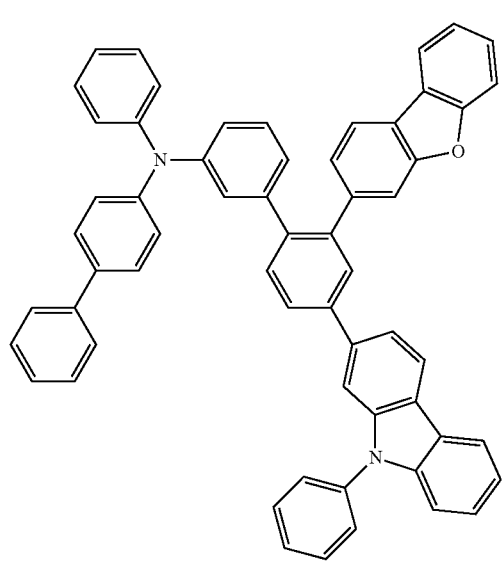
386
-continued
203
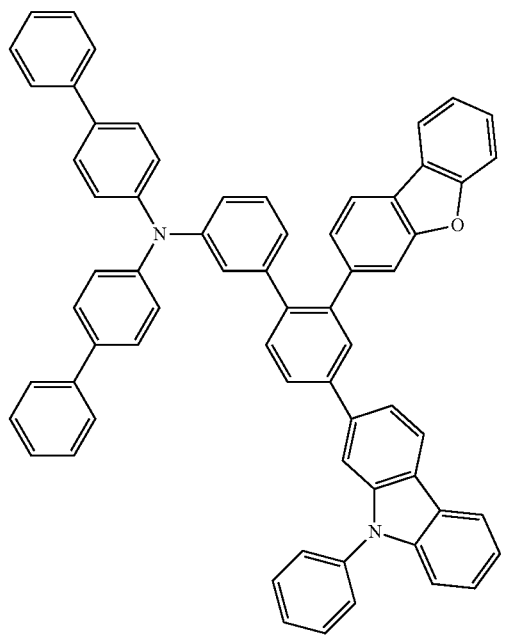
204
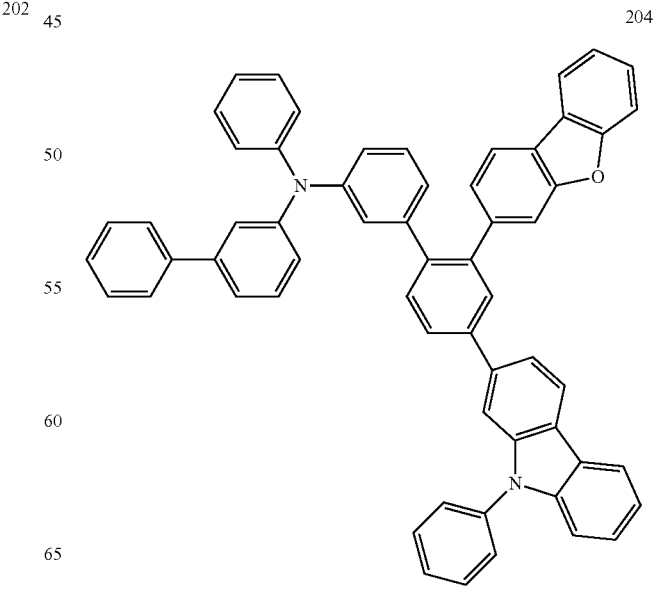

387
-continued
388
-continued
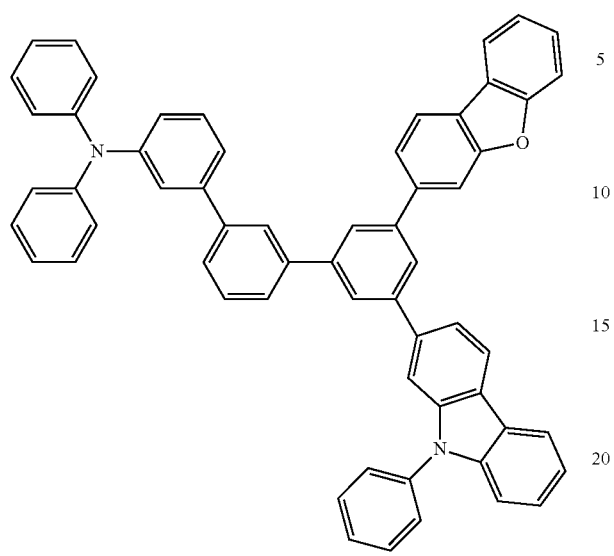
205
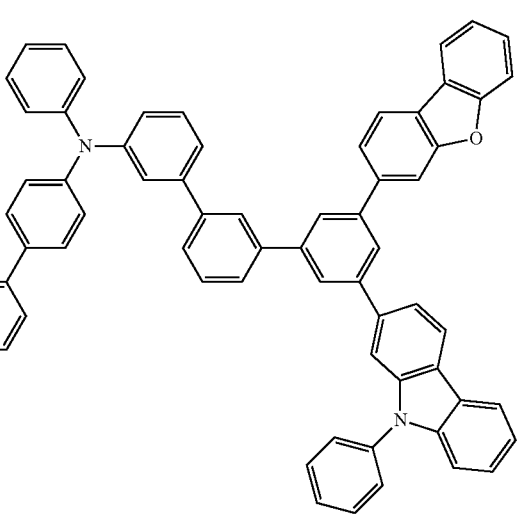
208
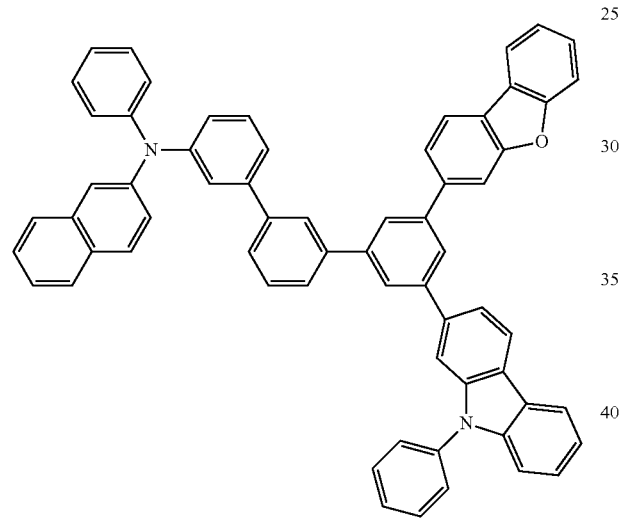
206
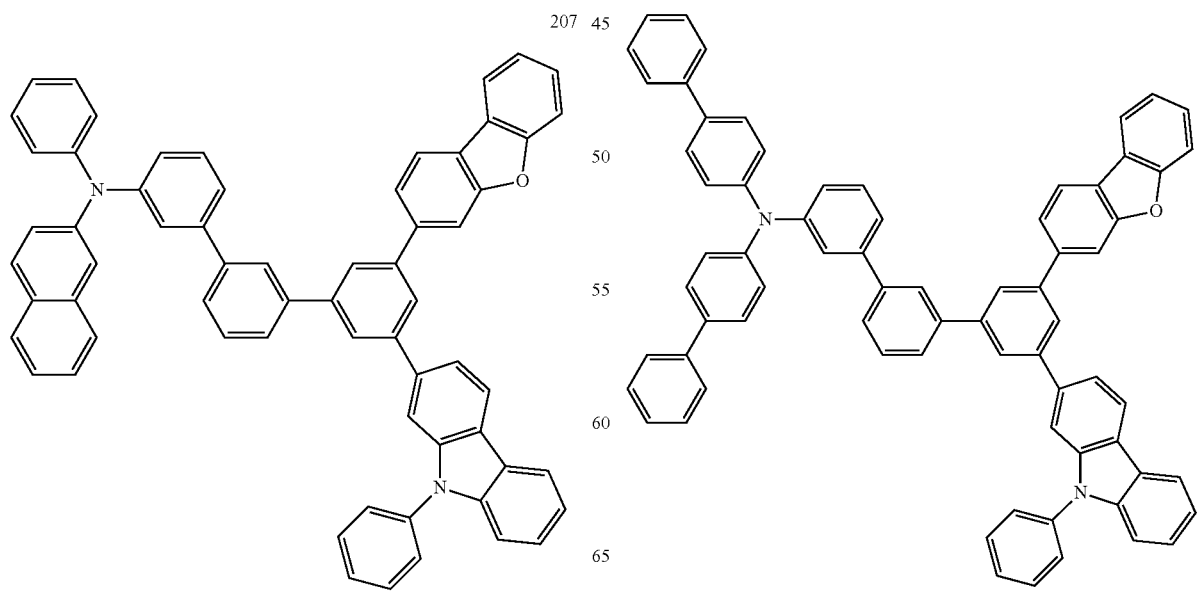
207
209

389
-continued
210
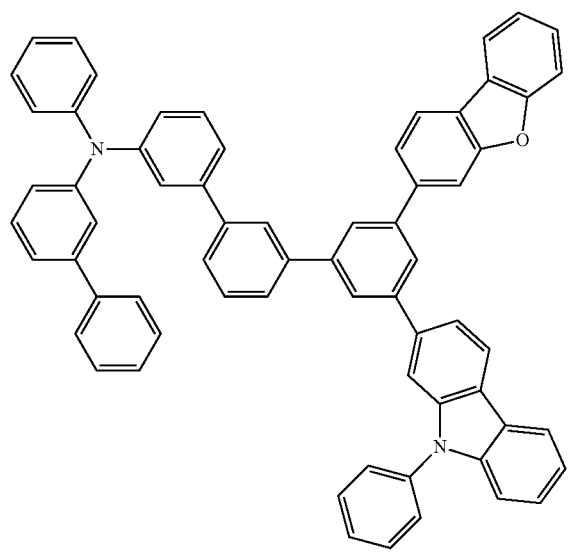
211
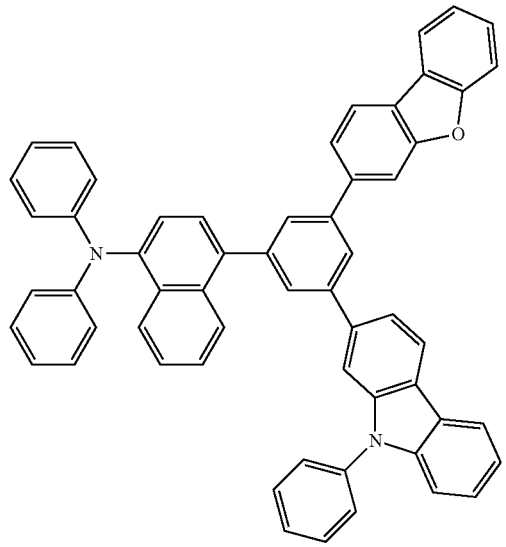
390
-continued
212
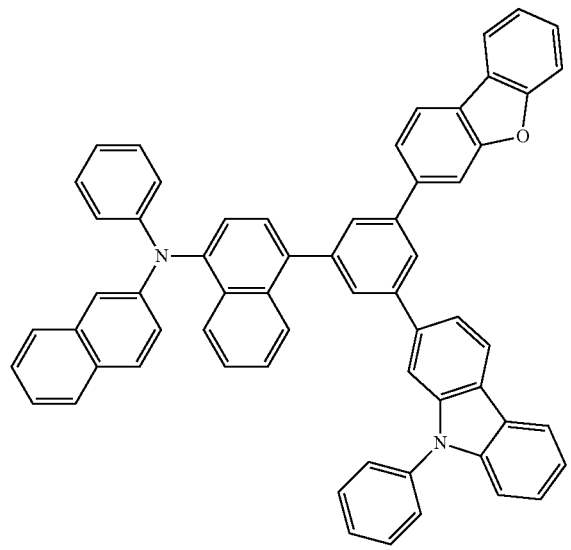
213
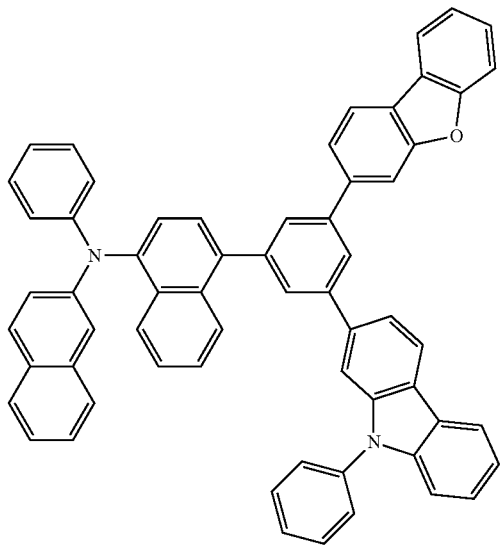

391
-continued
214
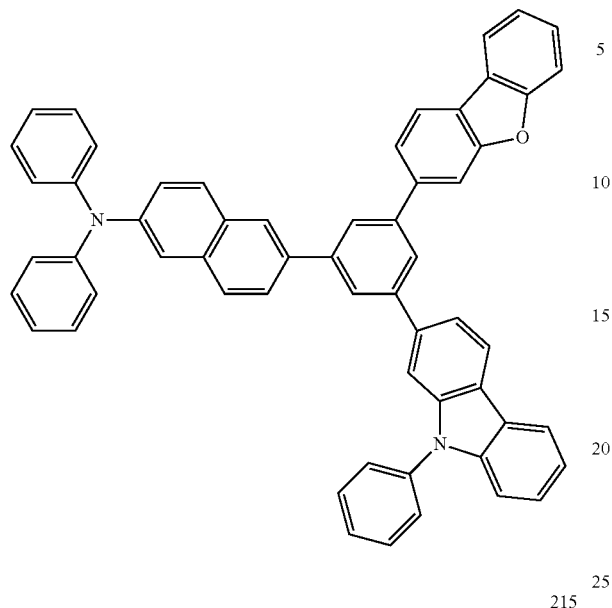
215
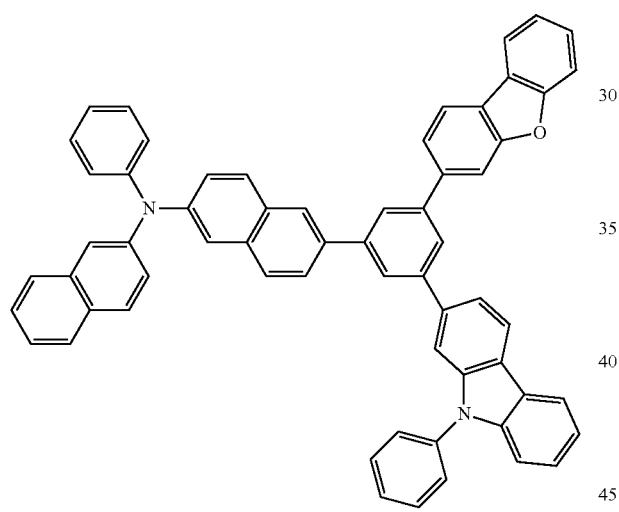
216
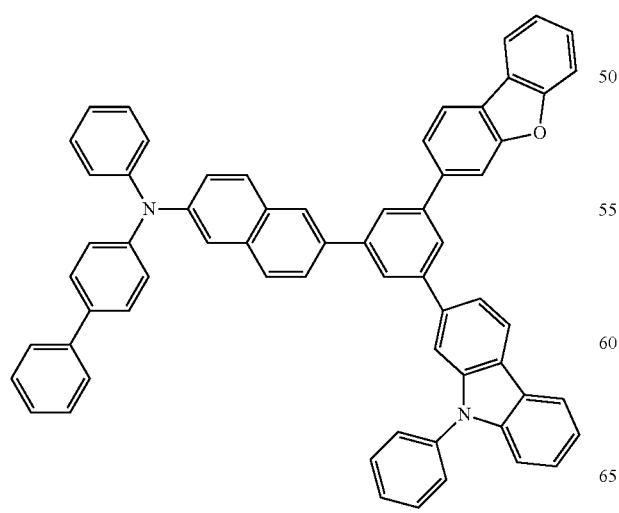
392
-continued
217
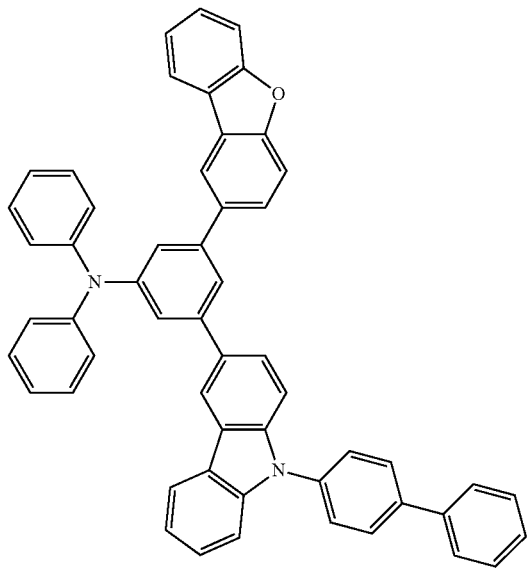
218
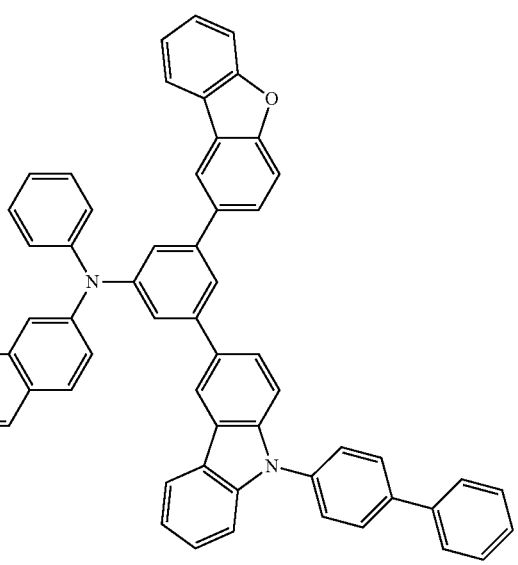

393
-continued
219
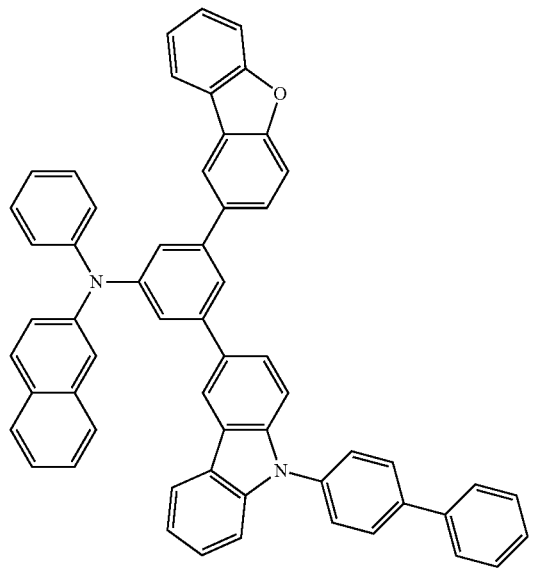
220
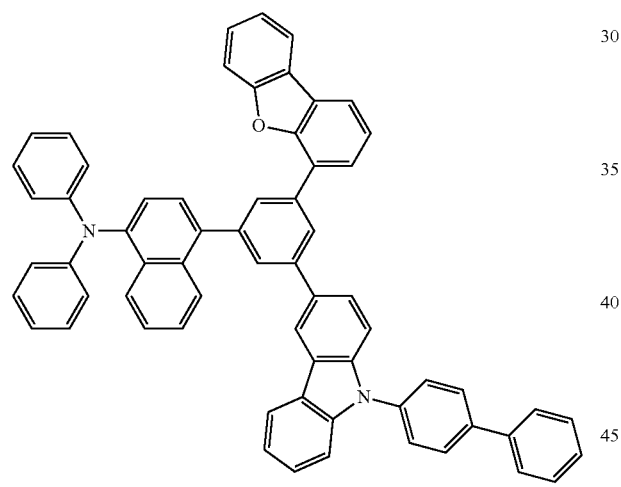
221
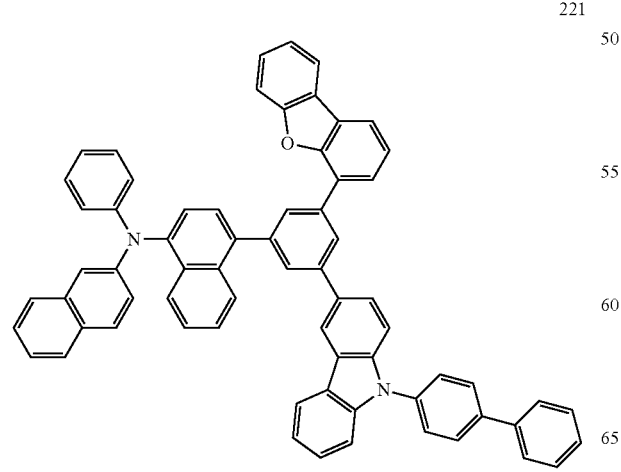
394
-continued
222
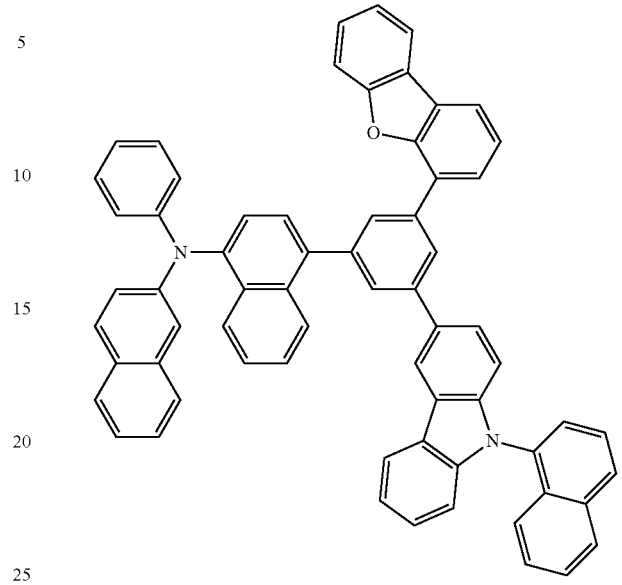
223
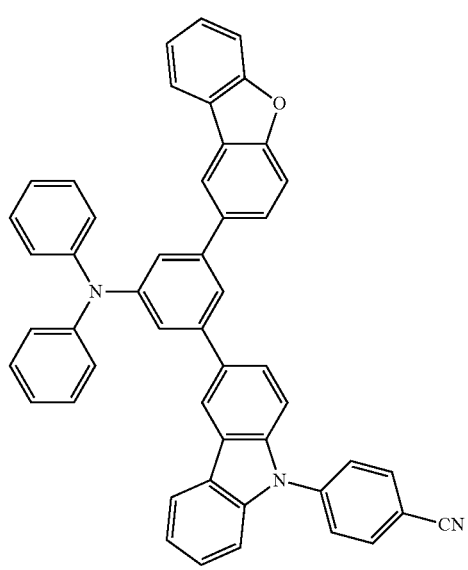

395
-continued
224
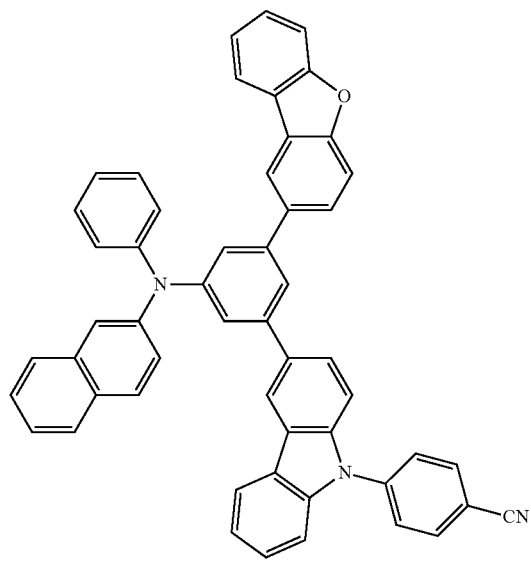
225
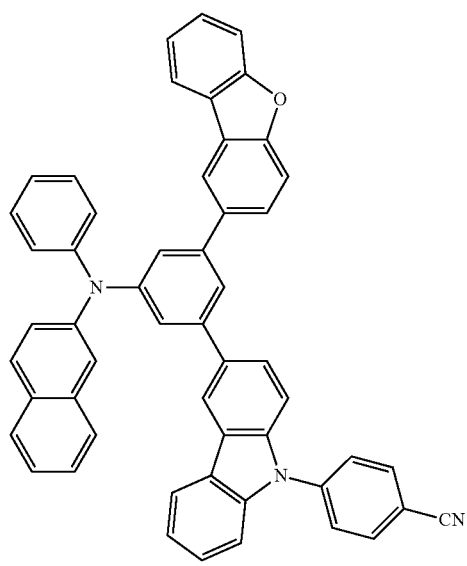
226
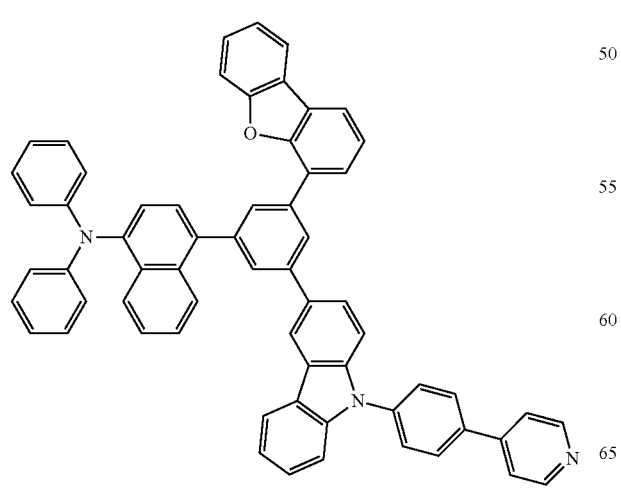
396
-continued
227
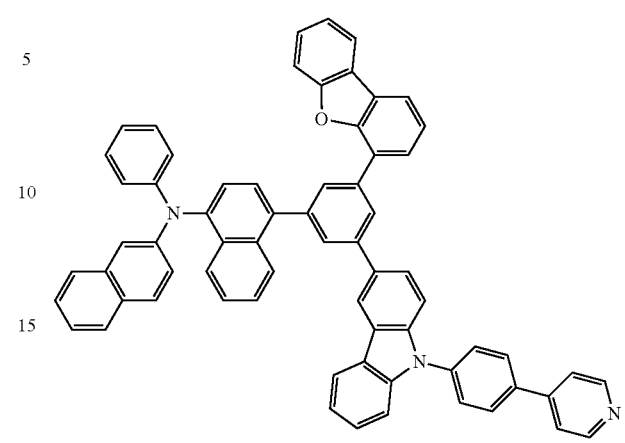
228
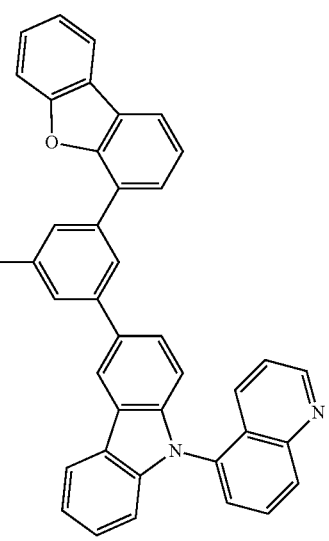
229

397
-continued
230
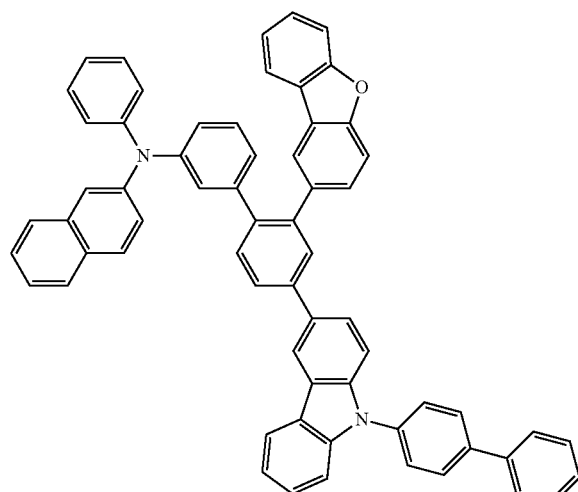
231
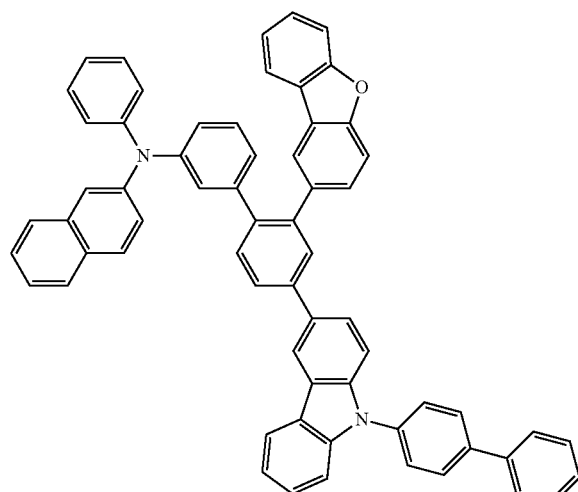
232
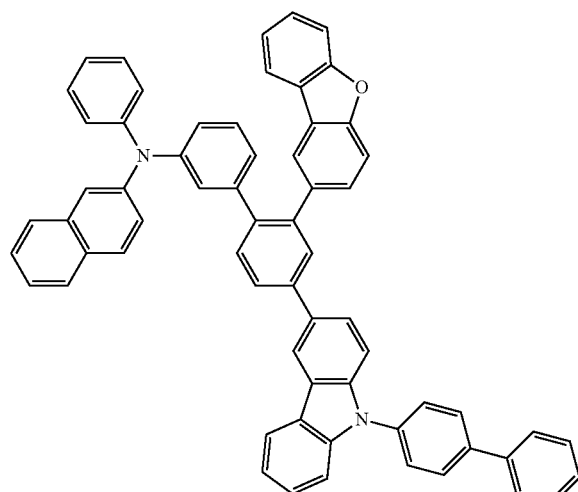
398
-continued
233
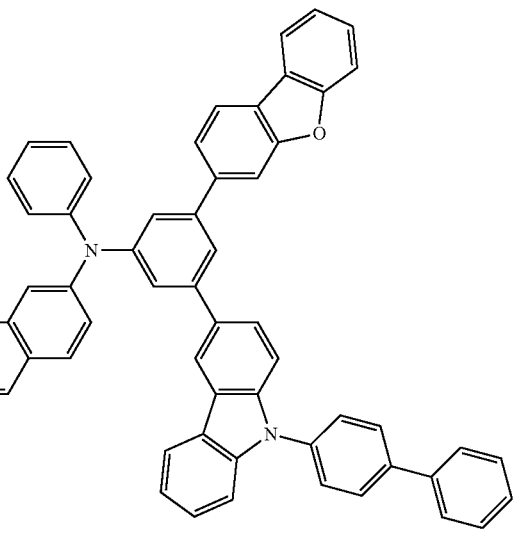
234
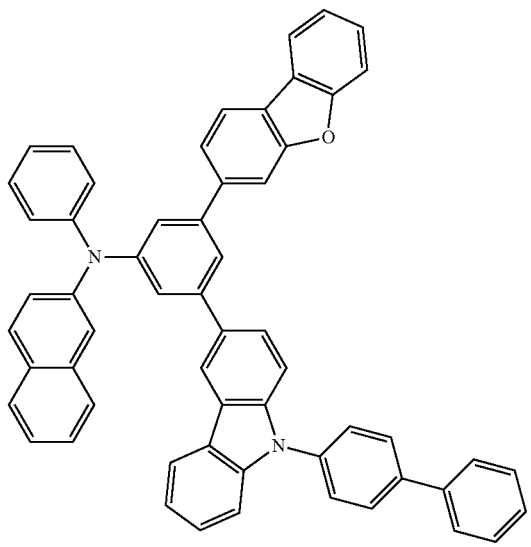

235
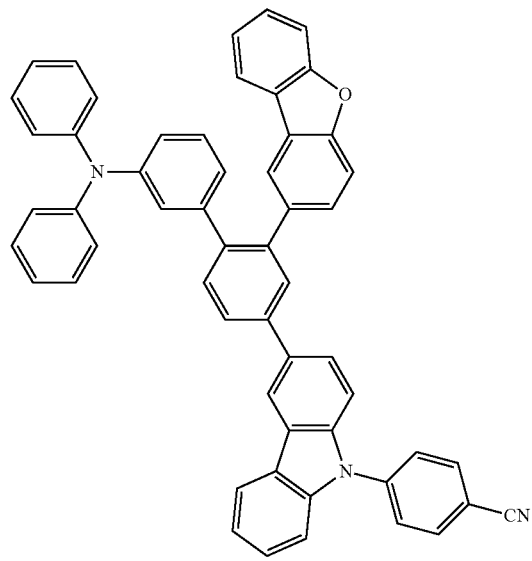
236
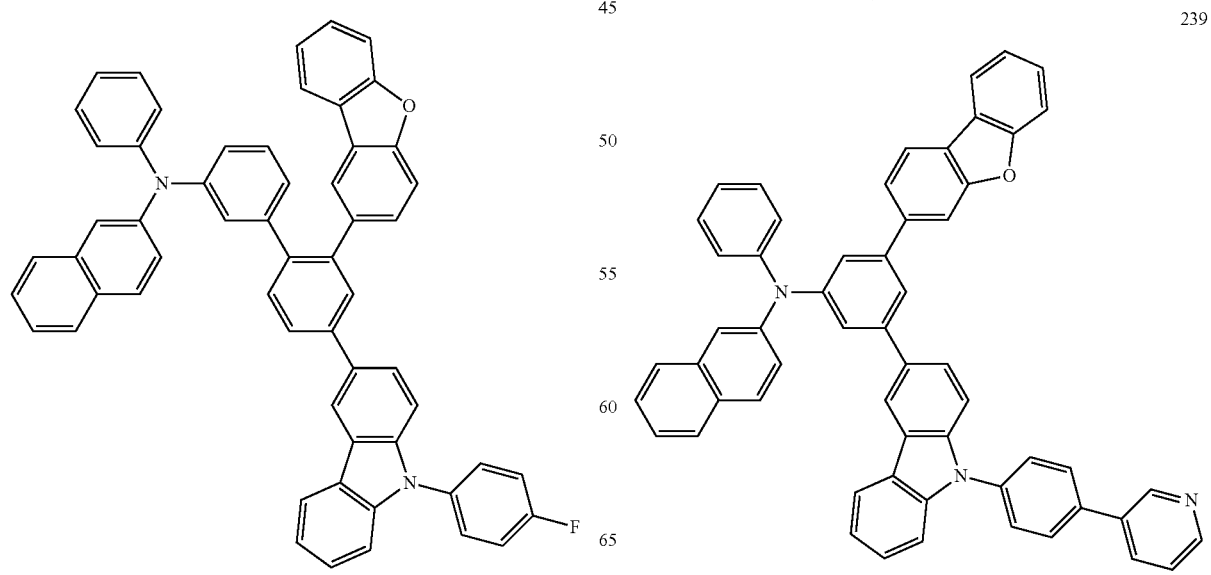
237
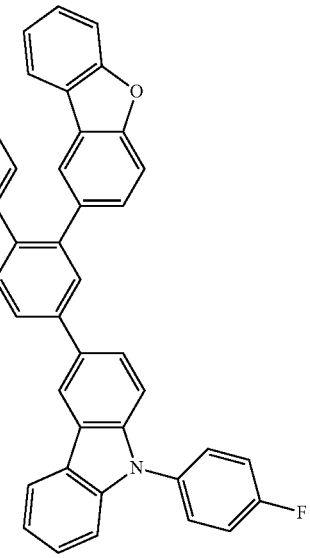
238
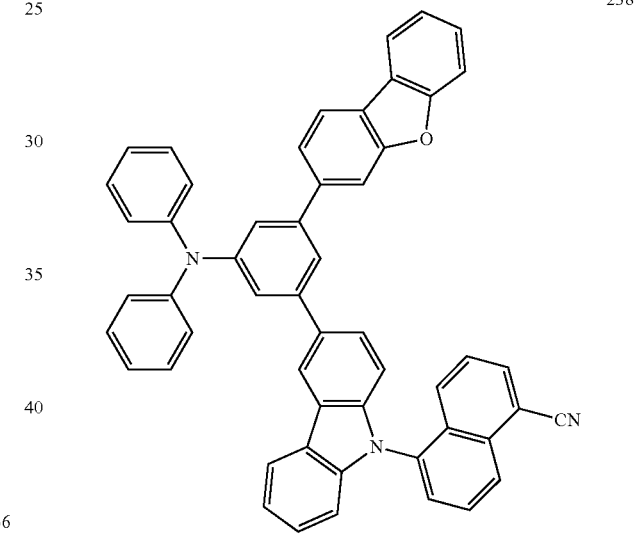
239
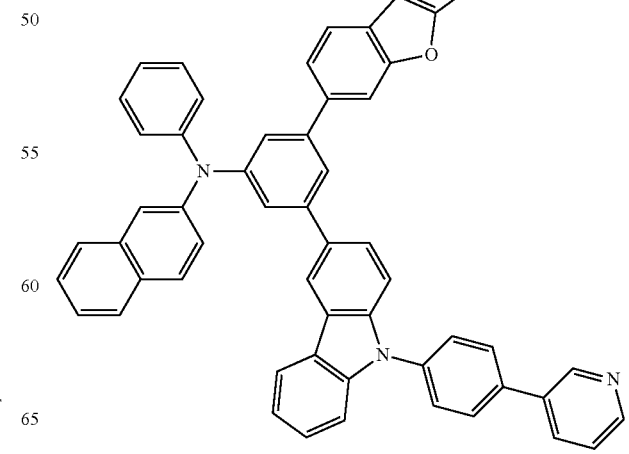

401
-continued
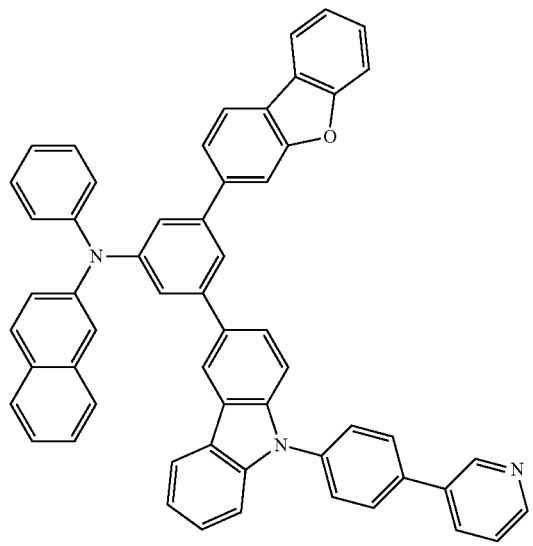
240
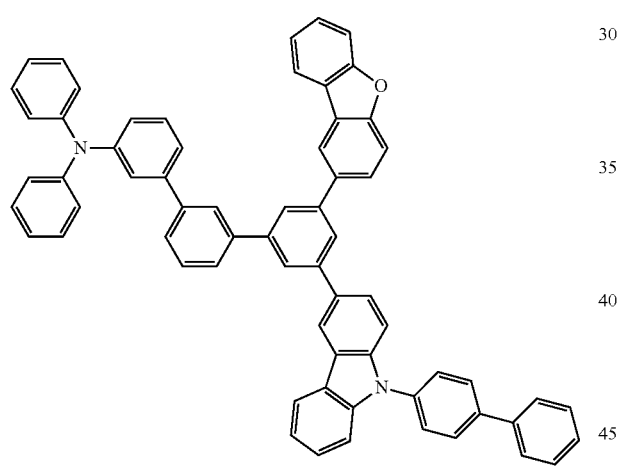
241
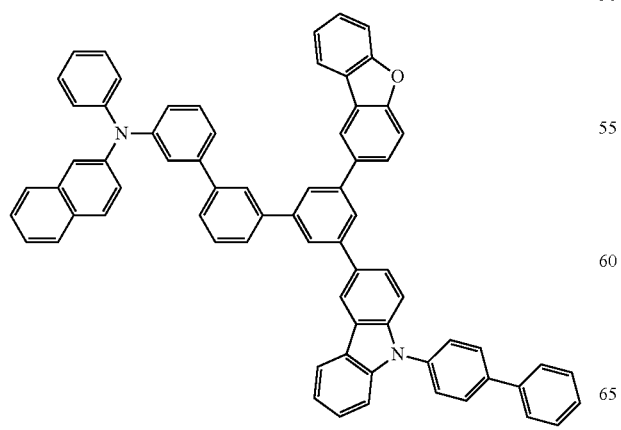
242
402
-continued
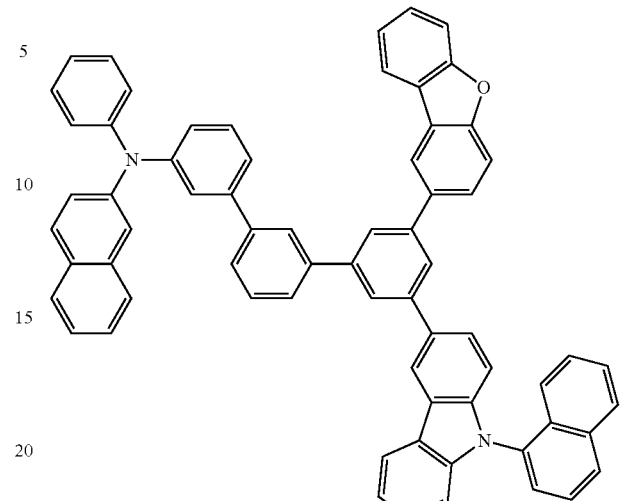
243
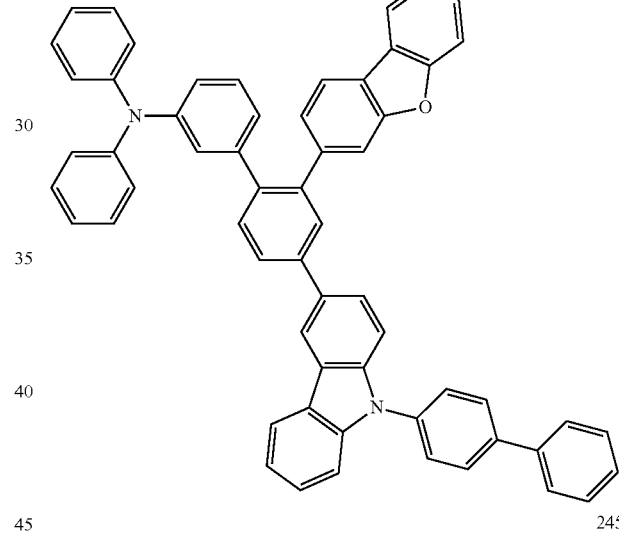
244
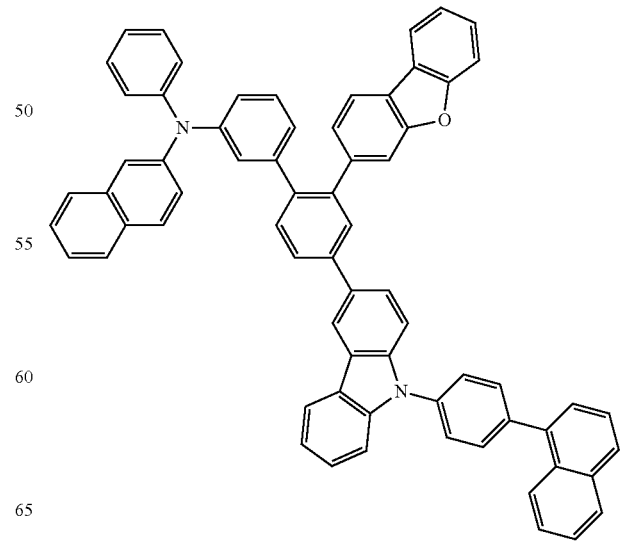
245

403
-continued
246
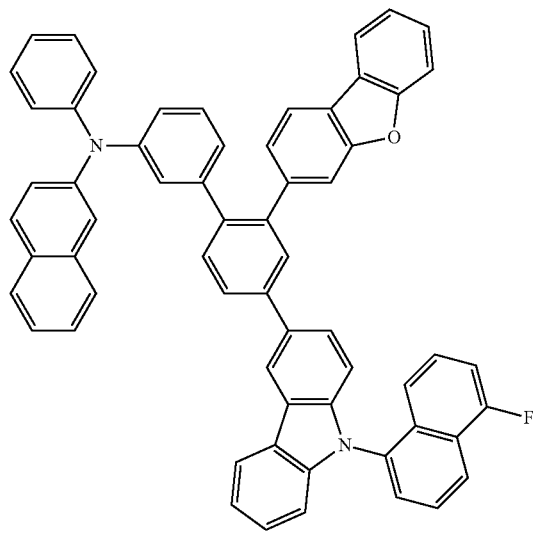
247
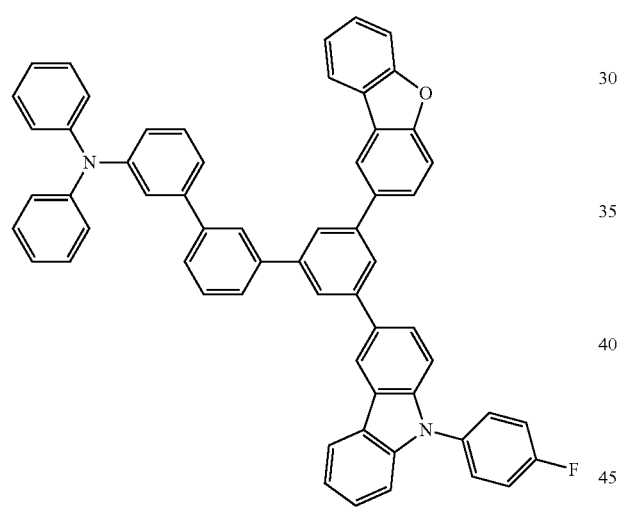
248
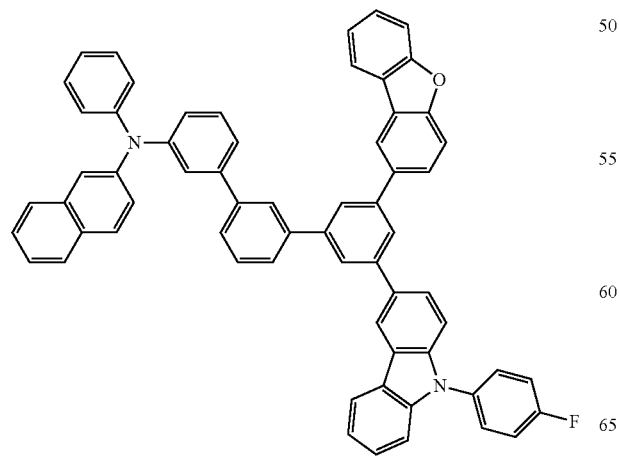
404
-continued
249
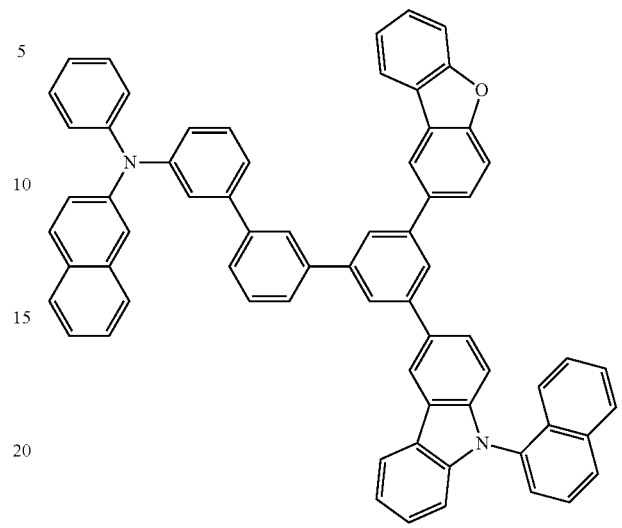
250
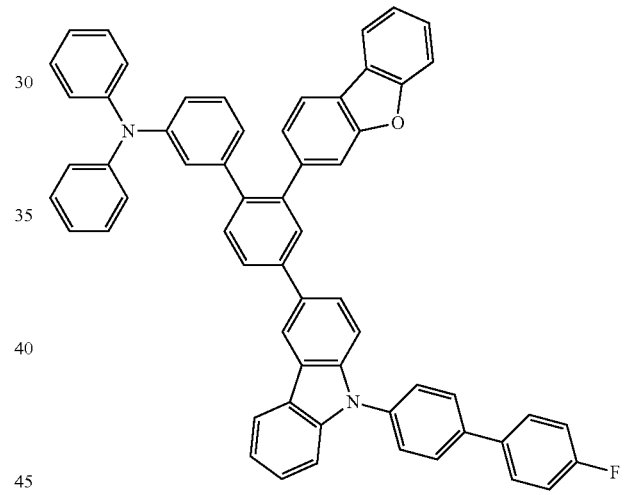
251
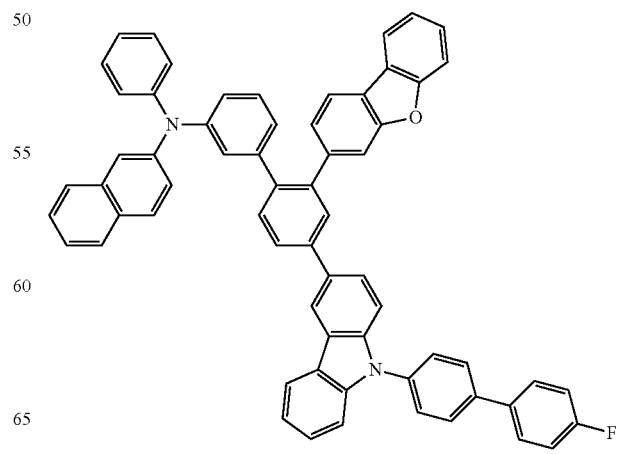

405
-continued
252
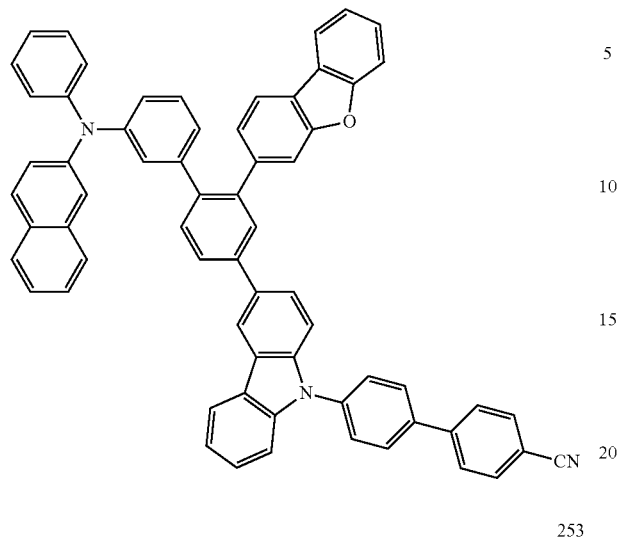
253
255
-continued
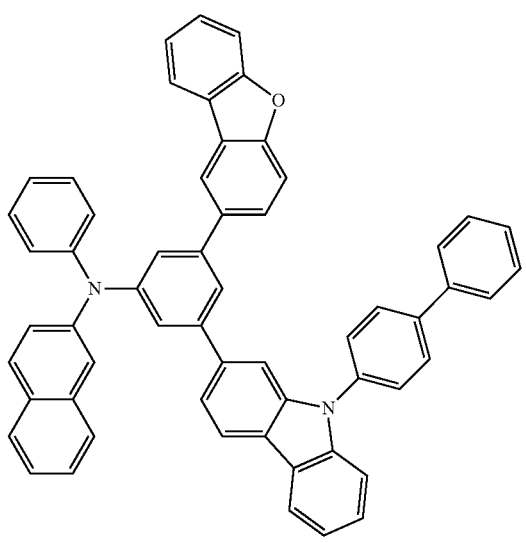
406
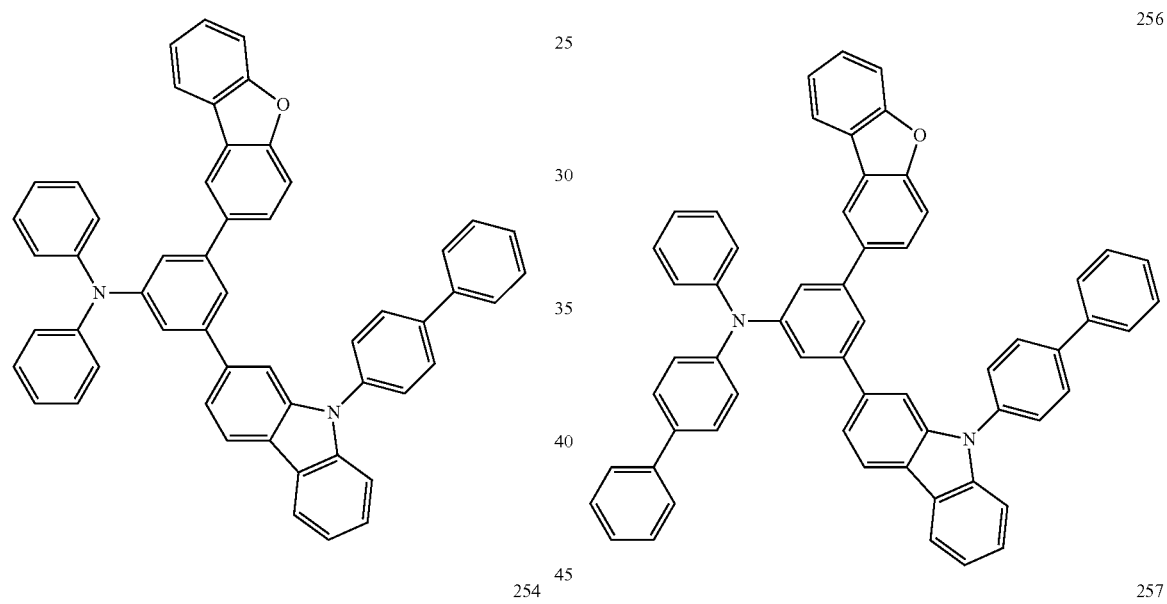
254
256
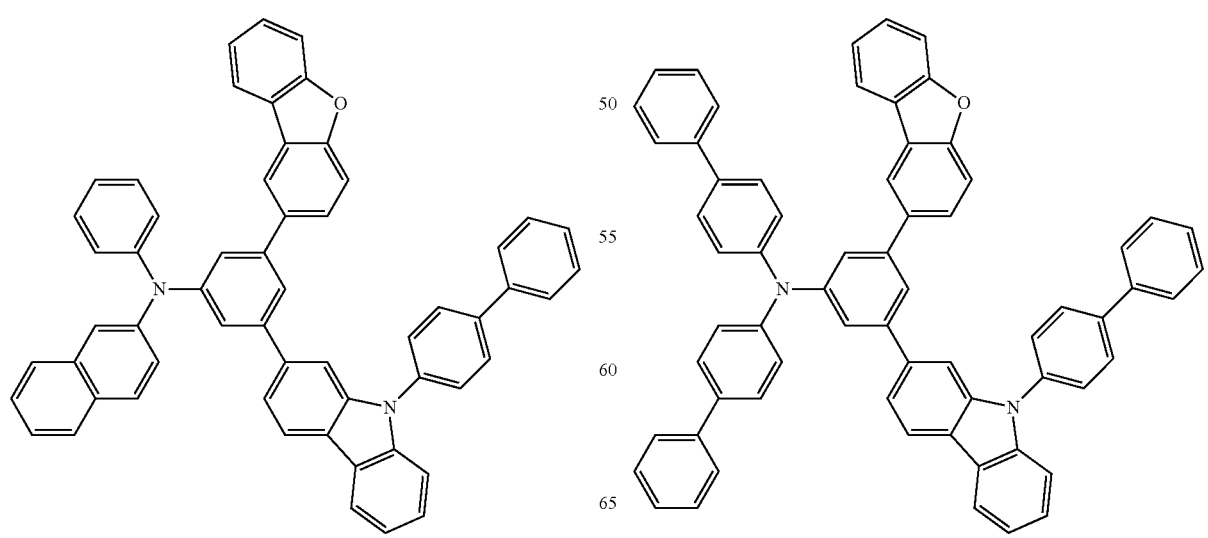
257

407
-continued
258
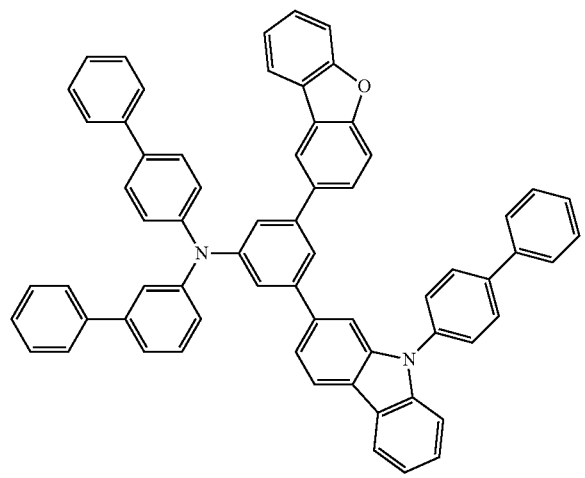
259
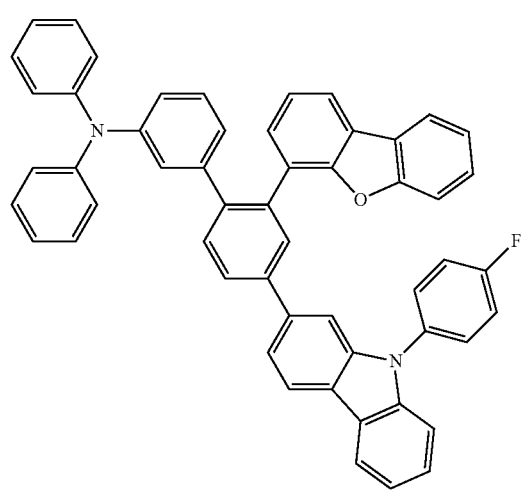
260
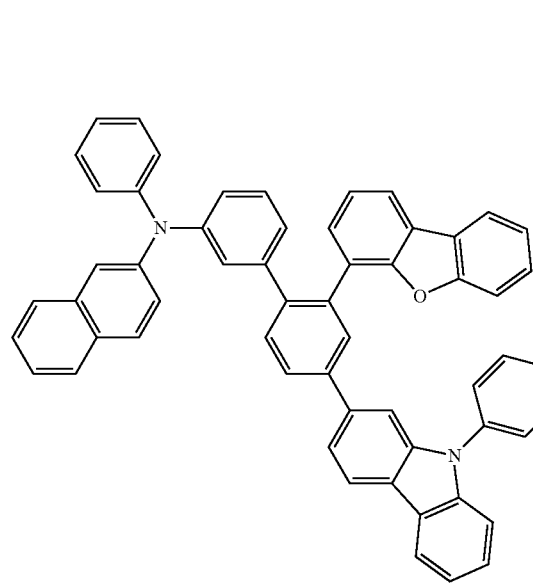
408
-continued
261
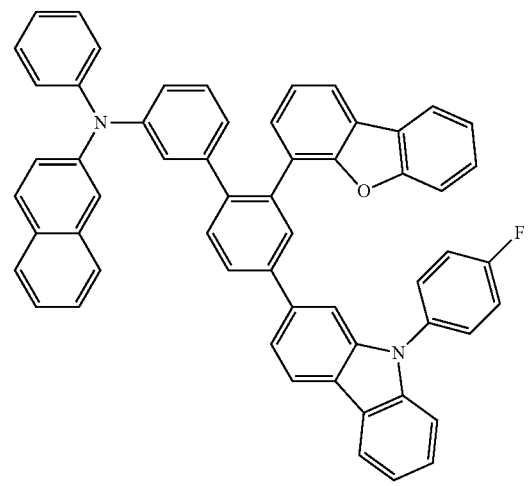
262
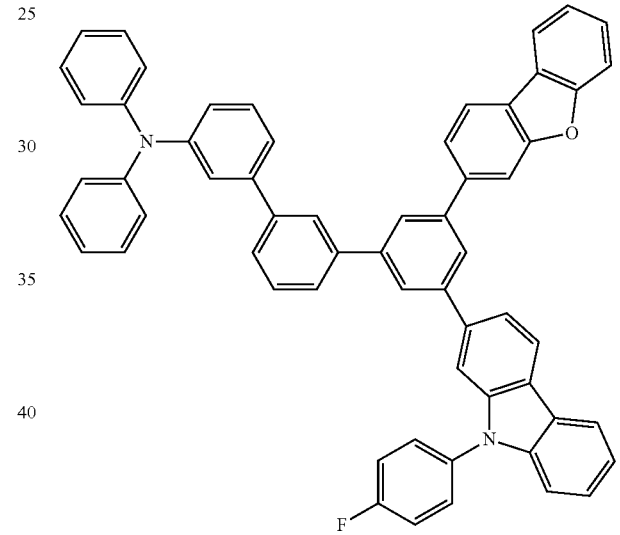
263
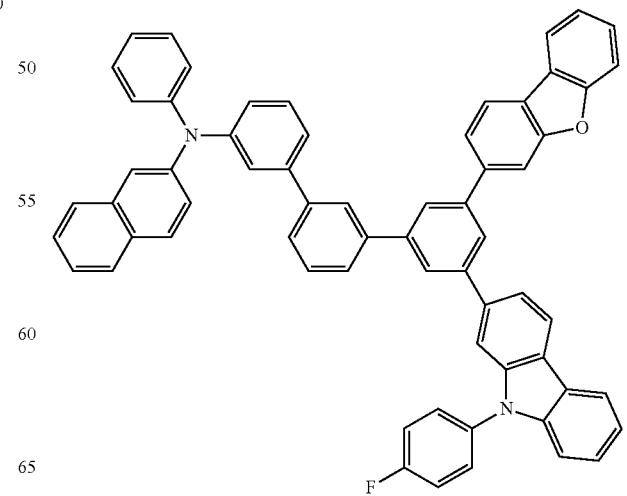

264
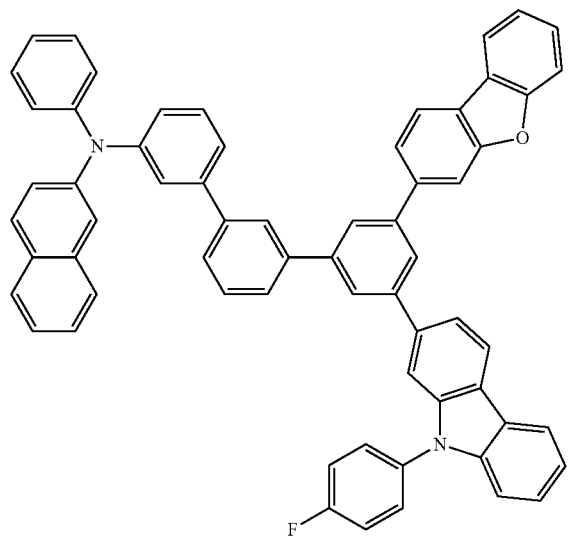
267
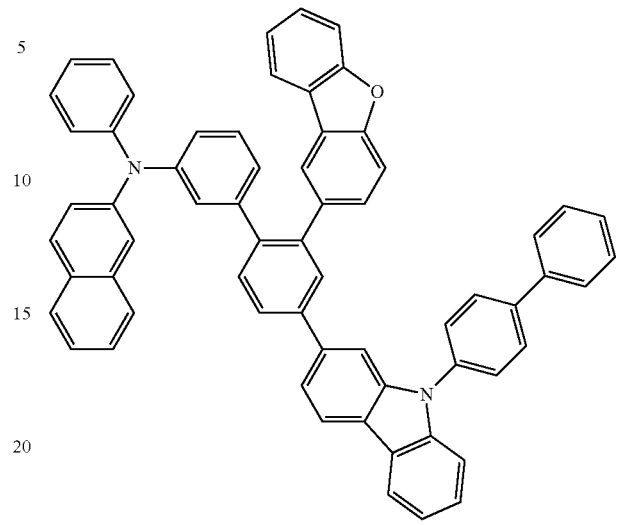
265
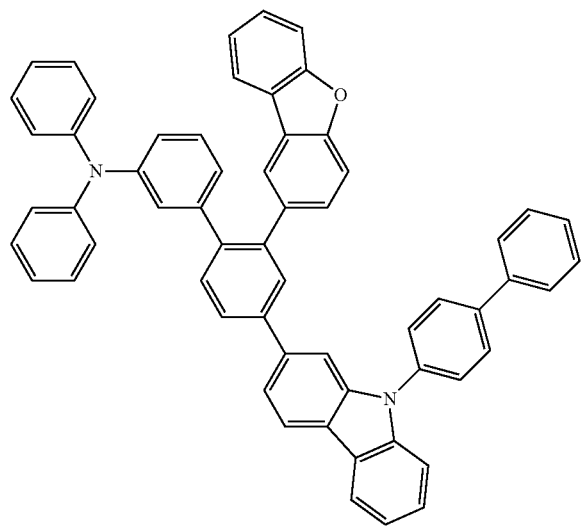
268
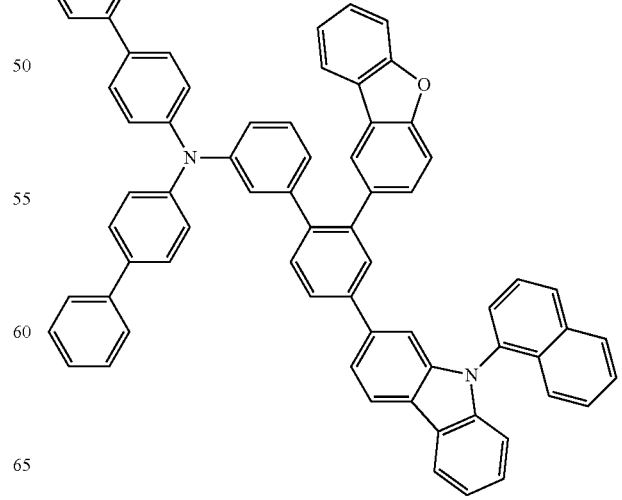
266
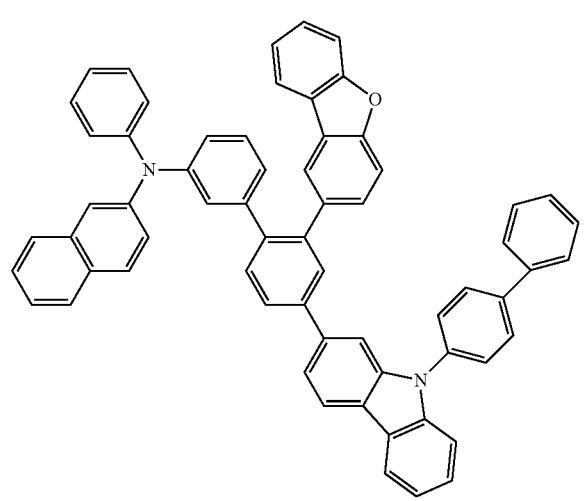
269
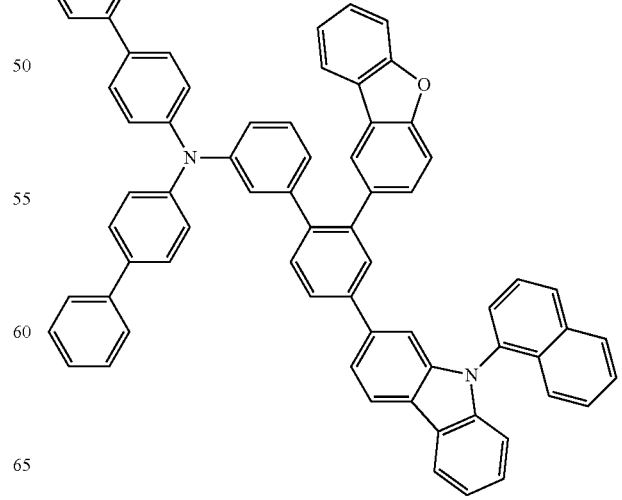

411
-continued
270
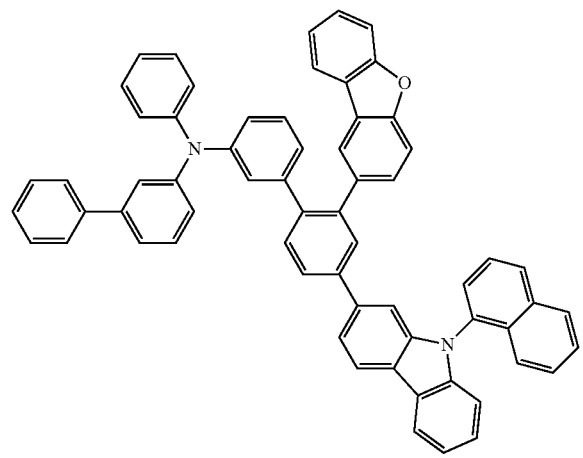
271
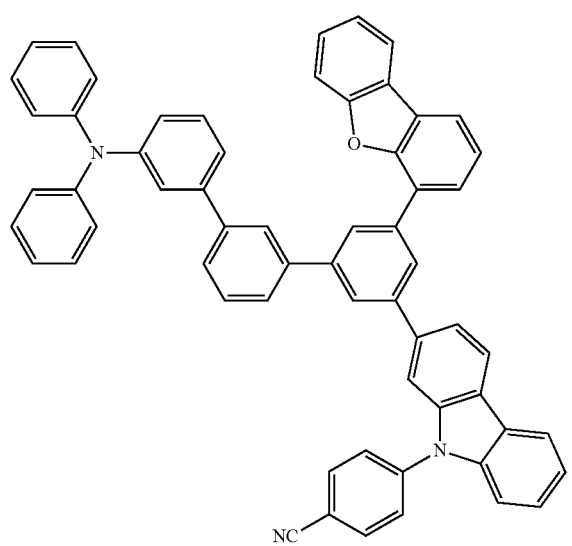
272
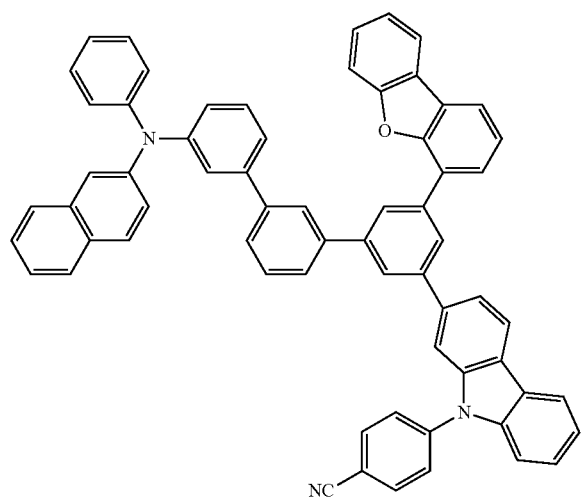
412
-continued
273
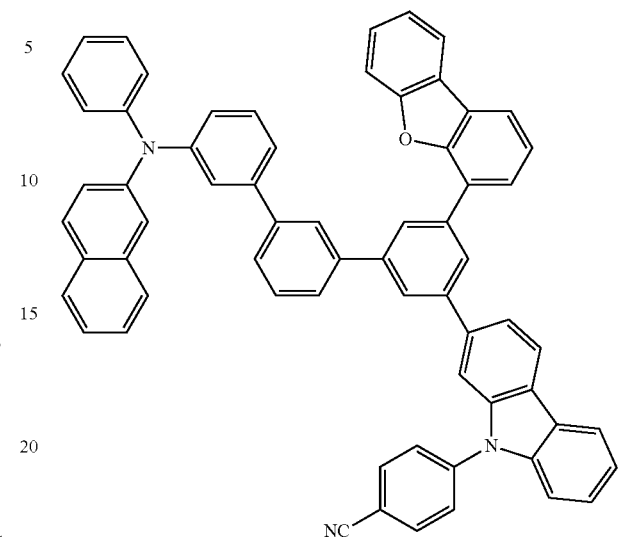
274
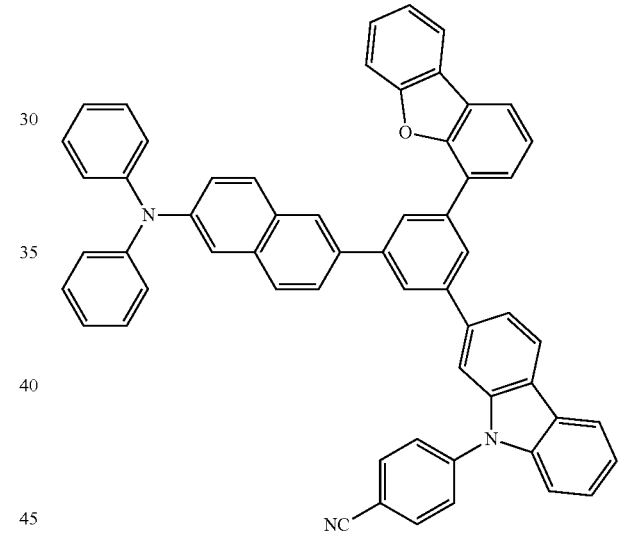
275
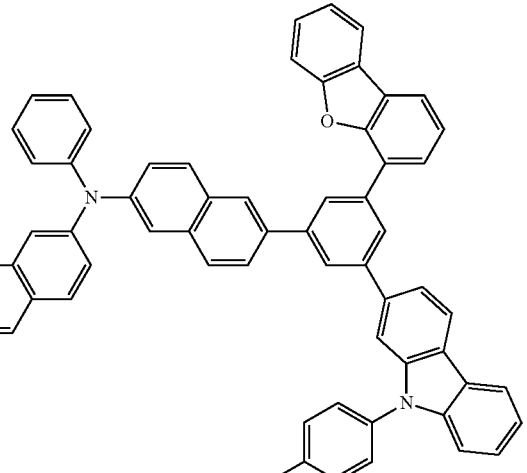

276
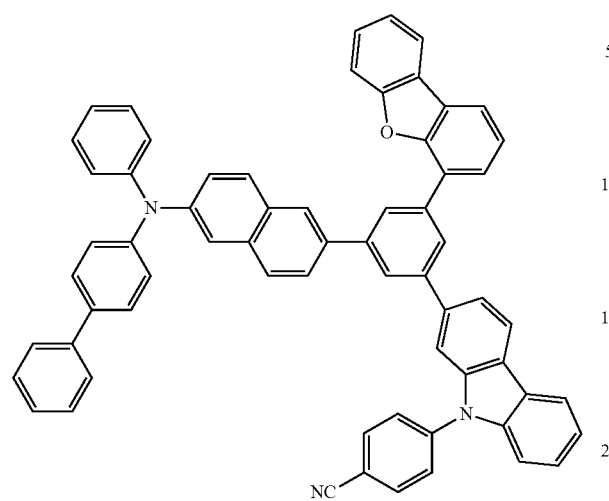
277
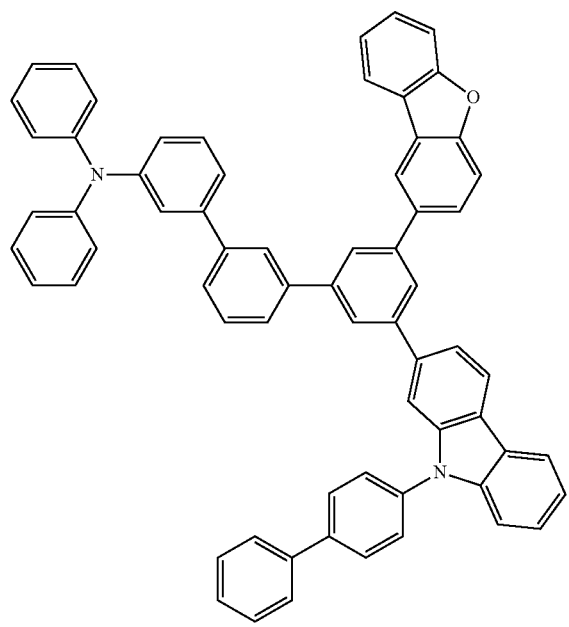
278
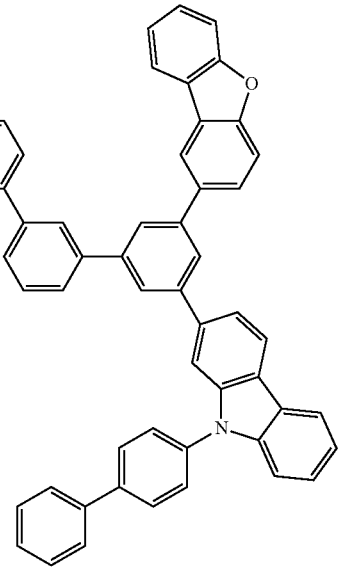
279
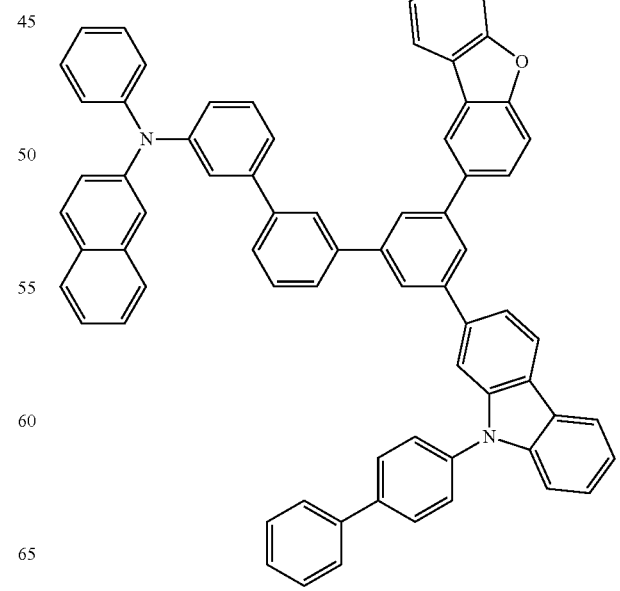

415
-continued
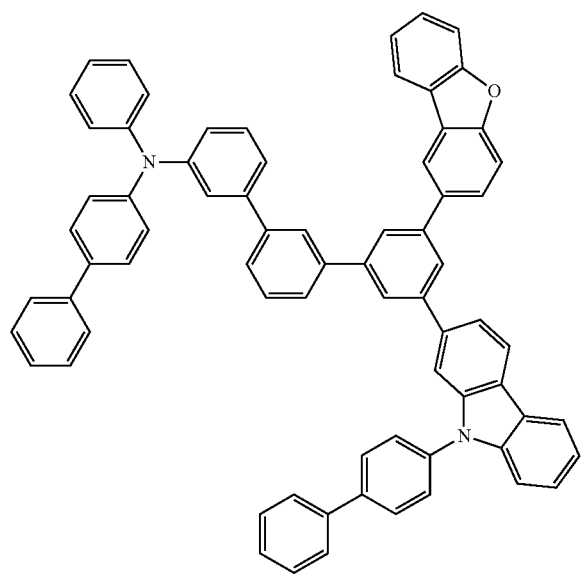
280
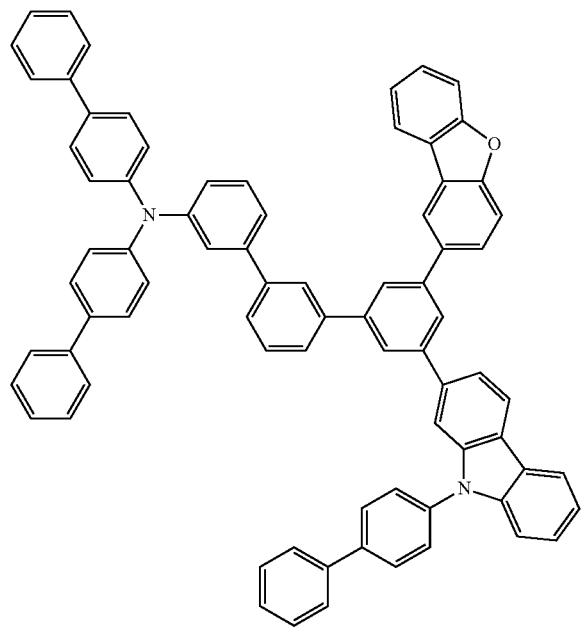
281
416
-continued
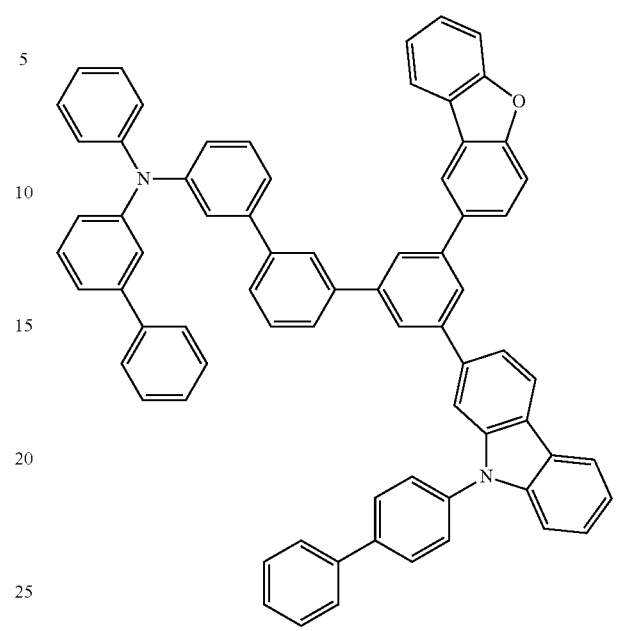
282
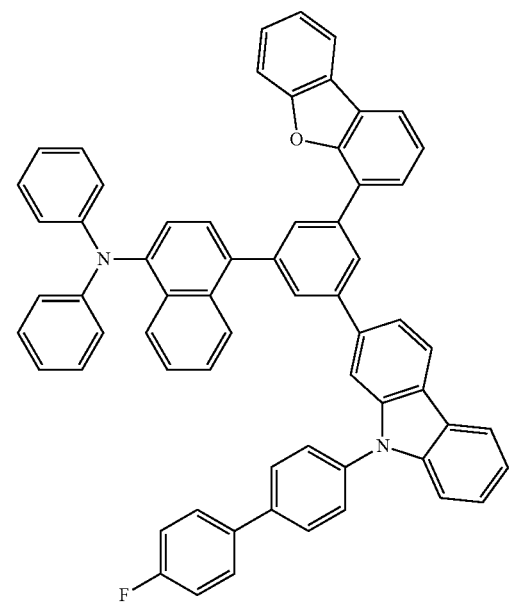
283

417
-continued

418
-continued

419
-continued
420
-continued
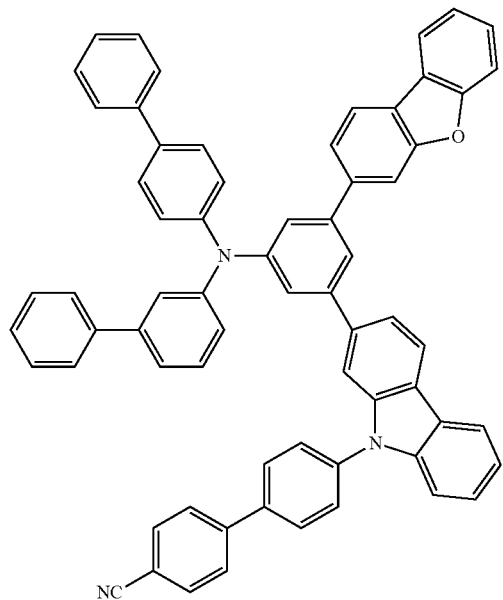
288
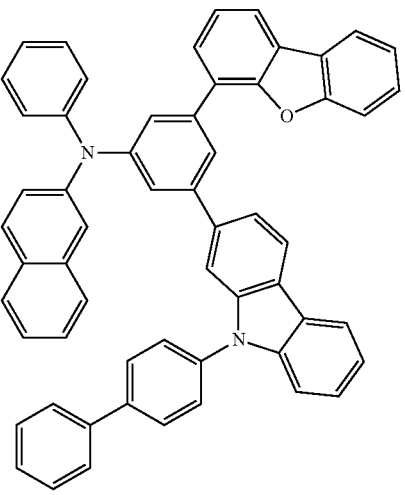
291
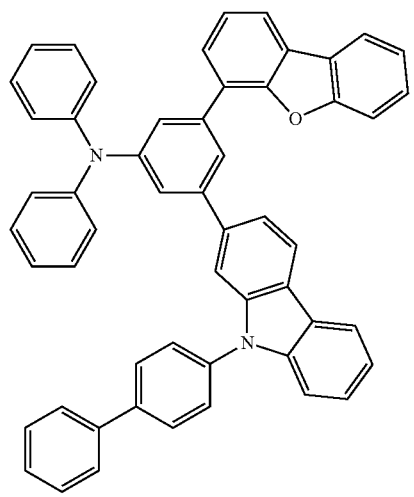
289
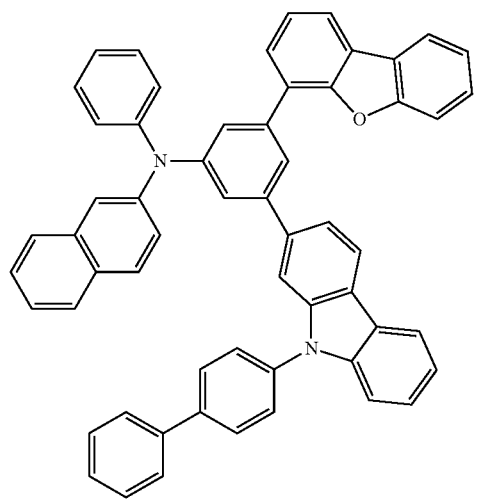
290
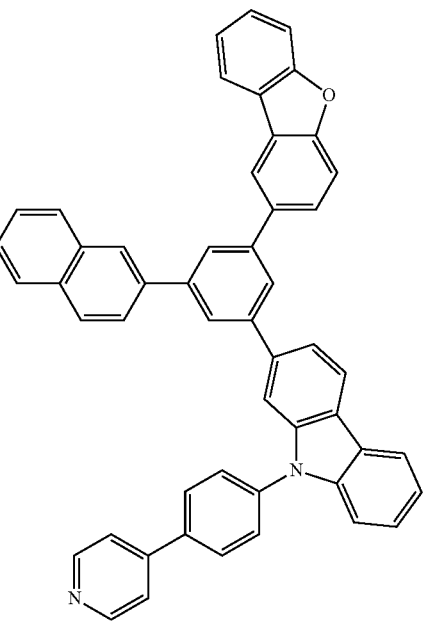
292

421
-continued
293
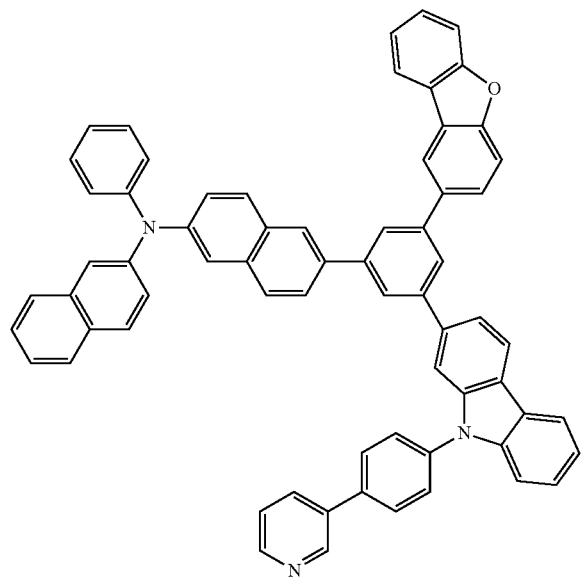
294
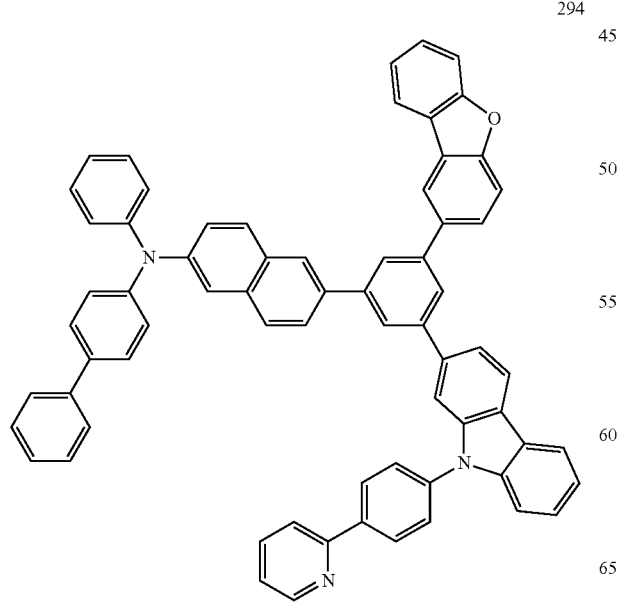
422
-continued
295
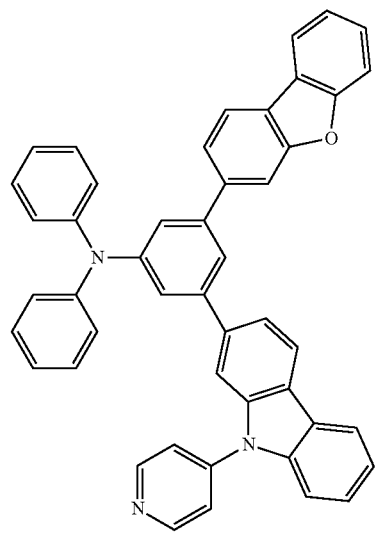
296
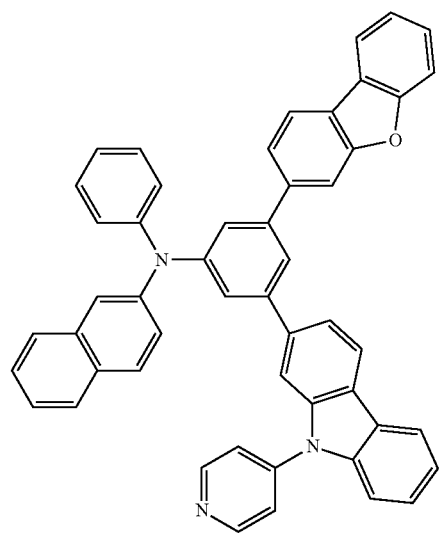
297
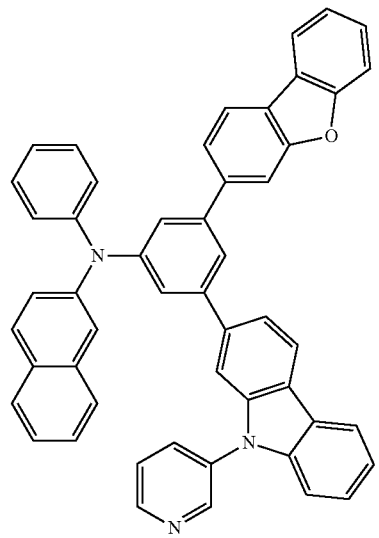

423
-continued

298

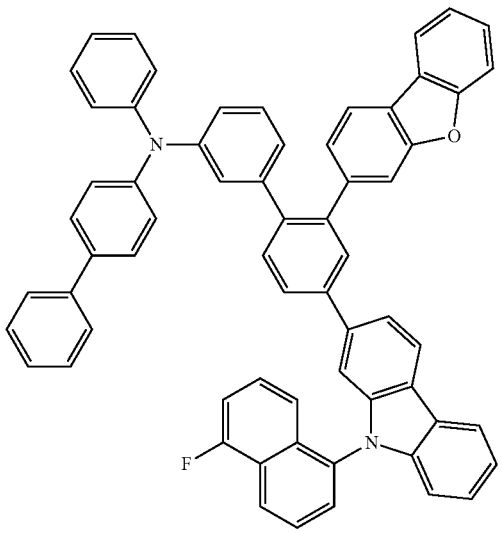

299

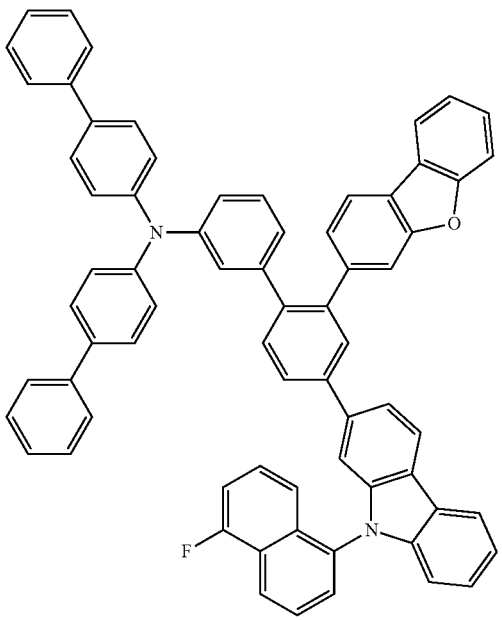

424
-continued

300

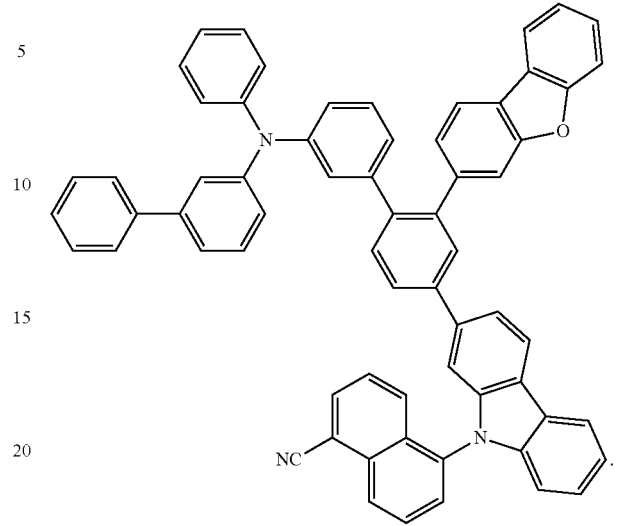

17. An organic light-emitting device, comprising:
a first electrode;
a second electrode facing the first electrode; and
an organic layer between the first electrode and the second electrode, the organic layer including an emission layer,
wherein the organic layer includes at least one amine-based compound as claimed in claim 1.

18. The organic light-emitting device as claimed in claim 17, wherein
the first electrode is an anode,
the second electrode is a cathode, and
the organic layer includes:
a hole transport region between the first electrode and the emission layer, the hole transport region including at least one of a hole injection layer, a hole transport layer, a buffer layer, and an electron blocking layer, and
an electron transport region between the emission layer and the second electrode, the electron transport region including at least one selected from a hole blocking layer, an electron transport layer, and an electron injection layer.

19. The organic light-emitting device as claimed in claim 18, wherein the amine-based compound is included in the hole transport region.

20. The organic light-emitting device as claimed in claim 19, wherein the hole transport region further includes a charge-generating material.

* * * * *